United States Patent
Carry et al.

(10) Patent No.: US 9,115,140 B2
(45) Date of Patent: Aug. 25, 2015

(54) THIENOPYRIMIDINE DERIVATIVES, PROCESSES FOR THE PREPARATION THEREOF AND THERAPEUTIC USES THEREOF

(71) Applicant: SANOFI, Paris (FR)

(72) Inventors: Jean-Christophe Carry, Paris (FR); Fabienne Chatreaux, Paris (FR); Stephanie Deprets, Paris (FR); Olivier Duclos, Paris (FR); Vincent Leroy, Paris (FR); Sergio Mallart, Paris (FR); Dominique Melon-Manguer, Paris (FR); Maria Mendez-Perez, Frankfurt am Main (DE); Fabrice Vergne, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/855,246

(22) Filed: Apr. 2, 2013

(65) Prior Publication Data

US 2013/0261106 A1 Oct. 3, 2013

(30) Foreign Application Priority Data

Apr. 3, 2012 (FR) ...................................... 12 53044

(51) Int. Cl.

| A01N 43/90 | (2006.01) |
| A61K 31/519 | (2006.01) |
| C07D 491/00 | (2006.01) |
| C07D 495/00 | (2006.01) |
| C07D 495/04 | (2006.01) |

(52) U.S. Cl.
CPC ............. *C07D 495/04* (2013.01); *A61K 31/519* (2013.01)

(58) Field of Classification Search
None
See application file for complete search history.

(56) References Cited

FOREIGN PATENT DOCUMENTS

| WO | 2009/062258 A1 | 5/2009 |
| WO | WO 2011/049332 A2 | 4/2011 |

OTHER PUBLICATIONS

Gellibert, F. et al., "Design of novel quinazoline derivatives and related analogues as potent and selective ALK5 inhibitors", Bioorganic & Medicinal Chemistry Letters (2009), vol. 19, No. 8, pp. 2277-2281.

*Primary Examiner* — Jeffrey H Murray
(74) *Attorney, Agent, or Firm* — Morrison & Foerster LLP

(57) ABSTRACT

The present invention relates to compounds of formula (I):

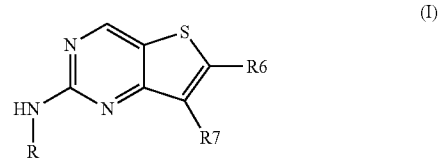

wherein R6 is —$CONH_2$ or a —$C(R_\alpha)(R_\beta)(OH)$ group; R is a substituted phenyl or heteroaryl group; R7 is an optionally substituted aryl or heteroaryl group.

Process for the preparation thereof and therapeutic use thereof.

15 Claims, No Drawings

THIENOPYRIMIDINE DERIVATIVES, PROCESSES FOR THE PREPARATION THEREOF AND THERAPEUTIC USES THEREOF

The present invention relates to novel thienopyrimidine derivatives, to processes for the preparation thereof, and also to the therapeutic uses thereof, in particular as anticancer agents via ALK kinase inhibition.

The present invention also relates to pharmaceutical compositions containing these derivatives, which have anticancer activity via ALK kinase modulation.

At the current time, most commercial compounds used in chemotherapy are cytotoxic compounds which pose considerable problems in terms of side effects and tolerance by patients. These effects could be limited insofar as the medicines used act selectively on cancer cells, with exclusion of healthy cells. One of the solutions for limiting the adverse effects of chemotherapy can therefore consist of the use of medicines which act on metabolic pathways or constituent elements of these pathways, expressed predominantly in cancer cells, and which would be expressed little or not at all in healthy cells. Protein kinases are a family of enzymes which catalyze the phosphorylation of hydroxyl groups of specific residues of proteins, such as tyrosine, serine or threonine residues. Such phosphorylations can widely modify the function of proteins: thus, protein kinases play an important role in the regulation of a large variety of cell processes, including in particular metabolism, cell proliferation, cell adhesion and motility, cell differentiation or cell survival, some protein kinases playing a central role in the initiation, development and completion of cell cycle events.

Among the various cell functions in which the activity of a protein kinase is involved, certain processes represent attractive targets for treating certain diseases. As an example, mention may particularly be made of angiogenesis and control of the cell cycle and also the control of cell proliferation, in which processes protein kinases can play an essential role. These processes are in particular essential for the growth of solid tumours and also other diseases. In particular, molecules which inhibit such kinases are capable of limiting undesired cell proliferations such as those observed in cancers, and can intervene in the prevention, regulation or treatment of neurodegenerative diseases such as Alzheimer's disease or else neuronal apoptosis.

The ALK kinase (or anaplastic lymphoma kinase) is a tyrosine kinase receptor, which belongs to the insulin receptor subfamily. ALK is expressed predominantly in the brain of newborn babies, which suggests a possible role for ALK in brain development.

ALK was initially identified in the form of a constitutively activated, oncogenic fusion protein in large cell anaplastic lymphomas. It has in particular been demonstrated that the mutant protein nucleophosmin (NMP)/ALK has an active tyrosine kinase domain responsible for its oncogenic activity (Falini, B. et al., Blood, 1999, 94, 3509-3515; Morris, S. W. et al., Brit. J. Haematol, 2001, 113, 275-295; Duyster et al.; Kutok & Aster). Recently, fusion proteins of similar forms have been identified in other types of human cancers: DLBCL diffuse large B-cell lymphoma, IMT inflammatory myofibroblastic tumour, ovarian cancer, breast cancer, colorectal cancer, glioblastoma, and also in non-small cell lung carcinomas (NSCLC). NSCLC cancers are common and lethal in human beings. Moreover, ALK gene amplifications and also active mutations have been found in neuroblastomas. In healthy adults, ALK expression is low and remains confined to neuronal tissues. ALK is therefore a therapeutic target in many types of cancers (Cheng and Ott, Anti-Cancer Agents in Medicinal Chemistry, 2010, 10, 236-249).

The objective of the present invention is to provide novel ALK kinase-inhibiting compounds intended for cancer treatment.

Thus, the present invention relates to compounds of formula (I):

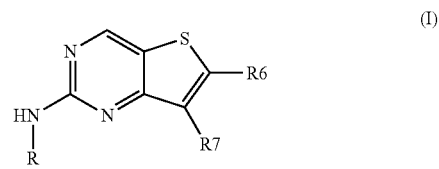

wherein:
R6 is —CONH$_2$ or a —C(R$_\alpha$)(R$_\beta$)(OH) group in which R$_\alpha$ and R$_\beta$ are, independently of one another, a hydrogen atom or a (C$_1$-C$_6$) alkyl group or together form, with the carbon atom which bears them, a 3- to 5-membered carbocycle;

R is a phenyl or heteroaryl group substituted with R1, R'1, R2 and R3;

R1 is a hydrogen atom or is selected from the following groups: (C$_1$-C$_6$)alkyl, (C$_1$-C$_6$)alkoxy, (C$_3$-C$_7$)cycloalkyl and aryl, these groups being optionally substituted with one or several substituents selected, independently in each instance, from: amino, hydroxyl, thiol, halogen, (C$_1$-C$_6$)alkyl, (C$_1$-C$_6$)alkoxy, (C$_1$-C$_6$)alkylthio, (C$_1$-C$_6$)alkylamino, aryloxy, aryl(C$_1$-C$_6$)alkoxy, cyano, halo(C$_1$-C$_6$)alkyl, carboxyl and carboxy(C$_1$-C$_6$) alkyl;

R'1 is a hydrogen atom or a (C$_1$-C$_6$)alkoxy group;

R2 is selected from:
  a hydrogen atom, a halogen atom, or a (C$_1$-C$_6$)alkyl, (C$_3$-C$_7$)cycloalkyl or (C$_1$-C$_6$)alkoxy group;
  a heterocycloalkyl, heterocycloalkyl-CH$_2$— or heteroaryl group;
    wherein each said heterocycloalkyl, heterocycloalkyl-CH$_2$— and heteroaryl group is optionally substituted with one or several substituents selected, independently in each instance, from: (C$_1$-C$_6$)alkyl, (C$_3$-C$_7$)cycloalkyl, (C$_1$-C$_6$)alkoxy, heterocycloalkyl, carboxy(C$_1$-C$_6$)alkyl, NR4R5 and OR4;
    said (C$_1$-C$_6$)alkyl group being optionally substituted with a halogen atom or a (C$_1$-C$_6$)alkoxy, heterocycloalkyl, NH$_2$ or OH group; and
      R4 and R5 being each, independently of one another, a hydrogen atom, a (C$_1$-C$_6$)alkyl group or a heterocycloalkyl group;
      or else R4 and R5 together form, with the nitrogen atom which bears them, a 4- to 7-membered ring;
  an NRaRb group, where Ra and Rb are, independently of one another:
    a hydrogen atom;
    a heterocycloalkyl group, said heterocycloalkyl group being optionally substituted with a (C$_1$-C$_6$)alkyl group; or
    a (C$_1$-C$_6$)alkyl group, said alkyl group being optionally substituted with an NR4R5 group;
      R4 and R5 being each, independently of one another, a hydrogen atom, a (C$_1$-C$_6$)alkyl group or a heterocycloalkyl group;

or else R4 and R5 together form, with the nitrogen atom which bears them, a 4- to 7-membered ring;

R3 is a hydrogen atom, a halogen atom or a $(C_1-C_6)$alkyl group;

wherein when R is a phenyl group, two adjacent substituents on the phenyl group may together form a heterocycloalkyl ring fused with the phenyl bearing them, this heterocycloalkyl being optionally substituted with one or several substituents selected, independently in each instance, from: an oxo group and a $(C_1-C_6)$alkyl group;

R7 is an aryl group or heteroaryl group, this group being optionally substituted with one or several substituents selected, independently in each instance, from: cyano, halogen, $(C_1-C_6)$alkyl, OR'4, $CH_2OH$, $CH_2NH_2$, $S(O)_nR'4$, R8 and OR8;

wherein:

R'4 is a hydrogen atom or a $(C_1-C_6)$alkyl or aryl group, said alkyl and aryl groups being optionally substituted with a halogen atom or an $NH_2$ or OH group;

n is 1 or 2; and

R8 is a halo$(C_1-C_6)$alkyl group.

In the compounds of general formula (I), the nitrogen atom(s) can optionally be in oxidized form (N-oxide).

The present invention also relates to compounds of formula (I'):

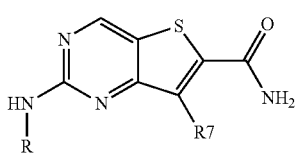

in which:

R is a phenyl or heteroaryl group substituted with R1, R'1, R2 and R3;

R1 is a hydrogen atom or is selected from the following groups: $(C_1-C_6)$alkyl, $(C_1-C_6)$alkoxy, $(C_3-C_7)$cycloalkyl and aryl, these groups being optionally substituted with one or several substituents selected, independently in each instance, from: amino, hydroxyl, thiol, halogen, $(C_1-C_6)$alkyl, $(C_1-C_6)$alkoxy, $(C_1-C_6)$alkylthio, $(C_1-C_6)$alkylamino, aryloxy, aryl$(C_1-C_6)$alkoxy, cyano, halo$(C_1-C_6)$alkyl, carboxyl and carboxy$(C_1-C_6)$alkyl;

R'1 is a hydrogen atom or a $(C_1-C_6)$alkoxy group;

R2 is selected from:

a hydrogen atom, a halogen atom, or a $(C_1-C_6)$alkyl, $(C_3-C_7)$cycloalkyl or $(C_1-C_6)$alkoxy group;

a heterocycloalkyl, heterocycloalkyl-$CH_2$— or heteroaryl group;

wherein each said heterocycloalkyl, heterocycloalkyl-$CH_2$— and heteroaryl group is optionally substituted with one or several substituents selected, independently in each instance, from: $(C_1-C_6)$alkyl, $(C_3-C_7)$cycloalkyl, $(C_1-C_6)$alkoxy, heterocycloalkyl, carboxy$(C_1-C_6)$alkyl, NR4R5 and OR4;

said $(C_1-C_6)$alkyl group being optionally substituted with a halogen atom or a $(C_1-C_6)$alkoxy, heterocycloalkyl, $NH_2$ or OH group; and an NRaRb group, where Ra and Rb are, independently of one another:

a hydrogen atom;

a heterocycloalkyl group, said heterocycloalkyl group being optionally substituted with a $(C_1-C_6)$alkyl group; or a $(C_1-C_6)$alkyl group, said alkyl group being optionally substituted with an NR4R5 group;

R4 and R5 being, independently of one another, a hydrogen atom, a $(C_1-C_6)$alkyl group or a heterocycloalkyl group;

or else R4 and R5 together form, with the nitrogen atom which bears them, a 4- to 7-membered ring;

R3 is a hydrogen atom, a halogen atom or a $(C_1-C_6)$alkyl group;

wherein when R is a phenyl group, two adjacent substituents on the phenyl group may together form a heterocycloalkyl ring fused with the phenyl bearing them, this heterocycloalkyl being optionally substituted with one or several substituents selected, independently in each instance, from: an oxo group and a $(C_1-C_6)$alkyl group;

R7 is an aryl or heteroaryl group, this group being optionally substituted with one or several substituents selected, independently in each instance, from: cyano, halogen, $(C_1-C_6)$alkyl, OR'4, $CH_2OH$, $CH_2NH_2$, $S(O)_nR'4$, R8 and OR8;

wherein:

R'4 is a hydrogen atom or a $(C_1-C_6)$alkyl or aryl group; said alkyl and aryl groups being optionally substituted with a halogen atom or an $NH_2$ or OH group;

n is 1 or 2;

R8 is a halo$(C_1-C_6)$alkyl group.

The present invention also relates to compounds of formula (I"):

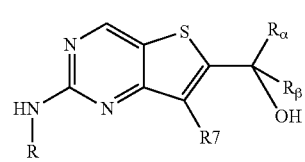

in which:

$R_\alpha$ and $R_\beta$ are, independently of one another, a hydrogen atom or a $(C_1-C_6)$alkyl group; or $R_\alpha$ and $R_\beta$ can together form, with the carbon atom bearing them, a 3- to 5-membered carbocycle;

R is a phenyl or heteroaryl group substituted with R1, R'1, R2 and R3;

R1 is a hydrogen atom or is selected from the following groups: $(C_1-C_6)$alkyl, $(C_1-C_6)$alkoxy, $(C_3-C_7)$cycloalkyl and aryl, these groups being optionally substituted with one or several substituents selected, independently in each instance, from: amino, hydroxyl, thiol, halogen, $(C_1-C_6)$alkyl, $(C_1-C_6)$alkoxy, $(C_1-C_6)$alkylthio, $(C_1-C_6)$alkylamino, aryloxy, aryl$(C_1-C_6)$alkoxy, cyano, halo$(C_1-C_6)$alkyl, carboxyl and carboxy$(C_1-C_6)$alkyl;

R'1 represents a hydrogen atom or a $(C_1-C_6)$alkoxy group;

R2 is selected from:

a hydrogen atom, a halogen atom, or a $(C_1-C_6)$alkyl, $(C_3-C_7)$cycloalkyl or $(C_1-C_6)$alkoxy group;

a heterocycloalkyl, heterocycloalkyl-$CH_2$— or heteroaryl group;

wherein each said heterocycloalkyl, heterocycloalkyl-$CH_2$— and heteroaryl group is optionally substituted with one or several substituents selected, independently in each instance, from: $(C_1-C_6)$alkyl, $(C_3-C_7)$cycloalkyl, $(C_1-C_6)$alkoxy, heterocycloalkyl, carboxy$(C_1-C_6)$alkyl, NR4R5 and OR4;

said alkyl group being optionally substituted with a halogen atom or a $(C_1-C_6)$alkoxy, heterocycloalkyl, $NH_2$ or OH group; and an NRaRb group, where Ra and Rb are, independently of one another:

a hydrogen atom;
a heterocycloalkyl group, said heterocycloalkyl group being optionally substituted with a $(C_1-C_6)$alkyl group; or
a $(C_1-C_6)$alkyl group, said alkyl group being optionally substituted with an NR4R5 group;
wherein:
R4 and R5 each is, independently of one another, a hydrogen atom, a $(C_1-C_6)$alkyl group or a heterocycloalkyl group;
or else R4 and R5 together form, with the nitrogen atom which bears them, a 4- to 7-membered ring;
R3 is a hydrogen atom, a halogen atom or a $(C_1-C_6)$alkyl group;
wherein when R is a phenyl group, two adjacent substituents on the phenyl group may together form a heterocycloalkyl ring fused with the phenyl bearing them, this heterocycloalkyl being optionally substituted with one or several substituents selected, independently in each instance, from: an oxo group and a $(C_1-C_6)$alkyl group;
R7 is an aryl group or heteroaryl group, this group being optionally substituted with one or several substituents selected, independently in each instance, from: cyano, halogen, $(C_1-C_6)$alkyl, OR'4, $CH_2OH$, $CH_2NH_2$, $S(O)_nR'4$, R8 and OR8;
wherein:
R'4 is a hydrogen atom or a $(C_1-C_6)$alkyl or aryl group, said alkyl and aryl groups being optionally substituted with a halogen atom or an $NH_2$ or OH group;
n is 1 or 2;
R8 is a halo$(C_1-C_6)$alkyl group.

Also within the present invention are the precursors (prodrugs) of the compounds of formula (I).

The compounds of formula (I), (I') or (I") can comprise one or more asymmetric carbon atoms. They can therefore exist in the form of enantiomers or of diastereoisomers. These enantiomers and diastereoisomers, and also mixtures thereof, including racemic mixtures, form part of the invention.

The compounds of formula (I), (I') or (I") can exist in the form of bases or of addition salts with acids. Such addition salts form part of the invention.

The compounds of formula (I), (I') or (I") can exist in the form of pharmaceutically acceptable salts.

These salts can be prepared with pharmaceutically acceptable acids, but the salts of other acids that are of use, for example, for purifying or isolating the compounds of formula (I), (I') or (I") also form part of the invention.

In the context of the present invention:
the expression "$C_t$—$C_z$ where t and z can take the values from 1 to 7" means a carbon-based chain which can have from t to z carbon atoms, for example $C_1$-$C_3$ means a carbon-based chain which can have from 1 to 3 carbon atoms;
the term "a halogen atom" means: a fluorine, a chlorine, a bromine or an iodine;
the term "an alkyl group" means: a linear or branched, saturated, hydrocarbon-based aliphatic group comprising, unless otherwise mentioned, from 1 to 12 carbon atoms. By way of examples, mention may be made of methyl, ethyl, n-propyl, isopropyl, butyl, isobutyl, tert-butyl or pentyl groups;
the term "a cycloalkyl group" means: a cyclic carbon-based group comprising, unless otherwise mentioned, from 3 to 6 carbon atoms. By way of examples, mention may be made of cyclopropyl, cyclobutyl, cyclopentyl, cyclohexyl, etc. groups;
the term "a haloalkyl group" means: an alkyl group as defined above, in which one or more of the hydrogen atoms is (are) replaced with a halogen atom. By way of example, mention may be made of fluoroalkyls, in particular $CF_3$ or $CHF_2$;
the term "an alkoxy group" means: an —O-alkyl radical where the alkyl group is as previously defined. By way of examples, mention may be made of —O—$(C_1-C_4)$ alkyl groups, and in particular the —O-methyl group, the —O-ethyl group as —O—$C_3$alkyl group, the —O-propyl group, the —O-isopropyl group, and as —O—$C_4$alkyl group, the —O-butyl, —O-isobutyl or —O-tert-butyl group;
the term "aryl group" means: a cyclic aromatic group comprising between 6 and 10 carbon atoms. By way of examples of aryl groups, mention may be made of phenyl or naphthyl groups;
the term "a heteroaryl" means: a 5- to 10-membered aromatic monocyclic or bicyclic group containing from 1 to 4 heteroatoms selected from O, S or N. By way of examples, mention may be made of imidazolyl, thiazolyl, oxazolyl, furanyl, thiophenyl, pyrazolyl, oxadiazolyl, tetrazolyl, pyridinyl, pyrazinyl, pyrimidinyl, pyridazinyl, indolyl, benzofuranyl, benzothiophenyl, benzoxazolyl, benzimidazolyl, indazolyl, benzothiazolyl, isobenzothiazolyl, benzotriazolyl, quinolinyl and isoquinolinyl groups;
by way of a heteroaryl comprising 5 to 6 atoms, including 1 to 4 nitrogen atoms, mention may in particular be made of the following representative groups: pyrrolyl, pyrazolyl, 1,2,3-triazolyl, 1,2,4-triazolyl, tetrazolyl and 1,2,3-triazinyl;
Mention may also be made, by way of heteroaryl, of thiophenyl, oxazolyl, furazanyl, 1,2,4-thiadiazolyl, naphthyridinyl, quinoxalinyl, phthalazinyl, imidazo[1,2-a]pyridine, imidazo[2,1-b]thiazolyl, cinnolinyl, benzofurazanyl, azaindolyl, benzimidazolyl, benzothiophenyl, thienopyridyl, thienopyrimidinyl, pyrrolopyridyl, imidazopyridyl, benzoazaindole, 1,2,4-triazinyl, indolizinyl, isoxazolyl, isoquinolinyl, isothiazolyl, purinyl, quinazolinyl, quinolinyl, isoquinolyl, 1,3,4-thiadiazolyl, thiazolyl, isothiazolyl, carbazolyl, and also the corresponding groups resulting from their fusion or from fusion with the phenyl nucleus;
the term "a heterocycloalkyl" means: a 4- to 10-membered, saturated or partially unsaturated, monocyclic or bicyclic group comprising from one to three heteroatoms selected from O, S or N; the heterocycloalkyl group may be attached to the rest of the molecule via a carbon atom or via a heteroatom; the term bicyclic heterocycloalkyl includes fused bicycles and spiro-type rings.

By way of saturated heterocycloalkyl comprising from 5 to 6 atoms, mention may be made of oxetanyl, tetrahydrofuranyl, dioxolanyl, pyrrolidinyl, azepinyl, oxazepinyl, pyrazolidinyl, imidazolidinyl, tetrahydrothiophenyl, dithiolanyl, thiazolidinyl, tetrahydropyranyl, tetrahydropyridinyl, dioxanyl, morpholinyl, piperidinyl, piperazinyl, tetrahydrothiopyranyl, dithianyl, thiomorpholinyl or isoxazolidinyl.

Among the heterocycloalkyls, mention may also be made, by way of examples, of bicyclic groups such as (8aR)-hexahydropyrrolo[1,2-a]pyrazin-2(1H)-yl, octahydroindozilinyl, diazepanyl, dihydroimidazopyrazinyl and diazabicycloheptanyl groups, or else diazaspiro rings such as 1,7-diazaspiro[4.4]non-7-yl or 1-ethyl-1,7-diazaspiro[4.4]non-7-yl.

When the heterocycloalkyl is substituted, the substitution(s) may be on one (or more) carbon atom(s) and/ or on the heteroatom(s). When the heterocycloalkyl comprises several substituents, they may be borne by one and the same atom or different atoms.

The abovementioned "alkyl", "cycloalkyl", "aryl", "heteroaryl" and "heterocycloalkyl" radicals can be substituted with one or more substituents. Among these substituents, mention may be made of the following groups: amino, hydroxyl, thiol, oxo, halogen, alkyl, alkoxy, alkylthio, alkylamino, aryloxy, arylalkoxy, cyano, trifluoromethyl, carboxy or carboxyalkyl;

the term "an alkylthio" means: an —S-alkyl group, the alkyl group being as defined above;

the term "an alkylamino" means: an —NH-alkyl group, the alkyl group being as defined above;

the term "an aryloxy" means: an —O-aryl group, the aryl group being as defined above;

the term "an arylalkoxy" means: an aryl-alkoxy- group, the aryl and alkoxy groups being as defined above;

the term "a carboxyalkyl" means: an HOOC-alkyl- group, the alkyl group being as defined above. As examples of carboxyalkyl groups, mention may in particular be made of carboxymethyl or carboxyethyl;

the term "a carboxyl" means: a COOH group;

the term "an oxo" means: "=O".

When an alkyl radical is substituted with an aryl group, the term "arylalkyl" or "aralkyl" radical is used. The "arylalkyl" or "aralkyl" radicals are aryl-alkyl- radicals, the aryl and alkyl groups being as defined above. Among the arylalkyl radicals, mention may in particular be made of the benzyl or phenethyl radicals.

Subgroup 1 is defined by the compounds of formula (I) for which:

R6 is —CONH$_2$ or a —C(R$_\alpha$)(R$_\beta$)(OH) group in which R$_\alpha$ and R$_\beta$ are, independently of one another, a hydrogen atom or a (C$_1$-C$_6$)alkyl group.

Subgroup 2 is defined by the compounds of formula (I) for which:

R6 is —CONH$_2$, —CH$_2$OH or C(CH$_3$)$_2$OH.

Subgroup 3 is defined by the compounds of formula (I) for which:

R is a phenyl, pyridinyl or pyrazolyl group substituted with R1, R'1, R2 and R3; R1, R'1, R2 and R3 being as defined in formula (I).

Subgroup 4 is defined by the compounds of formula (I) for which:

R is selected from the following groups:

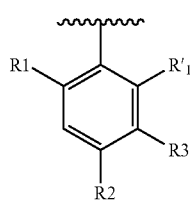

(A)

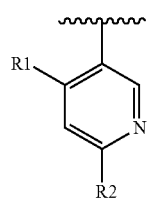

(B)

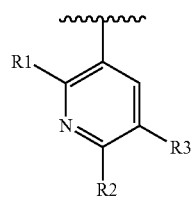

(C)

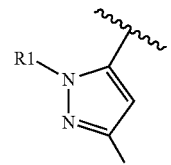

(D)

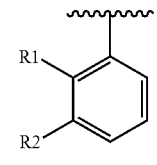

(E)

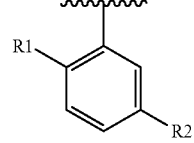

(F)

R1, R'1, R2 and R3 being as defined in formula (I).

Subgroup 5 is defined by the compounds of formula (I) for which:

R is an (A), (E) or (F) group

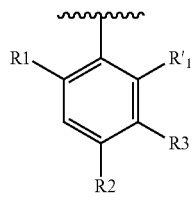

(A)

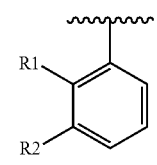

(E)

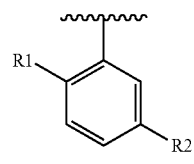

(F)

R1, R'1, R2 and R3 being as defined in formula (I).

Subgroup 6 is defined by the compounds of formula (I) for which:
R is an (A) group

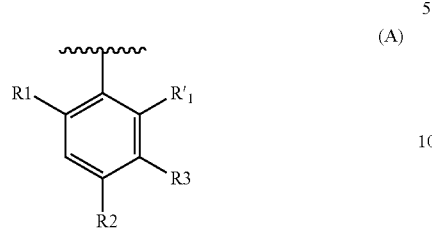

R1, R'1, R2 and R3 being as defined in formula (I).

Subgroup 7 is defined by the compounds of formula (I) for which:
R1 is a hydrogen atom or is selected from the following groups: $(C_1-C_6)$alkyl, such as methyl or isopropyl, $(C_1-C_6)$alkoxy, such as methoxy or isopropyloxy, $(C_3-C_7)$cycloalkyl, such as cyclobutyl, and aryl, such as phenyl.

Subgroup 8 is defined by the compounds of formula (I) for which:
R1 is an isopropyloxy group.

Subgroup 9 is defined by the compounds of formula (I) for which:
R'1 is an hydrogen atom or an isopropyloxy group.

Subgroup 10 is defined by the compounds of formula (I) for which:
R'1 is a hydrogen atom.

Subgroup 11 is defined by the compounds of formula (I) for which:
R2 is selected from:
  a hydrogen or chlorine atom, or a methyl, cyclopropyl or methoxy group;
  a pyrrolidinyl, piperidinyl, tetrahydropyridinyl, piperazinyl, tetrahydropyranyl, diazepan-1-yl, diazabicycloheptanyl, (8aR)-hexahydropyrrolo[1,2-a]pyrazin-2(1H)-yl, 1,7-diazaspiro[4.4]non-7-yl, octahydroindolizinyl, dihydroimidazopyrazinyl, piperazinyl-$CH_2$, pyrazolyl, imidazolyl, triazolyl or pyridinyl group;
  these groups being optionally substituted with one or more substituents selected, independently in each instance, from: $(C_1-C_6)$alkyl, $(C_3-C_7)$cycloalkyl, $(C_1-C_6)$alkoxy, heterocycloalkyl, carboxy$(C_1-C_6)$alkyl, NR4R5 and OR4;
    said $(C_1-C_6)$alkyl group being optionally substituted with a halogen atom or a $(C_1-C_6)$alkoxy, heterocycloalkyl, $NH_2$ or OH group; and
      R4 and R5 each is, independently of one another, a hydrogen atom, a $(C_1-C_6)$alkyl group, such as methyl or ethyl, or a heterocycloalkyl group, such as oxetanyl;
      or else R4 and R5 together form, with the nitrogen atom which bears them, a 4- to 7-membered ring, such as pyrrolidinyl;
  an NRaRb group, where Ra and Rb are, independently of one another:
    a hydrogen atom;
    a piperidinyl group or tetrahydropyranyl group, wherein each of said piperidinyl and tetrahydropyranyl groups is independently optionally substituted with a $(C_1-C_6)$alkyl group, such as methyl; or
    a methyl or ethyl group, said group being optionally substituted with an NR4R5 group;

wherein:
  R4 and R5 each is, independently of one another, a hydrogen atom, a $(C_1-C_6)$alkyl group, such as methyl or ethyl, or a heterocycloalkyl group, such as oxetanyl;
  or else R4 and R5 together form, with the nitrogen atom which bears them, a 4- to 7-membered ring, such as pyrrolidinyl;
R3 is a hydrogen atom, a halogen atom, such as a fluorine, or a $(C_1-C_6)$alkyl group, such as a methyl;
and when R corresponds to formula (A), R2 and R3 can together form an azepinyl or oxazepinyl ring fused with the phenyl bearing them, this azepinyl or oxazepinyl being optionally substituted with one or more substituents selected, independently in each instance, from: an oxo group and a $(C_1-C_6)$alkyl group, such as methyl.

Subgroup 12 is defined by the compounds of formula (I) for which:
R2 is a pyrrolidinyl, piperidinyl, tetrahydropyridinyl, piperazinyl, tetrahydropyranyl, 1,4-diazepan-1-yl, diazabicycloheptanyl, (8aR)-hexahydropyrrolo[1,2-a]pyrazin-2(1H)-yl, 1,7-diazaspiro[4.4]non-7-yl, octahydroindolizinyl, dihydroimidazopyrazinyl, piperazinyl-$CH_2$, pyrazolyl, imidazolyl, triazolyl or pyridinyl group;
these groups being optionally substituted with at least one substituent selected from: $(C_1-C_6)$alkyl, such as methyl, ethyl or isopropyl, $(C_3-C_7)$cycloalkyl, such as cyclopropyl, $(C_1-C_6)$alkoxy, such as methoxy, heterocycloalkyl, such as oxetanyl or pyrrolidinyl, carboxy$(C_1-C_6)$alkyl, such as $C(O)O(CH_3)_3$, NR4R5 and OH;
said alkyl group being optionally substituted with a $(C_1-C_6)$ alkoxy group, such as methoxy, or OH;
R4 and R5 being, independently of one another, a hydrogen atom, a $(C_1-C_6)$alkyl group, such as methyl or ethyl, or a heterocycloalkyl group, such as oxetanyl;
or else R4 and R5 together form, with the nitrogen atom which bears them, a 4- to 7-membered ring, such as pyrrolidinyl;
R3 is a hydrogen atom, a halogen atom, such as a fluorine, or a $(C_1-C_6)$alkyl group, such as a methyl.

Subgroup 13 is defined by the compounds of formula (I) for which:
R2 is a piperidinyl or piperazinyl group, these groups being optionally substituted with at least one substituent selected from: $(C_1-C_6)$alkyl, $(C_3-C_7)$cycloalkyl, $(C_1-C_6)$alkoxy, heterocycloalkyl, carboxy$(C_1-C_6)$alkyl, NR4R5 and OR4;
said alkyl group being optionally substituted with a halogen atom or a $(C_1-C_6)$alkoxy, heterocycloalkyl, $NH_2$ or OH group;
R4 and R5 being as defined in formula (I);
R3 is a hydrogen atom, a halogen atom, such as a fluorine, or a $(C_1-C_6)$alkyl group, such as a methyl.

Subgroup 14 is defined by the compounds of formula (I) for which:
R2 is a piperidinyl or piperazinyl group, these groups being optionally substituted with at least one substituent selected from: a methyl, ethyl, isopropyl, cyclopropyl, OH, oxetanyl, pyrrolidinyl, $C(O)O(CH_3)_3$, NR4R5 and OR4 group;
said methyl, ethyl and isopropyl groups being optionally substituted with a $(C_1-C_6)$alkoxy group, such as methoxy, or with an OH;
R4 and R5 being, independently of one another, a hydrogen atom, a $(C_1-C_6)$alkyl group, such as methyl, or a heterocycloalkyl group, such as oxetanyl;
R3 is a hydrogen or fluorine atom or a methyl.

Subgroup 15 is defined by the compounds of formula (I) for which:
R2 is a piperidinyl or piperazinyl group, these groups being optionally substituted with at least one substituent selected from: a methyl, ethyl or isopropyl group:
R3 is a hydrogen or fluorine atom or a methyl.

Subgroup 16 is defined by the compounds of formula (I) for which:
R2 is a group selected from the following groups:

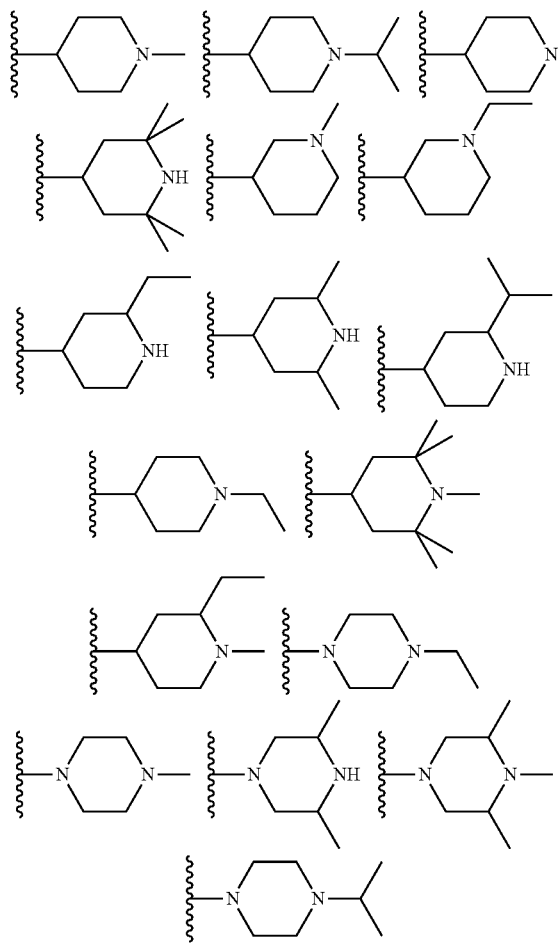

R3 is a hydrogen or fluorine atom or a methyl.

Subgroup 17 is defined by the compounds of formula (I) for which:
R7 is a phenyl, pyridinyl, thienyl, furanyl, pyrazolyl or pyrolyl group, this group being optionally substituted with one or more substituents selected, independently in each instance, from: cyano, halogen, $(C_1-C_6)$alkyl, OR'4, $CH_2OH$, $CH_2NH_2$, $S(O)_nR'4$, R8 and OR8;
wherein:
R'4 is a hydrogen atom or a $(C_1-C_6)$alkyl or aryl group, said alkyl and aryl groups being optionally substituted with a halogen atom or an $NH_2$ or OH group;
n is 1 or 2;
R8 is a halo$(C_1-C_6)$alkyl group.

Subgroup 18 is defined by the compounds of formula (I) for which:
R7 is a phenyl, pyridinyl, thienyl, furanyl, pyrazolyl or pyrolyl group, this group being optionally substituted with one or more substituents independently selected from: cyano, halogen, such as chlorine or fluorine, $(C_1-C_6)$alkyl, such as methyl, OR'4, $CH_2OH$, $CH_2NH_2$, $S(O)_nR'4$ and OR8;
wherein:
R'4 is a $(C_1-C_6)$alkyl group, such as methyl or ethyl;
n is 1;
R8 is a halo$(C_1-C_6)$alkyl group, such as $CF_3$ or $CHF_2$.

Subgroup 19 is defined by the compounds of formula (I) for which R, R6 and R7 are defined in one of subgroups 1 to 18 above.

Subgroup 20 is defined by the compounds of formula (I) for which:
$R_6$ is —$CONH_2$ or a —$C(R_\alpha)(R_\beta)(OH)$ group in which $R_\alpha$ and $R_\beta$ are, independently of one another, a hydrogen atom or a $(C_1-C_6)$alkyl group;
R is a phenyl, pyridinyl or pyrazolyl group substituted with R1, R'1, R2 and R3;
R1 is a hydrogen atom or is selected from the following groups: $(C_1-C_6)$alkyl, such as methyl or isopropyl, $(C_1-C_6)$alkoxy, such as methoxy or isopropyloxy, $(C_3-C_7)$cycloalkyl, such as cyclobutyl, and aryl, such as phenyl;
R'1 is a hydrogen atom or an isopropyloxy group;
R2 is selected from:
  a hydrogen or chlorine atom or a methyl, cyclopropyl or methoxy group;
  a pyrrolidinyl, piperidinyl, tetrahydropyridinyl, piperazinyl, tetrahydropyranyl, 1,4-diazepan-1-yl, diazabicycloheptanyl, (8aR)-hexahydropyrrolo[1,2-a]pyrazin-2(1H)-yl, 1,7-diazaspiro[4.4]non-7-yl, octahydroindolizinyl, dihydroimidazopyrazinyl, piperazinyl-$CH_2$, pyrazolyl, imidazolyl, triazolyl or pyridinyl group;
these groups being optionally substituted with one or more substituents independently selected from: $(C_1-C_6)$alkyl, $(C_3-C_7)$cycloalkyl, $(C_1-C_6)$alkoxy, heterocycloalkyl, carboxy$(C_1-C_6)$alkyl, NR4R5 and OR4;
  said alkyl group being optionally substituted with a halogen atom or a $(C_1-C_6)$alkoxy, heterocycloalkyl, $NH_2$ or OH group; and
  an NRaRb group, where Ra and Rb are, independently of one another:
    a hydrogen atom;
    a piperidinyl or tetrahydropyranyl group, said group being optionally substituted with a $(C_1-C_6)$alkyl group, such as methyl; or
    a methyl or ethyl group, said group being optionally substituted with an NR4R5 group;
R4 and R5 being, independently of one another, a hydrogen atom, a $(C_1-C_6)$alkyl group, such as methyl or ethyl, or a heterocycloalkyl group, such as oxetanyl;
or else R4 and R5 together form, with the nitrogen atom which bears them, a 4- to 7-membered ring, such as a pyrrolidinyl;
R3 is a hydrogen atom, a halogen atom, such as a fluorine, or a $(C_1-C_6)$alkyl group, such as a methyl;
wherein when R corresponds to formula (A), R2 and R3 may together form an azepinyl or oxazepinyl ring fused with the phenyl bearing them, this azepinyl or oxazepinyl ring being optionally substituted with at least one substituent selected from: an oxo group and a $(C_1-C_6)$alkyl group;
R7 is a phenyl, pyridinyl, thienyl, furanyl, pyrazolyl or pyrolyl group, this group being optionally substituted with one or more substituents selected, independently in each instance, from: cyano, halogen, $(C_1-C_6)$alkyl, OR'4, $CH_2OH$, $CH_2NH_2$, $S(O)_nR'4$, R8 and OR8;

wherein:
R'4 is a hydrogen atom or a (C$_1$-C$_6$)alkyl or aryl group, said alkyl and aryl groups being optionally substituted with a halogen atom or an NH$_2$ or OH group;
n is 1 or 2; and
R8 is a halo(C$_1$-C$_6$)alkyl group.

Subgroup 21 is defined by the compounds of formula (I) for which:
R6 is —CONH$_2$ or a —C(R$_\alpha$)(R$_\beta$)(OH) group in which R$_\alpha$ and R$_\beta$ are, independently of one another, a hydrogen atom or a (C$_1$-C$_6$)alkyl group;
R is selected from the following groups:

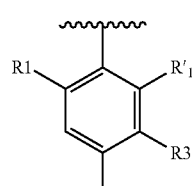
(A)

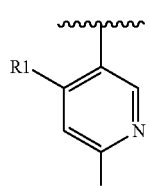
(B)

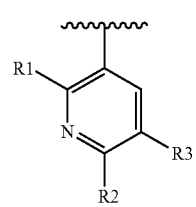
(C)

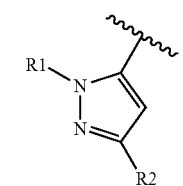
(D)

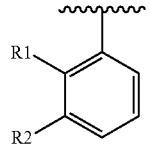
(E)

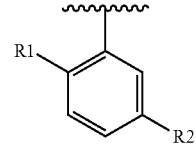
(F)

R1 is a hydrogen atom or is selected from the following groups: (C$_1$-C$_6$)alkyl, such as methyl or isopropyl, (C$_1$-C$_6$) alkoxy, such as methoxy or isopropyloxy, (C$_3$-C$_7$)cycloalkyl, such as cyclobutyl, and aryl, such as phenyl;
R'1 is a hydrogen atom or an isopropyloxy group;
R2 is a pyrrolidinyl, piperidinyl, tetrahydropyridinyl, piperazinyl, tetrahydropyranyl, 1,4-diazepan-1-yl, diazabicycloheptanyl, (8aR)-hexahydropyrrolo[1,2-a]pyrazin-2 (1H)-yl, 1,7-diazaspiro[4.4]non-7-yl, octahydroindolizinyl, dihydroimidazopyrazinyl, piperazinyl-CH$_2$, pyrazolyl, imidazolyl, triazolyl or pyridinyl group;
these groups being optionally substituted with one or more substituents selected, independently in each instance, from: (C$_1$-C$_6$)alkyl, such as methyl, ethyl or isopropyl, (C$_3$-C$_7$) cycloalkyl, such as cyclopropyl, (C$_1$-C$_6$)alkoxy, such as methoxy, heterocycloalkyl, such as oxetanyl or pyrrolidinyl, carboxy(C$_1$-C$_6$)alkyl, such as C(O)O(CH$_3$)$_3$, NR4R5 and OH;
said (C$_1$-C$_6$)alkyl group being optionally substituted with a (C$_1$-C$_6$)alkoxy group, such as methoxy, or OH;
wherein:
R4 and R5 each is, independently of one another, a hydrogen atom, a (C$_1$-C$_6$)alkyl group or a heterocycloalkyl group;
or else R4 and R5 together form, with the nitrogen atom which bears them, a 4- to 7-membered ring;
R3 is a hydrogen atom, a halogen atom, such as a fluorine, or a (C$_1$-C$_6$)alkyl group, such as a methyl;
R7 is a phenyl, pyridinyl, thienyl, furanyl, pyrazolyl or pyrolyl group, this group being optionally substituted with one or more substituents selected, independently in each instance, from: cyano, halogen, (C$_1$-C$_6$)alkyl, OR'4, CH$_2$OH, CH$_2$NH$_2$, S(O)$_n$R'4, R8 and OR8;
wherein:
R'4 is a hydrogen atom or a (C$_1$-C$_6$)alkyl or aryl group, said alkyl and aryl groups being optionally substituted with a halogen atom or an NH$_2$ or OH group;
n 1 or 2; and
R8 is a halo(C$_1$-C$_6$)alkyl group.

Subgroup 22 is defined by the compounds of formula (I) for which:
R6 is —CONH$_2$ or a —C(R$_\alpha$)(R$_\beta$)(OH) group in which R$_\alpha$ and R$_\beta$ are, independently of one another, a hydrogen atom or a (C$_1$-C$_6$)alkyl group;
R is an (A), (E) or (F) group

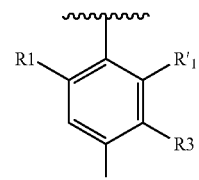
(A)

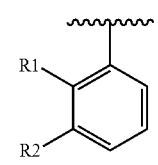
(E)

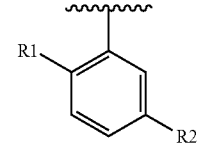
(F)

R1 is an isopropyloxy group;
R'1 is a hydrogen atom;
R2 is a piperidinyl or piperazinyl group, these groups being optionally substituted with one or more substituents selected, independently in each instance, from: a methyl, ethyl, isopropyl, cyclopropyl, OH, oxetanyl, pyrrolidinyl, C(O)O(CH$_3$)$_3$, NR4R5 and OR4 group;

said methyl, ethyl and isopropyl groups being optionally substituted with a (C$_1$-C$_6$)alkoxy group, such as methoxy, or with an OH;

wherein R4 and R5 each is, independently of one another, a hydrogen atom, a (C$_1$-C$_6$)alkyl group, such as methyl, or a heterocycloalkyl group, such as oxetanyl;

R3 is a hydrogen or fluorine atom or a methyl;

R7 is a phenyl, pyridinyl, thienyl, furanyl, pyrazolyl or pyrolyl group, this group being optionally substituted with one or more substituents selected, independently in each instance, from: cyano, halogen, such as chlorine or fluorine, (C$_1$-C$_6$)alkyl, such as methyl, OR'4, CH$_2$OH, CH$_2$NH$_2$, S(O)$_n$R'4 and OR8;

wherein:

R'4 is a (C$_1$-C$_6$)alkyl group, such as methyl or ethyl;

n is 1; and

R8 is a halo(C$_1$-C$_6$)alkyl group, such as CF$_3$ or CHF$_2$.

Subgroup 23 is defined by the compounds of formula (I') for which:

R is a phenyl, pyridinyl or pyrazolyl group substituted with R1, R'1, R2 and R3; R1, R'1, R2 and R3 being as defined in formula (I').

Subgroup 24 is defined by the compounds of formula (I') for which:

R is selected from the following groups:

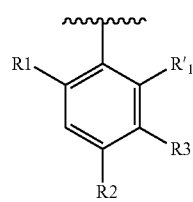
(A)

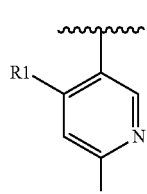
(B)

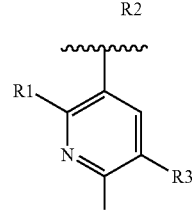
(C)

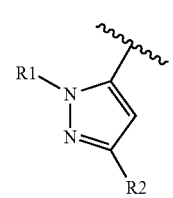
(D)

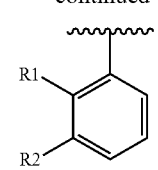
(E)

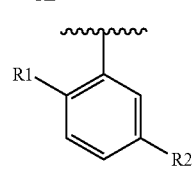
(F)

R1, R'1, R2 and R3 being as defined in formula (I').

Subgroup 25 is defined by the compounds of formula (I') for which:

R is an (A), (E) or (F) group

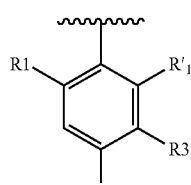
(A)

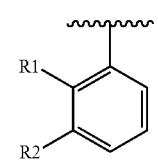
(E)

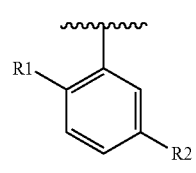
(F)

R1, R'1, R2 and R3 being as defined in formula (I').

Subgroup 26 is defined by the compounds of formula (I') for which:

R is an (A) group

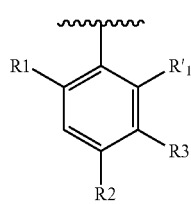
(A)

R1, R'1, R2 and R3 being as defined in formula (I').

Subgroup 27 is defined by the compounds of formula (I') for which:

R1 is a hydrogen atom or is selected from the following groups: (C$_1$-C$_6$)alkyl, such as methyl or isopropyl, (C$_1$-C$_6$) alkoxy, such as methoxy or isopropyloxy, (C$_3$-C$_7$)cycloalkyl, such as cyclobutyl, and aryl, such as phenyl.

Subgroup 28 is defined by the compounds of formula (I') for which:
R1 is an isopropyloxy group.
Subgroup 29 is defined by the compounds of formula (I') for which:
R'1 is a hydrogen atom or an isopropyloxy group.
Subgroup 30 is defined by the compounds of formula (I') for which:
R'1 is a hydrogen atom.
Subgroup 31 is defined by the compounds of formula (I') for which:
R2 is selected from:
  a hydrogen atom or a methyl, cyclopropyl or methoxy group;
  a pyrrolidinyl, piperidinyl, tetrahydropyridinyl, piperazinyl, tetrahydropyranyl, 1,4-diazepan-1-yl, diazabicycloheptanyl, (8aR)-hexahydropyrrolo[1,2-a]pyrazin-2(1H)-yl, 1,7-diazaspiro[4.4]non-7-yl, octahydroindolizinyl, dihydroimidazopyrazinyl, piperazinyl-CH$_2$, pyrazolyl, imidazolyl, triazolyl or pyridinyl group;
these groups being optionally substituted with one or several substituents independently selected from: $(C_1-C_6)$alkyl, $(C_3-C_7)$cycloalkyl, $(C_1-C_6)$alkoxy, heterocycloalkyl, carboxy$(C_1-C_6)$alkyl, NR4R5 and OR4;
said alkyl group being optionally substituted with a halogen atom or a $(C_1-C_6)$alkoxy, heterocycloalkyl, NH$_2$ or OH group; and
  an NRaRb group, where Ra and Rb are, independently of one another:
    a hydrogen atom;
    a piperidinyl or tetrahydropyranyl group, said group being optionally substituted with a $(C_1-C_6)$alkyl group, such as methyl; or
    a methyl or ethyl group, said alkyl group being optionally substituted with an NR4R5 group;
R4 and R5 being, independently of one another, a hydrogen atom, a $(C_1-C_6)$alkyl group, such as methyl or ethyl, or a heterocycloalkyl group, such as oxetanyl;
or else R4 and R5 together form, with the nitrogen atom which bears them, a 4- to 7-membered ring, such as a pyrrolidinyl;
R3 is a hydrogen atom, a halogen atom, such as a fluorine, or a $(C_1-C_6)$alkyl group, such as a methyl;
and when R corresponds to formula (A), R2 and R3 can together form an azepinyl or oxazepinyl ring, fused with the phenyl bearing them, this azepinyl or oxazepinyl ring being optionally substituted with at least one substituent selected from: an oxo group and a $(C_1-C_6)$alkyl group, such as methyl.
Subgroup 32 is defined by the compounds of formula (I') for which:
R2 is a pyrrolidinyl, piperidinyl, tetrahydropyridinyl, piperazinyl, tetrahydropyranyl, 1,4-diazepan-1-yl, diazabicycloheptanyl, (8aR)-hexahydropyrrolo[1,2-a]pyrazin-2(1H)-yl, 1,7-diazaspiro[4.4]non-7-yl, octahydroindolizinyl, dihydroimidazopyrazinyl, piperazinyl-CH$_2$, pyrazolyl, imidazolyl, triazolyl or pyridinyl group;
these groups being optionally substituted with one or several substituents independently selected from: $(C_1-C_6)$alkyl, such as methyl, ethyl or isopropyl, $(C_3-C_7)$cycloalkyl, such as cyclopropyl, $(C_1-C_6)$alkoxy, such as methoxy, heterocycloalkyl, such as oxetanyl or pyrrolidinyl, carboxy$(C_1-C_6)$alkyl, such as C(O)O(CH$_3$)$_3$, NR4R5 and OH;
said alkyl group being optionally substituted with a $(C_1-C_6)$ alkoxy group, such as methoxy, or OH;
R4 and R5 being, independently of one another, a hydrogen atom, a $(C_1-C_6)$alkyl group, such as methyl or ethyl, or a heterocycloalkyl group, such as oxetanyl;
or else R4 and R5 together form, with the nitrogen atom which bears them, a 4- to 7-membered ring, such as a pyrrolidinyl;
R3 is a hydrogen atom, a halogen atom, such as a fluorine, or a $(C_1-C_6)$alkyl group, such as a methyl.
Subgroup 33 is defined by the compounds of formula (I') for which:
R2 is a piperidinyl or piperazinyl group, these groups being optionally substituted with one or several substituents independently selected from: $(C_1-C_6)$alkyl, $(C_3-C_7)$cycloalkyl, $(C_1-C_6)$alkoxy, heterocycloalkyl, carboxy$(C_1-C_6)$alkyl, NR4R5 and OR4;
said alkyl group being optionally substituted with a halogen atom or a $(C_1-C_6)$alkoxy, heterocycloalkyl, NH$_2$ or OH group;
R4 and R5 being as defined in formula (I);
R3 is a hydrogen atom, a halogen atom, such as a fluorine, or a $(C_1-C_6)$alkyl group, such as a methyl.
Subgroup 34 is defined by the compounds of formula (I') for which:
R2 represents a piperidinyl or piperazinyl group, these groups being optionally substituted with one or several substituents independently selected from: a methyl, ethyl, isopropyl, cyclopropyl, OH, oxetanyl, pyrrolidinyl, C(O)O(CH$_3$)$_3$, NR4R5 and OR4 group;
said alkyl group being optionally substituted with a $(C_1-C_6)$ alkoxy group, such as methoxy, or with an OH;
R4 and R5 being, independently of one another, a hydrogen atom, a $(C_1-C_6)$alkyl group, such as methyl, or a heterocycloalkyl group, such as oxetanyl;
R3 is a hydrogen or fluorine atom or a methyl.
Subgroup 35 is defined by the compounds of formula (I') for which:
R2 is a piperidinyl group or piperazinyl group, these piperidinyl or piperazinyl groups being optionally substituted with one or more substituents selected, independently in each instance, from: a methyl, ethyl or isopropyl group;
R3 is a hydrogen or fluorine atom or a methyl.
Subgroup 36 is defined by the compounds of formula (I') for which:
R2 is a group selected from the following groups:

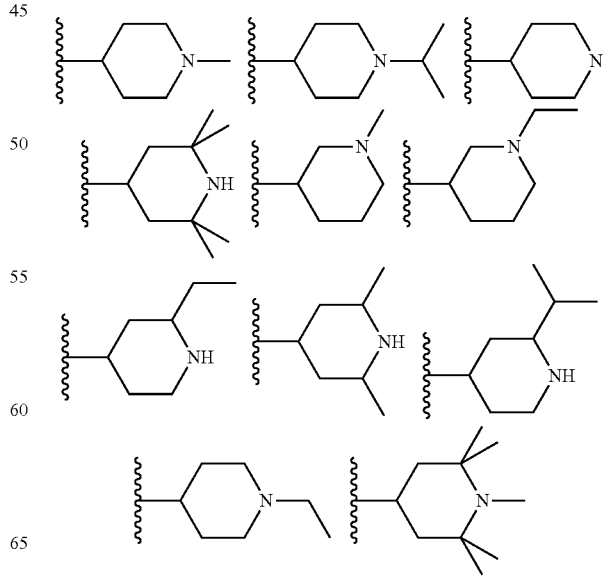

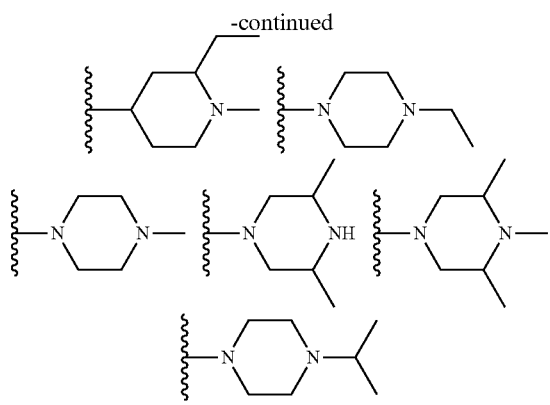

R3 is a hydrogen or fluorine atom or a methyl.

Subgroup 37 is defined by the compounds of formula (I') for which:

R7 is a phenyl, pyridinyl, thienyl, furanyl, pyrazolyl or pyrolyl group, this group being optionally substituted with one or more substituents selected, independently in each instance, from: cyano, halogen, $(C_1-C_6)$alkyl, OR'4, $CH_2OH$, $CH_2NH_2$, $S(O)_nR'4$, R8 and OR8;

wherein:
R'4 is a hydrogen atom or a $(C_1-C_6)$alkyl or aryl group, said alkyl and aryl groups being optionally substituted with a halogen atom or an $NH_2$ or OH group;
n is 1 or 2; and
R8 is a halo$(C_1-C_6)$alkyl group.

Subgroup 38 is defined by the compounds of formula (I') for which:

R7 is a phenyl, pyridinyl, thienyl, furanyl, pyrazolyl or pyrolyl group, this group being optionally substituted with one or more substituents selected, independently in each instance, from: cyano, halogen, such as chlorine or fluorine, $(C_1-C_6)$alkyl, such as methyl, OR'4, $CH_2OH$, $CH_2NH_2$, $S(O)_nR'4$ and OR8;

wherein:
R'4 is a $(C_1-C_6)$alkyl group, such as methyl or ethyl;
n is 1;
R8 is a halo$(C_1-C_6)$alkyl group, such as $CF_3$ or $CHF_2$.

Subgroup 39 is defined by the compounds of formula (I') for which R and R7 are defined in one of subgroups 23 to 38 above.

Subgroup 40 is defined by the compounds of formula (I') for which:

R is a phenyl, pyridinyl or pyrazolyl group substituted with R1, R'1, R2 and R3;

R1 is a hydrogen atom or is selected from the following groups: $(C_1-C_6)$alkyl, such as methyl or isopropyl, $(C_1-C_6)$alkoxy, such as methoxy or isopropyloxy, $(C_3-C_7)$cycloalkyl, such as cyclobutyl, and aryl, such as phenyl;

R'1 is a hydrogen atom or an isopropyloxy group;

R2 is selected from:
a hydrogen atom or a methyl, cyclopropyl or methoxy group;
a pyrrolidinyl, piperidinyl, tetrahydropyridinyl, piperazinyl, tetrahydropyranyl, 1,4-diazepan-1-yl, diazabicycloheptanyl, (8aR)-hexahydropyrrolo[1,2-a]pyrazin-2(1H)-yl, 1,7-diazaspiro[4.4]non-7-yl, octahydroindolizinyl, dihydroimidazopyrazinyl, piperazinyl-$CH_2$, pyrazolyl, imidazolyl, triazolyl or pyridinyl group;
these groups being optionally substituted with one or more substituents selected, independently in each instance, from:
$(C_1-C_6)$alkyl, $(C_3-C_7)$cycloalkyl, $(C_1-C_6)$alkoxy, heterocycloalkyl, carboxy$(C_1-C_6)$alkyl, NR4R5 and OR4;
said alkyl group being optionally substituted with a halogen atom or a $(C_1-C_6)$alkoxy, heterocycloalkyl, $NH_2$ or OH group; and
an NRaRb group, where Ra and Rb are, independently of one another:
a hydrogen atom;
a piperidinyl or tetrahydropyranyl group, said group being optionally substituted with a $(C_1-C_6)$alkyl group, such as methyl; or
a methyl or ethyl group, said alkyl group being optionally substituted with an NR4R5 group;
R4 and R5 are, independently of one another, a hydrogen atom, a $(C_1-C_6)$alkyl group, such as methyl or ethyl, or a heterocycloalkyl group, such as oxetanyl;
or else R4 and R5 together form, with the nitrogen atom which bears them, a 4- to 7-membered ring, such as a pyrrolidinyl;
R3 is a hydrogen atom, a halogen atom, such as a fluorine, or a $(C_1-C_6)$alkyl group, such as a methyl;
and when R corresponds to formula (A), R2 and R3 can together form an azepinyl or oxazepinyl ring, fused with the phenyl bearing them, this heterocycloalkyl being optionally substituted with at least one substituent selected from: an oxo group and a $(C_1-C_6)$alkyl group, such as methyl;
R7 is a phenyl, pyridinyl, thienyl, furanyl, pyrazolyl or pyrolyl group, this group being optionally substituted with one or more substituents selected, independently in each instance, from: cyano, halogen, $(C_1-C_6)$alkyl, OR'4, $CH_2OH$, $CH_2NH_2$, $S(O)_nR'4$, R8 and OR8;

wherein:
R'4 is a hydrogen atom or a $(C_1-C_6)$alkyl or aryl group, said alkyl and aryl groups being optionally substituted with a halogen atom or an $NH_2$ or OH group;
n is 1 or 2; and
R8 is a halo$(C_1-C_6)$alkyl group.

Subgroup 41 is defined by the compounds of formula (I') for which:

R is selected from the following groups:

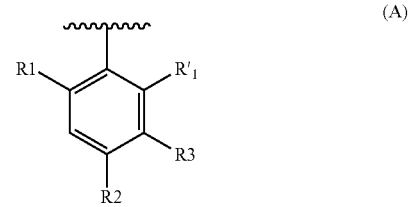

(A)

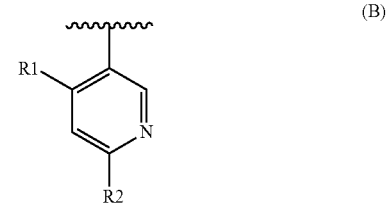

(B)

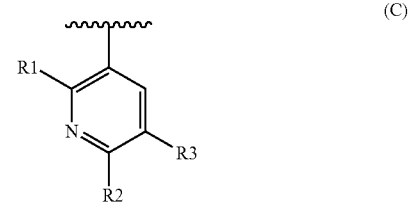

(C)

-continued

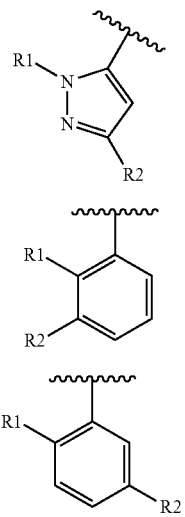

R1 is a hydrogen atom or is selected from the following groups: $(C_1-C_6)$alkyl, such as methyl or isopropyl, $(C_1-C_6)$ alkoxy, such as methoxy or isopropyloxy, $(C_3-C_7)$cycloalkyl, such as cyclobutyl, and aryl, such as phenyl;

R'1 is a hydrogen atom or an isopropyloxy group;

R2 is a pyrrolidinyl, piperidinyl, tetrahydropyridinyl, piperazinyl, tetrahydropyranyl, 1,4-diazepan-1-yl, diazabicycloheptanyl, (8aR)-hexahydropyrrolo[1,2-a]pyrazin-2 (1H)-yl, 1,7-diazaspiro[4.4]non-7-yl, octahydroindolizinyl, dihydroimidazopyrazinyl, piperazinyl-$CH_2$, pyrazolyl, imidazolyl, triazolyl or pyridinyl group;

these groups being optionally substituted with one or more substituents selected, independently in each instance, from: $(C_1-C_6)$alkyl, such as methyl, ethyl or isopropyl, $(C_3-C_7)$ cycloalkyl, such as cyclopropyl, $(C_1-C_6)$alkoxy, such as methoxy, heterocycloalkyl, such as oxetanyl or pyrrolidinyl, carboxy$(C_1-C_6)$alkyl, such as $C(O)O(CH_3)_3$, NR4R5 and OH;

said alkyl group being optionally substituted with a $(C_1-C_6)$ alkoxy group, such as methoxy, or OH;

R4 and R5 being, independently of one another, a hydrogen atom, a $(C_1-C_6)$alkyl group, such as methyl or ethyl, or a heterocycloalkyl group, such as oxetanyl;

or else R4 and R5 together form, with the nitrogen atom which bears them, a 4- to 7-membered ring, such as a pyrrolidinyl;

R3 is a hydrogen atom, a halogen atom, such as a fluorine, or a $(C_1-C_6)$alkyl group, such as a methyl;

R7 is a phenyl, pyridinyl, thienyl, furanyl, pyrazolyl or pyrolyl group, this group being optionally substituted with one or more substituents selected, independently in each instance, from: cyano, halogen, $(C_1-C_6)$alkyl, OR'4, $CH_2OH$, $CH_2NH_2$, $S(O)_nR'4$, R8 and OR8;

wherein:

R'4 is a hydrogen atom or a $(C_1-C_6)$alkyl or aryl group, said alkyl and aryl groups being optionally substituted with a halogen atom or an $NH_2$ or OH group;

n is 1 or 2;

R8 is a halo$(C_1-C_6)$alkyl group.

Subgroup 42 is defined by the compounds of formula (I') for which:
R is an (A), (E) or (F) group

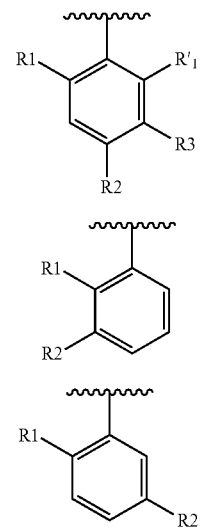

R1 is an isopropyloxy group;
R'1 is a hydrogen atom;
R2 is a piperidinyl or piperazinyl group, these groups being optionally substituted with one or more substituents selected, independently in each instance, from: a methyl, ethyl, isopropyl, cyclopropyl, OH, oxetanyl, pyrrolidinyl, $C(O)O(CH_3)_3$, NR4R5 and OR4 group; said alkyl group being optionally substituted with a $(C_1-C_6)$alkoxy group, such as methoxy, or with an OH;
R4 and R5 being, independently of one another, a hydrogen atom, a $(C_1-C_6)$alkyl group, such as methyl, or a heterocycloalkyl group, such as oxetanyl;
R3 is a hydrogen or fluorine atom or a methyl;
R7 is a phenyl, pyridinyl, thienyl, furanyl, pyrazolyl or pyrolyl group, this group being optionally substituted with one or more substituents selected, independently in each instance, from: cyano, halogen, such as chlorine or fluorine, $(C_1-C_6)$alkyl, such as methyl, OR'4, $CH_2OH$, $CH_2NH_2$, $S(O)_nR'4$ and OR8;
wherein:
R'4 is a $(C_1-C_6)$alkyl group, such as methyl or ethyl;
n is 1;
R8 is a halo$(C_1-C_6)$alkyl group, such as $CF_3$ or $CHF_2$.

Subgroup 43 is defined by the compounds of formula (I'') for which:
R is a phenyl, pyridinyl or pyrazolyl group substituted with R1, R'1, R2 and R3; R1, R'1, R2 and R3 being as defined in formula (I'').

Subgroup 44 is defined by the compounds of formula (I'') for which:
R is selected from the following groups:

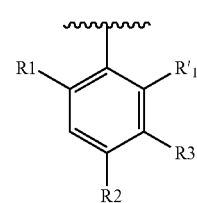

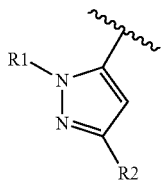

(D)

R1, R'1, R2 and R3 being as defined in formula (I'').

Subgroup 45 is defined by the compounds of formula (I'') for which:
R is a an (A) group (A)

R1, R'1, R2 and R3 being as defined in formula (I'').

Subgroup 46 is defined by the compounds of formula (I'') for which:
R1 is selected from the following groups: $(C_1$-$C_6)$alkyl, such as isopropyl, and $(C_1$-$C_6)$alkoxy, such as methoxy or isopropyloxy.

Subgroup 47 is defined by the compounds of formula (I'') for which:
R1 is an isopropyloxy group.

Subgroup 48 is defined by the compounds of formula (I'') for which:
R'1 is a hydrogen atom.

Subgroup 49 is defined by the compounds of formula (I'') for which:
R2 is selected from:
  a hydrogen or chlorine atom or a methyl group;
  a pyrrolidinyl, piperidinyl, piperazinyl, tetrahydropyranyl, 1,7-diazaspiro[4.4]non-7-yl or pyrazolyl group;
these groups being optionally substituted with at least one $(C_1$-$C_6)$alkyl group;
R3 is a hydrogen atom or a $(C_1$-$C_6)$alkyl group, such as a methyl.

Subgroup 50 is defined by the compounds of formula (I'') for which:
R2 is selected from a pyrrolidinyl, piperidinyl, piperazinyl, tetrahydropyranyl, 1,7-diazaspiro[4.4]non-7-yl or pyrazolyl group;
these groups being optionally substituted with at least one $(C_1$-$C_6)$alkyl group, such as methyl;
R3 is a hydrogen atom or a $(C_1$-$C_6)$alkyl group, such as a methyl.

Subgroup 51 is defined by the compounds of formula (I'') for which:
R2 is a piperidinyl or piperazinyl group, these groups being optionally substituted with at least one $(C_1$-$C_6)$alkyl group, such as methyl;
R3 is a hydrogen atom or a $(C_1$-$C_6)$alkyl group, such as a methyl.

Subgroup 52 is defined by the compounds of formula (I'') for which:
R2 is a group selected from the following groups:

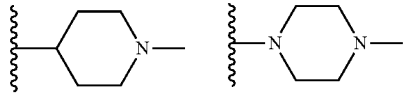

R3 is a hydrogen atom or a methyl.

Subgroup 53 is defined by the compounds of formula (I'') for which:
R7 is a phenyl or pyridinyl group, this group being optionally substituted with one or more substituents selected, independently in each instance, from: cyano, halogen, $(C_1$-$C_6)$alkyl, OR'4, $CH_2OH$, $CH_2NH_2$, $S(O)_nR'4$, R8 and OR8;
wherein:
  R'4 is a hydrogen atom or a $(C_1$-$C_6)$alkyl or aryl group, said alkyl and aryl groups being optionally substituted with a hydrogen atom or an $NH_2$ or OH group;
  n is 1 or 2;
  R8 is a halo$(C_1$-$C_6)$alkyl group.

Subgroup 54 is defined by the compounds of formula (I'') for which:
R7 is a phenyl or pyridinyl group, this group being optionally substituted with one or more substituents selected, independently in each instance, from: halogen, such as fluorine, $(C_1$-$C_6)$alkyl, such as methyl, OR'4 and OR8;
wherein:
  R'4 is a $(C_1$-$C_6)$alkyl group, such as methyl or ethyl;
  R8 is a halo$(C_1$-$C_6)$alkyl group, such as $CF_3$.

Subgroup 55 is defined by the compounds of formula (I'') for which R and R7 are defined in one of subgroups 43 to 54 above.

Subgroup 56 is defined by the compounds of formula (I'') for which:
R is a phenyl, pyridinyl or pyrazolyl group substituted with R1, R'1, R2 and R3;
R1 is selected from the following groups: $(C_1$-$C_6)$alkyl, such as isopropyl, $(C_1$-$C_6)$alkoxy, such as methoxy or isopropyloxy;
R'1 is a hydrogen atom;
R2 is selected from:
  a hydrogen or chlorine atom or a methyl group;
  a pyrrolidinyl, piperidinyl, piperazinyl, tetrahydropyranyl, 1,7-diazaspiro[4.4]non-7-yl or pyrazolyl group;
these groups being optionally substituted with at least one $(C_1$-$C_6)$alkyl group;
R3 is a hydrogen atom or a $(C_1$-$C_6)$alkyl group, such as a methyl;
R7 is a phenyl or pyridinyl group, this group being optionally substituted with one or more substituents selected, independently in each instance, from: cyano, halogen, $(C_1$-$C_6)$alkyl, OR'4, $CH_2OH$, $CH_2NH_2$, $S(O)_nR'4$, R8 and OR8;
wherein:
  R'4 is a hydrogen atom or a $(C_1$-$C_6)$alkyl or aryl group, said alkyl and aryl groups being optionally substituted with a halogen atom or an $NH_2$ or OH group;
  n is 1 or 2;
  R8 is a halo$(C_1$-$C_6)$alkyl group.

Subgroup 57 is defined by the compounds of formula (I") for which:
R is selected from the following groups:

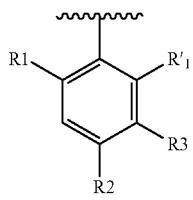

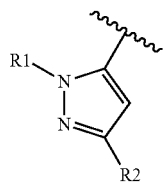

R1 is selected from the following groups: $(C_1-C_6)$alkyl, such as isopropyl, and $(C_1-C_6)$alkoxy, such as methoxy or isopropyloxy;
R'1 is a hydrogen atom;
R2 is a substituent selected from a pyrrolidinyl, piperidinyl, piperazinyl, tetrahydropyranyl, 1,7-diazaspiro[4.4]non-7-yl or pyrazolyl group;
these groups being optionally substituted with at least one $(C_1-C_6)$alkyl group, such as methyl;
R3 is a hydrogen atom or a $(C_1-C_6)$alkyl group, such as a methyl;
R7 is a phenyl or pyridinyl group, this group being optionally substituted with one or more substituents selected, independently in each instance, from: cyano, halogen, $(C_1-C_6)$alkyl, OR'4, CH$_2$OH, CH$_2$NH$_2$, S(O)$_n$R'4, R8 and OR8;
wherein:
R'4 is a hydrogen atom or a $(C_1-C_6)$alkyl or aryl group, said alkyl and aryl groups being optionally substituted with a halogen atom or an NH$_2$ or OH group;
n is 1 or 2;
R8 is a halo$(C_1-C_6)$alkyl group.
Subgroup 58 is defined by the compounds of formula (I") for which:
R is an (A) group

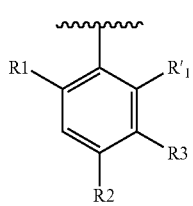

R1 is an isopropyloxy group;
R'1 is a hydrogen atom;
R2 is a piperidinyl or piperazinyl group, these groups being optionally substituted with at least one $(C_1-C_6)$alkyl group, such as methyl;
R3 is a hydrogen atom or a $(C_1-C_6)$alkyl group, such as a methyl;
R7 is a phenyl or pyridinyl group, this group being optionally substituted with one or more substituents selected, independently in each instance, from:
halogen, such as fluorine, $(C_1-C_6)$alkyl, such as methyl, OR'4 and OR8;
wherein:
R'4 is a $(C_1-C_6)$alkyl group, such as methyl or ethyl;
R8 is a halo$(C_1-C_6)$alkyl group, such as CF$_3$.
More particularly, the present invention relates to the following compounds:
2-({2-methoxy-4-[4-(pyrrolidin-1-yl)piperidin-1-yl]phenyl}amino)-7-phenylthieno-[3,2-d]pyrimidine-6-carboxamide;
2-({2-methyl-4-[4-(pyrrolidin-1-yl)piperidin-1-yl]phenyl}amino)-7-phenylthieno-[3,2-d]pyrimidine-6-carboxamide;
7-(3-chlorophenyl)-2-({2-methoxy-4-[4-(pyrrolidin-1-yl)piperidin-1-yl]phenyl}-amino)thieno[3,2-d]pyrimidine-6-carboxamide;
7-(4-chlorophenyl)-2-({2-methoxy-4-[4-(pyrrolidin-1-yl)piperidin-1-yl]phenyl}-amino)thieno[3,2-d]pyrimidine-6-carboxamide;
2-({2-methoxy-4-[4-(pyrrolidin-1-yl)piperidin-1-yl]phenyl}amino)-7-(thiophen-3-yl)thieno[3,2-d]pyrimidine-6-carboxamide;
2-({2-methoxy-4-[4-(pyrrolidin-1-yl)piperidin-1-yl]phenyl}amino)-7-(thiophen-2-yl)thieno[3,2-d]pyrimidine-6-carboxamide;
2-({2-methoxy-4-[4-(propan-2-yl)piperazin-1-yl]phenyl}amino)-7-phenylthieno-[3,2-d]pyrimidine-6-carboxamide;
2-({2-methoxy-4-[1-(propan-2-yl)piperidin-4-yl]phenyl}amino)-7-phenylthieno-[3,2-d]pyrimidine-6-carboxamide;
7-(2-methoxyphenyl)-2-{[4-(4-methylpiperazin-1-yl)-2-(propan-2-yloxy)phenyl]-amino}thieno[3,2-d]pyrimidine-6-carboxamide;
7-(4-fluoro-3-methoxyphenyl)-2-{[4-(4-methylpiperazin-1-yl)-2-(propan-2-yloxy)-phenyl]amino}thieno[3,2-d]pyrimidine-6-carboxamide;
7-(4-methoxyphenyl)-2-{[4-(4-methylpiperazin-1-yl)-2-(propan-2-yloxy)phenyl]-amino}thieno[3,2-d]pyrimidine-6-carboxamide;
7-(4-fluorophenyl)-2-{[4-(4-methylpiperazin-1-yl)-2-(propan-2-yloxy)phenyl]-amino}thieno[3,2-d]pyrimidine-6-carboxamide;
2-{[2-methoxy-5-methyl-4-(1-methylpiperidin-4-yl)phenyl]amino}-7-phenylthieno[3,2-d]pyrimidine-6-carboxamide;
7-(4-fluoro-2-methoxyphenyl)-2-{[2-methoxy-4-(4-methylpiperazin-1-yl)phenyl]-amino}thieno[3,2-d]pyrimidine-6-carboxamide;
2-{[2-methoxy-4-(4-methylpiperazin-1-yl)phenyl]amino}-7-(3-methoxyphenyl)-thieno[3,2-d]pyrimidine-6-carboxamide;
7-(2-methoxyphenyl)-2-{[4-(1-methylpiperidin-4-yl)-2-(propan-2-yloxy)phenyl]-amino}thieno[3,2-d]pyrimidine-6-carboxamide;
2-{[5-methyl-4-(1-methylpiperidin-4-yl)-2-(propan-2-yloxy)phenyl]amino}-7-phenylthieno[3,2-d]pyrimidine-6-carboxamide;
2-{[2-methoxy-5-methyl-4-(1-methylpiperidin-3-yl)phenyl]amino}-7-phenylthieno[3,2-d]pyrimidine-6-carboxamide;
2-({2-methoxy-4-[1-(propan-2-yl)piperidin-4-yl]phenyl}amino)-7-phenylthieno-[3,2-d]pyrimidine-6-carboxamide;
2-{[4-(1-methylpiperidin-4-yl)-2-(propan-2-yloxy)phenyl]amino}-7-(1-methyl-1H-pyrazol-5-yl)thieno[3,2-d]pyrimidine-6-carboxamide;

7-(2-ethoxyphenyl)-2-{[4-(1-methylpiperidin-4-yl)-2-(propan-2-yloxy)phenyl]-amino}thieno[3,2-d]pyrimidine-6-carboxamide;

7-(3-methoxyphenyl)-2-{[4-(1-methylpiperidin-4-yl)-2-(propan-2-yloxy)phenyl]-amino}thieno[3,2-d]pyrimidine-6-carboxamide;

2-{[5-methyl-4-(1-methylpiperidin-4-yl)-2-(propan-2-yloxy)phenyl]amino}-7-(pyridin-2-yl)thieno[3,2-d]pyrimidine-6-carboxamide;

2-{[4-(4-methyl-1,4-diazepan-1-yl)-2-(propan-2-yloxy)phenyl]amino}-7-phenylthieno[3,2-d]pyrimidine-6-carboxamide;

7-(2-fluoro-5-methoxyphenyl)-2-{[4-(1-methylpiperidin-4-yl)-2-(propan-2-yloxy)-phenyl]amino}thieno[3,2-d]pyrimidine-6-carboxamide;

7-(3-cyanophenyl)-2-{[4-(1-methylpiperidin-4-yl)-2-(propan-2-yloxy)phenyl]-amino}thieno[3,2-d]pyrimidine-6-carboxamide;

2-{[4-(1-methylpiperidin-4-yl)-2-(propan-2-yloxy)phenyl]amino}-7-[2-(trifluoromethoxy)phenyl]thieno[3,2-d]pyrimidine-6-carboxamide;

2-{[4-(1-methylpiperidin-4-yl)-2-(propan-2-yloxy)phenyl]amino}-7-phenylthieno-[3,2-d]pyrimidine-6-carboxamide;

2-({4-[(1S,4S)-5-methyl-2,5-diazabicyclo[2.2.1]hept-2-yl]-2-(propan-2-yloxy)-phenyl}amino)-7-phenylthieno[3,2-d]pyrimidine-6-carboxamide;

2-{[4-(1-methylpiperidin-4-yl)-2-(propan-2-yloxy)phenyl]amino}-7-(1-methyl-1,2,3,6-tetrahydropyridin-4-yl)thieno[3,2-d]pyrimidine-6-carboxamide;

7-(2-methoxyphenyl)-2-{[5-methyl-4-(1-methylpiperidin-4-yl)-2-(propan-2-yloxy)phenyl]amino}thieno[3,2-d]pyrimidine-6-carboxamide;

2-{[4-methoxy-2-(propan-2-yloxy)phenyl]amino}-7-phenylthieno[3,2-d]-pyrimidine-6-carboxamide;

2-{[4-(1-methylpiperidin-4-yl)-2-(propan-2-yloxy)phenyl]amino}-7-[3-(methylsulfinyl)phenyl]thieno[3,2-d]pyrimidine-6-carboxamide;

7-(2-methoxypyridin-3-yl)-2-{[4-(1-methylpiperidin-4-yl)-2-(propan-2-yloxy)-phenyl]amino}thieno[3,2-d]pyrimidine-6-carboxamide;

7-(2-cyanophenyl)-2-{[4-(1-methylpiperidin-4-yl)-2-(propan-2-yloxy)phenyl]-amino}thieno[3,2-d]pyrimidine-6-carboxamide;

2-{[4-(1H-imidazol-1-yl)-2-(propan-2-yloxy)phenyl]amino}-7-phenylthieno[3,2-d]pyrimidine-6-carboxamide;

2-{[4-{methyl[2-(pyrrolidin-1-yl)ethyl]amino}-2-(propan-2-yloxy)phenyl]amino}-7-phenylthieno[3,2-d]pyrimidine-6-carboxamide;

7-(2-methoxyphenyl)-2-{[6-(4-methylpiperazin-1-yl)-4-(propan-2-yloxy)pyridin-3-yl]amino}thieno[3,2-d]pyrimidine-6-carboxamide;

7-(2-methoxyphenyl)-2-{[6-(1-methylpiperidin-4-yl)-4-(propan-2-yloxy)pyridin-3-yl]amino}thieno[3,2-d]pyrimidine-6-carboxamide;

7-(5-fluoro-2-methoxyphenyl)-2-{[4-(1-methylpiperidin-4-yl)-2-(propan-2-yloxy)-phenyl]amino}thieno[3,2-d]pyrimidine-6-carboxamide;

7-(3-fluoro-2-methoxyphenyl)-2-{[4-(1-methylpiperidin-4-yl)-2-(propan-2-yloxy)-phenyl]amino}thieno[3,2-d]pyrimidine-6-carboxamide;

2-{[4-(1-methylpiperidin-4-yl)-2-(propan-2-yloxy)phenyl]amino}-7-[2-(methylsulfinyl)phenyl]thieno[3,2-d]pyrimidine-6-carboxamide;

2-({4-[3-(dimethylamino)pyrrolidin-1-yl]-2-(propan-2-yloxy)phenyl}amino)-7-(2-methoxyphenyl)thieno[3,2-d]pyrimidine-6-carboxamide;

7-(2-methoxyphenyl)-2-{[4-{methyl[2-(pyrrolidin-1-yl)ethyl]amino}-2-(propan-2-yloxy)phenyl]amino}thieno[3,2-d]pyrimidine-6-carboxamide;

7-(2-fluoro-3-methoxyphenyl)-2-{[4-(1-methylpiperidin-4-yl)-2-(propan-2-yloxy)-phenyl]amino}thieno[3,2-d]pyrimidine-6-carboxamide;

2-{[4-(1-ethylpiperidin-3-yl)-2-(propan-2-yloxy)phenyl]amino}-7-(2-methoxyphenyl)thieno[3,2-d]pyrimidine-6-carboxamide;

7-(2-fluorophenyl)-2-{[4-(1-methylpiperidin-4-yl)-2-(propan-2-yloxy)phenyl]-amino}thieno[3,2-d]pyrimidine-6-carboxamide;

2-{[4-(1-methylpiperidin-4-yl)-2-(propan-2-yloxy)phenyl]amino}-7-(1H-pyrrol-2-yl)thieno[3,2-d]pyrimidine-6-carboxamide;

7-[2-fluoro-5-(hydroxymethyl)phenyl]-2-{[4-(1-methylpiperidin-4-yl)-2-(propan-2-yloxy)phenyl]amino}thieno[3,2-d]pyrimidine-6-carboxamide;

2-{[4-(5-methoxy-1-methyl-1,2,3,6-tetrahydropyridin-4-yl)-2-(propan-2-yloxy)-phenyl]amino}-7-(2-methoxyphenyl)thieno[3,2-d]pyrimidine-6-carboxamide;

7-(4-fluoro-2-methoxyphenyl)-2-{[4-(4-methylpiperazin-1-yl)-2-(propan-2-yloxy)-phenyl]amino}thieno[3,2-d]pyrimidine-6-carboxamide;

2-{[4-(1H-imidazol-1-yl)-2-(propan-2-yloxy)phenyl]amino}-7-(2-methoxyphenyl)-thieno[3,2-d]pyrimidine-6-carboxamide;

2-methylpropan-2-yl 4-[5-{[6-carbamoyl-7-(2-methoxyphenyl)thieno-[3,2-d]pyrimidin-2-yl]amino}-1-(propan-2-yl)-1H-pyrazol-3-yl]piperidine-1-carboxylate;

7-(2-methoxyphenyl)-2-{[2-(propan-2-yloxy)-4-(2,2,6,6-tetramethylpiperidin-4-yl)phenyl]amino}thieno[3,2-d]pyrimidine-6-carboxamide;

2-{[4-(2,6-dimethylpiperidin-4-yl)-2-(propan-2-yloxy)phenyl]amino}-7-(2-methoxyphenyl)thieno[3,2-d]pyrimidine-6-carboxamide;

2-{[4-(2-ethylpiperidin-4-yl)-2-(propan-2-yloxy)phenyl]amino}-7-(2-methoxyphenyl)thieno[3,2-d]pyrimidine-6-carboxamide;

7-(2-methoxyphenyl)-2-{[4-(piperidin-4-yl)-2-(propan-2-yloxy)phenyl]amino}-thieno[3,2-d]pyrimidine-6-carboxamide;

7-(4-fluoro-2-methoxyphenyl)-2-{[4-(1-methylpiperidin-4-yl)-2-(propan-2-yloxy)-phenyl]amino}thieno[3,2-d]pyrimidine-6-carboxamide;

2-{[4-(3,5-dimethylpiperazin-1-yl)-2-(propan-2-yloxy)phenyl]amino}-7-(2-methoxyphenyl)thieno[3,2-d]pyrimidine-6-carboxamide;

7-(2-methoxyphenyl)-2-{[2-(propan-2-yloxy)-4-(3,4,5-trimethylpiperazin-1-yl)-phenyl]amino}thieno[3,2-d]pyrimidine-6-carboxamide;

2-({4-[(8aR)-hexahydropyrrolo[1,2-a]pyrazin-2(1H)-yl]-2-(propan-2-yloxy)-phenyl}amino)-7-(2-methoxyphenyl)thieno[3,2-d]pyrimidine-6-carboxamide;

7-(2-methoxyphenyl)-2-{[3-(piperidin-4-yl)-1-(propan-2-yl)-1H-pyrazol-5-yl]amino}thieno[3,2-d]pyrimidine-6-carboxamide;

2-({4-[(3R)-1-ethylpiperidin-3-yl]-2-(propan-2-yloxy)phenyl}amino)-7-(2-methoxyphenyl)thieno[3,2-d]pyrimidine-6-carboxamide;

2-({4-[(3S)-1-ethylpiperidin-3-yl]-2-(propan-2-yloxy)phenyl}amino)-7-(2-methoxyphenyl)thieno[3,2-d]pyrimidine-6-carboxamide;

2-{[4-(1-methylpiperidin-4-yl)-2-(propan-2-yloxy)phenyl]amino}-7-(thiophen-3-yl)thieno[3,2-d]pyrimidine-6-carboxamide;

7-(5-fluoro-2-methoxypyridin-4-yl)-2-{[4-(1-methylpiperidin-4-yl)-2-(propan-2-yloxy)phenyl]amino}thieno[3,2-d]pyrimidine-6-carboxamide;

7-(2-methoxyphenyl)-2-({2-(propan-2-yloxy)-4-[(2R,4S)-2-(propan-2-yl)-piperidin-4-yl]phenyl}amino)thieno[3,2-d]pyrimidine-6-carboxamide;

7-(2-methoxyphenyl)-2-({2-(propan-2-yloxy)-4-[(2R,4R)-2-(propan-2-yl)-piperidin-4-yl]phenyl}amino)thieno[3,2-d]pyrimidine-6-carboxamide;

7-(2-chlorophenyl)-2-{[4-(1-methylpiperidin-4-yl)-2-(propan-2-yloxy)phenyl]-amino}thieno[3,2-d]pyrimidine-6-carboxamide;

2-({4-[(8aR)-hexahydropyrrolo[1,2-a]pyrazin-2(1H)-yl]-2-(propan-2-yloxy)-phenyl}amino)-7-(2-methoxypyridin-3-yl)thieno[3,2-d]pyrimidine-6-carboxamide;

7-(3-chlorophenyl)-2-{[4-(1-methylpiperidin-4-yl)-2-(propan-2-yloxy)phenyl]-amino}thieno[3,2-d]pyrimidine-6-carboxamide;

7-(2-methylphenyl)-2-{[4-(1-methylpiperidin-4-yl)-2-(propan-2-yloxy)phenyl]-amino}thieno[3,2-d]pyrimidine-6-carboxamide;

2-{[4-(1-methylpiperidin-4-yl)-2-(propan-2-yloxy)phenyl]amino}-7-(1-methyl-1H-pyrazol-4-yl)thieno[3,2-d]pyrimidine-6-carboxamide;

7-(2,5-dimethoxyphenyl)-2-{[4-(1-methylpiperidin-4-yl)-2-(propan-2-yloxy)-phenyl]amino}thieno[3,2-d]pyrimidine-6-carboxamide;

7-[2-(difluoromethoxy)phenyl]-2-{[4-(1-methylpiperidin-4-yl)-2-(propan-2-yloxy)-phenyl]amino}thieno[3,2-d]pyrimidine-6-carboxamide;

2-{[4-(1-methylpiperidin-4-yl)-2-(propan-2-yloxy)phenyl]amino}-7-(1H-pyrazol-4-yl)thieno[3,2-d]pyrimidine-6-carboxamide;

2-({4-[3-(2-hydroxyethyl)-4-methylpiperazin-1-yl]-2-(propan-2-yloxy)-phenyl}amino)-7-(2-methoxyphenyl)thieno[3,2-d]pyrimidine-6-carboxamide;

7-(2-methoxypyridin-3-yl)-2-{[5-methyl-4-(1-methylpiperidin-4-yl)-2-(propan-2-yloxy)phenyl]amino}thieno[3,2-d]pyrimidine-6-carboxamide;

7-(2-methoxypyridin-3-yl)-2-{[4-(4-methylpiperazin-1-yl)-2-(propan-2-yloxy)-phenyl]amino}thieno[3,2-d]pyrimidine-6-carboxamide;

2-({4-[1-(2-hydroxyethyl)piperidin-4-yl]-2-(propan-2-yloxy)phenyl}amino)-7-(2-methoxyphenyl)thieno[3,2-d]pyrimidine-6-carboxamide;

7-(2-methoxyphenyl)-2-{[4-(3-methoxypyridin-4-yl)-2-(propan-2-yloxy)phenyl]-amino}thieno[3,2-d]pyrimidine-6-carboxamide;

7-(2-methoxyphenyl)-2-{[6-(4-methylpiperazin-1-yl)-2-(propan-2-yloxy)pyridin-3-yl]amino}thieno[3,2-d]pyrimidine-6-carboxamide;

7-(2-methoxyphenyl)-2-{[4-(1,2,2,6,6-pentamethylpiperidin-4-yl)-2-(propan-2-yloxy)phenyl]amino}thieno[3,2-d]pyrimidine-6-carboxamide;

2-({4-[(2S,4S)-2-ethyl-1-methylpiperidin-4-yl]-2-(propan-2-yloxy)phenyl}-amino)-7-(2-methoxyphenyl)thieno[3,2-d]pyrimidine-6-carboxamide;

2-({4-[(2S,4R)-2-ethyl-1-methylpiperidin-4-yl]-2-(propan-2-yloxy)phenyl}-amino)-7-(2-methoxyphenyl)thieno[3,2-d]pyrimidine-6-carboxamide;

7-(2-methoxypyridin-3-yl)-2-({2-(propan-2-yloxy)-4-[1-(propan-2-yl)piperidin-4-yl]phenyl}amino)thieno[3,2-d]pyrimidine-6-carboxamide;

7-(5-fluoro-2-methoxypyridin-3-yl)-2-{[4-(1-methylpiperidin-4-yl)-2-(propan-2-yloxy)phenyl]amino}thieno[3,2-d]pyrimidine-6-carboxamide;

7-(5-fluoro-2-methoxypyridin-3-yl)-2-({2-(propan-2-yloxy)-4-[1-(propan-2-yl)-piperidin-4-yl]phenyl}amino)thieno[3,2-d]pyrimidine-6-carboxamide;

7-(5-fluoro-2-methoxypyridin-3-yl)-2-{[5-methyl-4-(1-methylpiperidin-4-yl)-2-(propan-2-yloxy)phenyl]amino}thieno[3,2-d]pyrimidine-6-carboxamide;

7-(6-methoxypyridin-2-yl)-2-{[4-(1-methylpiperidin-4-yl)-2-(propan-2-yloxy)-phenyl]amino}thieno[3,2-d]pyrimidine-6-carboxamide;

7-(2-chlorophenyl)-2-({4-[1-(2-hydroxyethyl)piperidin-4-yl]-2-(propan-2-yloxy)-phenyl}amino)thieno[3,2-d]pyrimidine-6-carboxamide;

7-(2-methoxyphenyl)-2-{[6-(1-methylpiperidin-4-yl)-2-(propan-2-yloxy)pyridin-3-yl]amino}thieno[3,2-d]pyrimidine-6-carboxamide;

2-{[4-(1,7-diazaspiro[4.4]non-7-yl)-2-(propan-2-yloxy)phenyl]amino}-7-(2-methoxyphenyl)thieno[3,2-d]pyrimidine-6-carboxamide;

2-({4-[3-(diethylamino)pyrrolidin-1-yl]-2-(propan-2-yloxy)phenyl}amino)-7-(2-methoxypyridin-3-yl)thieno[3,2-d]pyrimidine-6-carboxamide;

2-({4-[3-(dimethylamino)pyrrolidin-1-yl]-2-(propan-2-yloxy)phenyl}amino)-7-(1-methyl-1H-pyrrol-2-yl)thieno[3,2-d]pyrimidine-6-carboxamide;

2-{[4-(1-methylpiperidin-4-yl)-2-(propan-2-yloxy)phenyl]amino}-7-(1-methyl-1H-pyrrol-2-yl)thieno[3,2-d]pyrimidine-6-carboxamide;

2-{[4-(1-methylpiperidin-4-yl)-2-(propan-2-yloxy)phenyl]amino}-7-(2-methylpyridin-3-yl)thieno[3,2-d]pyrimidine-6-carboxamide;

7-(furan-2-yl)-2-{[4-(1-methylpiperidin-4-yl)-2-(propan-2-yloxy)phenyl]amino}thieno[3,2-d]pyrimidine-6-carboxamide;

7-[5-(aminomethyl)furan-2-yl]-2-{[4-(1-methylpiperidin-4-yl)-2-(propan-2-yloxy)phenyl]amino}thieno[3,2-d]pyrimidine-6-carboxamide;

7-(2-methoxypyridin-3-yl)-2-{[5-methyl-4-(4-methylpiperazin-1-yl)-2-(propan-2-yloxy)phenyl]amino}thieno[3,2-d]pyrimidine-6-carboxamide;

2-{[4-(1-methylpiperidin-4-yl)-2-(propan-2-yloxy)phenyl]amino}-7-(1H-pyrrol-3-yl)thieno[3,2-d]pyrimidine-6-carboxamide;

2-({4-[3-(dimethylamino)pyrrolidin-1-yl]-2-(propan-2-yloxy)phenyl}amino)-7-(2-methoxypyridin-3-yl)thieno[3,2-d]pyrimidine-6-carboxamide;

7-(2-ethoxypyridin-3-yl)-2-({2-(propan-2-yloxy)-4-[1-(propan-2-yl)piperidin-4-yl]-phenyl}amino)thieno[3,2-d]pyrimidine-6-carboxamide;

7-(2-ethoxypyridin-3-yl)-2-{[5-methyl-4-(1-methylpiperidin-4-yl)-2-(propan-2-yloxy)phenyl]amino}thieno[3,2-d]pyrimidine-6-carboxamide;

7-(2-methoxyphenyl)-2-{[5-methyl-4-(4-methylpiperazin-1-yl)-2-(propan-2-yloxy)phenyl]amino}thieno[3,2-d]pyrimidine-6-carboxamide;

7-(2-ethoxypyridin-3-yl)-2-{[4-(1-methylpiperidin-4-yl)-2-(propan-2-yloxy)phenyl]amino}thieno[3,2-d]pyrimidine-6-carboxamide;

7-(2-ethoxypyridin-3-yl)-2-{[4-(4-methylpiperazin-1-yl)-2-(propan-2-yloxy)phenyl]amino}thieno[3,2-d]pyrimidine-6-carboxamide;

7-(2-methoxy-5-methylpyridin-3-yl)-2-{[4-(4-methylpiperazin-1-yl)-2-(propan-2-yloxy)phenyl]amino}thieno[3,2-d]pyrimidine-6-carboxamide;

7-(2-methoxy-5-methylpyridin-3-yl)-2-{[4-(1-methylpiperidin-4-yl)-2-(propan-2-yloxy)phenyl]amino}thieno[3,2-d]pyrimidine-6-carboxamide;

7-(5-fluoro-2-methoxypyridin-3-yl)-2-{[4-(4-methylpiperazin-1-yl)-2-(propan-2-yloxy)phenyl]amino}thieno[3,2-d]pyrimidine-6-carboxamide;

7-(2-methoxy-5-methylpyridin-3-yl)-2-{[5-methyl-4-(1-methylpiperidin-4-yl)-2-(propan-2-yloxy)phenyl]amino}thieno[3,2-d]pyrimidine-6-carboxamide;

2-{[4-(1-methylpiperidin-4-yl)-2-(propan-2-yloxy)phenyl]amino}-7-(1-methyl-1H-pyrazol-3-yl)thieno[3,2-d]pyrimidine-6-carboxamide;

2-({4-[3-(2-methoxyethyl)-4-methylpiperazin-1-yl]-2-(propan-2-yloxy)-phenyl}amino)-7-(2-methoxyphenyl)thieno[3,2-d]pyrimidine-6-carboxamide;

7-(2-methoxyphenyl)-2-{[4-{(3R)-3-[methyl(oxetan-3-yl)amino]piperidin-1-yl}-2-(propan-2-yloxy)phenyl]amino}thieno[3,2-d]pyrimidine-6-carboxamide;

7-(2-methylfuran-3-yl)-2-{[4-(1-methylpiperidin-4-yl)-2-(propan-2-yloxy)-phenyl]amino}thieno[3,2-d]pyrimidine-6-carboxamide;

7-(6-methoxypyridin-2-yl)-2-{[5-methyl-4-(1-methylpiperidin-4-yl)-2-(propan-2-yloxy)phenyl]amino}thieno[3,2-d]pyrimidine-6-carboxamide;

2-({4-[3-(dimethylamino)pyrrolidin-1-yl]-5-methyl-2-(propan-2-yloxy)-phenyl}amino)-7-(2-methoxypyridin-3-yl)thieno[3,2-d]pyrimidine-6-carboxamide;

2-({4-[3-(dimethylamino)pyrrolidin-1-yl]-5-methyl-2-(propan-2-yloxy)-phenyl}amino)-7-(2-methoxyphenyl)thieno[3,2-d]pyrimidine-6-carboxamide;

2-({3-[1-(oxetan-3-yl)piperidin-4-yl]-1-(propan-2-yl)-1H-pyrazol-5-yl}amino)-7-[2-(trifluoromethoxy)phenyl]thieno[3,2-d]pyrimidine-6-carboxamide;

7-(2-methoxy-6-methylpyridin-3-yl)-2-{[5-methyl-4-(1-methylpiperidin-4-yl)-2-(propan-2-yloxy)phenyl]amino}thieno[3,2-d]pyrimidine-6-carboxamide;

7-(2-methoxy-6-methylpyridin-3-yl)-2-{[4-(4-methylpiperazin-1-yl)-2-(propan-2-yloxy)phenyl]amino}thieno[3,2-d]pyrimidine-6-carboxamide;

7-(2-methoxy-6-methylpyridin-3-yl)-2-{[4-(1-methylpiperidin-4-yl)-2-(propan-2-yloxy)phenyl]amino}thieno[3,2-d]pyrimidine-6-carboxamide;

2-{[3-(1-ethylpiperidin-4-yl)-1-(propan-2-yl)-1H-pyrazol-5-yl]amino}-7-[2-(trifluoromethoxy)phenyl]thieno[3,2-d]pyrimidine-6-carboxamide;

2-({4-[(3R,4S)-3-hydroxy-1-methylpiperidin-4-yl]-2-(propan-2-yloxy)-phenyl}amino)-7-(2-methoxyphenyl)thieno[3,2-d]pyrimidine-6-carboxamide;

7-(2-methoxypyridin-3-yl)-2-({4-[(8S,8aS)-octahydroindolizin-8-yl]-2-(propan-2-yloxy)phenyl}amino)thieno[3,2-d]pyrimidine-6-carboxamide;

7-(2-methoxypyridin-3-yl)-2-({4-[(8R,8aS)-octahydroindolizin-8-yl]-2-(propan-2-yloxy)phenyl}amino)thieno[3,2-d]pyrimidine-6-carboxamide;

7-(2-methoxyphenyl)-2-{[4-(1-methyl-1H-pyrazol-4-yl)-2-(propan-2-yloxy)-phenyl]amino}thieno[3,2-d]pyrimidine-6-carboxamide;

7-(2-methoxypyridin-3-yl)-2-[(1-methyl-2-oxo-2,3,4,5-tetrahydro-1H-1-benzazepin-8-yl)amino]thieno[3,2-d]pyrimidine-6-carboxamide;

7-(2-methoxypyridin-3-yl)-2-{[4-(2-methyl-1H-imidazol-1-yl)-2-(propan-2-yloxy)-phenyl]amino}thieno[3,2-d]pyrimidine-6-carboxamide;

2-{[5-fluoro-4-(1-methylpiperidin-4-yl)-2-(propan-2-yloxy)phenyl]amino}-7-(2-methoxyphenyl)thieno[3,2-d]pyrimidine-6-carboxamide;

2-{[5-fluoro-4-(1-methylpiperidin-4-yl)-2-(propan-2-yloxy)phenyl]amino}-7-(2-methoxypyridin-3-yl)thieno[3,2-d]pyrimidine-6-carboxamide;

7-(2-methoxypyridin-3-yl)-2-{[5-methyl-4-(2-methyl-1H-imidazol-1-yl)-2-(propan-2-yloxy)phenyl]amino}thieno[3,2-d]pyrimidine-6-carboxamide;

7-(2-methoxyphenyl)-2-{[2-(propan-2-yloxy)-4-(1H-1,2,4-triazol-1-yl)phenyl]-amino}thieno[3,2-d]pyrimidine-6-carboxamide;

7-(2-methoxyphenyl)-2-[(1-phenyl-1H-pyrazol-5-yl)amino]thieno[3,2-d]pyrimidine-6-carboxamide;

7-(2-methoxyphenyl)-2-{[4-(1-methyl-1H-pyrazol-3-yl)-2-(propan-2-yloxy)-phenyl]amino}thieno[3,2-d]pyrimidine-6-carboxamide;

7-(2-methoxypyridin-3-yl)-2-{[3-methyl-1-(propan-2-yl)-1H-pyrazol-5-yl]amino}-thieno[3,2-d]pyrimidine-6-carboxamide;

7-(2-fluorophenyl)-2-{[5-methyl-4-(1-methylpiperidin-4-yl)-2-(propan-2-yloxy)-phenyl]amino}thieno[3,2-d]pyrimidine-6-carboxamide;

7-(2-methoxyphenyl)-2-[(1-methyl-2-oxo-2,3,4,5-tetrahydro-1H-1-benzazepin-8-yl)amino]thieno[3,2-d]pyrimidine-6-carboxamide;

7-(4-fluoro-2-methoxyphenyl)-2-{[3-(piperidin-3-yl)-1-(propan-2-yl)-1H-pyrazol-5-yl]amino}thieno[3,2-d]pyrimidine-6-carboxamide;

2-{[3-cyclopropyl-1-(propan-2-yl)-1H-pyrazol-5-yl]amino}-7-(2-methoxypyridin-3-yl)thieno[3,2-d]pyrimidine-6-carboxamide;

7-(4-fluoro-2-methoxyphenyl)-2-{[1-(propan-2-yl)-3-(pyridin-3-yl)-1H-pyrazol-5-yl]amino}thieno[3,2-d]pyrimidine-6-carboxamide;

7-(2-methoxypyridin-3-yl)-2-[(1-methyl-2-oxo-2,3,4,5-tetrahydro-1H-1-benzazepin-7-yl)amino]thieno[3,2-d]pyrimidine-6-carboxamide;

7-(4-fluoro-2-methoxyphenyl)-2-{[2-(propan-2-yloxy)-4-(1H-1,2,4-triazol-1-yl)-phenyl]amino}thieno[3,2-d]pyrimidine-6-carboxamide;

2-{[4-(2,4-dimethyl-1H-imidazol-1-yl)-2-(propan-2-yloxy)phenyl]amino}-7-(2-methoxypyridin-3-yl)thieno[3,2-d]pyrimidine-6-carboxamide;

2-{[4-methoxy-2-(propan-2-yloxy)phenyl]amino}-7-(2-methoxypyridin-3-yl)-thieno[3,2-d]pyrimidine-6-carboxamide;

2-[(3-cyclopropyl-1-phenyl-1H-pyrazol-5-yl)amino]-7-(2-methoxyphenyl)-thieno[3,2-d]pyrimidine-6-carboxamide;

2-{[4-(5,6-dihydroimidazo[1,2-a]pyrazin-7(8H)-yl)-2-(propan-2-yloxy)-phenyl]amino}-7-(2-methoxypyridin-3-yl)thieno[3,2-d]pyrimidine-6-carboxamide;

2-{[4-(1-cyclopropylpiperidin-4-yl)-2-(propan-2-yloxy)phenyl]amino}-7-(2-methoxyphenyl)thieno[3,2-d]pyrimidine-6-carboxamide;

2-{[4-(1-cyclopropylpiperidin-4-yl)-2-(propan-2-yloxy)phenyl]amino}-7-(5-fluoro-2-methoxyphenyl)thieno[3,2-d]pyrimidine-6-carboxamide;

2-{[4-(1-cyclopropylpiperidin-4-yl)-2-(propan-2-yloxy)phenyl]amino}-7-(2-methoxypyridin-3-yl)thieno[3,2-d]pyrimidine-6-carboxamide;

7-(2-methoxypyridin-3-yl)-2-{[4-(4-methyl-1H-imidazol-1-yl)-2-(propan-2-yloxy)-phenyl]amino}thieno[3,2-d]pyrimidine-6-carboxamide;

7-(4-fluoro-2-methoxyphenyl)-2-[(1-methyl-2-oxo-2,3,4,5-tetrahydro-1H-1-benzazepin-7-yl)amino]thieno[3,2-d]pyrimidine-6-carboxamide;

2-{[4-(4-methylpiperazin-1-yl)-2-(propan-2-yloxy)phenyl]amino}-7-(1-oxidopyridin-2-yl)thieno[3,2-d]pyrimidine-6-carboxamide;

2-{[4-(1-ethyl-1,7-diazaspiro[4.4]non-7-yl)-2-(propan-2-yloxy)phenyl]amino}-7-(2-methoxyphenyl)thieno[3,2-d]pyrimidine-6-carboxamide;

7-(2-ethoxypyridin-3-yl)-2-{[5-methyl-4-(4-methylpiperazin-1-yl)-2-(propan-2-yloxy)phenyl]amino}thieno[3,2-d]pyrimidine-6-carboxamide;

2-{[4-(3,5-dimethyl-1H-1,2,4-triazol-1-yl)-2-(propan-2-yloxy)phenyl]amino}-7-(2-methoxyphenyl)thieno[3,2-d]pyrimidine-6-carboxamide;

7-(5-fluoro-2-methoxypyridin-3-yl)-2-{[5-methyl-4-(4-methylpiperazin-1-yl)-2-(propan-2-yloxy)phenyl]amino}thieno[3,2-d]pyrimidine-6-carboxamide;

7-(2-methoxy-6-methylpyridin-3-yl)-2-{[4-(2-methyl-1H-imidazol-1-yl)-2-(propan-2-yloxy)phenyl]amino}thieno[3,2-d]pyrimidine-6-carboxamide;

7-(2-methoxyphenyl)-2-({4-[(4-methylpiperazin-1-yl)methyl]-2-(propan-2-yloxy)phenyl}amino)thieno[3,2-d]pyrimidine-6-carboxamide;

7-(2-methoxy-6-methylpyridin-3-yl)-2-{[5-methyl-4-(4-methylpiperazin-1-yl)-2-(propan-2-yloxy)phenyl]amino}thieno[3,2-d]pyrimidine-6-carboxamide;

7-(2-methoxyphenyl)-2-{[1-methyl-2-oxo-6-(propan-2-yloxy)-2,3,4,5-tetrahydro-1H-1-benzazepin-7-yl]amino}thieno[3,2-d]pyrimidine-6-carboxamide;

7-(2-methoxypyridin-3-yl)-2-{[1-methyl-2-oxo-6-(propan-2-yloxy)-2,3,4,5-tetrahydro-1H-1-benzazepin-7-yl]amino}thieno[3,2-d]pyrimidine-6-carboxamide;

7-(2-methoxyphenyl)-2-{[5-(4-methylpiperazin-1-yl)-2-(propan-2-yloxy)-phenyl]amino}thieno[3,2-d]pyrimidine-6-carboxamide;

7-(2-methoxyphenyl)-2-{[2-(propan-2-yloxy)-4-(tetrahydro-2H-pyran-4-ylamino)phenyl]amino}thieno[3,2-d]pyrimidine-6-carboxamide;

7-(3-methoxypyridin-2-yl)-2-{[5-methyl-4-(4-methylpiperazin-1-yl)-2-(propan-2-yloxy)phenyl]amino}thieno[3,2-d]pyrimidine-6-carboxamide;

2-{[4-(4-hydroxypiperidin-1-yl)-2-(propan-2-yloxy)phenyl]amino}-7-(2-methoxypyridin-3-yl)thieno[3,2-d]pyrimidine-6-carboxamide;

7-(2-methoxyphenyl)-2-({4-[(1-methylpiperidin-4-yl)amino]-2-(propan-2-yloxy)phenyl}amino)thieno[3,2-d]pyrimidine-6-carboxamide;

2-{[1-cyclobutyl-3-(1-ethylpiperidin-4-yl)-1H-pyrazol-5-yl]amino}-7-(4-fluoro-2-methoxyphenyl)thieno[3,2-d]pyrimidine-6-carboxamide;

7-(2-methoxypyridin-3-yl)-2-({4-[(4-methylpiperazin-1-yl)methyl]-2-(propan-2-yloxy)phenyl}amino)thieno[3,2-d]pyrimidine-6-carboxamide;

7-(2-methoxypyridin-3-yl)-2-{[4-(1-methylpyrrolidin-3-yl)-2-(propan-2-yloxy)phenyl]amino}thieno[3,2-d]pyrimidine-6-carboxamide;

7-(2-methoxyphenyl)-2-{[3-(4-methylpiperazin-1-yl)-2-(propan-2-yloxy)phenyl]amino}thieno[3,2-d]pyrimidine-6-carboxamide;

7-(5-fluoro-2-methoxypyridin-3-yl)-2-{[1-(propan-2-yl)-3-(tetrahydro-2H-pyran-4-yl)-1H-pyrazol-5-yl]amino}thieno[3,2-d]pyrimidine-6-carboxamide;

7-(5-fluoro-2-methoxypyridin-3-yl)-2-{[3-methyl-1-(propan-2-yl)-1H-pyrazol-5-yl]amino}thieno[3,2-d]pyrimidine-6-carboxamide;

7-(2-methoxypyridin-3-yl)-2-[(5-methyl-2,3,4,5-tetrahydro-1,5-benzoxazepin-7-yl)amino]thieno[3,2-d]pyrimidine-6-carboxamide;

2-{[1-(propan-2-yl)-3-(tetrahydro-2H-pyran-4-yl)-1H-pyrazol-5-yl]amino}-7-[2-(trifluoromethoxy)phenyl]thieno[3,2-d]pyrimidine-6-carboxamide;

7-(2-methoxypyridin-3-yl)-2-{[3-(4-methylpiperazin-1-yl)-2-(propan-2-yloxy)phenyl]amino}thieno[3,2-d]pyrimidine-6-carboxamide;

7-(2-methoxypyridin-3-yl)-2-{[5-(4-methylpiperazin-1-yl)-2-(propan-2-yloxy)phenyl]amino}thieno[3,2-d]pyrimidine-6-carboxamide;

7-(2-methoxypyridin-3-yl)-2-({4-[(1-methylpiperidin-4-yl)amino]-2-(propan-2-yloxy)phenyl}amino)thieno[3,2-d]pyrimidine-6-carboxamide;

2-{[4-(4-ethylpiperazin-1-yl)-2-(propan-2-yloxy)phenyl]amino}-7-(2-methoxypyridin-3-yl)thieno[3,2-d]pyrimidine-6-carboxamide;

7-(2-methoxyphenyl)-2-{[1-methyl-2-oxo-8-(propan-2-yloxy)-2,3,4,5-tetrahydro-1H-1-benzazepin-7-yl]amino}thieno[3,2-d]pyrimidine-6-carboxamide;

7-(2-methoxyphenyl)-2-{[1-(propan-2-yl)-3-(tetrahydro-2H-pyran-4-yl)-1H-pyrazol-5-yl]amino}thieno[3,2-d]pyrimidine-6-carboxamide;

7-(2-methoxypyridin-3-yl)-2-{[1-methyl-2-oxo-8-(propan-2-yloxy)-2,3,4,5-tetrahydro-1H-1-benzazepin-7-yl]amino}thieno[3,2-d]pyrimidine-6-carboxamide;

7-(2-methoxypyridin-3-yl)-2-{[4-(1-methyl-1H-pyrazol-4-yl)-2-(propan-2-yloxy)phenyl]amino}thieno[3,2-d]pyrimidine-6-carboxamide;

[7-(2-methoxyphenyl)-2-{[4-(1-methylpiperidin-4-yl)-2-(propan-2-yloxy)phenyl]amino}thieno[3,2-d]pyrimidin-6-yl]methanol;

[7-(2-methoxyphenyl)-2-{[4-(4-methylpiperazin-1-yl)-2-(propan-2-yloxy)phenyl]amino}thieno[3,2-d]pyrimidin-6-yl]methanol;

[7-(2-methoxy-6-methylpyridin-3-yl)-2-{[4-(4-methylpiperazin-1-yl)-2-(propan-2-yloxy)phenyl]amino}thieno[3,2-d]pyrimidin-6-yl]methanol;

[7-(5-fluoro-2-methoxypyridin-3-yl)-2-{[4-(4-methylpiperazin-1-yl)-2-(propan-2-yloxy)phenyl]amino}thieno[3,2-d]pyrimidin-6-yl]methanol;

[7-(2-ethoxypyridin-3-yl)-2-{[4-(4-methylpiperazin-1-yl)-2-(propan-2-yloxy)phenyl]amino}thieno[3,2-d]pyrimidin-6-yl]methanol;

[7-(2-methoxypyridin-3-yl)-2-{[5-methyl-4-(4-methylpiperazin-1-yl)-2-(propan-2-yloxy)phenyl]amino}thieno[3,2-d]pyrimidin-6-yl]methanol;

[7-(5-fluoro-2-methoxypyridin-3-yl)-2-{[5-methyl-4-(4-methylpiperazin-1-yl)-2-(propan-2-yloxy)phenyl]amino}thieno[3,2-d]pyrimidin-6-yl]methanol;

[7-(2-methoxy-6-methylpyridin-3-yl)-2-{[5-methyl-4-(4-methylpiperazin-1-yl)-2-(propan-2-yloxy)phenyl]amino}thieno[3,2-d]pyrimidin-6-yl]methanol;

[7-(2-methoxy-6-methylpyridin-3-yl)-2-{[1-(propan-2-yl)-3-(tetrahydro-2H-pyran-4-yl)-1H-pyrazol-5-yl]amino}thieno[3,2-d]pyrimidin-6-yl]methanol;

[7-(2-ethoxypyridin-3-yl)-2-{[5-methyl-4-(4-methylpiperazin-1-yl)-2-(propan-2-yloxy)phenyl]amino}thieno[3,2-d]pyrimidin-6-yl]methanol;

[7-(2-methoxyphenyl)-2-{[5-methyl-4-(4-methylpiperazin-1-yl)-2-(propan-2-yloxy)phenyl]amino}thieno[3,2-d]pyrimidin-6-yl]methanol;

[7-(2-methoxy-6-methylpyridin-3-yl)-2-{[4-(1-methyl-1,7-diazaspiro[4.4]non-7-yl)-2-(propan-2-yloxy)phenyl]amino}thieno[3,2-d]pyrimidin-6-yl]methanol;

[2-{[4-chloro-2-(propan-2-yloxy)phenyl]amino}-7-(2-methoxypyridin-3-yl)thieno[3,2-d]pyrimidin-6-yl]methanol;

(2-{[3-methyl-1-(propan-2-yl)-1H-pyrazol-5-yl]amino}-7-[2-(trifluoromethoxy)phenyl]thieno[3,2-d]pyrimidin-6-yl)methanol;

[7-(5-fluoro-2-methoxypyridin-3-yl)-2-{[3-methyl-1-(propan-2-yl)-1H-pyrazol-5-yl]amino}thieno[3,2-d]pyrimidin-6-yl]methanol;

(2-{[1-(propan-2-yl)-3-(tetrahydro-2H-pyran-4-yl)-1H-pyrazol-5-yl]amino}-7-[2-(trifluoromethoxy)phenyl]thieno[3,2-d]pyrimidin-6-yl)methanol;

[7-(2-methoxyphenyl)-2-{[1-(propan-2-yl)-3-(tetrahydro-2H-pyran-4-yl)-1H-pyrazol-5-yl]amino}thieno[3,2-d]pyrimidin-6-yl]methanol;

[7-(5-fluoro-2-methoxyphenyl)-2-{[3-methyl-1-(propan-2-yl)-1H-pyrazol-5-yl]amino}thieno[3,2-d]pyrimidin-6-yl]methanol;
[7-(5-fluoro-2-methoxyphenyl)-2-{[4-(4-methylpiperazin-1-yl)-2-(propan-2-yloxy)phenyl]amino}thieno[3,2-d]pyrimidin-6-yl]methanol;
(2-{[4-(4-methylpiperazin-1-yl)-2-(propan-2-yloxy)phenyl]amino}-7-[2-(trifluoromethoxy)phenyl]thieno[3,2-d]pyrimidin-6-yl)methanol;
[7-(2-methoxypyridin-3-yl)-2-{[4-(1-methyl-1H-pyrazol-4-yl)-2-(propan-2-yloxy)phenyl]amino}thieno[3,2-d]pyrimidin-6-yl]methanol;
[7-(2-methoxyphenyl)-2-{[4-(1-methyl-1H-pyrazol-4-yl)-2-(propan-2-yloxy)phenyl]amino}thieno[3,2-d]pyrimidin-6-yl]methanol;
[2-{[5-methyl-4-(4-methylpiperazin-1-yl)-2-(propan-2-yloxy)phenyl]amino}-7-(6-methylpyridin-3-yl)thieno[3,2-d]pyrimidin-6-yl]methanol;
[7-(2-methoxypyridin-3-yl)-2-{[4-(4-methylpiperazin-1-yl)-2-(propan-2-yloxy)phenyl]amino}thieno[3,2-d]pyrimidin-6-yl]methanol;
[7-(2-methoxyphenyl)-2-{[4-(1-methylpyrrolidin-3-yl)-2-(propan-2-yloxy)phenyl]amino}thieno[3,2-d]pyrimidin-6-yl]methanol;
2-(2-{[2-methoxy-4-(4-methylpiperazin-1-yl)phenyl]amino}-7-phenylthieno[3,2-d]pyrimidin-6-yl)propan-2-ol;
2-[2-{[2-methoxy-4-(4-methylpiperazin-1-yl)phenyl]amino}-7-(2-methoxyphenyl)thieno[3,2-d]pyrimidin-6-yl]propan-2-ol; and
2-[7-(4-fluoro-2-methoxyphenyl)-2-{[2-methoxy-4-(4-methylpiperazin-1-yl)phenyl]amino}thieno[3,2-d]pyrimidin-6-yl]propan-2-ol;

and pharmaceutically acceptable salts thereof.

The present invention also relates to a process for preparing a compound of formula (I) as defined above, characterized in that a thienopyrimidine of formula (II):

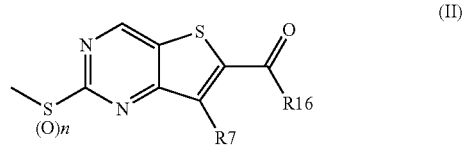

(II)

in which
R7 is as defined in formula (I) above;
n is 1 or 2; and
R16 is a $(C_1-C_6)$alkoxy group,
is reacted
a) with a compound of formula (IIIb) below:

(IIIb)

in which R is as defined in formula (I) above;
b) then step a) is followed:
either by a step of treating the mixture obtained with an aqueous ammonia solution, for example in a solvent such as methanol, which makes it possible to obtain the compounds of formula (I) in which R6 is —CONH$_2$;
or by a step of reducing the mixture obtained with a reducing agent, such as DIBALH, in a solvent such as toluene or THF, which makes it possible to obtain the compounds of formula (I) in which R6 is a —C(R$_\alpha$)(R$_\beta$)(OH) group where R$_\alpha$ and R$_\beta$ are hydrogen atoms;
or by a step of treating the mixture obtained with an excess of an organometallic derivative (R$_\alpha$MgX or R$_\beta$Li for example) in a solvent such as THF, which makes it possible to obtain the compounds of formula (I) in which R6 is a —C(R$_\alpha$)(R$_\beta$)(OH) group where R$_\alpha$ and R$_\beta$ are identical and are a $(C_1-C_6)$alkyl group.

According to one particular embodiment of step a), the reaction between the compounds (II) and (IIIb) is carried out in the presence of an organic or inorganic base, in a polar aprotic solvent.

The products of formula (II) can be prepared according to schemes 1 and 2 hereinafter.

Scheme 1

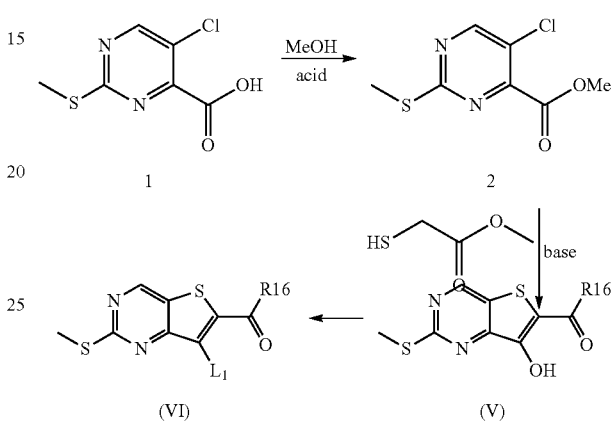

L1=leaving group such as OSO$_2$CF$_3$ or OTs.

The commercial 5-chloro-2-(methylsulfanyl)pyrimidine-4-carboxylic acid (1) is converted into ester (2) by reaction with methanol in the presence of acid as a catalyst. The treatment of the ester (2) with methyl sulfanylacetate in the presence of a base such as sodium hydride, potassium carbonate, sodium carbonate or caesium carbonate in a polar aprotic solvent such as DMF or THF gives a derivative (V). The derivative (V) can also be isolated in salt form. Finally, the hydroxyl group can be converted into a leaving group by reaction with a sulfonic anhydride or sulfonic acid chloride, in the presence of a base such as pyridine, potassium carbonate, sodium carbonate or caesium carbonate, in a polar aprotic solvent such as DMF or THF.

Scheme 2

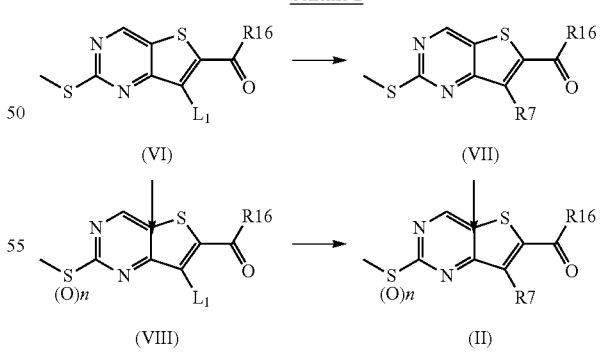

A Suzuki-type metallo-catalyzed coupling reaction on the compound (VI) makes it possible to install the (hetero)aryl R7 group in position 7. This reaction can precede or follow a reaction of oxidation of the sulfur with an oxidizing agent such as 3-chloroperbenzoic acid, aqueous hydrogen peroxide, sodium perborate tetrahydrate or sodium bromate in order to prepare the derivatives II (n=1, 2).

Alternatively, the products of formula (VII) can be prepared according to scheme 3, where R16 is a methoxy group.

temperature between ambient temperature and the reflux temperature, gives the derivative (VII).

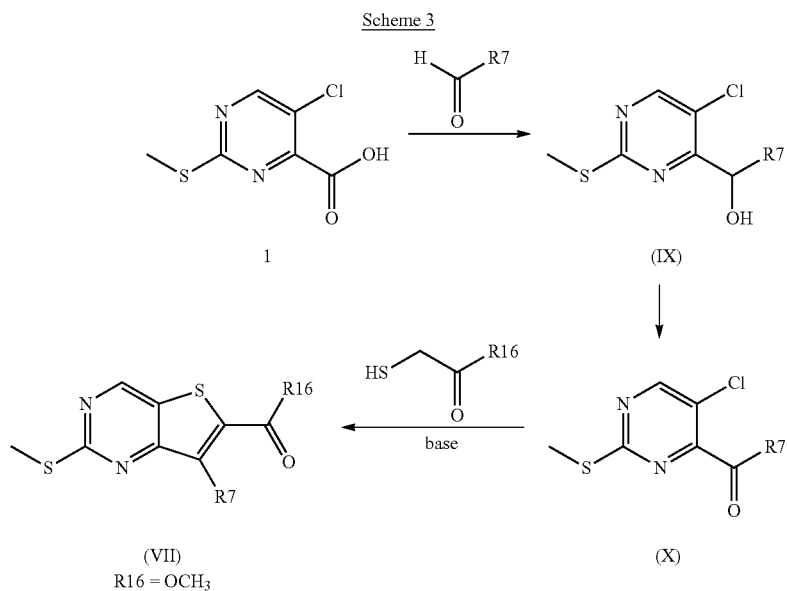

Scheme 3

Alternatively, the products of formula (I') can be prepared according to scheme 4.

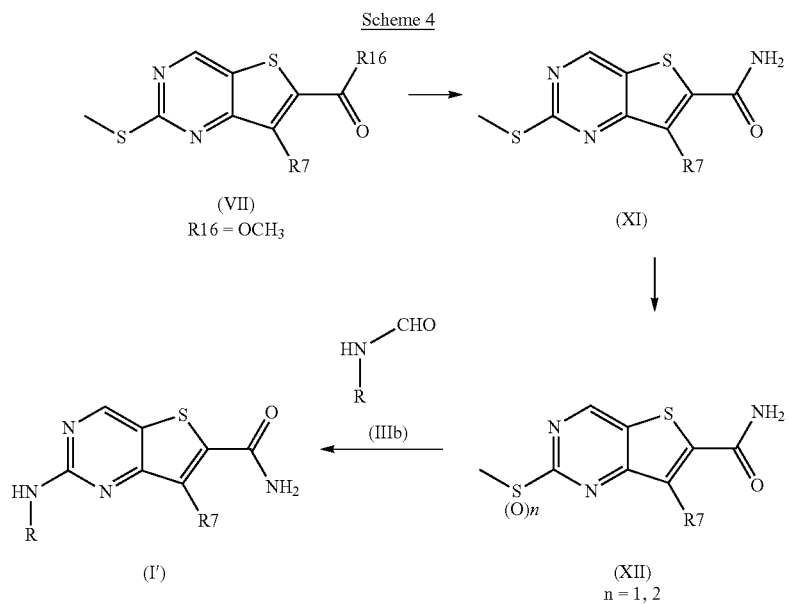

Scheme 4

Heating of the 5-chloro-2-(methylsulfanyl)pyrimidine-4-carboxylic acid (1) in the presence of an aldehyde, in an apolar solvent such as toluene, gives a benzyl alcohol (IX) (*J. Heterocyclic Chem.* 2003, 40, 219). Oxidation of the alcohol with manganese dioxide or a Swern-type reaction gives a ketone (X). Treatment of the ketone (X) with methyl sulfanylacetate in the presence of a base such as sodium hydride, potassium carbonate, sodium carbonate or caesium carbonate, in a polar aprotic solvent such as DMF or THF, at a Treatment of the derivatives (VII) for which R16 is a methoxy group, with an aqueous ammonia solution, in a solvent such as methanol, ethanol or water, gives carboxamide derivatives (XI). The sulfur is then oxidized with an oxidizing agent such as 3-chloroperbenzoic acid, aqueous hydrogen peroxide, sodium perborate tetrahydrate, magnesium monoperoxyphthalate or sodium bromate, in order to prepare the derivatives (XII) with n=1 or 2. Finally, the reaction of a compound of formula (IIIb) with the thienopyrimidine (XII) in the presence of an organic base such as DBU or BTTP, or an inorganic base such as sodium hydride, caesium carbonate or potassium carbonate, in a polar aprotic solvent such as DMF, DMA, DMSO or THF, gives the compounds (I').

Alternatively, the products of formula (I'') can be prepared according to scheme 5.

1,4-dibromobutane in a solvent such as THF (see, for example, *European Journal of Organic Chemistry* 2004, 24, 4995).

The sulfur of the compounds (XIII) is then oxidized with an oxidizing agent such as 3-chloroperbenzoic acid, aqueous

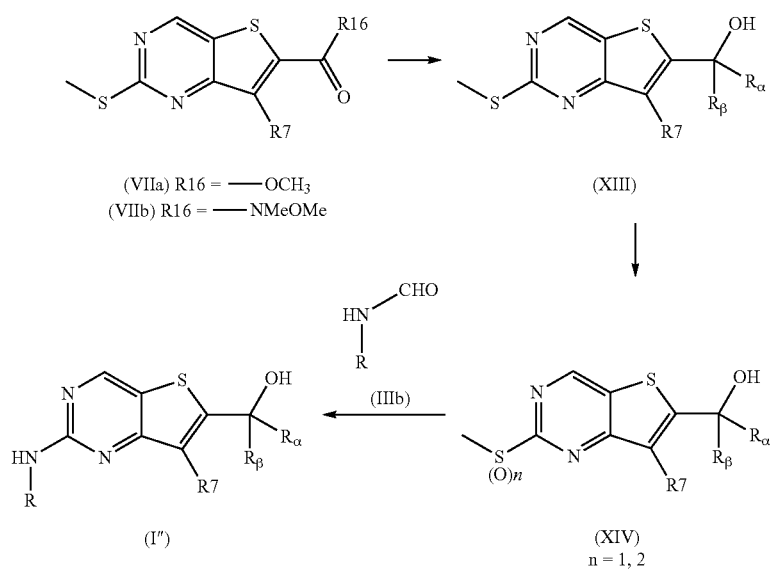

Reaction of the derivatives (VIIa) for which R16 is a methoxy group, with a reducing agent such as DIBALH, in a solvent such as THF or toluene, gives alcohol derivatives (XIII), for which the $R_\alpha$ and $R_\beta$ groups are hydrogen atoms.

Reaction of the derivatives (VIIa) for which R16 is a methoxy group, with an excess of an organometallic derivative ($R_\alpha MgX$ or $R_\alpha Li$, for example) in a solvent such as THF, gives alcohol derivatives (XIII) for which the $R_\alpha$ and $R_\beta$ groups are identical and are a ($C_1$-$C_6$)alkyl group.

Alcohol derivatives (XIII) for which the $R_\alpha$ and $R_\beta$ groups are alkyl groups that are different from one another can be obtained by means of a Weinreb amide (VIIb) for which R16 is $N(OCH_3)CH_3$ (obtained after hydrolysis of the ester (VIIa) with NaOH or LiOH and formation of the Weinreb amide according to the methods known to those skilled in the art), by addition of an organometallic derivative $R_\alpha MgX$ or $R_\alpha Li$, and then by treatment of the resulting ketone with another derivative $R_\alpha MgX$ or $R_\beta Li$.

Alcohol derivatives (XIII) for which one of the $R_\alpha$ or $R_\beta$ groups is a hydrogen and the other an alkyl group can be obtained by means of a Weinreb amide (VIIb) for which R16 is $N(OCH_3)CH_3$, by addition of an organometallic derivative RMgX or RLi, and then by treatment of the resulting ketone with a reducing agent such as sodium borohydride in methanol or DIBALH, in a solvent such as THF or toluene.

Alcohol derivatives (XIII) for which the $R_\alpha$ and $R_\beta$ groups together form, with the carbon atom which bears them, a 3-membered carbocycle can be obtained by reaction with ethylmagnesium bromide in the presence of titanium IV isopropoxide, in a solvent such as THF or ether (see, for example, *Tetrahedron* 2011, 67(33), 5979).

Alcohol derivatives (XIII) for which the $R_\alpha$ and $R_\beta$ groups together form, with the carbon atom which bears them, a 4- to 5-membered carbocycle can be obtained by reaction with the bismagnesium reagents derived from 1,3-dibromopropane or hydrogen peroxide, magnesium monoperoxyphthalate, sodium perborate tetrahydrate or sodium bromate, in order to prepare the derivatives (XIV) with n=1 or 2. Finally, the reaction of a compound of formula (IIIb) with the thienopyrimidine (XIV) in the presence of an organic base such as DBU or BTPP, or an inorganic base such as sodium hydride, caesium carbonate or potassium carbonate, in a polar aprotic solvent such as DMF, DMA, DMSO or THF, gives the compounds (I'').

The preparation of the compounds of formula (IIIb) can be carried out according to scheme 6.

Scheme 6

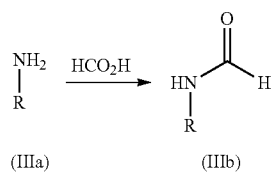

The products of formula (IIIb) can be prepared from the compounds (IIIa) by reaction with formic acid, optionally in the presence of acetic anhydride, at a temperature between ambient temperature and the reflux temperature. Most of the compounds (IIIa) are prepared according to the methods known to those skilled in the art.

The present invention also relates to the compounds of general formulae (II), (XII) and (XIV), as well as pharmaceutically acceptable salts thereof. These compounds are of use as synthesis intermediates for the preparation of the compounds of general formula (I).

Tables A and B hereinafter describe compounds of the invention, without, however, being limiting.

TABLE A

Compounds of formula (I')

(I')

[Structure: thieno[3,2-d]pyrimidine core with HN-R at 2-position, R7 at 7-position, and C(O)NH2 at 6-position]

| | R7 | R | R1 | R2 | R3 | R'1 |
|---|---|---|---|---|---|---|
| 1 | phenyl | (A) | OCH₃ | 4-(pyrrolidin-1-yl)piperidin-1-yl | H | H |
| 2 | phenyl | (A) | CH₃ | 4-(pyrrolidin-1-yl)piperidin-1-yl | H | H |
| 3 | 3-chlorophenyl | (A) | OCH₃ | 4-(pyrrolidin-1-yl)piperidin-1-yl | H | H |
| 4 | 4-chlorophenyl | (A) | OCH₃ | 4-(pyrrolidin-1-yl)piperidin-1-yl | H | H |
| 5 | thiophen-3-yl | (A) | OCH₃ | 4-(pyrrolidin-1-yl)piperidin-1-yl | H | H |
| 6 | thiophen-2-yl | (A) | OCH₃ | 4-(pyrrolidin-1-yl)piperidin-1-yl | H | H |
| 7 | phenyl | (A) | OCH₃ | 4-isopropylpiperazin-1-yl | H | H |
| 8 | phenyl | (A) | OCH₃ | 4-(1-isopropyl)piperidin-1-yl | H | H |

TABLE A-continued

Compounds of formula (I')

(I')

| | R7 | R | R1 | R2 | R3 | R'1 |
|---|---|---|---|---|---|---|
| 9 | 2-methoxyphenyl | (A) | isopropyloxy | 4-methylpiperazin-1-yl | H | H |
| 10 | 3-methoxy-4-fluorophenyl | (A) | isopropyloxy | 4-methylpiperazin-1-yl | H | H |
| 11 | 4-methoxyphenyl | (A) | isopropyloxy | 4-methylpiperazin-1-yl | H | H |
| 12 | 4-fluorophenyl | (A) | isopropyloxy | 4-methylpiperazin-1-yl | H | H |
| 13 | phenyl | (A) | OCH$_3$ | 1-methylpiperidin-4-yl | Me | H |
| 14 | 2-methoxy-4-fluorophenyl | (A) | isopropyloxy | 4-methylpiperazin-1-yl | H | H |
| 15 | 3-methoxyphenyl | (A) | OCH$_3$ | 4-methylpiperazin-1-yl | H | H |

TABLE A-continued

Compounds of formula (I')

| | R7 | R | R1 | R2 | R3 | R'1 |
|---|---|---|---|---|---|---|
| 16 | 2-methoxyphenyl | (A) | isopropyloxy | 1-methylpiperidin-4-yl | H | H |
| 17 | phenyl | (A) | isopropyloxy | 1-methylpiperidin-4-yl | Me | H |
| 18 | phenyl | (A) | OCH₃ | 1-methylpiperidin-3-yl | Me | H |
| 19 | 1-methyl-1H-pyrazol-5-yl | (A) | isopropyloxy | 1-methylpiperidin-4-yl | H | H |
| 20 | 2-ethoxyphenyl | (A) | isopropyloxy | 1-methylpiperidin-4-yl | H | H |
| 21 | 3-methoxyphenyl | (A) | isopropyloxy | 1-methylpiperidin-4-yl | H | H |
| 22 | pyridin-2-yl | (A) | isopropyloxy | 1-methylpiperidin-4-yl | Me | H |
| 23 | phenyl | (A) | isopropyloxy | 4-methyl-1,4-diazepan-1-yl | H | H |

TABLE A-continued

Compounds of formula (I')

(I') Structure: thieno[3,2-d]pyrimidine core with 2-(HN-R), 7-R7, 6-carboxamide (C(O)NH₂)

| | R7 | R | R1 | R2 | R3 | R'1 |
|---|---|---|---|---|---|---|
| 24 | 2-fluoro-5-methoxyphenyl | (A) | isopropyloxy | 1-methylpiperidin-4-yl | H | H |
| 25 | 3-cyanophenyl | (A) | isopropyloxy | 1-methylpiperidin-4-yl | H | H |
| 26 | 2-(trifluoromethoxy)phenyl | (A) | isopropyloxy | 1-methylpiperidin-4-yl | H | H |
| 27 | phenyl | (A) | isopropyloxy | 1-methylpiperidin-4-yl | H | H |
| 28 | phenyl | (A) | isopropyloxy | 5-methyl-2,5-diazabicyclo[2.2.1]heptan-2-yl | H | H |
| 29 | phenyl | (A) | isopropyloxy | 3-(dimethylamino)pyrrolidin-1-yl | H | H |
| 30 | 2-methoxyphenyl | (A) | isopropyloxy | 1-methylpiperidin-4-yl | Me | H |
| 31 | phenyl | (A) | isopropyloxy | OMe | H | H |

TABLE A-continued

Compounds of formula (I')

| | R7 | R | R1 | R2 | R3 | R'1 |
|---|---|---|---|---|---|---|
| 32 | 3-(methylsulfinyl)phenyl | (A) | isopropyloxy | 1-methylpiperidin-4-yl | H | H |
| 33 | 2-methoxypyridin-3-yl | (A) | isopropyloxy | 1-methylpiperidin-4-yl | H | H |
| 34 | 2-cyanophenyl | (A) | isopropyloxy | 1-methylpiperidin-4-yl | H | H |
| 35 | phenyl | (A) | isopropyloxy | imidazol-1-yl | H | H |
| 36 | phenyl | (A) | isopropyloxy | N-methyl-N-(2-(pyrrolidin-1-yl)ethyl)amino | H | H |
| 37 | 2-methoxyphenyl | (B) | isopropyloxy | 4-methylpiperazin-1-yl | — | H |
| 38 | 2-methoxyphenyl | (B) | isopropyloxy | 1-methylpiperidin-4-yl | — | H |
| 39 | 2-methoxy-5-fluorophenyl | (A) | isopropyloxy | 1-methylpiperidin-4-yl | H | H |

TABLE A-continued

Compounds of formula (I')

| | R7 | R | R1 | R2 | R3 | R'1 |
|---|---|---|---|---|---|---|
| 40 | 2-methoxy-3-fluorophenyl | (A) | isopropyloxy | 1-methylpiperidin-4-yl | H | H |
| 41 | 2-(methylsulfinyl)phenyl | (A) | isopropyloxy | 1-methylpiperidin-4-yl | H | H |
| 42 | 2-methoxyphenyl | (A) | isopropyloxy | 3-(dimethylamino)pyrrolidin-1-yl | H | H |
| 43 | 2-methoxyphenyl | (A) | isopropyloxy | N-methyl-2-(pyrrolidin-1-yl)ethylamino | H | H |
| 44 | 2-fluoro-3-methoxyphenyl | (A) | isopropyloxy | 1-methylpiperidin-4-yl | H | H |
| 45 | 2-methoxyphenyl | (A) | isopropyloxy | 1-ethylpiperidin-3-yl | H | H |
| 46 | 2-fluorophenyl | (A) | isopropyloxy | 1-methylpiperidin-4-yl | H | H |

TABLE A-continued

Compounds of formula (I')

(I')

[Structure of formula (I'): a thieno[3,2-d]pyrimidine core with HN(R) at the 2-position, R7 at the 3-position, and C(O)NH₂ at the 6-position]

| | R7 | R | R1 | R2 | R3 | R'1 |
|---|---|---|---|---|---|---|
| 47 | 2-pyrrolyl (HN) | (A) | isopropyloxy | 1-methylpiperidin-4-yl | H | H |
| 48 | 4-fluoro-3-(hydroxymethyl)phenyl | (A) | isopropyloxy | 1-methylpiperidin-4-yl | H | H |
| 49 | 2-methoxyphenyl | (A) | isopropyloxy | 3-methoxy-1-methyl-1,2,3,6-tetrahydropyridin-4-yl | H | H |
| 50 | 3-methoxy-4-fluorophenyl | (A) | isopropyloxy | 4-methylpiperazin-1-yl | H | H |
| 51 | 2-methoxyphenyl | (A) | isopropyloxy | imidazol-1-yl | H | H |
| 52 | 2-methoxyphenyl | (D) | isopropyl | 1-(tert-butoxycarbonyl)piperidin-4-yl | — | H |
| 53 | 2-methoxyphenyl | (A) | isopropyloxy | 2,2,6,6-tetramethylpiperidin-4-yl | H | H |
| 54 | 2-methoxyphenyl | (A) | isopropyloxy | 2,6-dimethylpiperidin-4-yl | H | H |

TABLE A-continued

Compounds of formula (I')

| | R7 | R | R1 | R2 | R3 | R'1 |
|---|---|---|---|---|---|---|
| 55 | 2-methoxyphenyl | (A) | isopropyloxy | 2-ethylpiperidin-4-yl | H | H |
| 56 | 2-methoxyphenyl | (A) | isopropyloxy | piperidin-4-yl | H | H |
| 57 | 2-methoxy-4-fluorophenyl | (A) | isopropyloxy | 1-methylpiperidin-4-yl | H | H |
| 58 | 2-methoxyphenyl | (A) | isopropyloxy | 3,5-dimethylpiperazin-1-yl | H | H |
| 59 | 2-methoxyphenyl | (A) | isopropyloxy | 2,4,6-trimethylpiperazin-1-yl | H | H |
| 60 | 2-methoxyphenyl | (A) | isopropyloxy | hexahydropyrrolo[1,2-a]pyrazin-2-yl | H | H |
| 61 | 2-methoxyphenyl | (D) | isopropyl | piperidin-4-yl | — | H |
| 62 | 2-methoxyphenyl | (A) | isopropyloxy | (3R)-1-ethylpiperidin-3-yl | H | H |

TABLE A-continued

Compounds of formula (I')

| | R7 | R | R1 | R2 | R3 | R'1 |
|---|---|---|---|---|---|---|
| 63 | 2-methoxyphenyl | (A) | isopropyloxy | (3R)-1-ethylpiperidin-3-yl | H | H |
| 64 | thiophen-3-yl | (A) | isopropyloxy | 1-methylpiperidin-4-yl | H | H |
| 65 | 5-fluoro-2-methoxypyridin-4-yl | (A) | isopropyloxy | 1-methylpiperidin-4-yl | H | H |
| 66 | 2-methoxyphenyl | (A) | isopropyloxy | (2,4-cis)-2-isopropylpiperidin-4-yl | H | H |
| 67 | 2-methoxyphenyl | (A) | isopropyloxy | (2,4-trans)-2-isopropylpiperidin-4-yl | H | H |
| 68 | 2-chlorophenyl | (A) | isopropyloxy | 1-methylpiperidin-4-yl | H | H |
| 69 | 2-methoxypyridin-3-yl | (A) | isopropyloxy | octahydropyrrolo[1,2-a]pyrazin-2-yl | H | H |
| 70 | 2-methoxyphenyl | (D) | isopropyl | 1-ethylpiperidin-4-yl | — | H |

TABLE A-continued

Compounds of formula (I')

(I')

| | R7 | R | R1 | R2 | R3 | R'1 |
|---|---|---|---|---|---|---|
| 71 | 3-chlorophenyl | (A) | isopropyloxy | 1-methylpiperidin-4-yl | H | H |
| 72 | 2-methylphenyl | (A) | isopropyloxy | 1-methylpiperidin-4-yl | H | H |
| 73 | 1-methyl-1H-pyrazol-4-yl | (A) | isopropyloxy | 1-methylpiperidin-4-yl | H | H |
| 74 | 2,5-dimethoxyphenyl | (A) | isopropyloxy | 1-methylpiperidin-4-yl | H | H |
| 75 | 2-(difluoromethoxy)phenyl | (A) | isopropyloxy | 1-methylpiperidin-4-yl | H | H |
| 76 | 1H-pyrazol-4-yl | (A) | isopropyloxy | 1-methylpiperidin-4-yl | H | H |
| 77 | 2-methoxyphenyl | (A) | isopropyloxy | 2-(2-hydroxyethyl)-4-methylpiperazin-1-yl | H | H |
| 78 | 2-methoxypyridin-3-yl | (A) | isopropyloxy | 1-methylpiperidin-4-yl | Me | H |

TABLE A-continued

Compounds of formula (I')

| | R7 | R | R1 | R2 | R3 | R'1 |
|---|---|---|---|---|---|---|
| 79 | 2-methoxypyridin-3-yl | (A) | isopropyloxy | 4-methylpiperazin-1-yl | H | H |
| 80 | 2-methoxyphenyl | (A) | isopropyloxy | 1-(2-hydroxyethyl)piperidin-4-yl | H | H |
| 81 | 2-methoxyphenyl | (A) | isopropyloxy | 3-methoxypyridin-4-yl | H | H |
| 82 | 2-methoxyphenyl | (C) | isopropyloxy | 4-methylpiperazin-1-yl | H | H |
| 83 | 2-methoxyphenyl | (A) | isopropyloxy | 1,2,2,6,6-pentamethylpiperidin-4-yl | H | H |
| 84 | 2-methoxyphenyl | (A) | isopropyloxy | (2,4-trans)-2-ethyl-1-methylpiperidin-4-yl | H | H |
| 85 | 2-methoxyphenyl | (A) | isopropyloxy | (2,4-cis)-2-ethyl-1-methylpiperidin-4-yl | H | H |
| 86 | 2-methoxypyridin-3-yl | (A) | isopropyloxy | 1-isopropylpiperidin-4-yl | H | H |

TABLE A-continued

Compounds of formula (I')

| | R7 | R | R1 | R2 | R3 | R'1 |
|---|---|---|---|---|---|---|
| 87 | 2-methoxy-5-fluoropyridin-3-yl | (A) | isopropyloxy | 1-methylpiperidin-4-yl | H | H |
| 88 | 2-methoxy-5-fluoropyridin-3-yl | (A) | isopropyloxy | 1-isopropylpiperidin-4-yl | H | H |
| 89 | 2-methoxy-5-fluoropyridin-3-yl | (A) | isopropyloxy | 1-methylpiperidin-4-yl | CH$_3$ | H |
| 90 | 6-methoxypyridin-2-yl | (A) | isopropyloxy | 1-methylpiperidin-4-yl | H | H |
| 91 | 2-chlorophenyl | (A) | isopropyloxy | 1-(2-hydroxyethyl)piperidin-4-yl | H | H |
| 92 | 2-methoxyphenyl | (C) | isopropyloxy | 1-methylpiperidin-4-yl | H | H |
| 93 | 2-methoxyphenyl | (A) | isopropyloxy | 2,7-diazaspiro[4.4]nonan-2-yl | H | H |
| 94 | 2-methoxypyridin-3-yl | (A) | isopropyloxy | 3-(diethylamino)pyrrolidin-1-yl | H | H |

TABLE A-continued

Compounds of formula (I')

| | R7 | R | R1 | R2 | R3 | R'1 |
|---|---|---|---|---|---|---|
| 95 | 1-methyl-pyrrol-2-yl | (A) | isopropyloxy | 3-(dimethylamino)pyrrolidin-1-yl | H | H |
| 96 | 1-methyl-pyrrol-2-yl | (A) | isopropyloxy | 1-methylpiperidin-4-yl | H | H |
| 97 | 2-methylpyridin-3-yl | (A) | isopropyloxy | 1-methylpiperidin-4-yl | H | H |
| 98 | furan-2-yl | (A) | isopropyloxy | 1-methylpiperidin-4-yl | H | H |
| 99 | 5-(aminomethyl)furan-2-yl | (A) | isopropyloxy | 1-methylpiperidin-4-yl | H | H |
| 100 | 2-methoxypyridin-3-yl | (A) | isopropyloxy | 4-methylpiperazin-1-yl | CH$_3$ | H |
| 101 | 1H-pyrrol-3-yl | (A) | isopropyloxy | 1-methylpiperidin-4-yl | H | H |
| 102 | 2-methoxypyridin-3-yl | (A) | isopropyloxy | 3-(dimethylamino)pyrrolidin-1-yl | H | H |

TABLE A-continued

Compounds of formula (I')

| | R7 | R | R1 | R2 | R3 | R'1 |
|---|---|---|---|---|---|---|
| 103 | 3-ethoxypyridin-2-yl | (A) | isopropyloxy | 1-isopropylpiperidin-4-yl | H | H |
| 104 | 3-ethoxypyridin-2-yl | (A) | isopropyloxy | 1-methylpiperidin-4-yl | CH₃ | H |
| 105 | 2-methoxyphenyl | (A) | isopropyloxy | 4-methylpiperazin-1-yl | CH₃ | H |
| 106 | 3-ethoxypyridin-2-yl | (A) | isopropyloxy | 1-methylpiperidin-4-yl | H | H |
| 107 | 3-ethoxypyridin-2-yl | (A) | isopropyloxy | 4-methylpiperazin-1-yl | H | H |
| 108 | 2-methoxy-5-methylpyridin-3-yl | (A) | isopropyloxy | 4-methylpiperazin-1-yl | H | H |
| 109 | 2-methoxy-5-methylpyridin-3-yl | (A) | isopropyloxy | 1-methylpiperidin-4-yl | H | H |
| 110 | 2-methoxy-5-fluoropyridin-3-yl | (A) | isopropyloxy | 4-methylpiperazin-1-yl | H | H |

TABLE A-continued

Compounds of formula (I')

| | R7 | R | R1 | R2 | R3 | R'1 |
|---|---|---|---|---|---|---|
| 111 | 2-methoxy-5-methylpyridin-3-yl | (A) | isopropyloxy | 1-methylpiperidin-4-yl | CH₃ | H |
| 112 | 1-methyl-1H-pyrazol-3-yl | (A) | isopropyloxy | 1-methylpiperidin-4-yl | H | H |
| 113 | 2-methoxyphenyl | (A) | isopropyloxy | 4-methyl-3-(2-methoxyethyl)piperazin-1-yl | H | H |
| 114 | 2-methoxyphenyl | (A) | isopropyloxy | 3-(N-methyl-N-oxetan-3-yl-amino)piperidin-1-yl | H | H |
| 115 | 2-methylfuran-3-yl | (A) | isopropyloxy | 1-methylpiperidin-4-yl | H | H |
| 116 | 6-methoxypyridin-2-yl | (A) | isopropyloxy | 1-methylpiperidin-4-yl | CH₃ | H |
| 117 | 2-methoxypyridin-3-yl | (A) | isopropyloxy | 3-(dimethylamino)pyrrolidin-1-yl | CH₃ | H |
| 118 | 2-methoxyphenyl | (A) | isopropyloxy | 3-(dimethylamino)pyrrolidin-1-yl | CH₃ | H |

TABLE A-continued

Compounds of formula (I')

| | R7 | R | R1 | R2 | R3 | R'1 |
|---|---|---|---|---|---|---|
| 119 | 2-(trifluoromethoxy)phenyl | (D) | isopropyl | 4-(oxetan-3-yl)piperidin-4-yl | — | H |
| 120 | 2-methoxy-6-methylpyridin-3-yl | (A) | isopropyloxy | 1-methylpiperidin-3-yl | CH₃ | H |
| 121 | 2-methoxy-6-methylpyridin-3-yl | (A) | isopropyloxy | 4-methylpiperazin-1-yl | H | H |
| 122 | 2-methoxy-6-methylpyridin-3-yl | (A) | isopropyloxy | 1-methylpiperidin-4-yl | H | H |
| 123 | 2-(trifluoromethoxy)phenyl | (D) | isopropyl | 1-ethylpiperidin-4-yl | — | H |
| 124 | 2-methoxyphenyl | (A) | isopropyloxy | 3-hydroxy-1-methylpiperidin-4-yl | H | H |
| 125 | 2-methoxypyridin-3-yl | (A) | isopropyloxy | indolizidinyl | H | H |
| 126 | 2-methoxypyridin-3-yl | (A) | isopropyloxy | indolizidinyl | H | H |

TABLE A-continued

Compounds of formula (I')

(I')

| | R7 | R | R1 | R2 | R3 | R'1 |
|---|---|---|---|---|---|---|
| 127 | 2-methoxyphenyl | (A) | isopropyloxy | 1-methylpyrazol-4-yl | H | H |
| 128 | 2-methoxypyridin-3-yl | (A) | H | 1-methyl-7-oxoazepan-3-yl | fused with phenyl | H |
| 129 | 2-methoxypyridin-3-yl | (A) | isopropyloxy | 2-methylimidazol-1-yl | H | H |
| 130 | 2-methoxyphenyl | (A) | isopropyloxy | 1-methylpiperidin-4-yl | F | H |
| 131 | 2-methoxypyridin-3-yl | (A) | isopropyloxy | 1-methylpiperidin-4-yl | F | H |
| 132 | 2-methoxypyridin-3-yl | (A) | isopropyloxy | 2-methylimidazol-1-yl | CH₃ | H |
| 133 | 2-methoxyphenyl | (A) | isopropyloxy | 1,2,4-triazol-1-yl | H | H |
| 134 | 2-methoxyphenyl | (D) | phenyl | H | — | H |

TABLE A-continued

Compounds of formula (I')

| R7 | R | R1 | R2 | R3 | R'1 |
|---|---|---|---|---|---|
| 135 2-methoxyphenyl | (A) | isopropyloxy | 1-methylpyrazol-3-yl | H | H |
| 136 2-methoxypyridin-3-yl | (D) | isopropyl | methyl | — | H |
| 137 2-fluorophenyl | (A) | isopropyloxy | 1-methylpiperidin-4-yl | CH$_3$ | H |
| 138 2-methoxyphenyl | (A) | H | 1-methyl-7-oxo-azepan-3-yl | fused with phenyl | H |
| 139 2-methoxy-4-fluorophenyl | (D) | isopropyl | piperidin-3-yl | — | H |
| 140 2-methoxypyridin-3-yl | (D) | isopropyl | cyclopropyl | — | H |
| 141 2-methoxy-4-fluorophenyl | (D) | isopropyl | pyridin-3-yl | — | H |

TABLE A-continued

Compounds of formula (I')

(I')

| | R7 | R | R1 | R2 | R3 | R'1 |
|---|---|---|---|---|---|---|
| 142 | 2-methoxypyridin-3-yl | (A) | H | 1-methyl-7-oxo-azepan-3-yl | fused with phenyl | H |
| 143 | 2-methoxy-4-fluorophenyl | (A) | isopropyloxy | 1H-1,2,4-triazol-1-yl | H | H |
| 144 | 2-methoxypyridin-3-yl | (A) | isopropyloxy | 2,4-dimethylimidazol-1-yl | H | H |
| 145 | 2-methoxypyridin-3-yl | (A) | isopropyloxy | methoxy | H | H |
| 146 | 2-methoxyphenyl | (D) | phenyl | cyclopropyl | — | H |
| 147 | 2-methoxypyridin-3-yl | (A) | isopropyloxy | 5,6,7,8-tetrahydroimidazo[1,2-a]pyrazin-7-yl | H | H |
| 148 | 2-methoxyphenyl | (A) | isopropyloxy | 1-cyclopropylpiperidin-4-yl | H | H |
| 149 | 2-methoxy-5-fluorophenyl | (A) | isopropyloxy | 1-cyclopropylpiperidin-4-yl | H | H |

TABLE A-continued

Compounds of formula (I')

| | R7 | R | R1 | R2 | R3 | R'1 |
|---|---|---|---|---|---|---|
| 150 | 2-methoxypyridin-3-yl | (A) | isopropyloxy | 1-cyclopropylpiperidin-4-yl | H | H |
| 151 | 2-methoxypyridin-3-yl | (A) | isopropyloxy | 4-methylimidazol-1-yl | H | H |
| 152 | 4-fluoro-2-methoxyphenyl | (A) | H | 1-methyl-2-oxo-azepan-3-yl | fused with phenyl | H |
| 153 | 2-pyridyl N-oxide | (A) | isopropyloxy | 4-methylpiperazin-1-yl | H | H |
| 154 | 2-methoxyphenyl | (A) | isopropyloxy | 2-ethyl-2,7-diazaspiro[4.4]nonan-7-yl | H | H |
| 155 | 2-ethoxypyridin-3-yl | (A) | isopropyloxy | 4-methylpiperazin-1-yl | CH₃ | H |
| 156 | 2-methoxyphenyl | (A) | isopropyloxy | 3,5-dimethyl-1,2,4-triazol-1-yl | H | H |
| 157 | 5-fluoro-2-methoxypyridin-3-yl | (A) | isopropyloxy | 4-methylpiperazin-1-yl | CH₃ | H |

TABLE A-continued

Compounds of formula (I')

| | R7 | R | R1 | R2 | R3 | R'1 |
|---|---|---|---|---|---|---|
| 158 | 2-methoxy-6-methylpyridin-3-yl | (A) | isopropyloxy | 2-methylimidazol-1-yl | H | H |
| 159 | 2-methoxyphenyl | (A) | isopropyloxy | (4-methylpiperazin-1-yl)methyl | H | H |
| 160 | 2-methoxy-6-methylpyridin-3-yl | (A) | isopropyloxy | 4-methylpiperazin-1-yl | CH₃ | H |
| 161 | 2-methoxyphenyl | (A) | H | N-methyl-azepan-2-one (fused with phenyl) | fused with phenyl | isopropyloxy |
| 162 | 2-methoxypyridin-3-yl | (A) | H | N-methyl-azepan-2-one (fused with phenyl) | fused with phenyl | isopropyloxy |
| 163 | 2-methoxyphenyl | (A) | isopropyloxy | 4-methylpiperazin-1-yl | H | H |
| 164 | 2-methoxyphenyl | (A) | isopropyloxy | tetrahydropyran-4-yl | H | H |

TABLE A-continued

Compounds of formula (I')

(I')

|  | R7 | R | R1 | R2 | R3 | R'1 |
|---|---|---|---|---|---|---|
| 165 | 3-methoxypyridin-2-yl | (A) | isopropyloxy | 4-methylpiperazin-1-yl | CH₃ | H |
| 166 | 2-methoxypyridin-3-yl | (A) | isopropyloxy | 4-hydroxypiperidin-1-yl | H | H |
| 167 | 2-methoxyphenyl | (A) | isopropyloxy | (1-methylpiperidin-4-yl)amino | H | H |
| 168 | 4-fluoro-2-methoxyphenyl | (D) | cyclobutyl | 1-ethylpiperidin-4-yl | — | H |
| 169 | 2-methoxypyridin-3-yl | (A) | isopropyloxy | (4-methylpiperazin-1-yl)methyl | H | H |
| 170 | 2-methoxypyridin-3-yl | (A) | isopropyloxy | 1-methylpyrrolidin-3-yl | H | H |
| 171 | 2-methoxyphenyl | (E) | isopropyloxy | 4-methylpiperazin-1-yl | — | H |
| 172 | 5-fluoro-2-methoxypyridin-3-yl | (D) | isopropyl | tetrahydropyran-4-yl | — | H |

TABLE A-continued

Compounds of formula (I')

|  | R7 | R | R1 | R2 | R3 | R'1 |
|---|---|---|---|---|---|---|
| 173 | 2-methoxy-5-fluoropyridin-3-yl | (D) | isopropyl | CH₃ | — | H |
| 174 | 2-methoxypyridin-3-yl | (A) | H | N-methyl-oxazepane | fused with phenyl | H |
| 175 | 2-(trifluoromethoxy)phenyl | (D) | isopropyl | tetrahydropyran-4-yl | — | H |
| 176 | 2-methoxypyridin-3-yl | (E) | isopropyloxy | 4-methylpiperazin-1-yl | — | H |
| 177 | 2-methoxypyridin-3-yl | (F) | isopropyloxy | 4-methylpiperazin-1-yl | — | H |
| 178 | 2-methoxypyridin-3-yl | (A) | isopropyloxy | (1-methylpiperidin-4-yl)amino | — | H |
| 179 | 2-methoxypyridin-3-yl | (A) | isopropyloxy | 4-ethylpiperazin-1-yl | H | H |
| 180 | 2-methoxyphenyl | (A) | isopropyloxy | 1-methyl-7-oxoazepane | fused with phenyl | H |

TABLE A-continued

Compounds of formula (I')

| | R7 | R | R1 | R2 | R3 | R'1 |
|---|---|---|---|---|---|---|
| 181 | 2-methoxyphenyl | (D) | isopropyl | tetrahydropyran-4-yl | — | H |
| 182 | 2-methoxypyridin-3-yl | (A) | isopropyloxy | 1-methyl-2-oxo-azepan-3-yl | fused with phenyl | H |
| 183 | 2-methoxypyridin-3-yl | (A) | isopropyloxy | 1-methyl-1H-pyrazol-4-yl | H | H |

TABLE B

Compounds of formula (I'')

| | R7 | R | R1 | R2 | R3 | Rα | Rβ | R'1 |
|---|---|---|---|---|---|---|---|---|
| 184 | 2-methoxyphenyl | (A) | isopropyloxy | 1-methylpiperidin-4-yl | H | H | H | H |
| 185 | 2-methoxyphenyl | (A) | isopropyloxy | 4-methylpiperazin-1-yl | H | H | H | H |
| 186 | 2-methoxy-6-methylpyridin-3-yl | (A) | isopropyloxy | 4-methylpiperazin-1-yl | H | H | H | H |

TABLE B-continued

Compounds of formula (I'')

| | R7 | R | R1 | R2 | R3 | Rα | Rβ | R'1 |
|---|---|---|---|---|---|---|---|---|
| 187 | 2-methoxy-5-fluoropyridin-3-yl | (A) | isopropyloxy | 4-methylpiperazin-1-yl | H | H | H | H |
| 188 | 2-ethoxypyridin-3-yl | (A) | isopropyloxy | 4-methylpiperazin-1-yl | H | H | H | H |
| 189 | 2-methoxypyridin-3-yl | (A) | isopropyloxy | 4-methylpiperazin-1-yl | CH₃ | H | H | H |
| 190 | 2-methoxy-5-fluoropyridin-3-yl | (A) | isopropyloxy | 4-methylpiperazin-1-yl | CH₃ | H | H | H |
| 191 | 2-methoxy-6-methylpyridin-3-yl | (A) | isopropyloxy | 4-methylpiperazin-1-yl | CH₃ | H | H | H |
| 192 | 2-methoxy-6-methylpyridin-3-yl | (D) | isopropyl | tetrahydropyran-4-yl | — | H | H | H |
| 193 | 2-ethoxypyridin-3-yl | (A) | isopropyloxy | 4-methylpiperazin-1-yl | CH₃ | H | H | H |
| 194 | 2-methoxyphenyl | (A) | isopropyloxy | 4-methylpiperazin-1-yl | CH₃ | H | H | H |

TABLE B-continued

Compounds of formula (I″)

| | R7 | R | R1 | R2 | R3 | Rα | Rβ | R′1 |
|---|---|---|---|---|---|---|---|---|
| 195 | 2-methoxy-6-methylpyridin-3-yl | (A) | isopropyloxy | 1-methyl-2,7-diazaspiro[4.4]nonan-7-yl | H | H | H | H |
| 196 | 2-methoxypyridin-3-yl | (A) | isopropyloxy | Cl | H | H | H | H |
| 197 | 2-(trifluoromethoxy)phenyl | (D) | isopropyl | CH₃ | — | H | H | H |
| 198 | 5-fluoro-2-methoxypyridin-3-yl | (D) | isopropyl | CH₃ | — | H | H | H |
| 199 | 2-(trifluoromethoxy)phenyl | (D) | isopropyl | tetrahydro-2H-pyran-4-yl | — | H | H | H |
| 200 | 2-methoxyphenyl | (D) | isopropyl | tetrahydro-2H-pyran-4-yl | — | H | H | H |
| 201 | 5-fluoro-2-methoxyphenyl | (D) | isopropyl | CH₃ | — | H | H | H |
| 202 | 5-fluoro-2-methoxyphenyl | (A) | isopropyloxy | 4-methylpiperazin-1-yl | H | H | H | H |

TABLE B-continued

Compounds of formula (I″)

| | R7 | R | R1 | R2 | R3 | Rα | Rβ | R'1 |
|---|---|---|---|---|---|---|---|---|
| 203 | 2-(trifluoromethoxy)phenyl | (A) | isopropyloxy | 4-methylpiperazin-1-yl | H | H | H | H |
| 204 | 2-methoxypyridin-3-yl | (A) | isopropyloxy | 1-methyl-1H-pyrazol-4-yl | H | H | H | H |
| 205 | 2-methoxyphenyl | (A) | isopropyloxy | 1-methyl-1H-pyrazol-4-yl | H | H | H | H |
| 206 | 6-methylpyridin-3-yl | (A) | isopropyloxy | 4-methylpiperazin-1-yl | CH₃ | H | H | H |
| 207 | 2-methoxypyridin-3-yl | (A) | isopropyloxy | 4-methylpiperazin-1-yl | H | H | H | H |
| 208 | 2-methoxyphenyl | (A) | isopropyloxy | 1-methylpyrrolidin-3-yl | H | H | H | H |
| 209 | phenyl | (A) | OCH₃ | 4-methylpiperazin-1-yl | H | CH₃ | CH₃ | H |
| 210 | 2-methoxyphenyl | (A) | OCH₃ | 4-methylpiperazin-1-yl | H | CH₃ | CH₃ | H |

TABLE B-continued

Compounds of formula (I")

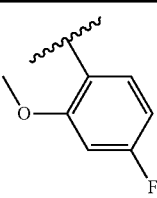

| R7 | R | R1 | R2 | R3 | Rα | Rβ | R'1 |
|---|---|---|---|---|---|---|---|
| 211  | (A) | OCH₃ | piperazine | H | CH₃ | CH₃ | H |

The following examples describe the preparation of certain compounds in accordance with the invention. These examples are not limiting and merely illustrate the present invention. The numbers of the compounds exemplified refer back to those given in the table hereinafter, which illustrates the chemical structures and the physical properties of some compounds according to the invention.

EXAMPLES

I—Materials and Methods

The $^1$H NMR spectra at 250, 400 and 500 MHz were performed on a Bruker Avance 250, Bruker Avance DRX-400 or Bruker Avance DPX-500 spectrometer with the chemical shifts (δ in ppm) in dimethyl sulfoxide-d6 (DMSO-d6) referenced at 2.5 ppm at the temperature of 303K.

The mass spectra (SM) were obtained by methods A to E.
Method A:
Waters UPLC-SQD apparatus; ionization: electrospray in positive and/or negative mode (ES+/−); chromatographic conditions: column: Acquity BEH C18 1.7 μm-2.1×50 mm; solvents: A: H₂O (0.1% formic acid) B: CH₃CN (0.1% formic acid); column temperature: 50° C.; flow rate: 1 ml/min; gradient (2 min): from 5 to 50% of B in 0.8 min; 1.2 min: 100% of B; 1.85 min: 100% of B; 1.95: 5% of B; retention time=Tr (min).
Method B:
Waters UPLC-SQD apparatus; ionization: electrospray in positive and/or negative mode (ES+/−); chromatographic conditions: column: Acquity BEH C18 1.7 μm-2.1×50 mm; solvents: A: H₂O (0.1% formic acid) B: CH₃CN (0.1% formic acid); column temperature: 50° C.; flow rate: 0.8 ml/min; gradient (2.5 min): from 5 to 100% of B in 1.8 min; 2.4 min: 100% of B; 2.45 min: 100% to 5% of B in 0.05 min; retention time=Tr (min).
Method C:
Waters UPLC-XEVO/QT of apparatus; ionization: electrospray in positive mode; chromatographic conditions: column: Acquity UPLC BEH C8 1.7 μm-2.1×100 mm; solvents: A: H₂O (0.1% formic acid) B: CH₃CN (0.1% formic acid); column temperature: 55° C.; flow rate: 0.55 ml/min; gradient (11 min): from 5 to 97% of B in 8.3 min; 8.6 min: 100% of B; 9 min: 5% of B; retention time=Tr (min).

Method D
Waters ZQ apparatus; ionization: electrospray in positive and/or negative mode (ES+/−); chromatographic conditions: column: XBridge C18 2.5 μm-3×50 mm; solvents: A: H₂O (0.1% formic acid) B: CH₃CN (0.1% formic acid); column temperature: 70° C.; flow rate: 0.9 ml/min; gradient (7 min): from 5 to 100% of B in 5.3 min; 5.5 min: 100% of B; 6.3 min: 5% of B; retention time=Tr (min).
Method E:
Waters UPLC-TOF apparatus; ionization: electrospray in positive mode; chromatographic conditions: column: Acquity UPLC BEH C8 1.7 μm-2.1×50 mm; solvents: A: H₂O (0.05% TFA) B: CH₃CN (0.035% TFA); column temperature: 40° C.; flow rate: 1.0 ml/min; gradient (3 min): T0: 98% of A; T1.6 min to T2.1 min: 100% B; T2.5 min to T3 min: 98% A.

The microwave oven used is a Biotage, Initiator™ Eight, 400 W max, 2450 MHz device or a CEM discover, 300 W max, device.

The H-cube used is a Thales-nanotechnology device.

II—Preparation of Compounds of Formulae (II) and (XII)

Example 1

Methyl 2-(methylsulfanyl)-7-{[(trifluoromethyl)sulfonyl]oxy}thieno[3,2-d]pyrimidine-6-carboxylate

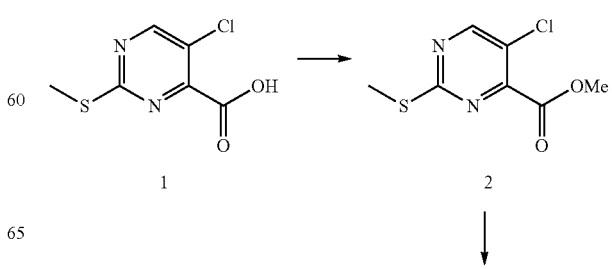

-continued

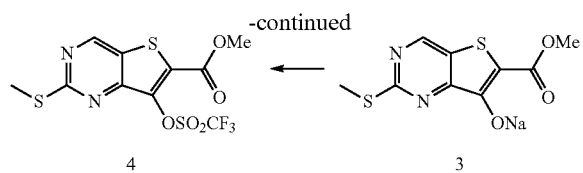

16.0 g of chloro(trimethyl)silane are added dropwise to a solution of 6.2 g of 5-chloro-2-(methylsulfanyl)pyrimidine-4-carboxylic acid 1 in 100 ml of methanol and 100 ml of dichloromethane. The mixture is stirred at ambient temperature for 20 h, and then concentrated under vacuum. The residue is taken up with water and extracted with dichloromethane. The organic phase is dried over magnesium sulfate and concentrated under vacuum so as to obtain 6.3 g of methyl 5-chloro-2-(methylsulfanyl)pyrimidine-4-carboxylate 2 in the form of a brown oil.

1.2 g of sodium hydride (60% in oil) are added slowly to a mixture of 6.0 g of methyl 5-chloro-2-(methylsulfanyl)pyrimidine-4-carboxylate 2 and 3.0 g of methyl sulfanylacetate in 60 ml of DMF. After 15 min at ambient temperature, the mixture is heated at 60° C. for 3 h, and then cooled to ambient temperature overnight. The resulting suspension is filtered and the solid is washed with ethyl acetate and dried under vacuum so as to obtain 3.6 g of sodium 6-(methoxycarbonyl)-2-(methylsulfanyl)thieno[3,2-d]pyrimidin-7-olate 3 in the form of a beige solid.

30 g of N-phenylbistrifluoromethanesulfonimide are added to a solution of 10.0 g of sodium 6-(methoxycarbonyl)-2-(methylsulfanyl)thieno[3,2-d]pyrimidin-7-olate 3 in 400 ml of anhydrous pyridine. The mixture is stirred at ambient temperature for 48 h, and then concentrated under reduced pressure. The reaction crude is solubilized in 400 ml of dichloromethane and then the organic phase is washed three times with 250 ml of water. The organic phase is dried over magnesium sulfate, filtered, and then concentrated under reduced pressure. The residue is purified on silica, elution being carried out with 15-30% of ethyl acetate in heptanes, so as to obtain 11.6 g of methyl 2-(methylsulfanyl)-7-{[(trifluoromethyl)sulfonyl]oxy}thieno[3,2-d]pyrimidine-6-carboxylate 4 in the form of a whitish powder. Rf=0.39 (heptane/ethyl acetate: 70/30).

Example 2

Methyl 2-(methylsulfonyl)-7-{[(trifluoromethyl)sulfonyl]oxy}thieno[3,2-d]pyrimidine-6-carboxylate

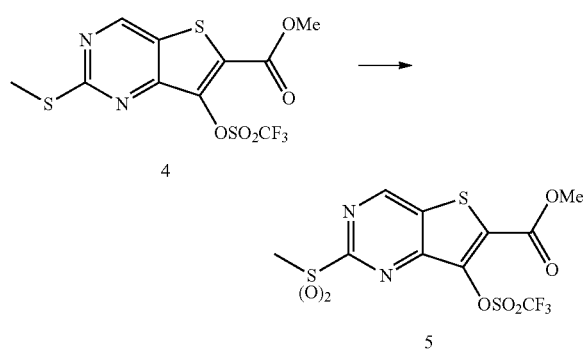

14.3 g of 3-chloroperbenzoic acid is added slowly, in fractions, to a solution of 10.0 g of methyl 2-(methylsulfanyl)-7-{[(trifluoromethyl)sulfonyl]oxy}thieno[3,2-d]pyrimidine-6-carboxylate 4 (example 1) in 140 ml of dichloromethane, cooled in an ice bath. The mixture is stirred for 6 h while cold, and then left at ambient temperature overnight. The mixture is then diluted with 400 ml of dichloromethane and treated with 300 ml of saturated sodium thiosulfate solution. After stirring and settling out, the aqueous phase is extracted with 2×100 ml of dichloromethane. The organic phases are washed with 400 ml of a saturated sodium bicarbonate solution, and then with 100 ml of a saturated sodium chloride solution. The organic phases are dried over magnesium sulfate, filtered, and then concentrated under vacuum so as to obtain 10.8 g of methyl 2-(methylsulfonyl)-7-{[(trifluoromethyl)sulfonyl]oxy}thieno[3,2-d]pyrimidine-6-carboxylate 5 in the form of a white powder. $^1$H NMR (DMSO-d6) δ 3.48 (s, 3H); 4.02 (s, 3H); 10.01 (s, 1H).

Example 3

Methyl 2-(methylsulfonyl)-7-phenylthieno[3,2-d]pyrimidine-6-carboxylate

A mixture of 253 mg of methyl 2-(methylsulfonyl)-7-{[(trifluoromethyl)sulfonyl]oxy}thieno[3,2-d]pyrimidine-6-carboxylate 5 (example 2), 110 mg of benzeneboronic acid, 392 mg of caesium carbonate and 49 mg of dichloropalladium(II)bis(diphenylphosphino)ferocene in 3.5 ml of toluene is heated at 90° C. for 30 min. The mixture is cooled and poured into water. The aqueous phase is extracted three times with dichloromethane. The organic phases are dried over magnesium sulfate, filtered, and then concentrated under vacuum. The residue is purified on 25 g of silica, elution being carried out with dichloromethane, so as to obtain 145 mg of methyl 2-(methylsulfonyl)-7-phenylthieno[3,2-d]pyrimidine-6-carboxylate in the form of a beige solid.

Example 4

Methyl 2-(methylsulfanyl)-7-phenylthieno[3,2-d]pyrimidine-6-carboxylate

Anhydrous dioxane is added, under argon, to a mixture of 2.5 g of methyl 2-(methylsulfanyl)-7-{[(trifluoromethyl)sulfonyl]oxy}thieno[3,2-d]pyrimidine-6-carboxylate 4 (example 1) and 0.785 g of phenylboronic acid. After the addition of 250 mg of dichloropalladium (dppf) and 4.09 g of BTPP, the mixture is refluxed for 20 h, and then cooled to ambient temperature. The mixture is filtered on silica gel, elution being carried out with ethyl acetate. The solvent is evaporated off under vacuum and the residue is triturated with an ethyl acetate/heptane mixture so as to obtain 1.6 g of methyl 2-(methylsulfanyl)-7-phenylthieno[3,2-d]pyrimidine-6-carboxylate in the form of a whitish precipitate.

Example 5

Methyl 7-[2-(difluoromethoxy)phenyl]-2-(methylsulfanyl)thieno[3,2-d]pyrimidine-6-carboxylate

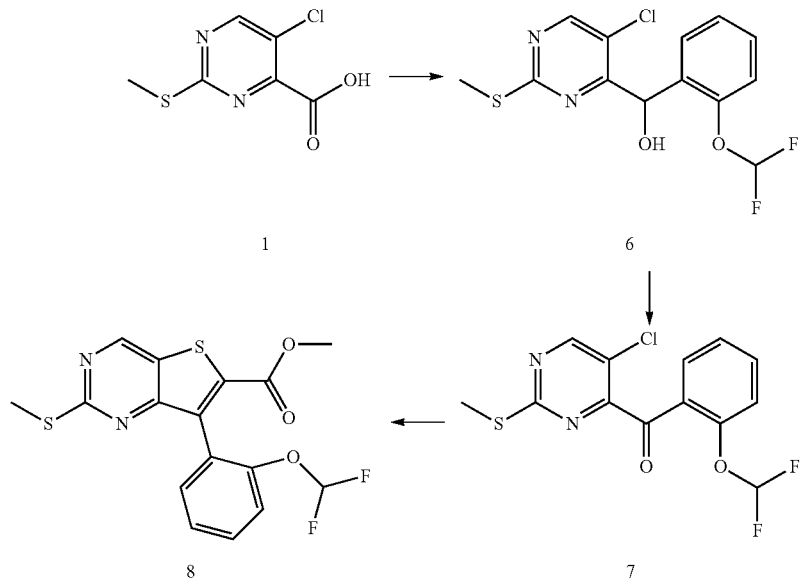

A mixture of 780 mg of 2-(difluoromethoxy)benzaldehyde and 300 mg of 5-chloro-2-(methylsulfanyl)pyrimidine-4-carboxylic acid 1 in 15 ml of anisole is microwave-heated at 130° C. for 45 min and then again for 15 min and again at 140° C. for 15 min. 160 mg of 5-chloro-2-(methylsulfanyl)pyrimidine-4-carboxylic acid 1 is then added and the mixture is again heated at 130° C. for 30 min. The mixture is concentrated under vacuum and purified on 40 g of silica, elution being carried out with 0-10% of ethyl acetate in heptane, so as to obtain 268 mg of [5-chloro-2-(methylsulfanyl)pyrimidin-4-yl][2-(difluoromethoxy)phenyl]methanol 6 in the form of a colourless oil.

A solution of 78 mg of DMSO in 0.5 ml of dichloromethane is added slowly, under argon, to a solution of 75 mg of oxalyl chloride in 2 ml of dichloromethane, cooled to −78° C. After 20 min at −78° C., a solution of 308 mg of [5-chloro-2-(methylsulfanyl)pyrimidin-4-yl][2-(difluoromethoxy)phenyl]methanol 6 in 2 ml of dichloromethane is added. After 1 h 30 at −78° C., 182 mg of triethylamine are slowly added and the mixture is left to return to ambient temperature for 30 min. The mixture is then poured into water and extracted three times with dichloromethane. The organic phases are dried over magnesium sulfate, filtered, and then concentrated under vacuum so as to obtain 303 mg of [5-chloro-2-(methylsulfanyl)pyrimidin-4-yl][2-(difluoromethoxy)phenyl]methanone 7 in the form of a pale yellow oil.

A mixture of 303 mg of [5-chloro-2-(methylsulfanyl)pyrimidin-4-yl][2-(difluoromethoxy)phenyl]methanone 7, 107 mg of methyl sulfanylacetate, 253 mg of potassium carbonate and 5 ml of acetonitrile is microwave-heated in a sealed tube at 60° C. for 4 h. The mixture is diluted with a 0.5 N aqueous hydrochloric acid solution and extracted twice with ethyl acetate and once with dichloromethane. The organic phases are dried over magnesium sulfate, filtered, and then concentrated under vacuum so as to obtain 343 mg of methyl 7-[2-(difluoromethoxy)phenyl]-2-(methylsulfanyl)thieno[3,2-d]pyrimidine-6-carboxylate 8 in the form of a pale yellow solid.

Example 6

Thiomethyl Oxidation

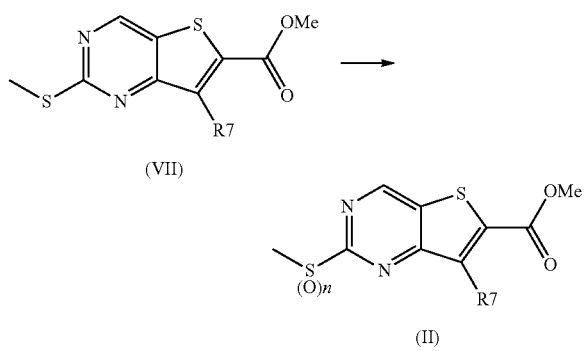

Example 6.1

Methyl 2-(methylsulfonyl)-7-phenylthieno[3,2-d]pyrimidine-6-carboxylate 2.3 g of 3-chloroperoxybenzoic acid (75%) are added slowly, in fractions, to a solution of 1.6 g of methyl 2-(methylsulfanyl)-7-phenylthieno[3,2-d]pyrimidine-6-carboxylate (example 4) in 25 ml of dichloromethane, cooled in an ice bath. The mixture is stirred for 2.5 h while cold, and then left at ambient temperature overnight. The mixture is then diluted with 80 ml of dichloromethane and treated with 60 ml of saturated sodium thiosulfate solution. After stirring and settling out, the aqueous phase is extracted with 60 ml of dichloromethane. The organic phases are washed with 60 ml of a saturated sodium bicarbonate solution, and then with 60 ml of a saturated sodium chloride solution. The organic phases are dried over magnesium sulfate, filtered, and then concentrated under vacuum so as to obtain the crude product, which is purified on 200 g of silica, elution being carried out with dichloromethane, so as to obtain 1.4 g of methyl 2-(methylsulfonyl)-7-phenylthieno[3,2-d]pyrimidine-6-carboxylate in the form of a white solid.

Example 6.2

Methyl 7-(1-methyl-1H-pyrazol-4-yl)-2-(methylsulfinyl)thieno[3,2-d]pyrimidine-6-carboxylate 230 mg of methyl 7-(1-methyl-1H-pyrazol-4-yl)-2-(methylsulfanyl)thieno[3,2-d]pyrimidine-6-carboxylate, prepared by analogy with the method described in example 4, are added to a mixture of 25 equivalents of hydrogen peroxide (30% in water) and 1.49 g of phenol. The reaction medium is stirred for 30 minutes at ambient temperature and then heated at 50° C. for 1 hour. The reaction medium is diluted in ethyl acetate and washed with a saturated aqueous NaHCO$_3$ solution and then with a saturated sodium chloride solution. The organic phase is dried over magnesium sulfate, filtered, and then concentrated under vacuum so as to obtain the crude product, which is purified on silica, elution being carried out with a 0-10% gradient of methanol in dichloromethane so as to obtain 170 mg of methyl 7-(1-methyl-1H-pyrazol-4-yl)-2-(methylsulfinyl)thieno[3,2-d]pyrimidine-6-carboxylate in the form of a beige solid.

Example 6.3

Methyl 7-(2-ethoxyphenyl)-2-(methylsulfonyl)thieno[3,2-d]pyrimidine-6-carboxylate A mixture of 330 mg of methyl 7-(2-ethoxyphenyl)-2-(methylsulfanyl)thieno[3,2-d]pyrimidine-6-carboxylate, prepared by analogy to the method described in example 4, and 634 mg of sodium perborate tetrahydrate in 15 ml of acetic acid is microwave-heated at 70° C. in a sealed tube for 1 h 30. The mixture is diluted with 5 volumes of water and the resulting precipitate is filtered off and washed with water. The solid is taken up with dichloromethane and 100 ml of a solution of sodium thiosulfate. The pH is adjusted to pH 8-9 by adding solid potassium carbonate and the aqueous phase is extracted with dichloromethane. The organic phases are dried over magnesium sulfate, filtered, and then concentrated under vacuum. This crude is purified on 40 g of silica, elution being carried out with dichloromethane, so as to obtain 296 mg of methyl 7-(2-ethoxyphenyl)-2-(methylsulfonyl)thieno[3,2-d]pyrimidine-6-carboxylate in the form of a yellow solid.

Example 6.4

Methyl 7-(6-methoxypyridin-2-yl)-2-(methylsulfinyl)thieno[3,2-d]pyrimidine-6-carboxylate 24 mg of sodium bromide and 18 mg of sodium bromate are added, with stirring, to a suspension of 55 mg of methyl 7-(6-methoxypyridin-2-yl)-2-(methylsulfanyl)thieno[3,2-d]pyrimidine-6-carboxylate, prepared by analogy to the method described in example 5, (at 50%) in 2 ml of water, and then 6.5 µl of concentrated sulfuric acid are slowly added. The yellow suspension rapidly turns orange. After 2 h 30 minutes of stirring at ambient temperature, the yellow suspension is filtered through a number 4 sintered glass filter. The yellow solid is dried under vacuum so as to obtain 28 mg of methyl 7-(6-methoxypyridin-2-yl)-2-(methylsulfinyl)thieno[3,2-d]pyrimidine-6-carboxylate.

Example 7

7-(4-Fluorophenyl)-2-(methylsulfonyl)thieno[3,2-d]pyrimidine-6-carboxamide

A mixture of 200 mg of methyl 2-(methylsulfanyl)-7-{[(trifluoromethyl)sulfonyl]oxy}thieno[3,2-d]pyrimidine-6-carboxylate 4 (example 1), 216 mg of 4-fluorophenylboronic acid, 19 mg of dichloropalladium (dppf) and 322 mg of BTPP in 2.5 ml of dioxane under argon is microwave-heated at 120° C. in a sealed tube for 1 h. The medium is taken up with dichloromethane and filtered. The organic phase is washed three times with water, then dried over magnesium sulfate, filtered, and then concentrated under vacuum so as to give a yellow solid. The crude is purified on 80 g of silica, elution being carried out with 0-20% of methanol in dichloromethane, so as to obtain 135 mg of methyl 7-(4-fluorophenyl)-2-(methylsulfanyl)thieno[3,2-d]pyrimidine-6-carboxylate in the form of a yellow solid.

A solution of 200 mg of methyl 7-(4-fluorophenyl)-2-(methylsulfanyl)thieno[3,2-d]pyrimidine-6-carboxylate in 75 ml of 7N ammoniacal methanol is stirred at ambient temperature for 64 h. The mixture is concentrated under vacuum so as to give 135 mg of 7-(4-fluorophenyl)-2-(methylsulfanyl)thieno[3,2-d]pyrimidine-6-carboxamide in the form of a yellow solid.

A mixture of 135 mg of 7-(4-fluorophenyl)-2-(methylsulfanyl)thieno[3,2-d]pyrimidine-6-carboxamide and 293 mg of sodium perborate tetrahydrate in 5 ml of acetic acid is microwave-heated at 70° C. in a sealed tube for 1 h 30. The mixture is taken up with dichloromethane and 100 ml of a sodium thiosulfate solution. The pH is adjusted to pH 8-9 by adding solid potassium carbonate and the aqueous phase is extracted with dichloromethane. The organic phases are dried over magnesium sulfate, filtered, and then concentrated under vacuum so as to obtain a beige solid. This crude is purified on 40 g of silica, elution being carried out with dichloromethane, so as to obtain 90 mg of 7-(4-fluorophenyl)-2-(methylsulfonyl)thieno[3,2-d]pyrimidine-6-carboxamide in the form of a white solid.

The compounds (II) and (XII) obtained according to examples 3 to 7 are described in table 1 hereinafter.

TABLE 1

| Compounds II/XII | Name | Prepared according to example No. | NMR | MS: conditions/ MH+/Tr |
|---|---|---|---|---|
| II-1 | Methyl 2-(methylsulfonyl)-7-phenylthieno[3,2-d]pyrimidine-6-carboxylate | 4/6.1 | 3.45 (s, 3 H); 3.89 (s, 3 H); 7.54 to 7.67 (m, 5 H); 10.00 (s, 1 H) | A 349 0.82 |

TABLE 1-continued

| Compounds II/XII | Name | Prepared according to example No. | NMR | MS: conditions/ MH+/Tr |
|---|---|---|---|---|
| II-2 | Methyl 7-(2-chlorophenyl)-2-(methylsulfonyl)thieno[3,2-d]pyrimidine-6-carboxylate | 4/6.1 | 3.37 (s, 3 H); 3.81 (s, 3 H); 7.46 to 7.59 (m, 3 H); 7.64 (broad d, J = 8.0 Hz, 1 H) 9.98 (s, 1 H) | A 383 0.87 |
| II-3 | Methyl 7-(3-chlorophenyl)-2-(methylsulfonyl)thieno[3,2-d]pyrimidine-6-carboxylate | 3 | 3.40 (s, 3 H); 3.85 (s, 3 H); 7.52 to 7.60 (m, 3 H); 7.70 (broad s, 1 H); 9.97 (s, 1 H) | A 383 0.93 |
| II-4 | Methyl 7-(4-chlorophenyl)-2-(methylsulfonyl)thieno[3,2-d]pyrimidine-6-carboxylate | 4/6.3 | 3.40 (s, 3 H); 3.85 (s, 3 H); 7.57 (d, J = 8 Hz, 2 H); 7.63 (d, J = 8 Hz, 2 H); 9.97 (s, 1 H) | B 383 1.22 |
| II-5 | Methyl 7-(2-methoxyphenyl)-2-(methylsulfonyl)thieno[3,2-d]pyrimidine-6-carboxylate | 3 | 3.37 (s, 3 H); 3.68 (s, 3 H); 3.80 (s, 3 H); 7.10 (broad t, J = 7.6 Hz, 1 H); 7.17 (dd, J = 2.0 and 7.6 Hz, 1 H); 7.44 (dd, J = 2.0 and 7.6 Hz, 1 H); 7.48 (m, 1 H); 9.92 (s, 1 H) | A 379 0.81 |
| II-6 | Methyl 7-(3-methoxyphenyl)-2-(methylsulfonyl)thieno[3,2-d]pyrimidine-6-carboxylate | 4/6.1 | 3.40 (s, 3 H); 3.80 (s, 3 H); 3.84 (s, 3 H); 7.07 (ddd, J = 1.0 and 2.7 and 8.3 Hz, 1 H); 7.13 (dt, J = 1.3 and 7.6 Hz, 1 H); 7.18 (dd, J = 1.7 and 2.4 Hz, 1 H); 7.42 (t, J = 7.9 Hz, 1 H); 9.94 (s, 1 H) | A 379 0.83 |
| XII-7 | 7-(4-Methoxyphenyl)-2-(methylsulfonyl)thieno[3,2-d]pyrimidine-6-carboxamide | 7 | 3.42 (s, 3 H); 3.84 (s, 3 H); 7.11 (broad d, J = 8.8 Hz, 2 H); 7.60 (broad d, J = 8.8 Hz, 2 H); 7.69 (broad s, 1 H); 8.05 (broad s, 1 H); 9.86 (s, 1 H) | A [M − H]− 362 0.57 |
| II-8 | Methyl 7-(2,5-dimethoxyphenyl)-2-(methylsulfonyl)thieno[3,2-d]pyrimidine-6-carboxylate | 3 | 3.39 (s, 3 H); 3.62 (s, 3 H); 3.75 (s, 3 H); 3.81 (s, 3 H); 7.00 to 7.11 (m, 3 H); 9.91 (s, 1 H) | A 409 0.82 |
| II-9 | Methyl 7-(3-fluoro-2-methoxyphenyl)-2-(methylsulfonyl)thieno[3,2-d]pyrimidine-6-carboxylate | 3 | 3.39 (s, 3 H); 3.67 (d, J = 2.2 Hz, 3 H); 3.82 (s, 3 H); 7.17 to 7.27 (m, 2 H); 7.39 to 7.48 (m, 1 H); 9.96 (s, 1 H) | A 397 0.86 |
| II-10 | Mthyl 7-(4-fluoro-2-methoxyphenyl)-2-(methylsulfonyl)thieno[3,2-d]pyrimidine-6-carboxylate | 3 | 3.38 (s, 3 H); 3.7 (s, 3 H); 3.8 (s, 3 H); 6.9 (m, 1 H), 7.1 (dd, J = 11.6 and 2.3 Hz, 1 H), 7.48 (dd, J = 8.2 and 6.6 Hz, 1 H), 9.9 (s, 1 H) | A 397 1.13 |
| II-11 | Methyl 7-(5-fluoro-2-methoxyphenyl)-2-(methylsulfonyl)thieno[3,2-d]pyrimidine-6-carboxylate | 3 | 3.38 (s, 3 H); 3.67 (s, 3 H); 3.82 (s, 3 H); 7.19 (m, 1 H); 7.28 to 7.37 (m, 2 H); 9.93 (s, 1 H) | A 397 0.84 |
| XII-12 | 7-(4-Fluoro-3-methoxyphenyl)-2-(methylsulfonyl)thieno[3,2-d]pyrimidine-6-carboxamide | 7 | 3.43 (s, 3 H); 3.87 (s, 3 H); 7.21 (ddd, J = 2.1 and 4.4 and 8.4 Hz, 1 H); 7.39 (dd, J = 8.4 and 11.5 Hz, 1 H); 7.52 (dd, J = 2.1 and 8.4 Hz, 1 H); 7.83 (broad s, 1 H); 8.10 (broad s, 1 H); 9.88 (s, 1 H) | A [M − H]− 380 0.60 |
| II-13 | Methyl 7-(2-fluoro-5-methoxyphenyl)-2-(methylsulfonyl)thieno[3,2-d]pyrimidine-6-carboxylate | 4/6.3 | 3.40 (s, 3 H); 3.78 (s, 3 H); 3.86 (s, 3 H); 7.11 (m, 1 H); 7.19 (dd, J = 3.2 and 5.9 Hz, 1 H); 7.30 (t, J = 9.3 Hz, 1 H); 9.97 (s, 1 H) | A 397 0.85 |
| II-14 | Methyl 7-(2-fluoro-3-methoxyphenyl)-2-(methylsulfonyl)thieno[3,2-d]pyrimidine-6-carboxylate | 3 | 3.38 (s, 3 H); 3.85 (s, 3 H); 3.91 (s, 3 H); 7.10 (m, 1 H); 7.21 to 7.40 (m, 2 H); 9.97 (s, 1 H) | A 397 0.82 |
| II-15 | Methyl 7-(2-ethoxyphenyl)-2-(methylsulfonyl)thieno[3,2-d]pyrimidine-6-carboxylate | 4/6.3 | 1.08 (t, J = 6.8 Hz, 3 H); 3.38 (s, 3 H); 3.80 (s, 3 H); 3.98 (q, J = 6.8 Hz, 2 H); 7.09 (t, J = 7.5 Hz, 1 H); 7.14 (d, J = 8.0 Hz, 1 H); 7.42 to 7.50 (m, 2 H); 9.92 (s, 1 H) | A 393 0.90 |
| II-16 | Methyl 7-(2-fluorophenyl)-2-(methylsulfonyl)thieno[3,2-d]pyrimidine-6-carboxylate | 3 | 3.38 (s, 3 H); 3.85 (s, 3 H); 7.34 to 7.41 (m, 2 H); 7.53 to 7.64 (m, 2 H); 9.97 (s, 1 H) | A 367 0.83 |
| XII-17 | 7-(4-Fluorophenyl)-2-(methylsulfonyl)thieno[3,2-d]pyrimidine-6-carboxamide | 7 | 3.42 (s, 3 H); 7.39 (broad t, J = 8.3 Hz, 2 H); 7.70 (broad dd, J = 5.5 and 8.3 Hz, 2 H); 7.87 (broad s, 1 H); 8.07 (broad s, 1 H); 9.88 (s, 1 H) | A 352 0.57 |
| II-18 | Methyl 7-[2-(difluoromethoxy)phenyl]-2-(methylsulfinyl)thieno[3,2-d]pyrimidine-6-carboxylate | 5/6.4 | 3.17 (s, 3 H), 3.8 (m, 1 H), 3.81 (s, 3 H), 7.35 (m, 2 H), 7.6 (m, 2 H), 9.9 (s, 1 H) | A 399 0.78 |

TABLE 1-continued

| Compounds II/XII | Name | Prepared according to example No. | NMR | MS: conditions/ MH+/Tr |
|---|---|---|---|---|
| II-19 | Methyl 2-(methylsulfonyl)-7[2-(trifluoromethoxy)-phenyl]thieno[3,2-d]pyrimidine-6-carboxylate | 4/6.3 | 3.37 (s, 3 H); 3.82 (s, 3 H); 7.51 to 7.72 (m, 4 H); 9.99 (s, 1 H) | A 433 0.95 |
| II-20 | Methyl 2-(methylsulfonyl)-7-[3-(trifluoromethoxy)-phenyl]thieno[3,2-d]pyrimidine-6-carboxylate | 4/6.3 | 3.39 (s, 3 H); 3.84 (s, 3 H); 7.52 (m, 1 H); 7.62 to 7.69 (m, 3 H); 9.96 (s, 1 H) | A 433 0.99 |
| II-21 | Methyl 7-(2-methylphenyl)-2-(methylsulfonyl)thieno[3,2-d]pyrimidine-6-carboxylate | 3 | 2.02 (s, 3 H); 3.34 (s, 3 H); 3.80 (s, 3 H); 7.20 to 7.42 (m, 4 H); 9.95 (s, 1 H) | A 363 0.87 |
| II-22 | Methyl 7-(2-cyanophenyl)-2-(methylsulfonyl)thieno[3,2-d]pyrimidine-6-carboxylate | 3 | 3.37 (s, 3 H); 3.85 (s, 3 H); 7.74 (m, 2 H); 7.89 (t, J = 7.8 Hz, 1 H); 8.04 (d, J = 7.8 Hz, 1 H); 10.01 (s, 1 H) | A 374 0.73 |
| II-23 | Methyl 7-(3-cyanophenyl)-2-(methylsulfonyl)thieno[3,2-d]pyrimidine-6-carboxylate | 4/6.3 | 3.40 (s, 3 H); 3.86 (s, 3 H); 7.75 (t, J = 7.8 Hz, 1 H); 7.95 (td, J = 1.5 and 7.8 Hz, 1 H); 7.99 (td, J = 1.5 and 7.8 Hz, 1 H); 8.13 (t, J = 1.5 Hz, 1 H); 9.97 (s, 1 H) | A 374 0.77 |
| II-24 | Methyl 7-[2-(methylsulfinyl)phenyl]-2-(methylsulfonyl)thieno[3,2-d]pyrimidine-6-carboxylate | 3 | | A 411 0.57 and 0.59 |
| II-25 | Methyl 7-[3-(methylsulfinyl)phenyl]-2-(methylsulfonyl)thieno[3,2-d]pyrimidine-6-carboxylate | 3 | | A 411 0.88 |
| II-26 | Methyl 7-[2-fluoro-5-(hydroxymethyl)phenyl]-2-(methylsulfonyl)thieno[3,2-d]pyrimidine-6-carboxylate | 3 | 3.39 (s, 3 H); 3.85 (s, 3 H); 4.56 (d, J = 5.7 Hz, 2 H); 5.30 (t, J = 5.7 Hz, 1 H); 7.32 (m, 1 H); 7.47 to 7.57 (m, 2 H); 9.97 (s, 1 H) | A 397 0.68 |
| II-27 | Methyl 2-(methylsulfonyl)-7-(thiophen-3-yl)thieno[3,2-d]pyrimidine-6-carboxylate | 3 | 3.45 (s, 3 H); 3.89 (s, 3 H); 7.52 (dd, J = 1.3 and 5.0 Hz, 1 H); 7.66 (dd, J = 3.1 and 5.0 Hz, 1 H); 8.08 (dd, J = 1.3 and 3.1 Hz, 1 H); 9.93 (s, 1 H) | C 355 4.35 |
| II-28 | Methyl 2-(methylsulfonyl)-7-(thiophen-2-yl)thieno[3,2-d]pyrimidine-6-carboxylate | 4/6.3 | | B 355 1.33 |
| II-29 | Methyl 7-(1-methyl-1H-pyrazol-5-yl)-2-(methylsulfonyl)-thieno[3,2-d]pyrimidine-6-carboxylate | 4/6.1 | | A 353 0.55 |
| II-30 | Methyl 2-(methylsulfonyl)-7-(1-oxidopyridin-2-yl)thieno[3,2-d]pyrimidine-6-carboxylate | 5/6.1 | | D 365 2.45 |
| II-31 | Methyl 7-(2-methoxypyridin-3-yl)-2-(methylsulfonyl)-thieno[3,2-d]pyrimidine-6-carboxylate | 3 | 3.38 (s, 3 H); 3.79 (s, 3 H); 3.83 (s, 3 H); 7.19 (dd, J = 5.1 and 7.3 Hz, 1 H); 7.90 (dd, J = 2.0 and 7.3 Hz, 1 H); 8.32 (dd, J = 2.0 and 5.1 Hz, 1 H); 9.95 (s, 1 H) | A 380 0.71 |
| II-32 | Methyl 7-(1-{[(2-methylpropan-2-yl)oxy]carbonyl}-1H-pyrrol-2-yl)-2-(methylsulfonyl)thieno[3,2-d]pyrimidine-6-carboxylate | 3 | | D 438 4.01 |
| II-33 | Methyl 7-(5-fluoro-2-methoxypyridin-4-yl)-2-(methylsulfonyl)thieno[3,2-d]pyrimidine-6-carboxylate | 3 | 2.90 (s, 3 H); 3.88 (s, 3 H); 3.92 (s, 3 H); 7.10 (d, J = 4.8 Hz, 1 H); 8.31 (broad s, 1 H); 9.91 (s, 1 H) | A 382 0.69 |
| II-34 | Methyl 7-(1-methyl-1H-pyrazol-4-yl)-2-(methylsulfonyl)thieno[3,2-d]pyrimidine-6-carboxylate | 4/6.2 | 3.51 (s, 3 H); 3.95 (s, 3 H); 3.99 (s, 3 H); 8.21 (s, 1 H); 8.49 (s, 1 H); 9.90 (s, 1 H) | A 353 0.60 |
| II-35 | Methyl 2-(methylsulfonyl)-7-(1H-pyrazol-4-yl)thieno[3,2-d]pyrimidine-6-carboxylate | 4/6.2 | 3.50 (s, 3 H); 3.95 (s, 3 H); 6.75 (broad m, 1 H); 8.30 (broad m, 1 H); 9.90 (s, 1 H); 13.20 (broad m, 1 H) | A 339 0.54 |
| II-36 | Methyl 7-(5-fluoro-2-methoxypyridin-3-yl)-2-(methylsulfonyl)thieno[3,2-d]pyrimidine-6-carboxylate | 3 | 3.40 (s, 3 H); 3.79 (s, 3 H); 3.86 (s, 3 H); 7.97 (dd, J = 3.0 and 8.5 Hz, 1 H); 8.32 (d, J = 3.0 Hz, 1 H); 9.97 (s, 1 H) | A 398 0.80 |

TABLE 1-continued

| Compounds II/XII | Name | Prepared according to example No. | NMR | MS: conditions/ MH+/Tr |
|---|---|---|---|---|
| II-37 | Methyl 7-(6-methoxypyridin-2-yl)-2-(methylsulfinyl)thieno[3,2-d]pyrimidine-6-carboxylate | 5/6.4 | 2.95 (s, 3 H); 3.81 (s, 3 H); 3.88 (s, 3 H) 6.92 (d, J = 8.0 Hz, 1 H); 7.69 (d, J = 8.0 Hz, 1 H); 7.91 (t, J = 8.0 Hz, 1 H); 9.89 (s, 1 H) | A 364 0.66 |
| II-38 | Methyl 7-(1-methyl-1H-pyrrol-2-yl)-2-(methylsulfonyl)-thieno[3,2-d]pyrimidine-6-carboxylate | 3 | 3.41 (s, 3 H); 3.48 (s, 3 H); 3.88 (s, 3 H); 6.19 (dd, J = 2.8 and 3.8 Hz, 1 H); 6.32 (dd, J = 2.0 and 3.8 Hz, 1 H); 7.01 (dd, J = 2.0 and 2.8 Hz, 1 H); 9.92 (s, 1 H) | A 352 0.74 |
| II-39 | Methyl 7-(2-methylpyridin-3-yl)-2-(methylsulfonyl)-thieno[3,2-d]pyrimidine-6-carboxylate | 3 | 2.21 (s, 3 H); 3.35 (s, 3 H); 3.81 (s, 3 H); 7.36 (dd, J = 5.1 and 7.3 Hz, 1 H); 7.70 (dd, J = 2.0 and 7.3 Hz, 1 H); 8.58 (dd, J = 2.0 and 5.1 Hz, 1 H); 9.98 (s, 1 H) | A 364 0.33 |
| II-40 | Methyl 7-(furan-2-yl)-2-(methylsulfonyl)thieno[3,2-d]pyrimidine-6-carboxylate | 4/6.1 | 3.51 (s, 3 H); 3.97 (s, 3 H); 6.78 (dd, J = 1.5 and 3.0 Hz, 1 H); 7.41 (dd, J = 0.8 and 3.0 Hz, 1 H); 7.97 (dd, J = 0.8 and 1.5 Hz, 1 H); 9.93 (s, 1 H) | A 339 0.74 |
| II-41 | Methyl 7-{5-[({[(2-methylpropan-2-yl)oxy]carbonyl}amino)methyl]furan-2-yl}-2-(methylsulfonyl)thieno[3,2-d]pyrimidine-6-carboxylate | 4/6.1 | 1.40 (s, 9 H); 3.51 (s, 3 H); 3.98 (s, 3 H); 4.22 (broad d, J = 5.5 Hz, 2 H); 6.48 (d, J = 3.5 Hz, 1 H); 7.38 (d, J = 3.5 Hz, 1 H); 9.91 (s, 1 H); 13.30 (broad m, 1 H) | A 468 0.92 |
| II-42 | Methyl 7-(2-methylfuran-3-yl)-2-(methylsulfinyl)thieno[3,2-d]pyrimidine-6-carboxylate | 4/6.2 | | D 337 3.39 |
| II-43 | Methyl 7-(1-{[(2-methylpropan-2-yl)oxy]carbonyl}-1H-pyrrol-3-yl)-2-(methylsulfonyl)-thieno[3,2-d]pyrimidine-6-carboxylate | 3 | 1.60 (s, 9 H); 3.50 (s, 3 H); 3.93 (s, 3 H); 6.89 (dd, J = 2.0 and 3.8 Hz, 1 H); 7.39 (dd, J = 2.8 and 3.8 Hz, 1 H); 8.15 (dd, J = 2.0 and 2.8 Hz, 1 H); 9.91 (s, 1 H) | A 438 1.03 |
| II-44 | Methyl 7-(2-ethoxypyridin-3-yl)-2-(methylsulfonyl)-thieno[3,2-d]pyrimidine-6-carboxylate | 3 | 1.15 (t, J = 7.1 Hz, 3 H); 3.40 (s, 3 H); 3.83 (s, 3 H); 4.29 (q, J = 7.0 Hz, 2 H); 7.19 (dd, J = 5.1 and 7.3 Hz, 1 H); 7.91 (dd, J = 2.0 and 7.3 Hz, 1 H); 8.30 (dd, J = 2.0 and 5.1 Hz, 1 H); 9.96 (s, 1 H) | A 394 0.79 |
| II-45 | Methyl 7-(2-methoxy-5-methylpyridin-3-yl)-2-(methylsulfonyl)thieno[3,2-d]pyrimidine-6-carboxylate | 3 | 2.30 (s, 3 H); 3.40 (s, 3 H); 3.75 (s, 3 H); 3.83 (s, 3 H); 7.74 (d, J = 3.0 Hz, 1 H); 8.11 (d, J = 3.0 Hz, 1 H); 9.94 (s, 1 H) | A 394 0.78 |
| II-46 | Methyl 7-(1-methyl-1H-pyrazol-3-yl)-2-(methylsulfonyl)-thieno[3,2-d]pyrimidine-6-carboxylate | 4/6.1 | 3.47 (s, 3 H); 3.88 (s, 3 H); 3.92 (s, 3 H); 6.89 (d, J = 2.0 Hz, 1 H); 7.87 (d, J = 2.0 Hz, 1 H); 9.91 (s, 1 H) | A 353 0.56 |
| II-47 | Methyl 7-(2-methoxy-6-methylpyridin-3-yl)-2-(methylsulfonyl)thieno[3,2-d]pyrimidine-6-carboxylate | 3 | 2.50 (s partially masked, 3 H); 3.39 (s, 3 H); 3.77 (s, 3 H); 3.83 (s, 3 H); 7.05 (d, J = 7.3 Hz, 1 H); 7.79 (d, J = 7.3 Hz, 1 H); 9.92 (s, 1 H) | A 394 0.84 |
| II-48 | Methyl 7-(3-methoxypyridin-2-yl)-2-(methylsulfinyl)thieno[3,2-d]pyrimidine-6-carboxylate | 5/6.4 | 2.86 (s, 3 H); 3.75 (s, 3 H); 3.78 (s, 3 H); 7.57 (dd, J = 8.0 and 5.0 Hz, 1 H); 7.71 (d, J = 8.0 Hz, 1 H); 8.32 (t, J = 5.0 Hz, 1 H); 9.89 (s, 1 H) | A 364 0.69 |
| II-49 | Methyl 7-(6-methylpyridin-3-yl)-2-(methylsulfinyl)thieno[3,2-d]pyrimidine-6-carboxylate | 3 | 2.58 (s, 3 H); 3.4 (s, 3 H); 3.85 (s, 3 H); 7.42 (d, J = 7 Hz, 1 H); 7.93 (dd, J = 7 and 1 Hz, 1 H); 8.65 (d, J = 1 Hz, 1 H); 9.95 (s, 1 H) | D 364 2.33 |
| II-50 | Methyl 2-(methylsulfonyl)-7-(pyridin-2-yl)thieno[3,2-d]pyrimidine-6-carboxylate | 5/6.1 | | A 350 0.78 |

III—Preparation of the Compounds of Formula (IIIa)

Example 8

Method 1: 4-(1-Methylpiperidin-4-yl)-2-(propan-2-yloxy)aniline

A mixture of 10.0 g of 4-bromo-2-fluoro-1-nitrobenzene, 44.4 g of caesium carbonate and 100 ml of isopropanol is heated at 85° C. (bath) for 1 h 30, and then left to cool to ambient temperature. The mixture is concentrated under vacuum and the residue is taken up with 400 ml of water and 300 ml of ethyl acetate. The aqueous phase is extracted with 100 ml of ethyl acetate and the combined organic phases are washed twice with 200 ml of water. The organic phases are dried over magnesium sulfate and concentrated under vacuum, so as to obtain 11.59 g of crude 4-bromo-1-nitro-2-(propan-2-yloxy)benzene in the form of a yellow oil which crystallizes. TLC: Rf=0.52 (dichloromethane/heptane (1/1)).

A mixture of 10.0 g of 4-bromo-1-nitro-2-(propan-2-yloxy)benzene, 5.78 g of 4-pyridylboronic acid, 12.2 g of sodium carbonate and 1.0 g of bis(triphenylphosphine)dichloropalladium, in 200 ml of dioxane and 35 ml of water, is heated at 110° C. (bath) for 9 h. The mixture is diluted with ethyl acetate and water. The aqueous phase is extracted twice with ethyl acetate and then with dichloromethane. The combined organic phases are dried over magnesium sulfate and concentrated under vacuum. The residue is purified on 330 g of silica, elution being carried out with ethyl acetate/heptane (1/1 to 4/1), so as to obtain 7.35 g of 4-[4-nitro-3-(propan-2-yloxy)phenyl]pyridine in the form of a pale yellow solid.

A mixture of 7.35 g of 4-[4-nitro-3-(propan-2-yloxy)phenyl]pyridine and 16.1 g of methyl iodide in 150 ml of acetonitrile is heated at 50° C. (bath) for 1 h. 2.5 ml of methyl iodide are added and the heating is continued for 1 h 50. The mixture is then concentrated under vacuum, so as to obtain 11.1 g of 1-methyl-4-[4-nitro-3-(propan-2-yloxy)phenyl]pyridinium iodide.

A solution of 10 g of 1-methyl-4-[4-nitro-3-(propan-2-yloxy)phenyl]pyridinium iodide in 280 ml of methanol is hydrogenated in an autoclave on 2.9 g of platinum oxide hydrate, at a hydrogen pressure of 15 bar and at ambient temperature for 4 h. The catalyst is removed by filtration on Clarcel and the mixture is concentrated under vacuum. The residue is taken up in 200 ml of ethyl acetate and washed with 200 ml of 1M sodium hydroxide and then with a saturated sodium chloride solution. The organic phase is dried over magnesium sulfate and concentrated under vacuum, so as to obtain 6.0 g of 4-(1-methylpiperidin-4-yl)-2-(propan-2-yloxy)aniline.

Method 2: 2-Methylpropan-2-yl 4-[4-amino-3-(propan-2-yloxy)phenyl]-2-ethylpiperidine-1-carboxylate 0.89 ml of diisopropylamine is introduced into 5 ml of THF. After cooling to −78° C., 2.45 ml of 2.5 M n-BuLi in hexane are added and the mixture is stirred for 15 minutes at −78° C. A solution of 1 g of 1-boc-2-ethylpiperidin-4-one in solution in 10 ml of THF is added dropwise. The reaction medium is stirred for 15 minutes at −78° C. and then N-phenylbis(trifluoromethanesulfonimide) in solution in 15 ml of THF is added. The reaction medium is brought back to ambient temperature and stirred for 16 hours at this temperature. The mixture is poured into 15 ml of a saturated aqueous sodium bicarbonate solution and then extracted with ethyl acetate, dried over magnesium sulfate, filtered and concentrated under reduced pressure. Purification is carried out by flash chromatography on silica gel (40-63 µm), elution being carried out with a dichloromethane/methanol (98/2) mixture. 870 mg of 2-methylpropan-2-yl 6-ethyl-4-{[(trifluoromethyl)sulfonyl]oxy}-3,6-dihydropyridine-1(2H)-carboxylate are obtained in the form of a pale yellow oil.

A mixture of 5 g of 4-bromo-1-nitro-2-(propan-2-yloxy)benzene, 5.65 g of potassium acetate, 5.85 g of bis(pinacolato)diborane and 704 mg of [1,1'-bis(diphenylphosphino)ferrocene]dichloropalladium(II) in 115 ml of dioxane is heated at 90° C. for 4 h 30. The reaction medium is poured into 250 ml of water and then extracted with twice 50 ml of water. The combined organic phases are dried over magnesium sulfate, filtered and evaporated. Purification is carried out by flash chromatography on silica gel (40-63 µm), elution being carried out with a dichloromethane/heptane (80/20) mixture. 2.5 g of 4,4,5,5-tetramethyl-2-[4-nitro-3-(propan-2-yloxy)phenyl]-1,3,2-dioxaborolane are obtained in the form of a yellow oil.

450 mg of 2-methylpropan-2-yl 6-ethyl-4-{[(trifluoromethyl)sulfonyl]oxy}-3,6-dihydropyridine-1(2H)-carboxylate are introduced into 27 ml of 1,4-dioxane. After sparging for 10 min with argon in the reaction medium, 843 mg of 4,4,5,5-tetramethyl-2-[4-nitro-3-(propan-2-yloxy)phenyl]-1,3,2-dioxaborolane, 100 mg of lithium chloride, 1.46 ml of a 2N solution of sodium carbonate and 203 mg of tetrakis(triphenylphosphine)palladium(0) are added. The reaction mixture is heated at 80° C. for 2 h. After cooling, the mixture is run into water, extracted with ethyl acetate, washed with a saturated sodium chloride solution, dried over magnesium sulfate, filtered and concentrated under reduced pressure. Purification is carried out by flash chromatography on silica gel (40-63 µm), elution being carried out with a mixture of heptane and ethyl acetate (90/10), and 470 mg of 2-methylpropan-2-yl 6-ethyl-4-[4-nitro-3-(propan-2-yloxy)phenyl]-3,6-dihydropyridine-1(2H)-carboxylate are obtained in the form of a yellow oil.

In a microwave tube, 470 mg of 2-methylpropan-2-yl 6-ethyl-4-[4-nitro-3-(propan-2-yloxy)phenyl]-3,6-dihydropyridine-1(2H)-carboxylate are introduced into 20 ml of methanol. 456 mg of ammonium formate and 385 mg of Pd/C (10%) are added. The reaction medium is microwave-heated at 80° C. for 5 minutes. The mixture is filtered on Clarcel and the Clarcel is rinsed with methanol. The filtrate is concentrated under reduced pressure. The residue is taken up with 30 ml of ethyl acetate and 3 ml of water. The organic phase is dried over magnesium sulfate, filtered and concentrated under reduced pressure, so as to obtain 370 mg of 2-methylpropan-2-yl 4-[4-amino-3-(propan-2-yloxy)phenyl]-2-ethylpiperidine-1-carboxylate in the form of a colourless oil.

Method 3: 4-(5-Methoxy-1-methyl-1,2,3,6-tetrahydropyridin-4-yl)-2-(propan-2-yloxy)aniline A mixture of 2.5 g of 4-bromo-1-nitro-2-(propan-2-yloxy)benzene, 2.58 g of 3-methoxy-4-(4,4,5,5-tetramethyl-1,3,2-dioxaborolan-2-yl)pyridine, 9.4 g of caesium carbonate and 703 mg of [1,1'-bis(diphenylphosphino)ferrocene]dichloropalladium(II), in 27 ml of dioxane and 8.8 ml of water, is microwave-heated at 130° C. for 20 minutes. The mixture is diluted with ethyl acetate and water. The aqueous phase is extracted with ethyl acetate (2×) and then with dichloromethane (2×10 ml). The combined organic phases are dried over magnesium sulfate and concentrated under vacuum. The residue is purified on 100 g of silica, elution being carried out with heptane/ethyl acetate (50/50 to 0/100), so as to obtain 2.63 g of 3-methoxy-4-[4-nitro-3-(propan-2-yloxy)phenyl]pyridine in the form of a brown solid.

A mixture of 3.41 g of 3-methoxy-4-[4-nitro-3-(propan-2-yloxy)phenyl]pyridine and 1.33 ml of methyl iodide in 55 ml of acetone is heated at 50° C. (bath) for 3 h 30. 147 µl of methyl iodide are added and the heating is continued at 50° C. for 50 minutes. The mixture is then concentrated under vacuum, so as to obtain 5.13 g of 3-methoxy-1-methyl-4-[4-nitro-3-(propan-2-yloxy)phenyl]pyridinium iodide in the form of a yellow solid.

672 mg of $NaBH_4$ are added, in portions, to a suspension of 5.09 g of 3-methoxy-1-methyl-4-[4-nitro-3-(propan-2-yloxy)phenyl]pyridinium iodide in 90 ml of ethanol brought to 5° C. the reaction medium is stirred for 30 minutes at ambient temperature. 50 ml of water and 100 ml of ethyl acetate are added. The two phases are separated, and the aqueous phase is washed with twice 50 ml of ethyl acetate. The combined organic phases are dried over magnesium sulfate, filtered and evaporated. Purification is carried out by flash chromatography on silica gel (40-63 µm), elution being carried out with a mixture of dichloromethane and acetone (95/5 to 80/20). 2.78 g of 5-methoxy-1-methyl-4-[4-nitro-3-(propan-2-yloxy)phenyl]-1,2,3,6-tetrahydropyridine are obtained in the form of a brown oil.

747 mg of zinc are added to a solution of 500 mg of 5-methoxy-1-methyl-4-[4-nitro-3-(propan-2-yloxy)phenyl]-1,2,3,6-tetrahydropyridine in 8 ml of acetic acid. The reaction medium is stirred for 1 hour at ambient temperature and then filtered on Clarcel. The Clarcel is rinsed with 8 ml of acetic acid, then 10 ml of ethanol and then of ethyl acetate. The filtrate is evaporated under reduced pressure and then the residue is taken up in 10 ml of ethyl acetate, 5 ml of water and 10 ml of a saturated aqueous sodium bicarbonate solution. 20 ml of ethyl acetate are added and the two phases are separated. The aqueous phase is extracted with ethyl acetate (2×10 ml). The combined organic phases are washed with a saturated aqueous sodium chloride solution, dried over magnesium sulfate and concentrated under vacuum. The residue is purified on 25 g of silica, elution being carried out with dichloromethane/acetone (100/0 to 95/5), so as to obtain 140 mg of 4-(5-methoxy-1-methyl-1,2,3,6-tetrahydropyridin-4-yl)-2-(propan-2-yloxy)aniline in the form of a brown oil.

Method 4: 4-[4-Amino-3-(propan-2-yloxy)phenyl]-1-methylpiperidin-3-ol 7.55 g of ammonium formate and 1.5 g of Pd/C (10%) are added to a solution of 5.75 g of 3-methoxy-4-[4-nitro-3-(propan-2-yloxy)phenyl]pyridine in 100 ml of methanol. The reaction medium is microwave-heated at 80° C. for 5 minutes. The mixture is filtered on Clarcel, and the Clarcel is rinsed with methanol. The filtrate is concentrated under reduced pressure. The residue is taken up with 60 ml of ethyl acetate and 20 ml of water. The 2 phases are separated, and the aqueous phase is extracted with twice 20 ml of ethyl acetate. The combined organic phases are dried over magnesium sulfate, filtered and evaporated, so as to give 5.35 g of 4-(3-methoxypyridin-4-yl)-2-(propan-2-yloxy)aniline in the form of a brown gum.

85 ml of a saturated aqueous sodium bicarbonate solution and then 3.81 ml of benzyl chloroformate are added to a solution of 4.6 g of 4-(3-methoxypyridin-4-yl)-2-(propan-2-yloxy)aniline in 115 ml of THF. The reaction medium is stirred overnight at ambient temperature and then 3.81 ml of benzyl chloroformate are added and the reaction medium is stirred at ambient temperature for 2 hours. 2.54 ml of benzyl chloroformate are added and the reaction medium is stirred for a further 2 hours at ambient temperature. The reaction medium is poured into 100 ml of ethyl acetate and 50 ml of water. The two phases are separated and the aqueous phase is extracted with twice 50 ml of ethyl acetate. The combined organic phases are dried over magnesium sulfate, filtered and evaporated under reduced pressure. The residue is purified on 100 g of silica, elution being carried out with dichloromethane/acetone (100/0 to 95/5), so as to give 3.12 g of benzyl [4-(3-methoxypyridin-4-yl)-2-(propan-2-yloxy)phenyl]carbamate in the form of a colourless oil.

A mixture of 3.58 g of benzyl [4-(3-methoxypyridin-4-yl)-2-(propan-2-yloxy)phenyl]carbamate and 1.14 ml of methyl iodide in 107 ml of acetone is heated at 50° C. (bath) for 1 h. 568 µl of methyl iodide are added and the heating is continued at 50° C. for 30 minutes. The mixture is then concentrated under vacuum, so as to give 4.57 g of 4-[4-{[(benzyloxy)carbonyl]amino}-3-(propan-2-yloxy)phenyl]-3-methoxy-1-methylpyridinium iodide in the form of a yellow solid.

486 mg of $NaBH_4$ are added, in portions, to a suspension of 4.57 g of 4-[4-{[(benzyloxy)carbonyl]amino}-3-(propan-2-yloxy)phenyl]-3-methoxy-1-methylpyridinium iodide in 100 ml of ethanol brought to 5° C. The reaction medium is stirred for 1 h 30 at ambient temperature. 50 ml of water, 50 ml of a saturated aqueous sodium bicarbonate solution and 100 ml of ethyl acetate are added. The two phases are separated, and the aqueous phase is washed with twice 50 ml of ethyl acetate. The combined organic phases are dried over magnesium sulfate, filtered and evaporated. Purification is carried out by flash chromatography on silica gel (40-63 µm), elution being carried out with a mixture of dichloromethane and (MeOH+10% $NH_4OH$) (99/1 to 90/10). 1.87 g of benzyl [4-(5-methoxy-1-methyl-1,2,3,6-tetrahydropyridin-4-yl)-2-(propan-2-yloxy)phenyl]carbamate are obtained in the form of an orangey-coloured oil.

30 ml of a 6N aqueous hydrochloric acid solution are added to a solution of 1.77 g of benzyl [4-(5-methoxy-1-methyl-1,2,3,6-tetrahydropyridin-4-yl)-2-(propan-2-yloxy)phenyl]carbamate in 60 ml of THF. The reaction medium is heated at 50° C. for 2 h 30 and then evaporated to dryness. The residue is taken up in 15 ml of water, 5 ml of a saturated aqueous sodium carbonate solution and 50 ml of ethyl acetate. The two phases are separated, and the aqueous phase is washed with twice 15 ml of ethyl acetate. The combined organic phases are dried over magnesium sulfate, filtered and evaporated, so as to give 1.7 g of benzyl [4-(1-methyl-3-oxopiperidin-4-yl)-2-(propan-2-yloxy)phenyl]carbamate in the form of a brown gum.

486 mg of $NaBH_4$ are added, in portions, to a suspension of 700 mg of benzyl [4-(1-methyl-3-oxopiperidin-4-yl)-2-(propan-2-yloxy)phenyl]carbamate in 35 ml of ethanol brought to 5° C. The reaction medium is stirred at ambient temperature for 50 minutes. 4 ml of water, 15 ml of a saturated aqueous sodium chloride solution and 40 ml of ethyl acetate are added. The two phases are separated, and the aqueous phase is washed with twice 20 ml of ethyl acetate. The combined organic phases are dried over magnesium sulfate, filtered and evaporated. Purification is carried out by flash chromatography on silica gel (40-63 µm), elution being carried out with a mixture of dichloromethane and (MeOH+10% $NH_4OH$) (99/1 to 90/10). 183 mg of benzyl [4-(3-hydroxy-1-methylpiperidin-4-yl)-2-(propan-2-yloxy)phenyl]carbamate (trans diastereoisomers) and 183 mg of benzyl [4-(3-hydroxy-1-methylpiperidin-4-yl)-2-(propan-2-yloxy)phenyl]carbamate (cis diastereoisomers) are obtained.

178 mg of benzyl [4-(3-hydroxy-1-methylpiperidin-4-yl)-2-(propan-2-yloxy)phenyl]carbamate (mixture of the cis diastereoisomers) are dissolved in 45 ml of methanol. The solution is filtered on 0.45 µm Acrodisc and then hydrogenated in an H-cube (Pd/C 10% cartridge and P $H_2$=1 atm). The reaction medium is evaporated to dryness under reduced pressure, so as to give 111 mg of 4-[4-amino-3-(propan-2-yloxy)phenyl]-1-methylpiperidin-3-ol in the form of an orangey-coloured solid (mixture of the cis diastereoisomers).

179 mg of benzyl [4-(3-hydroxy-1-methylpiperidin-4-yl)-2-(propan-2-yloxy)phenyl]carbamate (mixture of the trans diastereoisomers) are dissolved in 45 ml of methanol. The solution is filtered on 0.45 µm Acrodisc and then hydrogenated in an H-cube (Pd/C 10% cartridge and P $H_2$=1 atm). The reaction medium is evaporated to dryness under reduced pressure, so as to give 127 mg of 4-[4-amino-3-(propan-2-yloxy)phenyl]-1-methylpiperidin-3-ol in the form of a brown gum (mixture of the trans diastereoisomers).

Method 5: 2-Methylpropan-2-yl 4-[4-amino-3-(propan-2-yloxy)phenyl]piperidine-1-carboxylate A mixture of 3.26 g of 4-bromo-1-nitro-2-(propan-2-yloxy)benzene, 4.65 g of 2-methylpropan-2-yl 4-(4,4,5,5-tetramethyl-1,3,2-dioxaborolan-2-yl)-3,6-dihydropyridine-1(2H)-carboxylate, 12.5 ml of a 3M solution of sodium carbonate and 350 mg of bis(triphenylphosphine)dichloropalladium(II) in 41 ml of dioxane is refluxed for 1 h 30. The mixture is diluted with 150 ml of water and 200 ml of ethyl acetate. The aqueous phase is extracted three times with 200 ml of ethyl acetate. The combined organic phases are washed with 100 ml of a saturated sodium chloride solution, dried over magnesium sulfate and concentrated under vacuum. The residue is purified on 600 g of silica, elution being carried out with dichloromethane/ethyl acetate (99/1), so as to give 2.95 g of 2-methylpropan-2-yl 4-[4-nitro-3-(propan-2-yloxy)phenyl]-3,6-dihydropyridine-1(2H)-carboxylate in the form of a yellow solid.

A solution of 2.76 g of 2-methylpropan-2-yl 4-[4-nitro-3-(propan-2-yloxy)phenyl]-3,6-dihydropyridine-1(2H)-carboxylate in 60 ml of methanol is hydrogenated on 300 mg of palladium-on-carbon (10%) at a pressure of 10 bar and at ambient temperature for 3 h. The catalyst is removed by filtration on Celite and the filtrate is evaporated to dryness so as to obtain 2.44 g of 2-methylpropan-2-yl 4-[4-amino-3-(propan-2-yloxy)phenyl]piperidine-1-carboxylate in the form of a pink powder.

Method 6: 4-(4-Methylpiperazin-1-yl)-2-(propan-2-yloxy)aniline

A mixture of 18.0 g of 5-fluoro-2-nitrophenol, 29.0 g of caesium carbonate and 13.7 ml of 2-iodopropane in 119 ml of DMF is stirred at ambient temperature overnight. The mixture is concentrated under vacuum and the residue is taken up with 250 ml of water and extracted twice with 250 ml of ethyl acetate. The organic phases are washed twice with 200 ml of a saturated sodium chloride solution, dried over magnesium sulfate and concentrated under vacuum, so as to obtain 17 g of crude product. The crude product is purified on 400 g of silica, elution being carried out with cyclohexane/ethyl acetate (95/5), so as to obtain 13.0 g of 4-fluoro-1-nitro-2-(propan-2-yloxy)benzene in the form of a light yellow oil.

A mixture of 10.0 g of 4-fluoro-1-nitro-2-(propan-2-yloxy)benzene, 10.0 g of 1-methylpiperazine and 10.4 g of potassium carbonate in 93 ml of DMSO is stirred at ambient temperature overnight. The mixture is diluted with 160 ml of water and extracted three times with 150 ml of ethyl acetate. The organic phases are dried over magnesium sulfate and concentrated under vacuum. The residue is purified on 200 g of silica, elution being carried out with dichloromethane/methanol (98/2 then 95/5), so as to obtain 13.6 g of 1-methyl-4-[4-nitro-3-(propan-2-yloxy)phenyl]piperazine in the form of a yellow oil.

A mixture of 9.0 g of 1-methyl-4-[4-nitro-3-(propan-2-yloxy)phenyl]piperazine, 19.3 g of hydrazine hydrate and 1.7 g of 10% palladium-on-carbon in 205 ml of ethanol is heated at 80° C. (bath) for 45 min. The mixture is filtered and the filtrate is concentrated under vacuum, so as to obtain 13 g of an orangey-coloured oil. The residue is purified on 300 g of silica, elution being carried out with dichloromethane/methanol (95/5), so as to obtain 7.1 g of 4-(4-methylpiperazin-1-yl)-2-(propan-2-yloxy)aniline in the form of a brown oil.

Method 7: 1-[4-Amino-3-(propan-2-yloxy)phenyl]piperidin-4-yl acetate 4.75 g of di-tert-butyl dicarbonate are added to a mixture of 2 g of 4-hydroxypiperidine in 4 ml of water and 13.8 ml of a 2N aqueous sodium hydroxide solution. The reaction medium is stirred at ambient temperature for 2 hours and then 50 ml of chloroform are added. The two phases are separated and the organic phase is washed with an aqueous 25% $NH_4OH$ solution and then with a saturated aqueous sodium chloride solution. The organic phase is dried over magnesium sulfate, filtered and evaporated, so as to give 4 g of 2-methylpropan-2-yl 4-hydroxypiperidine-1-carboxylate in the form of a colourless oil. 2.84 g of acetic anhydride are added to a solution of 4.0 g of 2-methylpropan-2-yl 4-hydroxypiperidine-1-carboxylate in 6 ml of pyridine. The reaction medium is stirred for hours at ambient temperature and then concentrated to dryness. The residue is taken up in dichloromethane and an aqueous 25% $NH_4OH$ solution. The two phases are separated and the organic phase is washed with a saturated sodium chloride solution, dried over magnesium sulfate, filtered and evaporated. Purification is carried out by flash chromatography on silica gel (40-63 µm), elution being carried out with a mixture of dichloromethane and MeOH (95/5), so as to obtain 3 g of 2-methylpropan-2-yl 4-(acetyloxy)piperidine-1-carboxylate in the form of a colourless oil.

3 ml of trifluoroacetic acid are added to a solution of 3.18 g of 2-methylpropan-2-yl 4-(acetyloxy)piperidine-1-carboxylate in 40 ml of dichloromethane, cooled to 0° C. The reaction medium is stirred for 1 hour at 0° C. and then 1 hour at ambient temperature. 5 ml of trifluoroacetic acid are added and the reaction medium is stirred for 30 minutes at ambient temperature. The reaction medium is evaporated to dryness under reduced pressure, and the resulting product is taken up with dichloromethane and an aqueous 1% $NH_4OH$ solution. The organic phase is washed with a saturated aqueous sodium chloride solution, dried over magnesium sulfate, filtered and evaporated, so as to give 175 mg of piperidin-4-yl acetate in the form of a yellow oil.

A mixture of 1 g of 4-bromo-1-nitro-2-(propan-2-yloxy)benzene, 1.19 g of piperidin-4-yl acetate, 5.01 g of caesium carbonate, 86 mg of palladium acetate and 334 mg of 9,9-dimethyl-4,5-bis(diphenylphosphino)xanthene, in 50 ml of dioxane, is refluxed for 3 hours. The mixture is diluted with ethyl acetate and water. The aqueous phase is extracted with ethyl acetate (2×). The combined organic phases are dried over magnesium sulfate and concentrated under vacuum. The residue is purified on silica, elution being carried out with cyclohexane/ethyl acetate (80/80 to 50/50), so as to give 530 mg 1-[4-nitro-3-(propan-2-yloxy)phenyl]piperidin-4-yl acetate in the form of a brown solid.

622 mg of ammonium formate and 525 mg of Pd/C (10%) are added to a solution of 530 mg of 1-[4-nitro-3-(propan-2-yloxy)phenyl]piperidin-4-yl acetate in 13 ml of methanol. The reaction medium is microwave-heated at 80° C. for 5 minutes. The mixture is filtered on Clarcel, and the Clarcel is rinsed with methanol. The filtrate is concentrated under reduced pressure. The residue is taken up with 20 ml of ethyl acetate, 2 ml of water and 8 ml of a saturated aqueous sodium chloride solution. The two phases are separated and the aqueous phase is washed with 3 times 10 ml of ethyl acetate. The combined organic phases are dried over magnesium sulfate, filtered and evaporated. The residue is purified on silica, elution being carried out with dichloromethane/MeOH (95/5), so as to give 190 mg of 1-[4-amino-3-(propan-2-yloxy)phenyl]piperidin-4-yl acetate in the form of a brown oil.

Method 8: 2-(Propan-2-yloxy)-4-(1H-1,2,4-triazol-1-yl)aniline

A mixture of 1 g of 4-bromo-1-nitro-2-(propan-2-yloxy)benzene, 319 mg of triazole, 110 mg of copper (I) iodide, 585 mg of potassium carbonate and 84 mg of 8-hydroxyquinoline in 8 ml of DMSO is stirred overnight at ambient temperature and then heated at 120° C. for 3 hours. The reaction medium is poured into 10 ml of an aqueous 25% $NH_4OH$ solution, 40 ml of water and 10 ml of ethyl acetate. The mixture is stirred for 30 minutes at ambient temperature and then the two phases are separated. The aqueous phase is washed with twice 40 ml of ethyl acetate. The combined organic phases are dried over magnesium sulfate, filtered and evaporated. Purification is carried out by flash chromatography on silica gel (40-63 μm), elution being carried out with a mixture of dichloromethane and acetone (100/0 to 95/5). 695 mg of 1-[4-nitro-3-(propan-2-yloxy)phenyl]-1H-1,2,4-triazole are obtained in the form of a beige solid. 965 mg of ammonium formate and 172 mg of Pd/C (10%) are added to a solution of 691 mg of 1-[4-nitro-3-(propan-2-yloxy)phenyl]-1H-1,2,4-triazole in 14 ml of methanol. The reaction medium is microwave-heated at 80° C. for 5 minutes. The mixture is filtered on Clarcel, and the Clarcel is rinsed with methanol. The filtrate is concentrated under reduced pressure. The residue is taken up with 20 ml of ethyl acetate, 2 ml of water and 8 ml of a saturated aqueous sodium chloride solution. The two phases are separated and the aqueous phase is washed with 3 times 10 ml of ethyl acetate. The combined organic phases are dried over magnesium sulfate, filtered and evaporated, so as to give 589 mg of 2-(propan-2-yloxy)-4-(1H-1,2,4-triazol-1-yl)aniline in the form of a brown oil.

Method 9: 4-[3-(2-Methoxyethyl)-4-methylpiperazin-1-yl]-2-(propan-2-yloxy)aniline 974 mg of N,N-diisopropylethylamine and 724 mg of 2-(1-methylpiperazin-2-yl)ethanol are added to a suspension of 1 g of 4-fluoro-1-nitro-2-(propan-2-yloxy)benzene in 10 ml of acetonitrile. The reaction medium is microwave-heated at 110° C. for 6 hours and then concentrated to dryness under reduced pressure. Purification is carried out by flash chromatography on silica gel (40-63 microns), elution being carried out with a mixture of dichloromethane and methanol (100/0) to (90/10). 1.15 g of 2-{1-methyl-4-[4-nitro-3-(propan-2-yloxy)phenyl]piperazin-2-yl}ethanol are obtained in the form of a yellow oil.

42 microliters of mesyl chloride are added to a solution of 160 mg of 2-{1-methyl-4-[4-nitro-3-(propan-2-yloxy)phenyl]piperazin-2-yl}ethanol in 2 ml of dichloromethane and 0.2 ml of pyridine. The reaction medium is stirred at ambient temperature overnight and then concentrated under vacuum, under reduced pressure, so as to give 190 mg of 2-{1-methyl-4-[4-nitro-3-(propan-2-yloxy)phenyl]piperazin-2-yl}ethyl methanesulfonate in the form of an orangey-coloured oil.

51.1 mg of sodium methoxide are added to a solution of 2-{1-methyl-4-[4-nitro-3-(propan-2-yloxy)phenyl]piperazin-2-yl}ethyl methanesulfonate in 3 ml of methanol. The reaction medium is stirred for 10 minutes at ambient temperature and then 30 minutes at 90° C. in a microwave (CEM). The reaction medium is concentrated to dryness under reduced pressure, and taken up with water and ethyl acetate. The combined organic phases are dried over magnesium sulfate, filtered and evaporated. Purification is carried out by flash chromatography on silica gel (40-63 microns), elution being carried out with a mixture of dichloromethane and methanol (100/0) to (80/20). 100 mg of 2-(2-methoxyethyl)-1-methyl-4-[4-nitro-3-(propan-2-yloxy)phenyl]piperazine are obtained in the form of a yellow oil.

112 mg of ammonium formate and 10 mg of Pd/C (10%) are added to a solution of 100 mg of 2-(2-methoxyethyl)-1-methyl-4-[4-nitro-3-(propan-2-yloxy)phenyl]piperazine in 2 ml of methanol. The reaction medium is microwave-heated at 80° C. for 5 minutes. The mixture is filtered on Clarcel and the Clarcel is rinsed with methanol. The filtrate is concentrated under reduced pressure. The residue is taken up with 10 ml of ethyl acetate and 2 ml of water. The two phases are separated, and the aqueous phase is washed with twice 10 ml of ethyl acetate. The combined organic phases are dried over magnesium sulfate, filtered and evaporated, so as to obtain 80 mg of 4-[3-(2-methoxyethyl)-4-methylpiperazin-1-yl]-2-(propan-2-yloxy)aniline in the form of a brown oil.

Method 10: 5-Methyl-4-(4-methylpiperazin-1-yl)-2-(propan-2-yloxy)aniline 24.9 g of caesium carbonate, 745 mg of palladium acetate, 2.88 g of (9,9-dimethyl-9H-xanthene-4,5-diyl)bis(diphenylphosphane) and 4.89 g of 1-methylpiperazine are added to a solution of 7.62 g of 1-chloro-2-methyl-4-nitro-5-(propan-2-yloxy)benzene (prepared according to WO2008/073687, p. 31) in 380 ml of dioxane under argon. The mixture is refluxed for 5.5 h, and then cooled to ambient temperature. The mixture is combined with the crude product of one and the same reaction carried out on 1.89 g of 1-chloro-2-methyl-4-nitro-5-(propan-2-yloxy)benzene under the same conditions. The mixture is concentrated under vacuum and the residue is taken up with 100 ml of water, 200 ml of ethyl acetate and a little methanol. The mixture is filtered on Clarcel and the aqueous phase is extracted twice with 100 ml of ethyl acetate. The combined organic phases are washed with 100 ml of a saturated sodium chloride solution, dried over magnesium sulfate and concentrated under vacuum. The crude product is purified on 340 g of silica, elution being carried out with 0-100% of acetone in dichloromethane, so as to obtain 5.60 g of 1-methyl-4-[2-methyl-4-nitro-5-(propan-2-yloxy)phenyl]piperazine in the form of a black solid.

Two 20 ml tubes each containing a mixture of 614 mg of 1-methyl-4-[2-methyl-4-nitro-5-(propan-2-yloxy)phenyl]piperazine, 185 mg of 10% Pd on carbon and 793 mg of ammonium formate in 10 ml of methanol are microwave-heated at 80° C. (P 6-7 bar) for 5 min. The content of the tubes is combined and filtered on Clarcel. The Clarcel is washed with methanol and the filtrate is concentrated under vacuum. The residue is taken up with 20 ml of ethyl acetate, 2 ml of water and 8 ml of a saturated sodium chloride solution. The aqueous phase is extracted three times with 10 ml of ethyl acetate. The combined organic phases are washed with 10 ml of a saturated aqueous sodium chloride solution, dried over magnesium sulfate and concentrated under vacuum, so as to obtain 1.053 g of 5-methyl-4-(4-methylpiperazin-1-yl)-2-(propan-2-yloxy)aniline in the form of a light brown solid.

Method 11: 6-(1-Methylpiperidin-4-yl)-4-(propan-2-yloxy)pyridin-3-amine 3.38 g of sodium isopropoxide are added to a solution of 2.6 g of 2,4-dichloro-5-nitropyridine in 39 ml of DMF. The reaction medium is stirred at ambient temperature for 1 h 15 and 3.18 g of sodium isopropoxide are added. The reaction medium is stirred for a further 15 minutes and then the mixture is poured into 200 ml of water and extracted with ethyl acetate. The organic phase is dried over magnesium sulfate, filtered and concentrated under reduced pressure. Purification is carried out by flash chromatography on silica gel (40-63 microns), elution being carried out with a heptane/ethyl acetate mixture (90/10 to 80/20). 1.78 g of 2-chloro-5-nitro-4-(propan-2-yloxy)pyridine are obtained in the form of a pale yellow solid.

800 mg of 2-chloro-5-nitro-4-(propan-2-yloxy)pyridine are introduced into 62 ml of 1,4-dioxane. After sparging for 10 min with argon in the reaction mixture, 1.25 g of 1-methyl-4-(4,4,5,5-tetramethyl-1,3,2-dioxaborolan-2-yl)-1,2,3,6-tetrahydropyridine hydrochloride, 6.02 g of caesium carbonate, 6.2 ml of water and 467 mg of bis(triphenylphosphine)palladium(II) dichloride are added. The reaction mixture is heated at 100° C. for 16 h. After cooling, the mixture is run into water and extracted with ethyl acetate. The organic phase is washed with a saturated sodium chloride solution, dried over magnesium sulfate, filtered and concentrated under reduced pressure. Purification is carried out by flash chromatography on silica gel (40-63 microns), elution being carried out with a mixture of dichloromethane and methanol (90/10 to 80/20). 401 mg of 1'-methyl-5-nitro-4-(propan-2-yloxy)-1',2',3',6'-tetrahydro-2,4'-bipyridine are obtained in the form of a yellow gum.

In a microwave tube, 400 mg of 1'-methyl-5-nitro-4-(propan-2-yloxy)-1',2',3',6'-tetrahydro-2,4'-bipyridine are introduced into 30 ml of methanol. 546 mg of ammonium formate and 333 mg of Pd/C (10%) are added. The reaction medium is microwave-heated at 80° C. for 5 minutes. The mixture is filtered on Clarcel and the Clarcel is rinsed with methanol. The filtrate is concentrated under reduced pressure, so as to give 380 mg of 6-(1-methylpiperidin-4-yl)-4-(propan-2-yloxy)pyridin-3-amine in the form of a brown oil.

Method 12: 6-(4-Methylpiperazin-1-yl)-4-(propan-2-yloxy)pyridin-3-amine 383 mg of potassium carbonate and 185 mg of 1-methylpiperazine are added to a solution of 400 mg of 2-chloro-5-nitro-4-(propan-2-yloxy)pyridine in 3.7 ml of DMSO. The reaction medium is heated for 1 hour at 105° C. After cooling, the mixture is run into water, extracted with ethyl acetate, washed with a saturated sodium chloride solution, dried over magnesium sulfate, filtered and concentrated under reduced pressure. The residue is taken up in diisopropyl ether, and the insoluble material is filtered off and dried under vacuum, so as to give 481 mg of 1-methyl-4-[5-nitro-4-(propan-2-yloxy)pyridin-2-yl]piperazine in the form of an orangey-coloured solid.

In a microwave tube, 390 mg of 1-methyl-4-[5-nitro-4-(propan-2-yloxy)pyridin-2-yl]piperazine are introduced into 12 ml of methanol. 525 mg of ammonium formate and 210 mg of Pd/C (10%) are added. The reaction medium is microwave-heated at 80° C. for 5 minutes. The mixture is filtered on Clarcel and the Clarcel is rinsed with methanol. The filtrate is concentrated under reduced pressure, so as to give 340 mg of 6-(4-methylpiperazin-1-yl)-4-(propan-2-yloxy)pyridin-3-amine in the form of a brown oil.

Method 13: 6-(1-Methylpiperidin-4-yl)-2-(propan-2-yloxy)pyridin-3-amine 1.63 g of 6-chloro-3-nitropyridin-2-ol, 66 ml of heptane, 3.175 g of 2-iodopropane and 3.09 g of silver carbonate are introduced. The reaction medium is microwave-heated at 130° C. for 10 minutes and is then evaporated to dryness, bound to silica and purified by flash chromatography on silica gel (40-63 μm), elution being carried out with a mixture of heptane and ethyl acetate (90/10). 1.79 g of 6-chloro-3-nitro-2-(propan-2-yloxy)pyridine are obtained in the form of a beige solid.

1 g of 6-chloro-3-nitro-2-(propan-2-yloxy)pyridine is introduced into 78 ml of 1,4-dioxane. After sparging for 10 min with argon in the reaction medium, 2.16 g of 1-methyl-4-(4,4,5,5-tetramethyl-1,3,2-dioxaborolan-2-yl)-1,2,3,6-tetrahydropyridine hydrochloride, 7.5 g of caesium carbonate, 7.75 ml of water and 584 mg of bis(triphenylphosphine) palladium(II) dichloride are added. The reaction mixture is heated at 100° C. for 2 h. The mixture is concentrated under reduced pressure and bound to silica. Purification is carried out by flash chromatography on silica gel (40-63 μm), elution being carried out with a mixture of dichloromethane and methanol (90/10 to 80/20). 500 mg of 1-methyl-5-nitro-6-(propan-2-yloxy)-1',2',3',6'-tetrahydro-2,4'-bipyridine are obtained in the form of an orangey-coloured gum.

In a microwave tube, 300 mg of 1-methyl-5-nitro-6-(propan-2-yloxy)-1',2',3',6'-tetrahydro-2,4'-bipyridine are introduced into 22 ml of methanol. 410 mg of ammonium formate and 345 mg of Pd/C (10%) are added. The reaction medium is microwave-heated at 80° C. for 5 minutes. The mixture is filtered on Clarcel and the Clarcel is rinsed with methanol. The filtrate is concentrated under reduced pressure, so as to give 288 mg of 6-(1-methylpiperidin-4-yl)-2-(propan-2-yloxy)pyridin-3-amine in the form of a brown gum.

Method 14: 6-(4-Methylpiperazin-1-yl)-2-(propan-2-yloxy)pyridin-3-amine 463 mg of potassium carbonate and 224 mg of 1-methylpiperazine are added to a solution of 484 mg of 6-chloro-3-nitro-2-(propan-2-yloxy)pyridine in 4.45 ml of DMSO. The reaction medium is heated for 1 hour at 105° C. After cooling, the mixture is run into water and extracted with ethyl acetate. The organic phase is washed with a saturated sodium chloride solution, dried over magnesium sulfate, filtered and concentrated under reduced pressure. The residue is taken up in diisopropyl ether and the insoluble material is filtered off and dried under vacuum, so as to give 460 mg of 1-methyl-4-[5-nitro-6-(propan-2-yloxy)pyridin-2-yl]piperazine in the form of a yellow solid.

In a microwave tube, 500 mg of 1-methyl-4-[5-nitro-6-(propan-2-yloxy)pyridin-2-yl]piperazine are introduced into 15 ml of methanol. 675 mg of ammonium formate and 270 mg of Pd/C (10%) are added. The reaction medium is microwave-heated at 80° C. for 5 minutes. The mixture is filtered on Clarcel and the Clarcel is rinsed with methanol. The filtrate is concentrated under reduced pressure, so as to give 512 mg of 6-(4-methylpiperazin-1-yl)-2-(propan-2-yloxy)pyridin-3-amine in the form of a purple gum.

Method 15: 7-Amino-1-methyl-1,3,4,5-tetrahydro-2H-1-benzazepin-2-one 2 g of 1,3,4,5-tetrahydro-2H-1-benzazepin-2-one are added to a solution of 25 ml of nitric acid at 70% in water and of 35 ml of sulfuric acid cooled to 0° C. The reaction medium is stirred for 15 minutes at 0° C. and then poured into water (250 ml) and extracted with ethyl acetate. The organic phase is washed with a saturated aqueous sodium bicarbonate solution and with water, dried over magnesium sulfate, filtered and concentrated under reduced pressure. The residue is taken up with diisopropyl ether and the insoluble material is filtered off and dried under vacuum, so as to give 1.04 g of 7-nitro-1,3,4,5-tetrahydro-2H-1-benzazepin-2-one in the form of a beige solid.

202 mg of NaH (50%) are added to a solution of 771 mg of 7-nitro-1,3,4,5-tetrahydro-2H-1-benzazepin-2-one in 20 ml of DMF. The reaction medium is stirred for 15 minutes and then 583 mg of iodomethane are added. The mixture is stirred for 4 hours at ambient temperature and then run into ice-cold water and extracted with ethyl acetate. The organic phase is washed with a saturated sodium chloride solution, dried over magnesium sulfate, filtered and concentrated under reduced pressure. Purification is carried out by flash chromatography on silica gel (40-63 µm), elution being carried out with a heptane/ethyl acetate (80/20 to 50/50) mixture. 275 mg of 1-methyl-7-nitro-1,3,4,5-tetrahydro-2H-1-benzazepin-2-one are obtained in the form of a yellow solid.

In a microwave tube, 275 mg of 1-methyl-7-nitro-1,3,4,5-tetrahydro-2H-1-benzazepin-2-one are introduced into 26 ml of methanol. 473 mg of ammonium formate and 398 mg of Pd/C (10%) are added. The reaction medium is microwave-heated at 80° C. for 5 minutes. The mixture is filtered on Clarcel and the Clarcel is rinsed with methanol. The filtrate is concentrated under reduced pressure, so as to give 250 mg of 7-amino-1-methyl-1,3,4,5-tetrahydro-2H-1-benzazepin-2-one in the form of a purple gum.

Method 16: 7-Amino-1-methyl-6-(propan-2-yloxy)-1,3,4,5-tetrahydro-2H-1-benzazepin-2-one A mixture of 2.5 g of 5-hydroxy-1-tetralone, 30 ml of acetonitrile, 5 g of caesium carbonate and 3.87 ml of 2-iodopropane is heated for one hour at 80° C. and then evaporated to dryness. The residue is taken up in ethyl acetate and water. The organic phase is washed with a saturated sodium chloride solution, dried over magnesium sulfate, filtered and concentrated under reduced pressure, so as to give 4.87 g of 5-(propan-2-yloxy)-3,4-dihydronaphthalen-1(2H)-one in the form of an orangey-coloured oil.

A mixture of 4.39 g of 5-(propan-2-yloxy)-3,4-dihydronaphthalen-1(2H)-one and 1.74 g of sodium azide in 70 ml of TFA is refluxed for 2 hours. The reaction medium is poured into 250 ml of water, brought to pH 7 by adding potassium carbonate and extracted with ethyl acetate. The organic phase is dried over magnesium sulfate, filtered and evaporated under reduced pressure. Purification is carried out by flash chromatography on silica gel (40-63 µm), elution being carried out with a mixture of dichloromethane and MeOH (100/0 to 90/10). 2.87 g of 6-(propan-2-yloxy)-1,3,4,5-tetrahydro-2H-1-benzazepin-2-one are obtained in the form of a beige solid.

750 mg of potassium nitrate are added, in portions, to a solution of 1.3 g of 6-(propan-2-yloxy)-1,3,4,5-tetrahydro-2H-1-benzazepin-2-one in 13 ml of trifluoroacetic anhydride brought back to −5° C. The reaction medium is stirred for 5 minutes at −5° C. and then brought back to pH 5 by adding a saturated aqueous sodium bicarbonate solution. The mixture is extracted with ethyl acetate and the organic phase is dried over magnesium sulfate, filtered and concentrated under reduced pressure. Purification is carried out by flash chromatography on silica gel (40-63 µm), elution being carried out with a mixture of heptane and of ethyl acetate (80/20 to 50/50). 450 mg of 7-nitro-6-(propan-2-yloxy)-1,3,4,5-tetrahydro-2H-1-benzazepin-2-one are obtained in the form of a beige solid. 91 mg of sodium hydride at 50% are added to a solution of 445 mg of 7-nitro-6-(propan-2-yloxy)-1,3,4,5-tetrahydro-2H-1-benzazepin-2-one in 10 ml of DMF. The reaction medium is stirred for 10 minutes at ambient temperature and then 263 mg of iodomethane are added. The reaction medium is stirred for 1 hour at ambient temperature, poured into ice-cold water and extracted with ethyl acetate. The organic phase is dried over magnesium sulfate, filtered and evaporated under reduced pressure, so as to give 417 mg of 1-methyl-7-nitro-6-(propan-2-yloxy)-1,3,4,5-tetrahydro-2H-1-benzazepin-2-one in the form of a yellow gum.

567 mg of ammonium formate and 478 mg of Pd/C (10%) are added to a solution of 416 mg of 1-methyl-7-nitro-6-(propan-2-yloxy)-1,3,4,5-tetrahydro-2H-1-benzazepin-2-one in 30 ml of methanol. The reaction medium is microwave-heated at 80° C. for 5 minutes. The mixture is filtered on Clarcel, and the Clarcel is rinsed with methanol. The filtrate is concentrated under reduced pressure, so as to give 380 mg of 7-amino-1-methyl-6-(propan-2-yloxy)-1,3,4,5-tetrahydro-2H-1-benzazepin-2-one in the form of a colourless gum.

Method 17: 8-Amino-1-methyl-1,3,4,5-tetrahydro-2H-1-benzazepin-2-one 5 g of alpha-tetralone are added to 18.2 ml of sulfuric acid cooled to 0° C., while maintaining the temperature <10° C. A mixture of 1.87 ml of nitric acid at 70% in water and of 3.65 ml of sulfuric acid is added while maintaining the temperature <10° C. The reaction medium is stirred for 30 minutes at a temperature <10° C. and then stirred for one hour at ambient temperature. The reaction medium is poured into ice-cold water (250 ml). The insoluble material is filtered off under vacuum and dried, so as to give 5.2 g of 7-nitro-3,4-dihydronaphthalen-1(2H)-one in the form of a beige solid.

A mixture of 5 g of 7-nitro-3,4-dihydronaphthalen-1(2H)-one, 2.18 g of hydroxylamine hydrochloride, 4.29 g of sodium acetate in 90 ml of ethanol and 90 ml of water is refluxed for one hour. The reaction medium is brought back to ambient temperature and an aqueous 10% sodium bicarbonate solution is added until a pH of 7 is reached. The mixture is extracted with ethyl acetate and the organic phase is dried over magnesium sulfate, filtered and concentrated under reduced pressure. Purification is carried out by flash chromatography on silica gel (40-63 µm), elution being carried out with a mixture of heptane and of ethyl acetate (80/20 to 50/50). 1.14 g of (1E)-N-hydroxy-7-nitro-3,4-dihydronaphthalen-1(2H)-imine are obtained in the form of a yellow solid.

A mixture of 1.11 g of (1E)-N-hydroxy-7-nitro-3,4-dihydronaphthalen-1(2H)-imine and 13 g of polyphosphoric acid is heated at 125° C. for 16 hours. The reaction medium is poured into ice-cold water and extracted with ethyl acetate. The organic phase is washed with a saturated sodium chloride solution, dried over magnesium sulfate, filtered and concentrated under reduced pressure. 549 mg of 8-nitro-1,3,4,5-tetrahydro-2H-1-benzazepin-2-one are obtained in the form of a beige solid.

144 mg of NaH (50%) are added to a solution of 549 mg of 8-nitro-1,3,4,5-tetrahydro-2H-1-benzazepin-2-one in 15 ml of DMF. The reaction medium is stirred for 15 minutes and then 187 μl of iodomethane are added. The mixture is stirred for 16 hours at ambient temperature and then run into ice-cold water and extracted with ethyl acetate. The organic phase is washed with a saturated sodium chloride solution, dried over magnesium sulfate, filtered and concentrated under reduced pressure. The residue is taken up in diisopropyl ether and the insoluble material is filtered off and dried under vacuum, so as to give 405 mg of 1-methyl-8-nitro-1,3,4,5-tetrahydro-2H-1-benzazepin-2-one in the form of a beige solid.

696 mg of ammonium formate and 581 mg of Pd/C (10%) are added to a solution of 405 mg of 1-methyl-8-nitro-1,3,4,5-tetrahydro-2H-1-benzazepin-2-one in 39 ml of methanol. The reaction medium is microwave-heated at 80° C. for 5 minutes. The mixture is filtered on Clarcel, and the Clarcel is rinsed with methanol. The filtrate is concentrated under reduced pressure, so as to give 422 mg of 8-amino-1-methyl-1,3,4,5-tetrahydro-2H-1-benzazepin-2-one in the form of a colourless gum.

Method 18: 2-Isopropoxy-4-(4-methylpiperazin-1-ylmethyl)phenylamine 3.0 g of 3-hydroxy-4-nitrobenzaldehyde, 30 ml of acetonitrile, 5.9 g of caesium carbonate and 4.1 ml of 2-iodopropane are successively introduced into a three-necked round-bottomed flask under argon. The reaction mixture is heated at 70° C. for 17 h. After cooling to ambient temperature, the mixture is filtered through a sintered glass filter and the filtrate is concentrated to dryness under reduced pressure. The residue is taken up in a mixture of 50 ml of ethyl acetate and 15 ml of water, and then separated by settling out. The aqueous phase is separated and the organic phase is washed with 10 ml of water. The organic phase is then dried over magnesium sulfate and then concentrated to dryness under reduced pressure, so as to obtain 3.6 g of 3-isopropoxy-4-nitrobenzaldehyde in the form of a dark brown liquid.

3.25 ml of 1-methylpiperazine are added to a solution of 3.06 g of 3-isopropoxy-4-nitrobenzaldehyde in 15 ml of toluene and 0.34 ml of acetic acid in a three-necked round-bottomed flask under argon. The reaction mixture is stirred at ambient temperature for 1.5 h and then 5 ml of toluene are added, followed by 4.9 g of sodium triacetoxyborohydride by spatula. The reaction mixture is stirred at ambient temperature for 16 h, and then treated with 4.5 ml of methanol and 75 ml of a saturated sodium hydrogen carbonate solution. After stirring at ambient temperature for 30 min, the mixture is extracted with 30 ml and then 2×50 ml of ethyl acetate. The organic extracts are combined, washed with water, dried over magnesium sulfate, and then concentrated to dryness under reduced pressure, so as to give 4.24 g of 1-(3-isopropoxy-4-nitrobenzyl)-4-methylpiperazine in the form of a beige solid.

A mixture of 4.2 g of 1-(3-isopropoxy-4-nitrobenzyl)-4-methylpiperazine and 420 mg of 10% palladium-on-carbon in 145 ml of ethanol is hydrogenated at 25° C. under 1 bar for 3 h. The mixture is filtered on Clarcel and the Clarcel is rinsed with ethanol. The filtrate is concentrated to dryness under reduced pressure, so as to give 3.8 g of 2-isopropoxy-4-(4-methylpiperazin-1-ylmethyl)phenylamine in the form of a brown oil.

Method 19:
2-Isopropoxy-5-(4-methylpiperazin-1-yl)phenylamine

A mixture of 5.0 g of 5-bromo-2-fluoronitrobenzene, 14.8 g of caesium carbonate and 35.0 ml of 2-iodopropane is charged to two 20 ml microwave tubes, and irradiated at 60° C. with stirring for 1.5 h, and then stirred at ambient temperature overnight. The mixture is poured into 400 ml of water and then extracted three times with 300 ml of ethyl acetate. The organic extracts are combined and then concentrated to dryness under reduced pressure. The residue is reintroduced into a single-necked round-bottomed flask, into which 50 ml of 2-iodopropane and 10.0 g of caesium carbonate are added. The reaction mixture is heated at 95° C. for 10 min, and then at 60° C. for 3 h, and it is then stirred at ambient temperature overnight. The mixture is then poured into 400 ml of water and then extracted three times with 400 ml of ethyl acetate. The organic extracts are combined and then concentrated to dryness under reduced pressure, so as to obtain 5.6 g of 4-bromo-1-isopropoxy-2-nitrobenzene in the form of a brown oil.

A solution of 1.0 g of 4-bromo-1-isopropoxy-2-nitrobenzene in 36 ml of 1,4-dioxane is degassed with argon for 10 min, and then 0.69 g of 4,5-bis(diphenylphosphino)-9,9-dimethylxanthene (Xantphos), 0.70 g of tris(dibenzylideneacetone)dipalladium(0), 2.52 g of caesium carbonate and 0.86 ml of 1-methylpiperazine are successively added. The round-bottomed flask is rinsed with 2 ml of dioxane, and the reaction mixture is then heated at 90° C. for 43 h. After returning to ambient temperature, the mixture is diluted with 90 ml of ethyl acetate and then extracted with 90 ml of water. The organic phase is separated, dried over magnesium sulfate and concentrated to dryness under reduced pressure. The residue is purified by chromatography on a 70 g silica cartridge, elution being carried out with a 95/5 v/v then 50/50 v/v cyclohexane/ethyl acetate mixture, and then with a 95/5 v/v dichloromethane/methanol mixture at a flow rate of 50 ml/min, so as to obtain 0.57 g of 1-(4-isopropoxy-3-nitrophenyl)-4-methylpiperazine in the form of a brown oil.

A mixture of 0.57 g of 1-(4-isopropoxy-3-nitrophenyl)-4-methylpiperazine and 65 mg of 10% palladium-on-carbon in 200 ml of ethanol is hydrogenated at 25° C. under 1 bar for 22 h. The mixture is filtered on Clarcel and the Clarcel is rinsed with methanol. The filtrate is concentrated to dryness under reduced pressure and the residue is purified by chromatography on a 25 g silica cartridge, elution being carried out with pure dichloromethane and then successively with 98/2 and 95/5 v/v dichloromethane/methanol mixtures at a flow rate of 30 ml/min, so as to obtain 0.32 g of 2-isopropoxy-5-(4-methylpiperazin-1-yl)phenylamine in the form of a brown solid.

Method 20: 3-Isopropoxy-4-nitrophenyl)(tetrahydro-pyran-4-yl)amine

A mixture of 0.75 g of 5-fluoro-1-nitro-2-(propan-2-yloxy)benzene, 0.42 g of 4-aminotetrahydropyran and 0.8 g of potassium carbonate in 6 ml of DMSO is stirred at 50° C. overnight. The mixture is diluted with 100 ml of water and extracted three times with 50 ml of ethyl acetate. The organic phases are combined and then dried over magnesium sulfate and concentrated to dryness under reduced pressure. The residue is purified by chromatography on a 50 g silica column, elution being carried out with a dichloromethane/methanol (95/5 v/v) mixture, so as to obtain 0.69 g of (3-isopropoxy-4-nitrophenyl)(tetrahydropyran-4-yl)amine in the form of a yellow foam.

A mixture of 0.69 g of (3-isopropoxy-4-nitrophenyl)(tetrahydropyran-4-yl)amine and 0.1 g of 10% palladium-on-carbon in a mixture of 30 ml of ethanol and 10 ml of dichloromethane is hydrogenated at 22° C. under 2 bar for 15 h. The mixture is filtered and the filtrate is concentrated to dryness under reduced pressure. The residue is purified by chromatography on a 50 g silica column, elution being carried out with a dichloromethane/methanol (95/5 v/v) mixture, so as to obtain 0.4 g of (3-isopropoxy-4-nitrophenyl)(tetrahydropyran-4-yl)amine in the form of a purple oil.

Method 21: 2-Isopropoxy-3-(4-methylpiperazine-1-yl)phenylamine 1.23 g of potassium carbonate, 14.6 g of caesium carbonate, 22 ml of dimethylformamide and 1.0 g of 2-bromo-6-nitrophenol are successively introduced into a three-necked round-bottomed flask under argon. The resulting suspension is stirred at ambient temperature for 10 min, and then 0.91 ml of 2-iodopropane is added in one go. The round-bottomed flask is rinsed with 10 ml of dimethylformamide and then the reaction mixture is heated at 40° C. for 48 h. After cooling to ambient temperature, the mixture is treated with 50 ml of water and extracted four times with 30 ml of ethyl acetate. The organic extracts are combined and washed with 30 ml of saturated brine and then 30 ml of water. The organic phase is then dried over magnesium sulfate and then concentrated to dryness under reduced pressure. The residue is purified by chromatography on a 30 g silica cartridge, elution being carried out with a 95/5 v/v cyclohexane/ethyl acetate mixture at a flow rate of 30 ml/min, so as to obtain 1.04 g of 1-bromo-2-isopropoxy-3-nitrobenzene in the form of a yellow oil.

A solution of 1.04 g of 1-bromo-2-isopropoxy-3-nitrobenzene in 37 ml of 1,4-dioxane is degassed with argon for 10 min, and then 0.72 g of 4,5-bis(diphenylphosphino)-9,9-dimethylxanthene (Xantphos), 0.73 g of tris(dibenzylideneacetone)dipalladium(0), 2.62 g of caesium carbonate and 0.90 ml of 1-methylpiperazine are successively added. The round-bottomed flask is rinsed with 3 ml of dioxane, and then the reaction mixture is heated at 90° C. for 19 h. After returning to ambient temperature, the mixture is diluted with 90 ml of ethyl acetate and then extracted with 90 ml of water. The organic phase is separated, dried over magnesium sulfate and concentrated to dryness under reduced pressure. The residue is purified by chromatography on a 90 g silica cartridge, elution being carried out with a 98/2 v/v dichloromethane/methanol mixture, at a flow rate of 50 ml/min, so as to obtain 0.31 g of 1-(2-isopropoxy-3-nitrophenyl)-4-methylpiperazine in the form of a brown oil.

A mixture of 0.80 g of 1-(2-isopropoxy-3-nitrophenyl)-4-methylpiperazine and 91 mg of 10% palladium-on-carbon in 300 ml of ethanol is hydrogenated at 25° C. under 1 bar for 22 h. The mixture is filtered on Clarcel and the Clarcel is rinsed with ethanol. The filtrate is concentrated to dryness under reduced pressure and the residue is purified by chromatography on a 50 g silica cartridge, elution being carried out with pure dichloromethane and then successively with 98/2 and 95/5 v/v dichloromethane/methanol mixtures at a flow rate of 30 ml/min, so as to obtain 0.60 g of 2-isopropoxy-3-(4-methylpiperazine-1-yl)phenylamine in the form of a yellow powder.

Method 22: 2-Isopropoxy-N4-(1-methylpiperidin-4-yl)benzene-1,4-diamine 1.7 g of potassium carbonate and 1.0 g of 4-amino-1-methylpiperidine are successively added to a solution of 1.6 g of 4-fluoro-2-isopropoxy-1-nitrobenzene in 13.5 ml of dimethyl sulfoxide. The reaction mixture is heated at 120° C. for 3 h and is then cooled to ambient temperature and poured into a mixture of 150 ml of ice-cold water and 100 ml of ethyl acetate. After settling out, the organic phase is separated and the aqueous phase is extracted twice with 70 ml of ethyl acetate. The organic extracts are combined, dried over magnesium sulfate and then concentrated to dryness under reduced pressure. The residue is purified by chromatography on a 90 g silica cartridge, elution being carried out with a 97.5/2/0.5 v/v/v dichloromethane/methanol/20% aqueous ammonia mixture at a flow rate of 50 ml/min, so as to obtain 1.5 g of (3-isopropoxy-4-nitrophenyl)(1-methylpiperidin-4-yl)amine in the form of a bright yellow oil.

A mixture of 1.49 g of (3-isopropoxy-4-nitrophenyl)(1-methylpiperidin-4-yl)amine and 150 mg of 10% palladium-on-carbon in 60 ml of ethanol is hydrogenated at 25° C. under 1 bar for 3 h. The mixture is filtered on Clarcel and the Clarcel is rinsed with ethanol. The filtrate is concentrated to dryness under reduced pressure and the residue is purified by chromatography on a 70 g silica cartridge, elution being carried out with a 96.5/3/0.5 v/v/v dichloromethane/methanol/28% aqueous ammonia mixture at a flow rate of 50 ml/min, so as to obtain 0.9 g of 2-isopropoxy-N4-(1-methylpiperidin-4-yl)benzene-1,4-diamine in the form of a brown liquid.

Method 23: 2-Methylpropan-2-yl 7-[4-amino-3-(propan-2-yloxy)phenyl]-1,7-diazaspiro[4.4]nonane-1-carboxylate A mixture of 3.0 g of tert-butyl 1,7-diazaspiro[4.4]nonane-1-carboxylate and 2.64 g of 4-fluoro-1-nitro-2-(propan-2-yloxy)benzene (obtained according to method 6), and 2.75 g of potassium carbonate in DMSO is stirred at ambient temperature overnight. The mixture is taken up with ethyl acetate and washed twice with 10 volumes of water. The organic phase is dried over magnesium sulfate and concentrated under vacuum. The crude product is purified on 120 g of silica, elution being carried out with dichloromethane, so as to obtain 3.40 g of 2-methylpropan-2-yl 7-[4-nitro-3-(propan-2-yloxy)phenyl]-1,7-diazaspiro[4.4]nonane-1-carboxylate in the form of a dark yellow solid.

A mixture of 400 mg of 2-methylpropan-2-yl 7-[4-nitro-3-(propan-2-yloxy)phenyl]-1,7-diazaspiro[4.4]nonane-1-carboxylate, 592 mg of hydrazine hydrate and 52.5 mg of 10% palladium-on-carbon in 10 ml of ethanol is refluxed for 1 h. The mixture is filtered and the filtrate is concentrated under reduced pressure, so as to obtain 365 mg of 2-methylpropan-2-yl 7-[4-amino-3-(propan-2-yloxy)phenyl]-1,7-diazaspiro[4.4]nonane-1-carboxylate in the form of a mauve gum.

Method 24: 4-(1-Methyl-1,7-diazaspiro[4.4]non-7-yl)-2-(propan-2-yloxy)aniline

A mixture of 1.42 g of 4-fluoro-1-nitro-2-(propan-2-yloxy)benzene, 1.0 g of 1-methyl-1,7-diazaspiro[4,4]nonane and 1.48 g of potassium carbonate in 10 ml of DMSO is stirred at ambient temperature overnight. The mixture is diluted with 160 ml of water and extracted three times with 100 ml of ethyl acetate. The organic phases are dried over magnesium sulfate and concentrated under vacuum. The yellow oily residue is purified on silica, with an elution gradient with dichloromethane/methanol (100/0 then 90/10), so as to obtain 160 mg of 1-methyl-7-[4-nitro-3-(propan-2-yloxy)phenyl]-1,7-diazaspiro[4.4]nonane in the form of an orangey-coloured oil.

A mixture of 160 mg of 1-methyl-7-[4-nitro-3-(propan-2-yloxy)phenyl]-1,7-diazaspiro[4.4]nonane, 301 mg of hydrazine hydrate and 27 mg of 10% palladium-on-carbon in 30 ml of ethanol is heated at 80° C. (bath) for 2 h. The mixture is filtered and the filtrate is concentrated under vacuum, so as to obtain 141 mg of 4-(1-methyl-1,7-diazaspiro[4.4]non-7-yl)-2-(propan-2-yloxy)aniline in the form of a brown oil.

Method 25: 4-(1-Ethyl-1,7-diazaspiro[4.4]non-7-yl)-2-(propan-2-yloxy)aniline 0.33 ml of trifluoroacetic acid is added to a solution of 300 mg of 2-methylpropan-2-yl 7-[4-nitro-3-(propan-2-yloxy)phenyl]-1,7-diazaspiro[4.4]nonane-1-carboxylate in 30 ml of dichloromethane. The mixture is stirred at ambient temperature for 15 hours and then 3 ml of trifluoroacetic acid are again added. After stirring for 15 hours, the reaction mixture is run into 50 ml of a saturated potassium carbonate solution. The aqueous phase is extracted three times with 50 ml of dichloromethane. The organic phases are combined, dried over anhydrous magnesium sulfate, filtered and then concentrated to dryness under reduced pressure, so as to give a yellow oil. The residue is purified by chromatography on silica gel, elution being carried out with dichloromethane/methanol (100/0 to 95/5), so as to obtain 221 mg of 7-[4-nitro-3-(propan-2-yloxy)phenyl]-1,7-diazaspiro[4.4]nonane in the form of a yellow solid.

1.0 ml of acetaldehyde is added to a solution of 500 mg of 7-[4-nitro-3-(propan-2-yloxy)phenyl]-1,7-diazaspiro[4.4]nonane in 20 ml of 1,4-dichloroethane, cooled in a bath of ice-cold water. After 30 minutes, 1.12 g of sodium triacetoxyborohydride are added in small portions and the mixture is left to return to ambient temperature. The mixture is stirred at ambient temperature for 15 hours. 1 ml of acetaldehyde is then added and the mixture is stirred for 7 h. The mixture is concentrated to dryness under reduced pressure and the residue is diluted in 100 ml of dichloromethane. The organic phase is washed three times with 50 ml of water and the organic phase is dried over anhydrous magnesium sulfate, filtered and then concentrated to dryness under reduced pressure. The residue is purified by chromatography on silica gel, elution being carried out with a dichloromethane/isopropanol gradient: 100/0 to 50/50, and then by further chromatography on silica gel, elution being carried out with a dichloromethane/acetone gradient: 100/0 to 50/50, so as to obtain a yellow oil. This oil is taken up with ether, and the precipitate obtained is filtered off. The filtrate is concentrated to dryness under reduced pressure, so as to give 250 mg of 1-ethyl-7-[4-nitro-3-(propan-2-yloxy)phenyl]-1,7-diazaspiro[4.4]nonane in the form of a yellow oil.

A mixture of 250 mg of 1-ethyl-7-[4-nitro-3-(propan-2-yloxy)phenyl]-1,7-diazaspiro[4.4]nonane, 450 mg of hydrazine hydrate and 40 mg of 10% palladium-on-carbon in 10 ml of ethanol is heated at 80° C. (bath) for 4 h 30 min. 450 mg of hydrazine hydrate are then added and the reflux is maintained for 1 h. The mixture is filtered and the filtrate is concentrated under vacuum, so as to obtain 230 mg of 4-(1-ethyl-1,7-diazaspiro[4.4]non-7-yl)-2-(propan-2-yloxy)aniline in the form of a brown oil.

Method 26: 4-[(8aR)-Hexahydropyrrolo[1,2-a]pyrazin-2(1H)-yl]-2-(propan-2-yloxy)aniline A mixture of 1.0 g of 4-fluoro-1-nitro-2-(propan-2-yloxy)benzene, 634 mg of (R)-1,4-diazabicyclo[4,3,0]nonane and 1.04 g of potassium carbonate in 7 ml of DMSO is stirred at ambient temperature for 21 hours. The reaction medium is run into 15 ml of water and the mixture is then extracted three times with 30 ml of ethyl acetate. The organic phases are dried over magnesium sulfate, filtered and concentrated under vacuum, so as to obtain 1.44 g of (8aR)-2-[4-nitro-3-(propan-2-yloxy)phenyl]octahydropyrrolo[1,2-a]pyrazine in the form of an orangey-coloured oily residue.

A mixture of 1.38 g of (8aR)-2-[4-nitro-3-(propan-2-yloxy)phenyl]octahydropyrrolo[1,2-a]pyrazine, 2.72 g of hydrazine hydrate and 240 mg of 10% palladium-on-carbon (240 mg, 5 mol %) in 30 ml of ethanol is heated at 80° C. (bath) for 1 h 30. The mixture is filtered on Clarcel and the filtrate is concentrated under vacuum, so as to obtain 1.23 g of 4-[(8aR)-hexahydropyrrolo[1,2-a]pyrazin-2(1H)-yl]-2-(propan-2-yloxy)aniline in the form of a purple oil.

Method 27: 2-{4-[4-Amino-3-(propan-2-yloxy)phenyl]piperidin-1-yl}ethanol

A mixture of 100 mg of 4-[4-nitro-3-(propan-2-yloxy)phenyl]pyridine (see method 1) and 0.075 ml of 2-iodoethanol in 1.7 ml of acetonitrile is heated at 85° C. (bath) for 1 h. 75 µl of 2-iodoethanol are then added and the heating is continued for 15 h at 91° C. The mixture is then concentrated under vacuum, so as to obtain a solid which is taken up with 10 ml of ethyl ether. The resulting heterogeneous mixture is filtered and the solid is rinsed with ethyl ether and dried under reduced pressure, so as to obtain 147 mg of 1-(2-hydroxyethyl)-4-[4-nitro-3-(propan-2-yloxy)phenyl]pyridinium iodide in the form of a solid. 44 g of sodium borohydride are added, at a temperature of about 0° C. (ice/water bath) to a solution of 0.142 g of 1-(2-hydroxyethyl)-4-[4-nitro-3-(propan-2-yloxy)phenyl]pyridinium iodide in 2.6 ml of methanol. After 30 minutes, a few drops of water are added and the mixture is left to return to ambient temperature. The mixture is concentrated to dryness under reduced pressure and then diluted with 150 ml of ethyl acetate. The organic phase is washed successively with 120 ml of a saturated sodium hydrogen carbonate solution and then 70 ml of a saturated sodium chloride solution. The organic phase is dried over anhydrous magnesium sulfate, filtered and then concentrated to dryness under reduced pressure, so as to obtain 90 mg of 2-{4-[4-nitro-3-(propan-2-yloxy)phenyl]-3,6-dihydropyridin-1(2H)-yl}ethanol.

A mixture of 150 mg of 10% palladium-on-carbon and 400 mg of 2-{4-[4-nitro-3-(propan-2-yloxy)phenyl]-3,6-dihydropyridin-1(2H)-yl}ethanol in 15 ml of ethanol is heated at 80° C. with stirring. 1.25 g of ammonium formate are then added in two portions. After stirring at 80° C. for 1 h, the mixture is allowed to return to ambient temperature and is filtered on Clarcel. The Clarcel is rinsed with 200 ml of ethanol and the filtrate is concentrated under vacuum, so as to obtain a residue which is solubilised in 150 ml of dichloromethane. The organic phase is washed three times with 70 ml of a saturated potassium carbonate solution, and the aqueous phase is extracted twice with 100 ml of dichloromethane. The combined organic phases are dried over magnesium sulfate, filtered and concentrated under vacuum, so as to obtain 330 mg of 2-{4-[4-amino-3-(propan-2-yloxy)phenyl]piperidin-1-yl}ethanol used without further purification.

Method 28: (3R)-1-[4-Amino-3-(propan-2-yloxy)phenyl]-N-methyl-N-(oxetan-3-yl)piperidin-3-amine A mixture of 3.0 g of 4-fluoro-1-nitro-2-(propan-2-yloxy)benzene, 5.0 g of (R)-3-Boc-aminopiperidine and 3.12 g of potassium carbonate in 28 ml of DMSO is stirred at ambient temperature overnight. The mixture is diluted with 30 ml of water and extracted three times with 60 ml of ethyl acetate. The organic phases are dried over magnesium sulfate and concentrated under vacuum. The residue is purified by flash chromatography on silica gel, using a dichloromethane/ethyl acetate (98/2 to 90/10) elution gradient, so as to obtain 5.71 g of 2-methylpropan-2-yl {(3R)-1-[4-nitro-3-(propan-2-yloxy)phenyl]piperidin-3-yl}carbamate in the form of a yellow solid.

6.25 ml of trifluoroacetic acid are added, at a temperature of about 20° C., to 5.32 g of 2-methylpropan-2-yl {(3R)-1-[4-nitro-3-(propan-2-yloxy)phenyl]piperidin-3-yl}carbamate in solution in 106 ml of dichloromethane, and the mixture is left to stir for 15 h. A further 2 ml of trifluoroacetic acid are added and the stirring is continued for 1 h. The mixture is concentrated under reduced pressure, so as to obtain an oily residue which is precipitated by adding ethyl ether. The solid obtained is filtered off and then washed with ethyl ether, so as to obtain 5.42 g of (3R)-1-[4-nitro-3-(propan-2-yloxy)phenyl]piperidin-3-amine trifluoroacetate in the form of a yellow solid.

5.11 g of (3R)-1-[4-nitro-3-(propan-2-yloxy)phenyl]piperidin-3-amine trifluoroacetate are added to 40 ml of a saturated potassium carbonate solution and then the mixture is extracted three times with 50 ml of dichloromethane. The combined organic phases are dried over magnesium sulfate, filtered and concentrated under vacuum so as to give 3.60 g of (3R)-1-[4-nitro-3-(propan-2-yloxy)phenyl]piperidin-3-amine in the form of a yellow solid.

2 ml of 3-oxetanone are added, at a temperature of about 20° C., to a solution of 1.50 g of (3R)-1-[4-nitro-3-(propan-2-yloxy)phenyl]piperidin-3-amine in 54 ml of 1,4-dichloroethane, under an argon atmosphere. After stirring of the mixture, 3.69 g of sodium triacetoxyborohydride are added in small portions and the reaction mixture is heated at 70° C. for 3 h. After returning to ambient temperature, 70 ml of a dilute sodium hydrogen carbonate solution are added. The aqueous phase is extracted twice with 80 ml of dichloromethane. The combined organic phases are dried over magnesium sulfate, filtered and concentrated under vacuum, so as to obtain an orangey-coloured oily residue. The residue is purified by chromatography on silica gel, using a dichloromethane/isopropanol (98/2 to 94/6) elution gradient, so as to obtain 1.2 g of (3R)-1-[4-nitro-3-(propan-2-yloxy)phenyl]-N-(oxetan-3-yl)piperidin-3-amine in the form of an orangey-coloured gum.

65 μl of iodomethane are added, at a temperature of about 20° C., under an argon atmosphere and with magnetic stirring, to a mixture of 293 mg of (3R)-1-[4-nitro-3-(propan-2-yloxy)phenyl]-N-(oxetan-3-yl)piperidin-3-amine and 427 mg of caesium carbonate in 8 ml of anhydrous DMF. After stirring for 3 hours, 100 μl of iodomethane are added and the mixture is left to stir for a further 2 h. 10 ml of water are then added and the mixture is then extracted three times with 15 ml of ethyl acetate. The combined organic phases are dried over magnesium sulfate, filtered and concentrated under vacuum so as to give an oily yellow residue. The residue is purified by flash chromatography on silica gel, using a dichloromethane/methanol (98/2) eluent, so as to obtain 47 mg of (3R)—N-methyl-1-[4-nitro-3-(propan-2-yloxy)phenyl]-N-(oxetan-3-yl)piperidin-3-amine in the form of an orangey-yellow solid.

24 mg of palladium-on-carbon (10%) and then 0.269 ml of hydrazine hydrate are added to a solution of 161 mg of (3R)—N-methyl-1-[4-amino-3-(propan-2-yloxy)phenyl]-N-(oxetan-3-yl)piperidin-3-amine in 4 ml of ethanol. This mixture is heated at between 85° C./90° C. with magnetic stirring for 1 h 30, then 24 mg of palladium-on-carbon (10%) are added while continuing the refluxing for 2 h. 24 mg of palladium-on-carbon (10%) and 0.269 ml of hydrazine hydrate are again added. The mixture is heated for 1 h at 85° C./90° C., and then allowed to return to ambient temperature and the mixture is filtered through a Whatman AutoCup sintered glass funnel. The filtrate is concentrated under vacuum so as to obtain 136 mg of (3R)-1-[4-amino-3-(propan-2-yloxy)phenyl]-N-methyl-N-(oxetan-3-yl)piperidin-3-amine in the form of an orangey-yellow solid which is used for the subsequent step without further purification.

Rf=0.61 (TLC, silica support), eluent dichloromethane/MeOH (95/5), UV 254 nm.

Method 29: 2-Methylpropan-2-yl 4-[5-amino-1-(propan-2-yl)-1H-pyrazol-3-yl]piperidine-1-carboxylate 1.82 ml of triethylamine are added to a solution of 3.18 g of 4-(2-cyanoacetyl)piperidine-1-carboxylic acid tert-butyl ester and 1.41 g of isopropylhydrazine hydrochloride in 70 ml of ethanol under an argon atmosphere. The mixture is refluxed with magnetic stirring for 3 hours, and then concentrated to dryness under reduced pressure. The residue is taken up in a mixture of 100 ml of water and 100 ml of ethyl acetate, and then the organic phase is washed twice with 100 ml of water. The combined aqueous phases are extracted twice with 100 ml of ethyl acetate. The combined organic phases are dried over magnesium sulfate, filtered and concentrated under reduced pressure, so as to obtain 3.9 g of 2-methylpropan-2-yl 4-[5-amino-1-(propan-2-yl)-1H-pyrazol-3-yl]piperidine-1-carboxylate in the form of a solid.

Method 30: 1-(Propan-2-yl)-3-(tetrahydro-2H-pyran-4-yl)-1H-pyrazol-5-amine 26.8 ml of a 1M solution of LiHMDS in THF are introduced into 25 ml of anhydrous THF under an argon atmosphere. The mixture is maintained at a temperature of about −78° C., and then 1.47 ml of acetonitrile in solution in 3 ml of anhydrous THF are added. The reaction mixture is kept stirring at −78° C. for 40 minutes and then a solution of 3.0 g of methyl tetrahydropyran-4-carboxylate in 3 ml of THF is added. After stirring for 2 hours at −78° C., the mixture is left to return to ambient temperature for 15 hours and it is then diluted with 200 ml of a water/ice mixture. The pH is adjusted to a value of about 3 by adding 2N HCl, and then the mixture is extracted three times with 150 ml of ethyl acetate. The combined organic phases are dried over anhydrous magnesium sulfate, filtered and then concentrated to dryness under reduced pressure, so as to give 3.18 g of 3-oxo-3-(tetrahydro-2H-pyran-4-yl)propanenitrile in the form of a light brown oil.

0.43 ml of triethylamine is added to a solution of 640 mg of 3-oxo-3-(tetrahydro-2H-pyran-4-yl)propanenitrile and 347 mg of isopropylhydrazine hydrochloride in 8 ml of ethanol under an argon atmosphere. The mixture is refluxed with magnetic stirring for 1 h and then concentrated to dryness under reduced pressure. The residue is taken up in 100 ml of ethyl acetate and the organic phase is washed twice with 40 ml of a saturated sodium hydrogen carbonate solution. The combined aqueous phases are extracted twice with 50 ml of ethyl acetate. The combined organic phases are dried over magnesium sulfate, filtered and concentrated under reduced pressure, so as to obtain 536 mg of 1-(propan-2-yl)-3-(tetrahydro-2H-pyran-4-yl)-1H-pyrazol-5-amine.

Method 31: 4-Methoxy-2-(propan-2-yloxy)aniline

A mixture of 5.0 g of 4-fluoro-1-nitro-2-(propan-2-yloxy)benzene, 4.07 g of sodium methoxide and 200 mg of 18C6 in 100 ml of methanol is heated at 65° C. for 2 h. The mixture is then concentrated and the residue is taken up with a mixture of water and ethyl acetate. The aqueous phase is extracted three times with ethyl acetate. The combined organic phases are dried over anhydrous magnesium sulfate, filtered and then concentrated to dryness under reduced pressure, so as to obtain 5.0 g of 1-nitro-4-methoxy-2-(propan-2-yloxy)benzene.

A solution of 5.0 g of 1-nitro-4-methoxy-2-(propan-2-yloxy)benzene in 300 ml of methanol is hydrogenated on 2.5 g of platinum oxide at a hydrogen pressure of 15 bar, for 2 h at ambient temperature. The mixture is filtered and the filtrate is concentrated to dryness under reduced pressure, so as to obtain 4.36 g of 4-methoxy-2-(propan-2-yloxy)aniline.

Method 32: 4-Chloro-2-(propan-2-yloxy)aniline

A mixture of 1.0 g of 4-chloro-2-fluoronitrobenzene and 9.3 g of caesium carbonate in 10 ml of 2-propanol is heated at 60° C. for 24 h. The mixture is then concentrated and the residue is taken up with 100 ml of a mixture of water and ethyl acetate. The aqueous phase is extracted three times with 50 ml of ethyl acetate. The combined organic phases are washed with 50 ml of a saturated sodium chloride solution, dried over anhydrous magnesium sulfate, filtered and then concentrated to dryness under reduced pressure. The residue is purified on 90 g of silica, elution being carried out with 95/5 heptane/ethyl acetate, so as to obtain 885 mg of 4-chloro-1-nitro-2-(propan-2-yloxy)benzene in the form of a yellow solid.

A mixture of 2.55 g of 4-chloro-1-nitro-2-(propan-2-yloxy)benzene in 40 ml of acetic acid is heated at 50° C., and then 7 ml of water and 2.64 g of iron powder are added. The mixture is stirred for 1 h at 50° C., and then cooled to ambient temperature and filtered on Celite. The Celite is rinsed three times with 20 ml of methanol, and the filtrate is concentrated under reduced pressure. The residue is taken up in 50 ml of 1N sodium hydroxide and 50 ml of dichloromethane. The aqueous phase is extracted twice with 50 ml of dichloromethane. The combined organic phases are dried over anhydrous magnesium sulfate, filtered and then concentrated to dryness under reduced pressure, so as to obtain 2.25 g of 4-chloro-2-(propan-2-yloxy)aniline in the form of a green oil.

Method 33: 4-(4-Methyl-1,4-diazepan-1-yl)-2-(propan-2-yloxy)aniline

A mixture of 250 mg of 4-bromo-1-nitro-2-(propan-2-yloxy)benzene, 1.13 g of caesium carbonate, 197 mg of N-methylhomopiperazine, 47.5 mg of tris(dibenzylideneacetone)dipalladium(0) and 50 mg of 9,9-dimethyl-4,5-bis(diphenylphosphino)xanthene in 5 ml of 1,4-dioxane is microwave-heated in a sealed tube, at 150° C. for 30 min, and then 200° C. for 10 min. The mixture is diluted with ethyl acetate and filtered on Clarcel. The Clarcel is washed with ethyl acetate and the organic phase is washed with water. The organic phase is dried over anhydrous magnesium sulfate, filtered and then concentrated to dryness under reduced pressure. The residue is purified on 12 g of silica, elution being carried out with 0-5% methanol in dichloromethane, so as to obtain 110 mg of 4-(4-methyl-1,4-diazepan-1-yl)-2-(propan-2-yloxy)nitrobenzene in the form of an orangey-coloured oil.

A solution of 267 mg of 4-(4-methyl-1,4-diazepan-1-yl)-2-(propan-2-yloxy)nitrobenzene in 90 ml of methanol is hydrogenated using an H-cube, on a cartridge of 10% palladium-on-carbon, at a flow rate of 1 ml/min. The hydrogenated solution is concentrated under reduced pressure, so as to obtain 220 mg of 4-(4-methyl-1,4-diazepan-1-yl)-2-(propan-2-yloxy)aniline in the form of a grey oil.

Method 34 7-Amino-1-methyl-8-(propan-2-yloxy)-1,3,4,5-tetrahydro-2H-1-benzazepin-2-one A suspension of 2.0 g of 7-hydroxy-3,4-dihydronaphthalen-1(2H)-one, 4.04 g of caesium carbonate and 3.15 ml of 2-iodopropane in 23 ml of acetonitrile is heated for 1 hour at 80° C. The reaction medium is brought back to ambient temperature and then evaporated to dryness. The residue is taken up with 100 ml of water and 100 ml of ethyl acetate. The organic phase is dried over magnesium sulfate, filtered and evaporated under reduced pressure, so as to obtain 2.24 g of 7-(propan-2-yloxy)-3,4-dihydronaphthalen-1(2H)-one in the form of an orangey-coloured oil.

900 mg of sodium azide are added at ambient temperature to a solution of 2.24 g of 7-(propan-2-yloxy)-3,4-dihydronaphthalen-1(2H)-one in 35 ml of trifluoroacetic acid. The reaction medium is refluxed for 3 hours and is then brought back to ambient temperature. The reaction medium is poured into 100 ml of water and the pH is adjusted to pH 7 by adding sodium carbonate. The mixture is extracted twice with 100 ml of ethyl acetate. The combined organic phases are dried over magnesium sulfate, filtered and evaporated. The residue is purified by flash chromatography on silica gel, elution being carried out with dichloromethane and then a dichloromethane/methanol (9/1) mixture, so as to obtain 346 mg of 8-(propan-2-yloxy)-1,3,4,5-tetrahydro-2H-1-benzazepin-2-one in the form of an orangey-coloured oil.

460 mg of potassium nitrate are added to a solution of 797 mg of 8-(propan-2-yloxy)-1,3,4,5-tetrahydro-2H-1-benzazepin-2-one in 8 ml of trifluoroacetic anhydride, cooled to −5° C. The reaction medium is stirred for 5 minutes at −5° C., brought back to pH 7 by adding a saturated aqueous sodium hydrogen carbonate solution, and then extracted with 100 ml of ethyl acetate. The organic phase is dried over magnesium sulfate, filtered and evaporated. The residue is purified by flash chromatography on silica gel, elution being carried out with a heptane/ethyl acetate (1/1) mixture, so as to obtain 489 mg of 7-nitro-8-(propan-2-yloxy)-1,3,4,5-tetrahydro-2H-1-benzazepin-2-one in the form of a yellow solid. 100 mg of sodium hydride at 60% are added to a solution of 485 mg of 7-nitro-8-(propan-2-yloxy)-1,3,4,5-tetrahydro-2H-1-benzazepin-2-one in 8 ml of DMF, cooled to 0° C. The reaction medium is stirred for 5 minutes and then 263 mg of iodomethane are added. The reaction medium is brought back to ambient temperature and stirred for 1 hour at this temperature. The reaction medium is poured into 100 ml of ice-cold water and the mixture is extracted with 100 ml of ethyl acetate. The organic phase is dried over magnesium sulfate, filtered and evaporated. The residue is purified by flash chromatography on silica gel, elution being carried out with a heptane/ethyl acetate (1/1) mixture, so as to obtain 318 mg of 1-methyl-7-nitro-8-(propan-2-yloxy)-1,3,4,5-tetrahydro-2H-1-benzazepin-2-one in the form of a yellow solid.

In a microwave tube, 316 mg of 1-methyl-7-nitro-8-(propan-2-yloxy)-1,3,4,5-tetrahydro-2H-1-benzazepin-2-one are introduced into 20 ml of methanol. 443 mg of ammonium formate and 363 mg of Pd/C (10%) are added. The reaction medium is microwave-heated at 80° C. for 5 minutes. The mixture is filtered on Clarcel and the Clarcel is rinsed with methanol. The filtrate is concentrated under reduced pressure, so as to obtain 280 mg of 7-amino-1-methyl-8-(propan-2-yloxy)-1,3,4,5-tetrahydro-2H-1-benzazepin-2-one in the form of a colourless gum.

Method 35: 4-(1,2,2,6,6-Pentamethylpiperidin-4-yl)-2-(propan-2-yloxy)aniline

180 μl of formaldehyde and 3.4 ml of formic acid are added to a solution of 500 mg of 2,2,6,6-tetramethyl-4-[4-nitro-3-(propan-2-yloxy)phenyl]-1,2,3,6-tetrahydropyridine (obtained according to method 2) in 15 ml of DMSO. The tube is microwave-heated at 100° C. for 5 minutes. After cooling, the mixture is run into water and extracted with ethyl acetate. The organic phase is washed with a saturated sodium chloride solution, dried over magnesium sulfate, filtered and concentrated under reduced pressure. Purification is carried out by flash chromatography on silica gel, elution being carried out with a mixture of dichloromethane and methanol (95/5), so as to obtain 230 mg of 1,2,2,6,6-pentamethyl-4-[4-nitro-3-(propan-2-yloxy)phenyl]-1,2,3,6-tetrahydropyridine in the form of a yellow oil. In a microwave tube, 230 mg of 1,2,2,6,6-pentamethyl-4-[4-nitro-3-(propan-2-yloxy)phenyl]-1,2,3,6-tetrahydropyridine are introduced into 11.5 ml of methanol. 262 mg of ammonium formate and 221 mg of Pd/C (10%) are added. The reaction medium is microwave-heated at 80° C. for 5 minutes. The mixture is filtered on Clarcel and the Clarcel is rinsed with methanol. The filtrate is concentrated under reduced pressure and the residue is purified by flash chromatography on alumina, elution being carried out with a dichloromethane/methanol (98/2) mixture, so as to obtain 120 mg of 4-(1,2,2,6,6-pentamethylpiperidin-4-yl)-2-(propan-2-yloxy)aniline in the form of a yellow oil.

Method 36: 4-(1-Methyl-1H-pyrazol-3-yl)-2-(propan-2-yloxy)aniline 1.02 g of 3-iodo-1-methyl-1H-pyrazole are introduced into 33 ml of 1-4-dioxane. After sparging with argon for 10 min in the reaction medium, 1.5 g of 4,4,5,5-tetramethyl-2-[4-nitro-3-(propan-2-yloxy)phenyl]-1,3,2-dioxaborolane (obtained as in method 2), 4.77 g of caesium carbonate, 6.5 ml of water and 179 mg of [1,1'-bis(diphenylphosphino)ferrocene]dichloropalladium(II) are added. The reaction medium is heated for 1 hour at 90° C. and is then diluted with ethyl acetate and water. The aqueous phase is extracted twice with ethyl acetate. The combined organic phases are dried over magnesium sulfate and concentrated under vacuum. The residue is purified by flash chromatography on silica gel, elution being carried out with dichloromethane and then a dichloromethane/methanol (98/2) mixture, so as to give 865 mg of 1-methyl-3-[4-nitro-3-(propan-2-yloxy)phenyl]-1H-pyrazole in the form of an orange oil.

In a microwave tube, 860 mg of 1-methyl-3-[4-nitro-3-(propan-2-yloxy)phenyl]-1H-pyrazole are introduced into 30 ml of methanol. 1.25 g of ammonium formate and 1.05 g of Pd/C (10%) are added. The reaction medium is microwave-heated at 80° C. for 3 times 7 minutes. The mixture is filtered on Clarcel and the Clarcel is rinsed with methanol. The filtrate is concentrated under reduced pressure and the residue is taken up with 30 ml of ethyl acetate and 3 ml of water. The organic phase is dried over magnesium sulfate, filtered and concentrated under reduced pressure. The residue is purified by flash chromatography on silica gel, elution being carried out with a dichloromethane/methanol (95/5) mixture, so as to obtain 110 mg of 4-(1-methyl-1H-pyrazol-3-yl)-2-(propan-2-yloxy)aniline in the form of a purple oil.

The compounds (IIIa) obtained according to Example 8 (methods 1 to 36) are described in Table 2.

TABLE 2

| Compounds IIIa | Name | Method |
|---|---|---|
| IIIa-1 | 2-Methoxy-4-[1-(propan-2-yl)piperidin-4-yl]aniline | WO2009/020990 p92 |
| IIIa-2 | 2-Methoxy-5-methyl-4-(1-methylpiperidin-4-yl)aniline | Analogy with WO2008/073687 p48 |
| IIIa-3 | 4-(1-Methylpiperidin-4-yl)-2-(propan-2-yloxy)aniline | Method 1 |
| IIIa-4 | 2-Methylpropan-2-yl 4-[4-amino-3-(propan-2-yloxy)phenyl]piperidine-1-carboxylate | Method 5 |
| IIIa-5 | 2-(Propan-2-yloxy)-4-[1-(propan-2-yl)piperidin-4-yl]aniline | Method 1 |
| IIIa-6 | 4-(1-Cyclopropylpiperidin-4-yl)-2-(propan-2-yloxy)aniline | Method 2 |
| IIIa-7 | 5-Methyl-4-(1-methylpiperidin-4-yl)-2-(propan-2-yloxy)aniline | WO2008/073687 p48 |
| IIIa-8 | 4-(5-Methoxy-1-methyl-1,2,3,6-tetrahydropyridin-4-yl)-2-(propan-2-yloxy)aniline | Method 3 |
| IIIa-9 | 2-(Propan-2-yloxy)-4-(2,2,6,6-tetramethylpiperidin-4-yl)aniline | Method 2 |
| IIIa-10 | 4-(1,2,2,6,6-Pentamethylpiperidin-4-yl)-2-(propan-2-yloxy)aniline | Method 35 |
| IIIa-11 | 2-Methylpropan-2-yl 4-[4-amino-3-(propan-2-yloxy)phenyl]-2,6-dimethylpiperidine-1-carboxylate | Method 2 |
| IIIa-12 | 2-Methylpropan-2-yl 2-ethyl-4-[4-(formylamino)-3-(propan-2-yloxy)phenyl]piperidine-1-carboxylate | Method 2 |
| IIIa-13 | 4-[2-Ethyl-1-methylpiperidin-4-yl]-2-(propan-2-yloxy)aniline | Method 35 |
| IIIa-14 | (cis)-4-[4-Amino-3-(propan-2-yloxy)phenyl]-1-methylpiperidin-3-ol | Method 4 |
| IIIa-15 | 2-Methylpropan-2-yl 4-[4-(formylamino)-3-(propan-2-yloxy)phenyl]-2-(propan-2-yl)piperidine-1-carboxylate | Method 2 |
| IIIa-16 | 2-{4-[4-Amino-3-(propan-2-yloxy)phenyl]piperidin-1-yl}ethanol | Method 27 |
| IIIa-17 | 5-Fluoro-4-(1-methylpiperidin-4-yl)-2-(propan-2-yloxy)aniline | Method 1 |
| IIIa-18 | 2-Methoxy-5-methyl-4-(1-methylpiperidin-3-yl)aniline | Method 1 |
| IIIa-19 | 4-(1-Ethylpiperidin-3-yl)-2-(propan-2-yloxy)aniline | Method 1 |
| IIIa-20 | 4-(Octahydroindolizin-8-yl)-2-(propan-2-yloxy)aniline | Method 2 |
| IIIa-21 | 2-Methoxy-4-[4-(pyrrolidin-1-yl)piperidin-1-yl]aniline | US2006/46990 p6 |
| IIIa-22 | 2-Methyl-4-[4-(pyrrolidin-1-yl)piperidin-1-yl]aniline | Method 6 |
| IIIa-23 | 2-Methoxy-4-[4-(propan-2-yl)piperazin-1-yl]aniline | WO2009/020990 p102 |
| IIIa-24 | 2-Methoxy-4-(4-methylpiperazin-1-yl)aniline | WO2004/080980 p138 |
| IIIa-25 | 4-(4-Methylpiperazin-1-yl)-2-(propan-2-yloxy)aniline | Method 6 |

TABLE 2-continued

| Compounds IIIa | Name | Method |
|---|---|---|
| IIIa-26 | 5-Methyl-4-(4-methylpiperazin-1-yl)-2-(propan-2-yloxy)aniline | Method 10 |
| IIIa-27 | 4-(3,5-Dimethylpiperazin-1-yl)-2-(propan-2-yloxy)aniline | Method 6 |
| IIIa-28 | 2-(Propan-2-yloxy)-4-(3,4,5-trimethylpiperazin-1-yl)aniline | Method 35 |
| IIIa-29 | 4-(5,6-Dihydroimidazo[1,2-a]pyrazin-7(8H)-yl)-2-(propan-2-yloxy)aniline | Method 6 |
| IIIa-30 | 2-{4-[4-Amino-3-(propan-2-yloxy)phenyl]-1-methylpiperazin-2-yl}ethanol | Method 6 |
| IIIa-31 | 4-[3-(2-Methoxyethyl)-4-methylpiperazin-1-yl]-2-(propan-2-yloxy)aniline | Method 9 |
| IIIa-32 | 4-(4-Methyl-1,4-diazepan-1-yl)-2-(propan-2-yloxy)aniline | Method 33 |
| IIIa-33 | 4-[(1S,4S)-5-Methyl-2,5-diazabicyclo[2.2.1]hept-2-yl]-2-(propan-2-yloxy)aniline | Method 6 |
| IIIa-34 | 1-[4-Amino-3-(propan-2-yloxy)phenyl]-N,N-dimethylpyrrolidin-3-amine | Method 6 |
| IIIa-35 | 1-[4-Amino-2-methyl-5-(propan-2-yloxy)phenyl]-N,N-dimethylpyrrolidin-3-amine | Method 7 |
| IIIa-36 | 1-[4-Amino-3-(propan-2-yloxy)phenyl]-N,N-diethylpyrrolidin-3-amine | Method 6 |
| IIIa-37 | 4-(1H-Imidazol-1-yl)-2-(propan-2-yloxy)aniline | Method 6 |
| IIIa-38 | 4-(2-Methyl-1H-imidazol-1-yl)-2-(propan-2-yloxy)aniline | Method 6 |
| IIIa-39 | 5-Methyl-4-(2-methyl-1H-imidazol-1-yl)-2-(propan-2-yloxy)aniline | Method 8 |
| IIIa-40 | 4-(4-Methyl-1H-imidazol-1-yl)-2-(propan-2-yloxy)aniline | Method 6 |
| IIIa-41 | 4-(2,4-Dimethyl-1H-imidazol-1-yl)-2-(propan-2-yloxy)aniline | Method 6 |
| IIIa-42 | 2-(Propan-2-yloxy)-4-(1H-1,2,4-triazol-1-yl)aniline | Method 8 |
| IIIa-43 | N~4~-methyl-2-(propan-2-yloxy)-N~4~-[2-(pyrrolidin-1-yl)ethyl]benzene-1,4-diamine | Method 6 |
| IIIa-44 | 4-[(8aR)-Hexahydropyrrolo[1,2-a]pyrazin-2(1H)-yl]-2-(propan-2-yloxy)aniline | Method 26 |
| IIIa-45 | 2-Methylpropan-2-yl 7-[4-amino-3-(propan-2-yloxy)phenyl]-1,7-diazaspiro[4.4]nonane-1-carboxylate | Method 23 |
| IIIa-46 | 4-(1-Ethyl-1,7-diazaspiro[4.4]non-7-yl)-2-(propan-2-yloxy)aniline | Method 25 |
| IIIa-47 | (3R)-1-[4-Amino-3-(propan-2-yloxy)phenyl]-N-methyl-N-(oxetan-3-yl)piperidin-3-amine | Method 28 |
| IIIa-48 | 4-(3-Methoxypyridin-4-yl)-2-(propan-2-yloxy)aniline | Method 3 |
| IIIa-49 | 4-(1-Methyl-1H-pyrazol-4-yl)-2-(propan-2-yloxy)aniline | Method 36 |
| IIIa-50 | 4-(1-Methyl-1H-pyrazol-3-yl)-2-(propan-2-yloxy)aniline | Method 36 |
| IIIa-51 | 4-Methoxy-2-(propan-2-yloxy)aniline | Method 31 |
| IIIa-52 | 8-Amino-1-methyl-1,3,4,5-tetrahydro-2H-1-benzazepin-2-one | Method 17 |
| IIIa-53 | 7-Amino-1-methyl-1,3,4,5-tetrahydro-2H-1-benzazepin-2-one | Method 15 |
| IIIa-54 | 6-(4-Methylpiperazin-1-yl)-4-(propan-2-yloxy)pyridin-3-amine | Method 12 |
| IIIa-55 | 6-(1-Methylpiperidin-4-yl)-4-(propan-2-yloxy)pyridin-3-amine | Method 11 |
| IIIa-56 | 6-(4-Methylpiperazin-1-yl)-2-(propan-2-yloxy)pyridin-3-amine | Method 14 |
| IIIa-57 | 6-(1-Methylpiperidin-4-yl)-2-(propan-2-yloxy)pyridin-3-amine | Method 13 |
| IIIa-58 | 2-Methylpropan-2-yl 4-[5-amino-1-(propan-2-yl)-1H-pyrazol-3-yl]piperidine-1-carboxylate | Method 29 |
| IIIa-59 | 2-Methylpropan-2-yl 3-[5-(formylamino)-1-(propan-2-yl)-1H-pyrazol-3-yl]piperidine-1-carboxylate | Method 29 |
| IIIa-60 | 1-Phenyl-1H-pyrazol-5-amine | [827-85-7] |
| IIIa-61 | 3-Cyclopropyl-1-phenyl-1H-pyrazol-5-amine | [175137-45-8] |
| IIIa-62 | 1-(Propan-2-yl)-3-(pyridin-3-yl)-1H-pyrazol-5-amine | Method 29 |
| IIIa-63 | 3-Cyclopropyl-1-(propan-2-yl)-1H-pyrazol-5-amine | Method 29 |
| IIIa-64 | 3-Methyl-1-(propan-2-yl)-1H-pyrazol-5-amine | [1124-16-9] |
| IIIa-65 | 7-Amino-1-methyl-6-(propan-2-yloxy)-1,3,4,5-tetrahydro-2H-1-benzazepin-2-one | Method 16 |
| IIIa-66 | 4-[(4-Methylpiperazin-1-yl)methyl]-2-(propan-2-yloxy)aniline | Method 18 |
| IIIa-67 | 4-(3,5-Dimethyl-1H-1,2,4-triazol-1-yl)-2-(propan-2-yloxy)aniline | Method 8 |

TABLE 2-continued

| Compounds IIIa | Name | Method |
|---|---|---|
| IIIa-68 | 5-(4-Methylpiperazin-1-yl)-2-(propan-2-yloxy)aniline | Method 19 |
| IIIa-69 | 2-(Propan-2-yloxy)-N~4~-(tetrahydro-2H-pyran-4-yl)benzene-1,4-diamine | Method 20 |
| IIIa-70 | 1-[4-Amino-3-(propan-2-yloxy)phenyl]piperidin-4-yl acetate | Method 7 |
| IIIa-71 | 4-(1-Methylpyrrolidin-3-yl)-2-(propan-2-yloxy)aniline | Method 2 |
| IIIa-72 | 1-(Propan-2-yl)-3-(tetrahydro-2H-pyran-4-yl)-1H-pyrazol-5-amine | Method 30 |
| IIIa-73 | N~4~-(1-Methylpiperidin-4-yl)-2-(propan-2-yloxy)benzene-1,4-diamine | Method 22 |
| IIIa-74 | 2-Methylpropan-2-yl 4-(5-amino-1-cyclobutyl-1H-pyrazol-3-yl)piperidine-1-carboxylate | Method 29 |
| IIIa-75 | 3-(4-Methylpiperazin-1-yl)-2-(propan-2-yloxy)aniline | Method 21 |
| IIIa-76 | 5-Methyl-2,3,4,5-tetrahydro-1,5-benzoxazepin-7-amine | Analogy with US20100173823 p36 |
| IIIa-77 | 4-(4-Ethylpiperazin-1-yl)-2-(propan-2-yloxy)aniline | Method 6 |
| IIIa-78 | 7-Amino-1-methyl-8-(propan-2-yloxy)-1,3,4,5-tetrahydro-2H-1-benzazepin-2-one | Method 34 |
| IIIa-79 | 4-Chloro-2-(propan-2-yloxy)aniline | Method 32 |
| IIIa-80 | 4-(1-Methyl-1,7-diazaspiro[4.4]non-7-yl)-2-(propan-2-yloxy)aniline | Method 6 |

IV—Formation of the Compounds of Formula (IIIb)

Example 9

Example 9.1

N-[4-(1-Methylpiperidin-4-yl)-2-(propan-2-yloxy)phenyl]formamide

A solution of 12.3 g of acetic anhydride is added slowly to 19 ml of formic acid at ambient temperature. After one hour of stirring, a solution of 6.0 g of 4-(1-methylpiperidin-4-yl)-2-(propan-2-yloxy)aniline in 28 ml of formic acid is added dropwise. The mixture is stirred at ambient temperature for 2 h and then concentrated under vacuum and taken up with water. The aqueous phase is neutralized with a saturated sodium bicarbonate solution and extracted three times with 100 ml of dichoromethane. The organic phases are dried over magnesium sulfate, filtered and concentrated under vacuum. The crude product is triturated with ethyl ether and the solid is filtered off, so as to obtain 5.0 g of N-[4-(1-methylpiperidin-4-yl)-2-(propan-2-yloxy)phenyl]formamide.

Example 9.2

N-[5-Methyl-4-(4-methylpiperazin-1-yl)-2-(propan-2-yloxy)phenyl]formamide

A mixture of 0.53 g of 5-methyl-4-(1-methylpiperidin-4-yl)-2-(propan-2-yloxy)aniline in 5.7 ml of formic acid is refluxed for 20 h. The mixture is cooled, diluted with water and neutralized with a saturated sodium hydrogen carbonate solution. The aqueous phase is extracted with ethyl acetate. The organic phase is dried over magnesium sulfate and concentrated under vacuum. The crude product is purified on 50 g of silica, elution being carried out with methanol in dichloromethane (97/3 and 1% $NH_4OH$), so as to obtain 0.56 g of N-[5-methyl-4-(4-methylpiperazin-1-yl)-2-(propan-2-yloxy)phenyl]formamide.

The compounds (IIIb) obtained according to Example 9 are described in Table 3.

TABLE 3

| Compounds IIIb | Name | MS Method | MH+ | Tr |
|---|---|---|---|---|
| IIIb-1 | N-{2-Methoxy-4-[1-(propan-2-yl)piperidin-4-yl]phenyl}formamide | D | 277 | 0.83 |
| IIIb-2 | N-[2-Methoxy-5-methyl-4-(1-methylpiperidin-4-yl)phenyl]formamide | A | 263 | 0.28 |
| IIIb-3 | N-[4-(1-Methylpiperidin-4-yl)-2-(propan-2-yloxy)phenyl]formamide | A | 277 | 0.37 |
| IIIb-4 | 2-Methylpropan-2-yl 4-[4-(formylamino)-3-(propan-2-yloxy)phenyl]piperidine-1-carboxylate | A | 363 | 1.08 |
| IIIb-5 | N-{2-(Propan-2-yloxy)-4-[1-(propan-2-yl)piperidin-4-yl]phenyl}formamide | A | 305 | 0.44 |
| IIIb-6 | N-[4-(1-Cyclopropylpiperidin-4-yl)-2-(propan-2-yloxy)phenyl]formamide | A | 303 | 0.55 |
| IIIb-7 | N-[5-Methyl-4-(1-methylpiperidin-4-yl)-2-(propan-2-yloxy)phenyl]formamide | A | 291 | 0.39 |
| IIIb-8 | N-[4-(5-Methoxy-1-methyl-1,2,3,6-tetrahydropyridin-4-yl)-2-(propan-2-yloxy)phenyl]formamide | A | 305 | 0.40 |
| IIIb-9 | N-[2-(Propan-2-yloxy)-4-(2,2,6,6-tetramethylpiperidin-4-yl)phenyl]formamide | A | 319 | 0.52 |
| IIIb-10 | N-[4-(1,2,2,6,6-Pentamethylpiperidin-4-yl)-2-(propan-2-yloxy)phenyl]formamide | A | 333 | 0.48 |

TABLE 3-continued

| Compounds IIIb | Name | MS Method | MH+ | Tr |
|---|---|---|---|---|
| IIIb-11 | 2-Methylpropan-2-yl 4-[4-(formylamino)-3-(propan-2-yloxy)phenyl]-2,6-dimethylpiperidine-1-carboxylate | C | 391 | 6.28 |
| IIIb-12 | 2-Methylpropan-2-yl 2-ethyl-4-[4-(formylamino)-3-(propan-2-yloxy)phenyl]piperidine-1-carboxylate | C | 391 | 6.26 |
| IIIb-13 | N-[4-(2-Ethyl-1-methylpiperidin-4-yl)-2-(propan-2-yloxy)phenyl]formamide | A | 305 | 0.55 |
| IIIb-14 | (cis)-4-[4-(Formylamino)-3-(propan-2-yloxy)phenyl]-1-methylpiperidin-3-yl formate | A | 321 | 0.33 and 0.36 |
| IIIb-15 | 2-Methylpropan-2-yl 4-[4-(formylamino)-3-(propan-2-yloxy)phenyl]-2-(propan-2-yl)piperidine-1-carboxylate | A | 405 | 1.19 |
| IIIb-16 | 2-{4-[4-(Formylamino)-3-(propan-2-yloxy)phenyl]piperidin-1-yl}ethyl formate | A | 335 | 0.39 |
| IIIb-17 | N-[5-Fluoro-4-(1-methylpiperidin-4-yl)-2-(propan-2-yloxy)phenyl]formamide | A | 295 | 0.41 |
| IIIb-18 | N-[2-Methoxy-5-methyl-4-(1-methylpiperidin-3-yl)phenyl]formamide | A | 263 | 0.31 |
| IIIb-19 | N-[4-(1-Ethylpiperidin-3-yl)-2-(propan-2-yloxy)phenyl]formamide | A | 291 | 0.41 |
| IIIb-20 | N-[4-(Octahydroindolizin-8-yl)-2-(propan-2-yloxy)phenyl]formamide | A | 303 | 0.41 |
| IIIb-21 | N-{2-Methoxy-4-[4-(pyrrolidin-1-yl)piperidin-1-yl]phenyl}formamide | E | 304 | 0.83 |
| IIIb-22 | N-{2-Methyl-4-[4-(pyrrolidin-1-yl)piperidin-1-yl]phenyl}formamide | E | 288 | 0.78 |
| IIIb-23 | N-{2-Methoxy-4-[4-(propan-2-yl)piperazin-1-yl]phenyl}formamide | | | |
| IIIb-24 | N-[2-Methoxy-4-(4-methylpiperazin-1-yl)phenyl]formamide | A | 250 | 0.20 |
| IIIb-25 | N-[4-(4-Methylpiperazin-1-yl)-2-(propan-2-yloxy)phenyl]formamide | A | 278 | 0.32 |
| IIIb-26 | N-[5-Methyl-4-(4-methylpiperazin-1-yl)-2-(propan-2-yloxy)phenyl]formamide | A | 292 | 0.39 |
| IIIb-27 | N-[4-(3,5-Dimethylpiperazin-1-yl)-2-(propan-2-yloxy)phenyl]formamide | A | 292 | 0.39 |
| IIIb-28 | N-[2-(Propan-2-yloxy)-4-(3,4,5-trimethylpiperazin-1-yl)phenyl]formamide | A | 306 | 0.38 |
| IIIb-29 | N-[4-(5,6-Dihydroimidazo[1,2-a]pyrazin-7(8H)-yl)-2-(propan-2-yloxy)phenyl]formamide | A | 301 | 0.55 |
| IIIb-30 | N-{4-[3-(2-Hydroxyethyl)-4-methylpiperazin-1-yl]-2-(propan-2-yloxy)phenyl}formamide | D | 322 | 0.93 |
| IIIb-31 | N-{4-[3-(2-Methoxyethyl)-4-methylpiperazin-1-yl]-2-(propan-2-yloxy)phenyl}formamide | D | 336 | 2.22 |
| IIIb-32 | N-[4-(4-Methyl-1,4-diazepan-1-yl)-2-(propan-2-yloxy)phenyl]formamide | B | 292 | 0.46 |
| IIIb-33 | N-{4-[(1S,4S)-5-Methyl-2,5-diazabicyclo[2.2.1]hept-2-yl]-2-(propan-2-yloxy)phenyl}formamide | B | 290 | 0.43 |
| IIIb-34 | N-{4-[3-(Dimethylamino)pyrrolidin-1-yl]-2-(propan-2-yloxy)phenyl}formamide | A | 292 | 0.37 |
| IIIb-35 | N-{4-[3-(Dimethylamino)pyrrolidin-1-yl]-5-methyl-2-(propan-2-yloxy)phenyl}formamide | D | 306 | 2.58 |
| IIIb-36 | N-{4-[3-(Diethylamino)pyrrolidin-1-yl]-2-(propan-2-yloxy)phenyl}formamide | D | 320 | 2.26 |
| IIIb-37 | N-[4-(1H-Imidazol-1-yl)-2-(propan-2-yloxy)phenyl]formamide | D | 246 | 1.12 |
| IIIb-38 | N-[4-(2-Methyl-1H-imidazol-1-yl)-2-(propan-2-yloxy)phenyl]formamide | A | 260 | 0.36 |
| IIIb-39 | N-[5-Methyl-4-(2-methyl-1H-imidazol-1-yl)-2-(propan-2-yloxy)phenyl]formamide | D | 274 | 1.28 |
| IIIb-40 | N-[4-(4-Methyl-1H-imidazol-1-yl)-2-(propan-2-yloxy)phenyl]formamide | D | 260 | 1.61 |
| IIIb-41 | N-[4-(2,4-Dimethyl-1H-imidazol-1-yl)-2-(propan-2-yloxy)phenyl]formamide | D | 274 | 1.79 |
| IIIb-42 | N-[2-(Propan-2-yloxy)-4-(1H-1,2,4-triazol-1-yl)phenyl]formamide | A | 247 | 0.56 |
| IIIb-43 | N-[4-{Methyl[2-(pyrrolidin-1-yl)ethyl]amino}-2-(propan-2-yloxy)phenyl]formamide | B | 306 | 0.51 |

TABLE 3-continued

| Compounds IIIb | Name | MS Method | MH+ | Tr |
|---|---|---|---|---|
| IIIb-44 | N-{4-[(8aR)-Hexahydropyrrolo[1,2-a]pyrazin-2(1H)-yl]-2-(propan-2-yloxy)phenyl}formamide | A | 304 | 0.39 |
| IIIb-45 | N-[4-(1-Formyl-1,7-diazaspiro[4.4]non-7-yl)-2-(propan-2-yloxy)phenyl]formamide | A | 332 | 1.36 |
| IIIb-46 | N-[4-(1-Ethyl-1,7-diazaspiro[4.4]non-7-yl)-2-(propan-2-yloxy)phenyl]formamide | B | 332 | 0.55 |
| IIIb-47 | N-[4-{(3R)-3-[Methyl(oxetan-3-yl)amino]piperidin-1-yl}-2-(propan-2-yloxy)phenyl]formamide | B | 348 | 0.52 |
| IIIb-48 | N-[4-(3-Methoxypyridin-4-yl)-2-(propan-2-yloxy)phenyl]formamide | A | 287 | 0.47 |
| IIIb-49 | N-[4-(1-Methyl-1H-pyrazol-4-yl)-2-(propan-2-yloxy)phenyl]formamide | A | 260 | 0.66 |
| IIIb-50 | N-[4-(1-Methyl-1H-pyrazol-3-yl)-2-(propan-2-yloxy)phenyl]formamide | A | 260 | 0.70 |
| IIIb-51 | N-[4-Methoxy-2-(propan-2-yloxy)phenyl]formamide | D | 210 | 0.38 |
| IIIb-52 | N-(1-Methyl-2-oxo-2,3,4,5-tetrahydro-1H-1-benzazepin-8-yl)formamide | D | 219 | 2.63 |
| IIIb-53 | N-(1-Methyl-2-oxo-2,3,4,5-tetrahydro-1H-1-benzazepin-7-yl)formamide | A | 219 | 0.60 |
| IIIb-54 | N-[6-(4-Methylpiperazin-1-yl)-4-(propan-2-yloxy)pyridin-3-yl]formamide | D | 279 | 0.32 |
| IIIb-55 | N-[6-(1-Methylpiperidin-4-yl)-4-(propan-2-yloxy)pyridin-3-yl]formamide | A | 278 | 0.14 |
| IIIb-56 | N-[6-(4-Methylpiperazin-1-yl)-2-(propan-2-yloxy)pyridin-3-yl]formamide | D | 279 | 0.98 |
| IIIb-57 | N-[6-(1-Methylpiperidin-4-yl)-2-(propan-2-yloxy)pyridin-3-yl]formamide | D | 278 | 1.93 |
| IIIb-58 | 2-Methylpropan-2-yl 4-[5-(formylamino)-1-(propan-2-yl)-1H-pyrazol-3-yl]piperidine-1-carboxylate | A | 337 | 0.82 |
| IIIb-59 | 2-Methylpropan-2-yl 3-[5-(formylamino)-1-(propan-2-yl)-1H-pyrazol-3-yl]piperidine-1-carboxylate | D | 337 | 3.76 |
| IIIb-60 | N-(1-Phenyl-1H-pyrazol-5-yl)formamide | A | 188 | 0.39 |
| IIIb-61 | N-(3-Cyclopropyl-1-phenyl-1H-pyrazol-5-yl)formamide | D | 228 | 3.20 |
| IIIb-62 | N-[1-(Propan-2-yl)-3-(pyridin-3-yl)-1H-pyrazol-5-yl]formamide | A | 231 | 0.29 |
| IIIb-63 | N-[3-Cyclopropyl-1-(propan-2-yl)-1H-pyrazol-5-yl]formamide | A | 194 | 0.49 |
| IIIb-64 | N-[3-Methyl-1-(propan-2-yl)-1H-pyrazol-5-yl]formamide | A | 168 | 0.33 |
| IIIb-65 | N-[1-Methyl-2-oxo-6-(propan-2-yloxy)-2,3,4,5-tetrahydro-1H-1-benzazepin-7-yl]formamide | A | 277 | 0.81 |
| IIIb-66 | N-{4-[(4-Methylpiperazin-1-yl)methyl]-2-(propan-2-yloxy)phenyl}formamide | A | 292 | 0.47 |
| IIIb-67 | N-[4-(3,5-Dimethyl-1H-1,2,4-triazol-1-yl)-2-(propan-2-yloxy)phenyl]formamide | A | 275 | 0.78 |
| IIIb-68 | N-[5-(4-Methylpiperazin-1-yl)-2-(propan-2-yloxy)phenyl]formamide | B | 278 | 0.55 |
| IIIb-69 | N-[4-(Formylamino)-3-(propan-2-yloxy)phenyl]-N-(tetrahydro-2H-pyran-4-yl)formamide | B | 307 | 0.82 |
| IIIb-70 | 1-[4-(Formylamino)-3-(propan-2-yloxy)phenyl]piperidin-4-yl acetate | A | 321 | 0.87 |
| IIIb-71 | N-[4-(1-Methylpyrrolidin-3-yl)-2-(propan-2-yloxy)phenyl]formamide | D | 263 | 0.88 |
| IIIb-72 | N-[1-(Propan-2-yl)-3-(tetrahydro-2H-pyran-4-yl)-1H-pyrazol-5-yl]formamide | A | 238 | 0.66 |
| IIIb-73 | N-[4-(Formylamino)-3-(propan-2-yloxy)phenyl]-N-(1-methylpiperidin-4-yl)formamide | A | 320 | 0.52 |
| IIIb-74 | 2-Methylpropan-2-yl 4-[1-cyclobutyl-5-(formylamino)-1H-pyrazol-3-yl]piperidine-1-carboxylate | B | 349 | 1.26 |
| IIIb-75 | N-[3-(4-Methylpiperazin-1-yl)-2-(propan-2-yloxy)phenyl]formamide | B | 278 | 0.55 |
| IIIb-76 | N-(5-Methyl-2,3,4,5-tetrahydro-1,5-benzoxazepin-7-yl)formamide | D | 207 | 1.49 |
| IIIb-77 | N-[4-(4-Ethylpiperazin-1-yl)-2-(propan-2-yloxy)phenyl]formamide | A | 292 | 0.65 |
| IIIb-78 | N-[1-Methyl-2-oxo-8-(propan-2-yloxy)-2,3,4,5-tetrahydro-1H-1-benzazepin-7-yl]formamide | D | 277 | 3.16 |

TABLE 3-continued

| Compounds IIIb | Name | MS Method | MH+ | Tr |
|---|---|---|---|---|
| IIIb-79 | N-[4-Chloro-2-(propan-2-yloxy)phenyl]formamide | A | 214 | 1.19 |
| IIIb-80 | N-[4-(1-Methyl-1,7-diazaspiro[4.4]non-7-yl)-2-(propan-2-yloxy)phenyl]formamide | A | 318 | 0.69 |

V—Preparation of the Compounds of Formula (I)

Example 10

7-(2-Methoxyphenyl)-2-{[4-(1-methylpiperidin-4-yl)-2-(propan-2-yloxy)-phenyl]amino}thieno[3,2-d]pyrimidine-6-carboxamide (I-16)

A mixture of 527 mg of N-[4-(1-methylpiperidin-4-yl)-2-(propan-2-yloxy)phenyl]formamide and 953 mg of 1-[N-(2-methylpropan-2-yl)-P,P-di(pyrrolidin-1-yl)phosphorimidoyl]-pyrrolidine (BTPP) in 10 ml of anhydrous DMF is stirred at ambient temperature for 30 min, and then a solution of 577 mg of methyl 7-(2-methoxyphenyl)-2-(methylsulfonyl)thieno[3,2-d]pyrimidine-6-carboxylate in 15 ml of anhydrous DMF is slowly added. The mixture is stirred at ambient temperature for 48 h, and then diluted with ethyl acetate and washed three times with water. The organic phase is dried over magnesium sulfate, filtered and concentrated under vacuum. The crude product is purified on 80 g of silica, elution being carried out with 5-10% of methanol in dichloromethane, so as to obtain 615 mg of methyl 7-(2-methoxyphenyl)-2-{[4-(1-methylpiperidin-4-yl)-2-(propan-2-yloxy)phenyl]amino}thieno[3,2-d]pyrimidine-6-carboxylate in the form of a yellow solid. The crude product is diluted with 600 ml of 7N ammoniacal methanol and the solution is stirred at ambient temperature for 48 h, and then concentrated under vacuum. The residue is solubilized with 100 ml of hot ethyl acetate and the solution is left to cool in order to obtain a suspension. The suspension is cooled in an ice bath and filtered. The solid is washed with ethyl ether and dried under vacuum, so as to obtain 477 mg of 7-(2-methoxyphenyl)-2-{[4-(1-methylpiperidin-4-yl)-2-(propan-2-yloxy)phenyl]amino}thieno[3,2-d]pyrimidine-6-carboxamide in the form of a yellow solid.

Example 11

2-{[4-(1-Methylpiperidin-4-yl)-2-(propan-2-yloxy)phenyl]amino}-7-(1H-pyrazol-4-yl)thieno[3,2-d]pyrimidine-6-carboxamide (I-76)

123 mg of N,N-diisopropylethylamine, 181 mg of HATU and 14 mg of ammonium chloride are added to a solution of 117 mg of 2-{[4-(1-methylpiperidin-4-yl)-2-(propan-2-yloxy)phenyl]amino}-7-(1H-pyrazol-4-yl)thieno[3,2-d]pyrimidine-6-carboxylic acid in 6 ml of dimethylformamide. The reaction medium is stirred for 16 hours at ambient temperature and then concentrated to dryness under reduced pressure. Purification is carried out by flash chromatography on alumina, elution being carried out with a mixture of dichloromethane and methanol (+10% NH$_4$OH) (95/5). The product resulting from the column purification is taken up in methanol and is purified by preparative thin layer chromatography (eluent: dichloromethane/methanol (+10% NH$_4$OH) (95/5)), so as to give 23 mg of 2-{[4-(1-methylpiperidin-4-yl)-2-(propan-2-yloxy)phenyl]amino}-7-(1H-pyrazol-4-yl)thieno[3,2-d]pyrimidine-6-carboxamide in the form of a yellow solid.

Example 12

7-(4-Fluorophenyl)-2-{[4-(4-methylpiperazin-1-yl)-2-(propan-2-yloxy)phenyl]amino}thieno[3,2-d]pyrimidine-6-carboxamide (I-12)

27 mg of sodium hydride (at 60%) are added to a solution of 126 mg of N-[4-(4-methylpiperazin-1-yl)-2-(propan-2-yloxy)phenyl]formamide in 2 ml of dimethylformamide. The suspension is stirred at ambient temperature for 30 min, and is then diluted with 1 ml of dimethylformamide, and a solution of 80 mg of 7-(4-fluorophenyl)-2-(methylsulfonyl)thieno[3,2-d]pyrimidine-6-carboxamide in 2 ml of dimethylformamide is added. The mixture is stirred at ambient temperature for 30 min, and then diluted with 50 ml of methanol. The mixture is stirred at ambient temperature for 1 h, and then concentrated under vacuum. The residue is purified on 40 g of silica, elution being carried out with 0-20% of methanol in dichloromethane, and then by high performance liquid chromatography (Macherey-Nagel 250×40 mm reverse phase C18 Nucleodur 10µ column. Eluent: MeCN containing 0.07% TFA and H$_2$O containing 0.07% TFA. 10% MeCN hold: 3 min, gradient up to 95% MeCN in 37 min and then 95% MeCN hold of 8 min. Flow rate: 70 ml/min). The fractions containing the expected material are loaded on to a 2 g Varian Bond Elut SCX cartraige (preconditioned with MeOH). Washing the cartridge four times with methanol, followed by elution of the expected material with 2N ammonia in methanol gives, after drying, 10 mg of 7-(4-fluorophenyl)-2-{[4-(4-methylpiperazin-1-yl)-2-(propan-2-yloxy)phenyl]amino}thieno[3,2-d]pyrimidine-6-carboxamide.

The compounds (I') obtained according to Examples 10 to 12 are described in Table 4.

TABLE 4

| Compound I' | Compound II | Compound IIIb | Name | NMR | MS conditions/MH+/Tr |
|---|---|---|---|---|---|
| I-1 | II-1 | IIIb-21 | 2-({2-Methoxy-4-[4-(pyrrolidin-1-yl)piperidin-1-yl]phenyl}amino)-7-phenylthieno[3,2-d]pyrimidine-6-carboxamide | 1.85 to 2.25 (m, 8 H); 2.88 (m, 1 H); 3.10 (m, 2 H); 3.23 to 3.858 (partially masked m, 6 H); 3.87 (s, 3 H); 6.55 to 7.00 (broad m, 2 H); 7.48 (t, J = 7.7 Hz, 1 H); 7.53 (t, J = 7.7 Hz, 2 H); 7.58 (broad s, 1 H); 7.68 (d, J = 7.7 Hz, 2 H); | E 529 0.78 |

TABLE 4-continued

| Compound I' | Compound II | Compound IIIb | Name | NMR | MS conditions/ MH+/Tr |
|---|---|---|---|---|---|
| | | | | 7.87 (broad s, 1 H); 8.02 (broad m, 1 H); 8.11 (broad s, 1 H); 9.21 (s, 1 H); 10.48 (broad m, 1 H) | |
| I-2 | II-1 | IIIb-22 | 2-({2-Methyl-4-[4-(pyrrolidin-1-yl)piperidin-1-yl]phenyl}amino)-7-phenylthieno[3,2-d]pyrimidine-6-carboxamide | 1.82 to 2.27 (m, 8 H); 2.20 (s, 3 H); 2.85 (m, 1 H); 3.10 (m, 2 H); 3.25 to 3.85 (partially masked m, 6 H); 6.80 to 7.10 (broad m, 2 H); 7.38 to 7.55 (m, 5 H); 7.60 (d, J = 7.7 Hz, 2 H); 7.84 (m, 1 H); 8.70 (s, 1 H); 9.16 (s, 1 H); 10.68 (broad m, 1 H) | E 513 0.70 |
| I-3 | II-3 | IIIb-21 | 7-(3-Chlorophenyl)-2-({2-methoxy-4-[4-(pyrrolidin-1-yl)piperidin-1-yl]phenyl}amino)thieno[3,2-d]pyrimidine-6-carboxamide | 1.78 to 2.30 (m, 8 H); 2.93 to 3.85 (m, 9 H); 3.81 (s, 3 H); 6.70 to 7.20 (broad m, 2 H); 7.45 (m, 3 H); 7.70 (s, 1 H); 7.79 (s, 1 H); 7.83 (s, 1 H); 8.09 (m, 1 H); 8.20 (s, 1 H); 9.19 (s, 1 H); 11.08 (broad m, 1 H) | E 563 1.03 |
| I-4 | II-4 | IIIb-21 | 7-(4-Chlorophenyl)-2-({2-methoxy-4-[4-(pyrrolidin-1-yl)piperidin-1-yl]phenyl}amino)thieno[3,2-d]pyrimidine-6-carboxamide | 1.80 to 2.23 (m, 8 H); 2.65 to 3.90 (partially masked m, 9 H); 3.82 (s, 3 H); 6.45 to 6.90 (broad m, 2 H); 7.58 (d, J = 8.8 Hz, 2 H); 7.67 (d, J = 8.8 Hz, 2 H); 7.77 (s, 1 H); 7.87 (m, 2 H); 8.12 (s, 1 H); 9.19 (s, 1 H); 11.70 (broad m, 1 H) | E 563 1.05 |
| I-5 | II-27 | IIIb-21 | 2-({2-Methoxy-4-[4-(pyrrolidin-1-yl)piperidin-1-yl]phenyl}amino)-7-(thiophen-3-yl)thieno[3,2-d]pyrimidine-6-carboxamide | 1.83 to 2.40 (m, 8 H); 3.00 to 3.92 (m, 9 H); 3.85 (s, 3 H); 6.70 to 7.22 (broad m, 2 H); 7.52 (d, J = 4.0 Hz, 1 H); 7.69 (m, 1 H); 7.82 (s, 1 H); 7.98 (s, 1 H); 8.07 (m, 1 H); 8.10 (broad m, 1 H); 8.30 (s, 1 H); 9.21 (s, 1 H); 11.09 (broad m, 1 H) | E 535 0.68 |
| I-6 | II-28 | IIIb-21 | 2-({2-Methoxy-4-[4-(pyrrolidin-1-yl)piperidin-1-yl]phenyl}amino)-7-(thiophen-2-yl)thieno[3,2-d]pyrimidine-6-carboxamide | 1.88 to 2.34 (m, 8 H); 3.00 to 3.94 (m, 9 H); 3.89 (s, 3 H); 6.78 to 7.22 (broad m, 2 H); 7.20 (m, 1 H); 7.63 (m, 1 H); 7.72 (m, 1 H); 8.02 (s, 1 H); 8.10 (s, 1 H); 8.22 (broad m, 1 H); 8.31 (s, 1 H); 9.21 (s, 1 H); 11.94 (broad m, 1 H) | E 535 0.69 |
| I-7 | II-1 | IIIb-23 | 2-({2-Methoxy-4-[4-(propan-2-yl)piperazin-1-yl]phenyl}amino)-7-phenylthieno[3,2-d]pyrimidine-6-carboxamide | 1.31 (d, J = 6.0 Hz, 6 H); 3.15 (m, 4 H); 3.50 (m, 3 H); 3.80 (m, 2 H); 3.84 (s, 3 H); 6.48 (broad d, J = 8.5 Hz, 1 H); 6.70 (broad s, 1 H); 7.46 (t, J = 7.6 Hz, 1 H); 7.51 (t, J = 7.6 Hz, 2 H); 7.58 (broad s, 1 H); 7.66 (d, J = 7.6 Hz, 2 H); 7.85 (broad s, 1 H); 7.98 (d, J = 8.5 Hz, 1 H); 8.10 (broad s, 1 H); 9.20 (s, 1 H); 10.55 (broad m, 1 H) | E 503 0.81 |
| I-8 | II-1 | IIIb-1 | 2-({2-Methoxy-4-[1-(propan-2-yl)piperidin-4-yl]phenyl}amino)-7-phenylthieno[3,2-d]pyrimidine-6-carboxamide | 1.00 (d, J = 6.4 Hz, 6 H); 1.55 to 1.69 (m, 2 H); 1.69 to 1.78 (m, 2 H); 2.13 to 2.25 (m, 2 H); 2.35 to 2.47 (m, 1 H); 2.70 (quin, J = 6 Hz, 1 H); 2.82 to 2.94 (m, 2 H); 3.85 (s, 3 H); 6.71 (dd, J = 1.5 and 8.3 Hz, 1 H); 6.89 (d, J = 1.5 Hz, 1 H); 7.40 to 7.59 (m, 4 H); 7.65 (d, J = 6.8 Hz, 2 H); 7.84 (broad s, 1 H); 8.05 (s, 1 H); 8.12 (d, J = 8.3 Hz, 1 H); 9.23 (s, 1 H) | A 502 0.65 |
| I-9 | II-5 | IIIb-25 | 7-(2-Methoxyphenyl)-2-{[4-(4-methylpiperazin-1-yl)-2-(propan-2-yloxy)phenyl]amino}thieno[3,2-d]pyrimidine-6-carboxamide | 1.26 (d, J = 6.1 Hz, 6 H); 2.23 (s, 3 H); 2.42 to 2.48 (m, 4 H); 3.01 to 3.10 (m, 4 H); 3.70 (s, 3 H); 4.65 (quin, J = 6.1 Hz, 1 H); 6.30 (dd, J = 2.4 and 8.8 Hz, 1 H); 6.61 (d, J = 2.4 Hz, 1 H); 6.82 to 6.93 (m, 1 H); 7.12 (t, J = 7.2 Hz, 1 H); 7.18 (d, J = 8.1 Hz, 1 H); 7.42 to 7.53 (m, 2 H); 7.71 (broad s, 1 H); 7.77 (s, 1 H); 7.97 (d, J = 9.0 Hz, 1 H); 9.16 (s, 1 H) | A 533 0.65 |
| I-10 | II-12 | IIIb-25 | 7-(4-Fluoro-3-methoxyphenyl)-2-{[4-(4-methylpiperazin-1-yl)-2-(propan-2-yloxy)phenyl]amino}thieno[3,2-d]pyrimidine-6-carboxamide | 1.25 (d, J = 6.1 Hz, 6 H); 2.23 (s, 3 H); 2.44 to 2.48 (m, 4 H); 3.02 to 3.12 (m, 4 H); 3.82 (s, 3 H); 4.65 (quin, J = 5.9 Hz, 1 H); 6.37 (dd, J = 2.3 and 8.9 Hz, 1 H); 6.64 (d, J = 2.2 Hz, 1 H); 7.17 (ddd, J = 2.0 and 4.3 and 8.4 Hz, 1 H); 7.35 (dd, J = 8.3 and 11.5 Hz, 1 H); 7.46 (dd, J = 2.0 and 8.6 Hz, 1 H); 7.59 (broad s, 1 H); 7.86 (broad s, 1 H); 7.91 (s, 1 H); 8.01 (d, J = 8.1 Hz, 1 H); 9.19 (s, 1 H) | A 551 0.67 |

TABLE 4-continued

| Compound I' | Compound II | Compound IIIb | Name | NMR | MS conditions/ MH+/Tr |
|---|---|---|---|---|---|
| I-11 | II-7 | IIIb-25 | 7-(4-Methoxyphenyl)-2-{[4-(4-methylpiperazin-1-yl)-2-(propan-2-yloxy)phenyl]amino}thieno[3,2-d]pyrimidine-6-carboxamide | 1.27 (d, J = 5.9 Hz, 6 H); 2.24 (s, 3 H); 2.44 to 2.48 (m, 4 H); 3.06 to 3.12 (m, 4 H); 3.84 (s, 3 H); 4.66 (spt, J = 6.1 Hz, 1 H); 6.43 (dd, J = 2.4 and 8.8 Hz, 1 H); 6.64 (d, J = 2.2 Hz, 1 H); 7.09 (d, J = 8.6 Hz, 2 H); 7.46 (broad s, 1 H); 7.60 (d, J = 8.6 Hz, 2 H); 7.81 (broad s, 1 H); 7.84 (s, 1 H); 8.06 (d, J = 8.8 Hz, 1 H); 9.16 (s, 1 H) | A 533 0.67 |
| I-12 | II-17 | IIIb-25 | 7-(4-Fluorophenyl)-2-{[4-(4-methylpiperazin-1-yl)-2-(propan-2-yloxy)phenyl]amino}thieno[3,2-d]pyrimidine-6-carboxamide | 1.27 (d, J = 5.9 Hz, 6 H); 2.23 (s, 3 H); 2.43 to 2.48 (m, 4 H); 3.05 to 3.12 (m, 4 H); 4.66 (spt, J = 6.1 Hz, 1 H); 6.44 (dd, J = 2.4 and 8.8 Hz, 1 H); 6.64 (d, J = 2.4 Hz, 1 H); 7.32 to 7.40 (m, 2 H); 7.62 to 7.73 (m, 3 H); 7.83 (broad s, 1 H); 7.87 (s, 1 H); 8.01 (d, J = 8.8 Hz, 1 H); 9.19 (s, 1 H) | A 521 0.67 |
| I-13 | II-1 | IIIb-2 | 2-{[2-Methoxy-5-methyl-4-(1-methylpiperidin-4-yl)phenyl]amino}-7-phenylthieno[3,2-d]pyrimidine-6-carboxamide | 1.49 to 1.80 (m, 4 H); 1.89 to 2.05 (m, 2 H); 2.13 (s, 3 H); 2.20 (s, 3 H); 2.53 to 2.64 (m, 1 H); 2.87 (d, J = 11.2 Hz, 2 H); 3.83 (s, 3 H); 6.82 (s, 1 H); 7.38 to 7.57 (m, 4 H); 7.59 to 7.70 (m, J = 6.8 Hz, 2 H); 7.85 (broad s, 1 H); 8.00 (d, J = 9.3 Hz, 2 H); 9.23 (s, 1 H) | A 488 0.62 |
| I-14 | II-10 | IIIb-24 | 7-(4-Fluoro-2-methoxyphenyl)-2-{[2-methoxy-4-(4-methylpiperazin-1-yl)phenyl]amino}thieno[3,2-d]pyrimidine-6-carboxamide | 2.23 (s, 3 H); 2.42 to 2.49 (m, 4 H); 3.04 to 3.14 (m, 4 H); 3.70 (s, 3 H); 3.80 (s, 3 H); 6.37 (dd, J = 2.4 and 9.0 Hz, 1 H); 6.61 (d, J = 2.4 Hz, 1 H); 6.94 (td, J = 2.4 and 8.4 Hz, 1 H); 7.01 to 7.16 (m, 2 H); 7.46 (dd, J = 7.1 and 8.6 Hz, 1 H); 7.72 (broad s, 1 H); 7.80 (d, J = 8.6 Hz, 1 H); 7.96 (s, 1 H); 9.14 (s, 1 H) | A 523 0.57 |
| I-15 | II-6 | IIIb-24 | 2-{[2-Methoxy-4-(4-methylpiperazin-1-yl)phenyl]amino}-7-(3-methoxyphenyl)thieno[3,2-d]pyrimidine-6-carboxamide | 2.23 (s, 3 H); 2.45 to 2.49 (m, 4 H); 3.08 to 3.13 (m, 4 H); 3.79 (s, 3 H); 3.81 (s, 3 H); 6.37 (dd, J = 2.3 and 8.7 Hz, 1 H); 6.63 (d, J = 2.4 Hz, 1 H); 7.02 (dd, J = 2.2 and 8.1 Hz, 1 H); 7.18 (d, J = 7.8 Hz, 1 H); 7.24 (s, 1 H); 7.41 (t, J = 7.8 Hz, 1 H); 7.59 (broad s, 1 H); 7.83 to 7.94 (m, 2 H); 8.04 (s, 1 H); 9.17 (s, 1 H) | A 505 0.58 |
| I-16 | II-5 | IIIb-3 | 7-(2-Methoxyphenyl)-2-{[4-(1-methylpiperidin-4-yl)-2-(propan-2-yloxy)phenyl]amino}thieno[3,2-d]pyrimidine-6-carboxamide | 1.29 (d, J = 6.1 Hz, 6 H); 1.56 to 1.74 (m, 4 H); 1.88 to 1.98 (m, 2 H); 2.19 (s, 3 H); 2.30 to 2.43 (m, 1 H); 2.80 to 2.90 (m, 2 H); 3.70 (s, 3 H); 4.67 (spt, J = 6.0 Hz, 1H); 6.60 (d, J = 8.3 Hz, 1 H); 6.87 (d, J = 1.2 Hz, 1 H); 6.90 (broad s, 1 H); 7.13 (t, J = 7.3 Hz, 1 H); 7.20 (d, J = 8.1 Hz, 1 H); 7.36 to 7.58 (m, 2 H); 7.73 (broad s, 1 H); 7.86 (s, 1 H); 8.13 (d, J = 8.3 Hz, 1 H); 9.21 (s, 1 H) | A 532 0.69 |
| I-17 | II-1 | IIIb-7 | 2-{[5-Methyl-4-(1-methylpiperidin-4-yl)-2-(propan-2-yloxy)phenyl]amino}-7-phenylthieno[3,2-d]pyrimidine-6-carboxamide | 1.29 (d, J = 5.9 Hz, 6 H); 1.53 to 1.75 (m, 4 H); 1.96 (td, J = 2.9 and 11.1 Hz, 2 H); 2.12 (s, 3 H); 2.19 (s, 3 H); 2.53 to 2.60 (m, 1 H); 2.82 to 2.91 (m, 2 H); 4.63 (quin, J = 6.1 Hz, 1 H); 6.82 (s, 1 H); 7.38 to 7.58 (m, 4 H); 7.67 (d, J = 7.3 Hz, 2 H); 7.80 to 7.95 (m, 2 H); 8.12 (s, 1 H); 9.25 (s, 1 H) | A 516 0.67 |
| I-18 | II-1 | IIIb-18 | 2-{[2-Methoxy-5-methyl-4-(1-methylpiperidin-3-yl)phenyl]amino}-7-phenylthieno[3,2-d]pyrimidine-6-carboxamide | 1.35 to 1.48 (m, 1 H); 1.54 to 1.74 (m, 3 H); 1.90 (t, J = 11.0 Hz, 2 H); 2.14 (s, 3 H); 2.18 (s, 3 H); 2.64 to 2.92 (m, 3 H); 3.83 (s, 3 H); 6.83 (s, 1 H); 7.42 to 7.56 (m, 4 H); 7.65 (d, J = 7.8 Hz, 2 H); 7.87 (broad s, 1 H); 8.00 (s, 1 H); 8.03 (s, 1 H); 9.24 (s, 1 H) | A 488 0.64 |
| I-19 | II-29 | IIIb-3 | 2-{[4-(1-Methylpiperidin-4-yl)-2-(propan-2-yloxy)phenyl]amino}-7-(1-methyl-1H-pyrazol-5-yl)thieno[3,2-d]pyrimidine-6-carboxamide | 1.28 (d, J = 5.9 Hz, 6 H); 1.57 to 1.76 (m, 4 H); 1.86 to 2.00 (m, 2 H); 2.19 (s, 3 H); 2.35 to 2.45 (m, 1 H); 2.80 to 2.90 (m, 2 H); 3.69 (s, 3 H); 4.66 (quin, J = 6.1 Hz, 1 H); 6.47 (d, J = 2.0 Hz, 1 H); 6.67 (dd, J = 1.7 and 8.3 Hz, 1 H); 6.89 (d, J = 1.5 Hz, 1 H); 7.44 (broad s, 1 H); 7.58 (d, J = 2.0 Hz, 1 H); 7.93 (broad s, 1 H); 8.00 (d, J = 8.3 Hz, 1 H); 8.05 (s, 1 H); 9.26 (s, 1 H) | A 506 0.61 |

TABLE 4-continued

| Compound I' | Compound II | Compound IIIb | Name | NMR | MS conditions/ MH+/Tr |
|---|---|---|---|---|---|
| I-20 | II-15 | IIIb-3 | 7-(2-Ethoxyphenyl)-2-{[4-(1-methylpiperidin-4-yl)-2-(propan-2-yloxy)phenyl]amino}thieno[3,2-d]pyrimidine-6-carboxamide | 1.13 (t, J = 7.0 Hz, 3 H); 1.29 (d, J = 6.1 Hz, 6 H); 1.56 to 1.74 (m, 4 H); 1.88 to 1.98 (m, 2 H); 2.19 (s, 3 H); 2.29 to 2.43 (m, 1 H); 2.80 to 2.88 (m, 2 H); 4.00 (q, J = 7.1 Hz, 2 H); 4.67 (quin, J = 6.1 Hz, 1 H); 6.60 (dd, J = 1.5 and 8.3 Hz, 1 H); 6.87 (d, J = 1.5 Hz, 1 H); 6.91 (broad s, 1 H); 7.06 to 7.21 (m, 2 H); 7.40 to 7.52 (m, 2 H); 7.73 (broad s, 1 H); 7.86 (s, 1 H); 8.15 (d, J = 8.3 Hz, 1 H); 9.21 (s, 1 H) | A 546 0.72 |
| I-21 | II-6 | IIIb-3 | 7-(3-Methoxyphenyl)-2-{[4-(1-methylpiperidin-4-yl)-2-(propan-2-yloxy)phenyl]amino}thieno[3,2-d]pyrimidine-6-carboxamide | 1.30 (d, J = 5.9 Hz, 6 H); 1.55 to 1.82 (m, 4 H); 1.93 to 2.08 (m, 2 H); 2.22 (broad s, 3 H); 2.35 to 2.47 (m, 1 H); 2.81 to 2.98 (m, 2 H); 3.81 (s, 3 H); 4.68 (quin, J = 5.4 Hz, 1 H); 6.66 (d, J = 8.1 Hz, 1 H); 6.90 (s, 1 H); 7.06 (dd, J = 2.0 and 8.3 Hz, 1 H); 7.21 (d, J = 7.8 Hz, 1 H); 7.28 (d, J = 1.7 Hz, 1 H); 7.44 (t, J = 7.8 Hz, 1 H); 7.56 (broad s, 1 H); 7.87 (broad s, 1 H); 7.95 (s, 1 H); 8.27 (d, J = 8.3 Hz, 1 H); 9.24 (s, 1 H) | A 532 0.70 |
| I-22 | II-50 | IIIb-7 | 2-{[5-Methyl-4-(1-methylpiperidin-4-yl)-2-(propan-2-yloxy)phenyl]amino}-7-(pyridin-2-yl)thieno[3,2-d]pyrimidine-6-carboxamide | 1.30 (d, J = 5.9 Hz, 6 H); 1.55 to 1.82 (m, 4 H); 1.93 to 2.08 (m, 2 H); 2.22 (broad s, 3 H); 2.35 to 2.47 (m, 1 H); 2.81 to 2.98 (m, 2 H); 3.81 (s, 3 H); 4.68 (quin, J = 5.4 Hz, 1 H); 6.66 (d, J = 8.1 Hz, 1 H); 6.90 (s, 1 H); 7.06 (dd, J = 2.0 and 8.3 Hz, 1 H); 7.21 (d, J = 7.8 Hz, 1 H); 7.28 (d, J = 1.7 Hz, 1 H); 7.44 (t, J = 7.8 Hz, 1 H); 7.56 (broad s, 1 H); 7.87 (broad s, 1 H); 7.95 (s, 1 H); 8.27 (d, J = 8.3 Hz, 1 H); 9.24 (s, 1 H) | B 517 0.78 |
| I-23 | II-1 | IIIb-32 | 2-{[4-(4-Methyl-1,4-diazepan-1-yl)-2-(propan-2-yloxy)phenyl]amino}-7-phenylthieno[3,2-d]pyrimidine-6-carboxamide | 1.25 (d, J = 6.1 Hz, 6 H); 1.89 (dq, J = 5.7 and 5.9 Hz, 2 H); 2.27 (s, 3 H); 2.45 (m, 2 H); 2.62 (m, 2 H); 3.31 to 3.51 (masked m, 4 H); 4.60 (qd, J = 5.9 and 6.0 Hz, 1 H); 6.17 (dd, J = 2.4 and 9.3 Hz, 1 H); 6.34 (d, J = 2.7 Hz, 1 H); 7.43 (m, 1 H); 7.51 (m, 3 H); 7.66 (d, J = 6.8 Hz, 2 H); 7.76 to 7.89 (m, 3 H); 9.14 (s, 1 H) | A 517 0.68 |
| I-24 | II-13 | IIIb-3 | 7-(2-Fluoro-5-methoxyphenyl)-2-{[4-(1-methylpiperidin-4-yl)-2-(propan-2-yloxy)phenyl]amino}thieno[3,2-d]pyrimidine-6-carboxamide | 1.29 (d, J = 5.9 Hz, 6 H); 1.65 (m, 4 H); 1.95 (m, 2 H); 2.19 (s, 3 H); 2.37 (m, 1 H); 2.85 (m, 2 H); 3.79 (s, 3 H); 4.67 (quin, J = 6.1 Hz, 1 H); 6.62 (dd, J = 2.0 and 8.3 Hz, 1 H); 6.89 (s, 1 H); 7.08 (dt, J = 3.5 and 9.0 Hz, 1 H); 7.20 (dd, J = 3.2 and 5.9 Hz, 1 H); 7.27 (t, J = 9.3 Hz, 1 H); 7.56 (broad s, 1 H); 7.77 (broad s, 1 H); 7.96 (s, 1 H); 8.19 (d, J = 8.3 Hz, 1 H); 9.26 (s, 1 H) | A 550 0.70 |
| I-25 | II-23 | IIIb-3 | 7-(3-Cyanophenyl)-2-{[4-(1-methylpiperidin-4-yl)-2-(propan-2-yloxy)phenyl]amino}thieno[3,2-d]pyrimidine-6-carboxamide | 1.30 (d, J = 5.9 Hz, 6 H); 1.59 to 1.76 (m, 4 H); 1.95 (td, J = 2.9 and 11.6 Hz, 2 H); 2.19 (s, 3 H); 2.39 (m, 1 H); 2.85 (d, J = 11.2 Hz, 2 H); 4.68 (spt, J = 6.2 Hz, 1 H); 6.81 (dd, J = 2.0 and 8.3 Hz, 1 H); 6.92 (d, J = 2.2 Hz, 1 H); 7.72 (t, J = 7.8 Hz, 1 H); 7.91 (m, 4 H); 8.03 (s, 1 H); 8.17 (d, J = 8.3 Hz, 1 H); 9.27 (s, 1 H) | A 527 0.68 |
| I-26 | II-19 | IIIb-3 | 2-{[4-(1-Methylpiperidin-4-yl)-2-(propan-2-yloxy)phenyl]amino}-7-[2-(trifluoromethoxy)phenyl]thieno[3,2-d]pyrimidine-6-carboxamide | 1.28 (d, J = 5.9 Hz, 6 H); 1.59 to 1.78 (m, 4 H); 2.11 (m, 2 H); 2.28 (broad s, 3 H); 2.42 (m, 1 H); 2.95 (m, 2 H); 4.66 (spt, J = 6.0 Hz, 1 H); 6.61 (dd, J = 1.7 and 8.1 Hz, 1 H); 6.88 (d, J = 2.0 Hz, 1 H); 7.46 (broad s, 1 H); 7.50 (dt, J = 1.6 and 8.1 Hz, 1 H); 7.56 (td, J = 1.2 and 7.3 Hz, 1 H); 7.62 (td, J = 2.0 and 7.6 Hz, 1 H); 7.69 (dd, J = 2.0 and 7.3 Hz, 1 H); 7.75 (broad s, 1 H); 7.93 (s, 1 H); 8.07 (d, J = 8.3 Hz, 1 H); 9.26 (s, 1 H) | A 586 0.76 |
| I-27 | II-1 | IIIb-3 | 2-{[4-(1-Methylpiperidin-4-yl)-2-(propan-2-yloxy)phenyl]amino}-7-phenylthieno[3,2-d]pyrimidine-6-carboxamide | 1.30 (d, J = 6.1 Hz, 6 H); 1.57 to 1.75 (m, 4 H); 1.94 (td, J = 2.4 and 11.4 Hz, 2 H); 2.19 (s, 3 H); 2.39 (m, 1 H); 2.86 (m, 2 H); 4.68 (spt, J = 6.1 Hz, 1 H); 6.68 (dd, J = 1.6 and 8.4 Hz, 1 H); 6.90 (d, J = 2.0 Hz, 1 H); 7.47 (t, J = 7.3 Hz, 1 H); | A 502 0.69 |

TABLE 4-continued

| Compound I' | Compound II | Compound IIIb | Name | NMR | MS conditions/ MH+/Tr |
|---|---|---|---|---|---|
| | | | | 7.55 (m, 3 H); 7.67 (d, J = 7.1 Hz, 2 H); 7.85 (broad s, 1 H); 7.94 (s, 1 H); 8.24 (d, J = 8.3 Hz, 1 H); 9.24 (s, 1 H) | |
| I-28 | II-1 | IIIb-33 | 2-({4-[(1S,4S)-5-methyl-2,5-diazabicyclo[2.2.1]hept-2-yl]-2-(propan-2-yloxy)phenyl}amino)-7-phenylthieno[3,2-d]pyrimidine-6-carboxamide | 1.25 (d, J = 5.9 Hz, 6 H); 1.74 to 1.98 (m, 2 H); 2.33 (broad s, 3 H); 2.61 (broad s, 1 H); 2.82 (m, 1 H); 3.13 (m, 1 H); 3.32 (masked m, 1 H); 3.51 (broad s, 1 H); 4.30 (broad s, 1 H); 4.61 (m, 1 H); 6.07 (d, J = 9.1 Hz, 1 H); 6.26 (broad s, 1 H); 7.32 to 7.60 (m, 4 H); 7.66 (d, J = 7.4 Hz, 2 H); 7.76 to 7.97 (m, 3 H); 9.14 (s, 1 H) | A 515 0.66 |
| I-29 | II-1 | IIIb-34 | 2-({4-[3-(Dimethylamino)pyrrolidin-1-yl]-2-(propan-2-yloxy)phenyl}amino)-7-phenylthieno[3,2-d]pyrimidine-6-carboxamide | 1.26 (d, J = 5.9 Hz, 6 H); 1.79 (m, 1 H); 2.12 (m, 1 H); 2.21 (s, 6 H); 2.79 (m, 1 H); 3.02 (t, J = 8.4 Hz, 1 H); 3.25 (masked m, 2 H); 3.41 (m, 1 H); 4.63 (m, 1 H); 6.03 (dd, J = 2.7 and 8.8 Hz, 1 H); 6.23 (d, J = 2.2 Hz, 1 H); 7.39 to 7.57 (m, 4 H); 7.66 (d, J = 7.1 Hz, 2 H); 7.79 (s, 1 H); 7.81 (broad s, 1 H); 7.92 (d, J = 8.3 Hz, 1 H); 9.14 (s, 1 H) | A 517 0.68 |
| I-30 | II-5 | IIIb-7 | 7-(2-Methoxyphenyl)-2-{[5-methyl-4-(1-methylpiperidin-4-yl)-2-(propan-2-yloxy)phenyl]amino}thieno[3,2-d]pyrimidine-6-carboxamide | 1.28 (d, J = 5.9 Hz, 6 H); 1.54 to 1.71 (m, 4 H); 1.95 (m, 2 H); 2.04 (s, 3 H); 2.19 (s, 3 H); 2.54 (masked m, 1 H); 2.85 (d, J = 11.0 Hz, 2 H); 3.69 (s, 3 H); 4.62 (m, 1 H); 6.79 (s, 1 H); 6.82 (broad s, 1 H); 7.13 (t, J = 7.3 Hz, 1 H); 7.20 (d, J = 8.1 Hz, 1 H); 7.48 (m, 2 H); 7.74 (broad s, 1 H); 7.81 (s, 1 H); 8.02 (s, 1 H); 9.21 (s, 1 H) | A 546 0.67 |
| I-31 | II-1 | IIIb-51 | 2-{[4-Methoxy-2-(propan-2-yloxy)phenyl]amino}-7-phenylthieno[3,2-d]pyrimidine-6-carboxamide | 1.28 (d, J = 6.1 Hz, 6 H); 3.73 (s, 3 H); 4.64 (spt, J = 6.0 Hz, 1 H); 6.40 (dd, J = 2.3 and 8.9 Hz, 1 H); 6.63 (d, J = 2.2 Hz, 1 H); 7.46 (t, J = 7.1 Hz, 1 H); 7.53 (m, 3 H); 7.66 (d, J = 7.3 Hz, 2 H); 7.83 (broad s, 1 H); 7.90 (s, 1 H); 8.09 (d, J = 8.8 Hz, 1 H); 9.20 (s, 1 H) | A 435 1.06 |
| I-32 | II-25 | IIIb-3 | 2-{[4-(1-Methylpiperidin-4-yl)-2-(propan-2-yloxy)phenyl]amino}-7-[3-(methylsulfinyl)phenyl]thieno[3,2-d]pyrimidine-6-carboxamide | 1.29 (d, J = 5.9 Hz, 6 H); 1.55 to 1.78 (m, 4 H); 1.91 to 2.02 (m, 2 H); 2.20 (s, 3 H); 2.34 to 2.45 (m, 1 H); 2.79 (s, 3 H); 2.82 to 2.93 (m, 2 H); 4.68 (spt, J = 5.9 Hz, 1 H); 6.72 (dd, J = 1.5 and 8.3 Hz, 1 H); 6.89 (d, J = 1.2 Hz, 1 H); 7.67 to 7.81 (m, 4 H); 7.88 (broad s, 1 H); 7.92 to 8.01 (m, 2 H); 8.16 (d, J = 8.3 Hz, 1 H); 9.27 (s, 1 H) | A 564 0.62 |
| I-33 | II-31 | IIIb-3 | 7-(2-Methoxypyridin-3-yl)-2-{[4-(1-methylpiperidin-4-yl)-2-(propan-2-yloxy)phenyl]amino}thieno[3,2-d]pyrimidine-6-carboxamide | 1.29 (d, J = 6.1 Hz, 6 H); 1.53 to 1.77 (m, 4 H); 1.91 to 2.05 (m, 2 H); 2.21 (s, 3 H); 2.34 to 2.46 (m, 1 H); 2.78 to 2.95 (m, 2 H); 3.80 (s, 3 H); 4.67 (spt, J = 6.1 Hz, 1 H); 6.64 (d, J = 8.3 Hz, 1 H); 6.88 (s, 1 H); 7.18 (dd, J = 5.0 and 7.2 Hz, 1 H); 7.47 (broad s, 1 H); 7.70 (broad s, 1 H); 7.86 to 7.95 (m, 2 H); 8.11 (d, J = 8.1 Hz, 1 H); 8.28 (dd, J = 1.7 and 4.9 Hz, 1 H); 9.23 (s, 1 H) | A 533 0.64 |
| I-34 | II-22 | IIIb-3 | 7-(2-Cyanophenyl)-2-{[4-(1-methylpiperidin-4-yl)-2-(propan-2-yloxy)phenyl]amino}thieno[3,2-d]pyrimidine-6-carboxamide | 1.31 (d, J = 6.1 Hz, 6 H); 1.62 to 1.80 (m, 4 H); 2.03 (m, 2 H); 2.24 (s, 3 H); 2.44 (partially masked m, 1 H); 2.91 (m, 2 H); 4.70 (m, 1 H); 6.81 (dd, J = 1.3 and 8.6 Hz, 1 H); 6.95 (d, J = 1.3 Hz, 1 H); 7.64 (t, J = 7.8 Hz, 1 H); 7.78 (t, J = 7.8 Hz, 1 H); 7.88 (d, J = 7.8 Hz, 1 H); 8.13 (s, 1 H); 8.26 (d, J = 8.6 Hz, 1 H); 8.46 (s, 1 H); 8.52 (s, 1 H); 8.80 (d, J = 7.8 Hz, 1 H); 9.28 (s, 1 H) | A 525 0.64 |
| I-35 | II-1 | IIIb-37 | 2-{[4-(1H-Imidazol-1-yl)-2-(propan-2-yloxy)phenyl]amino}-7-phenylthieno[3,2-d]pyrimidine-6-carboxamide | 1.35 (d, J = 5.9 Hz, 6 H); 4.87 (spt, J = 6.1 Hz, 1 H); 7.07 (m, 2 H); 7.31 (d, J = 2.4 Hz, 1 H); 7.48 (t, J = 7.3 Hz, 1 H); 7.58 (m, 3 H); 7.69 (d, J = 6.8 Hz, 2 H); 7.71 (s, 1 H); 7.87 (broad s, 1 H); 8.10 (s, 1 H); 8.21 (s, 1 H); 8.46 (d, J = 8.8 Hz, 1 H); 9.30 (s, 1 H) | A 471 0.68 |
| I-36 | II-1 | IIIb-43 | 2-{[4-{Methyl[2-(pyrrolidin-1-yl)ethyl]amino}-2-(propan-2-yloxy)phenyl]amino}-7- | (70-30 conformer mixture): 1.27 (d, J = 6.4 Hz, 6 H); 1.74 (m, 4 H); 2.66 (m, 6 H); 2.87 (s, 3 H); 3.40 (t, J = 7.1 Hz, 2 H); 4.56 (m, 1 H); 6.21 (dd, J = 2.9 and | A 531 0.71 |

TABLE 4-continued

| Compound I' | Compound II | Compound IIIb | Name | NMR | MS conditions/ MH+/Tr |
|---|---|---|---|---|---|
| | | | phenylthieno[3,2-d]pyrimidine-6-carboxamide | 8.8 Hz, 0.7 H); 6.26 (m, 0.3 H); 6.37 (d, J = 2.4 Hz, 0.3 H); 6.40 (d, J = 2.9 Hz, 0.7 H); 7.34 to 7.55 (m, 5 H); 7.65 (m, 3 H); 7.92 (d, J = 8.8 Hz, 1 H) 9.11 (s, 1 H) | |
| I-37 | II-5 | IIIb-54 | 7-(2-Methoxyphenyl)-2-{[6-(4-methylpiperazin-1-yl)-4-(propan-2-yloxy)pyridin-3-yl]amino}thieno[3,2-d]pyrimidine-6-carboxamide | 1.19 (d, J = 5.9 Hz, 6 H); 2.25 (s, 3 H); 2.43 (broad s, 4 H); 3.42 (broad s, 4 H); 3.69 (s, 3 H); 4.75 (spt, J = 5.9 Hz, 1 H); 6.38 (s, 1 H); 6.74 (broad s, 1 H); 7.05 (t, J = 7.5 Hz, 1 H); 7.13 (d, J = 8.1 Hz, 1 H); 7.38 (dd, J = 1.7 and 7.6 Hz, 1 H); 7.40 to 7.47 (m, 1 H); 7.69 (broad s, 1 H); 7.97 (s, 1 H); 8.27 (s, 1 H); 9.09 (s, 1 H) | A 534 0.46 |
| I-38 | II-5 | IIIb-55 | 7-(2-Methoxyphenyl)-2-{[6-(1-methylpiperidin-4-yl)-4-(propan-2-yloxy)pyridin-3-yl]amino}thieno[3,2-d]pyrimidine-6-carboxamide | 1.25 (d, J = 5.9 Hz, 6 H); 1.70 to 1.78 (m, 4 H); 1.88 to 2.00 (m, 2 H); 2.19 (s, 3 H); 2.52 to 2.56 (m, 1 H); 2.79 to 2.92 (m, 2 H); 3.70 (s, 3 H); 4.78 (quin, J = 6.4 Hz, 1 H); 6.80 (broad s, 1 H); 6.89 (s, 1 H); 7.07 (t, J = 7.3 Hz, 1 H); 7.15 (d, J = 8.1 Hz, 1 H); 7.40 (dd, J = 1.2 and 7.6 Hz, 1 H); 7.43 to 7.49 (m, 1 H); 7.72 (broad s, 1 H); 8.07 (s, 1 H); 8.82 (s, 1 H); 9.19 (s, 1 H) | A 533 0.44 |
| I-39 | II-11 | IIIb-3 | 7-(5-Fluoro-2-methoxyphenyl)-2-{[4-(1-methylpiperidin-4-yl)-2-(propan-2-yloxy)phenyl]amino}thieno[3,2-d]pyrimidine-6-carboxamide | 1.29 (d, J = 6.1 Hz, 6 H); 1.57 to 1.75 (m, 4 H); 1.95 (m, 2 H); 2.20 (s, 3 H); 2.38 (m, 1 H); 2.86 (m, 2 H); 3.68 (s, 3 H); 4.67 (spt, J = 6.2 Hz, 1 H); 6.62 (dd, J = 1.5 and 8.3 Hz, 1 H); 6.88 (d, J = 1.5 Hz, 1 H); 7.15 (dd, J = 4.6 and 9.3 Hz, 1 H); 7.25 (broad s, 1 H); 7.30 (td, J = 3.2 and 8.8 Hz, 1 H); 7.37 (dd, J = 3.2 and 9.3 Hz, 1 H); 7.70 (broad s, 1 H); 7.92 (s, 1 H); 8.16 (d, J = 8.3 Hz, 1 H); 9.22 (s, 1 H) | A 550 0.70 |
| I-40 | II-9 | IIIb-3 | 7-(3-Fluoro-2-methoxyphenyl)-2-{[4-(1-methylpiperidin-4-yl)-2-(propan-2-yloxy)phenyl]amino}thieno[3,2-d]pyrimidine-6-carboxamide | 1.27 (d, J = 6.1 Hz, 6 H); 1.56 to 1.73 (m, 4 H); 1.94 (m, 2 H); 2.19 (s, 3 H); 2.37 (m, 1 H); 2.85 (m, 2 H); 3.65 (m, 3 H); 4.65 (spt, J = 6.0 Hz, 1 H); 6.60 (dd, J = 1.5 and 8.8 Hz, 1 H); 6.87 (d, J = 1.0 Hz, 1 H); 7.26 (m, 3 H); 7.39 (ddd, J = 2.3 and 7.7 and 12.0 Hz, 1 H); 7.76 (broad s, 1 H); 7.92 (s, 1 H); 8.06 (d, J = 8.3 Hz, 1 H); 9.23 (s, 1 H) | A 550 0.69 |
| I-41 | II-24 | IIIb-3 | 2-{[4-(1-Methylpiperidin-4-yl)-2-(propan-2-yloxy)phenyl]amino}-7-[2-(methylsulfinyl)phenyl]thieno[3,2-d]pyrimidine-6-carboxamide | (70/30 rotamer mixture): 1.25 (m, 6 H); 1.56 to 1.71 (m, 4 H); 1.93 (m, 2 H); 2.18 (s, 3 H); 2.35 (m, 1.9 H); 2.54 (s, 2.1 H); 2.84 (d, J = 11.0 Hz, 2 H); 4.62 (m, 1 H); 6.47 (d, J = 9.3 Hz, 0.7 H); 6.55 (d, J = 8.6 Hz, 0.3 H); 6.84 (s, 1 H); 7.24 (broad s, 1 H); 7.37 (d, J = 7.1 Hz, 0.7 H); 7.46 (d, J = 7.1 Hz, 0.3 H); 7.64 (t, J = 7.5 Hz, 0.7 H); 7.70 (d, J = 7.8 Hz, 0.3H); 7.75 to 7.94 (m, 3.7 H); 8.06 (m, 1.3 H); 9.92 (m, 1 H) | A 564 0.60 |
| I-42 | II-5 | IIIb-34 | 2-({4-[3-(Dimethylamino)pyrrolidin-1-yl]-2-(propan-2-yloxy)phenyl}amino)-7-(2-methoxyphenyl)thieno[3,2-d]pyrimidine-6-carboxamide | 1.26 (d, J = 6.1 Hz, 6 H); 1.79 (m, 1 H); 2.11 (m, 1 H); 2.21 (s, 6 H); 2.47 (masked m, 1 H); 2.78 (quin, J = 7.8 Hz, 1 H); 3.00 (t, J = 8.3 Hz, 1 H); 3.19 (m, 1 H); 3.38 (t, J = 8.1 Hz, 1 H); 3.70 (s, 3 H); 4.62 (spt, J = 6.0 Hz, 1 H); 5.94 (dd, J = 1.8 and 8.4 Hz, 1 H); 6.21 (d, J = 2.4 Hz, 1 H); 6.82 (broad s, 1 H); 7.11 (t, J = 7.1 Hz, 1 H); 7.17 (d, J = 8.3 Hz, 1 H); 7.47 (m, 2 H); 7.68 (m, 2 H); 7.83 (d, J = 8.6 Hz, 1 H); 9.11 (s, 1 H) | A 547 0.67 |
| I-43 | II-5 | IIIb-43 | 7-(2-Methoxyphenyl)-2-{[4-{methyl[2-(pyrrolidin-1-yl)ethyl]amino}-2-(propan-2-yloxy)phenyl]amino}thieno[3,2-d]pyrimidine-6-carboxamide | 1.26 (d, J = 6.1 Hz, 6 H); 1.68 (m, 4 H); 2.48 (masked m, 4 H); 2.54 (m, 2 H); 2.86 (s, 3 H); 3.38 (t, J = 7.5 Hz, 2 H); 3.70 (s, 3 H); 4.58 (spt, J = 6.1 Hz, 1 H); 6.10 (dd, J = 2.4 and 8.6 Hz, 1 H); 6.35 (d, J = 2.2 Hz, 1 H); 6.84 (broad s, 1 H); 7.10 (t, J = 7.5 Hz, 1 H); 7.16 (d, J = 8.3 Hz, 1 H); 7.44 (m, 2 H); 7.70 (m, 2 H); 7.83 (d, J = 8.6 Hz, 1 H); 9.12 (s, 1 H) | A 561 0.70 |

TABLE 4-continued

| Compound I' | Compound II | Compound IIIb | Name | NMR | MS conditions/ MH+/Tr |
|---|---|---|---|---|---|
| I-44 | II-14 | IIIb-3 | 7-(2-Fluoro-3-methoxyphenyl)-2-{[4-(1-methylpiperidin-4-yl)-2-(propan-2-yloxy)phenyl]amino}thieno[3,2-d]pyrimidine-6-carboxamide | 1.29 (d, J = 6.1 Hz, 6 H); 1.66 (m, 4 H); 1.95 (m, 2 H); 2.20 (s, 3 H); 2.37 (m, 1 H); 2.86 (m, 2 H); 3.93 (s, 3 H); 4.67 (spt, J = 6.0 Hz, 1 H); 6.61 (dd, J = 1.6 and 7.9 Hz, 1 H); 6.88 (d, J = 2.0 Hz, 1 H); 7.13 (m, 1 H); 7.28 (m, 2 H); 7.53 (broad s, 1 H); 7.77 (broad s, 1 H); 7.93 (s, 1 H); 8.15 (d, J = 8.3 Hz, 1 H); 9.25 (s, 1 H) | A 550 0.69 |
| I-45 | II-5 | IIIb-19 | 2-{[4-(1-Ethylpiperidin-3-yl)-2-(propan-2-yloxy)phenyl]amino}-7-(2-methoxyphenyl)thieno[3,2-d]pyrimidine-6-carboxamide | 1.00 (t, J = 7.1 Hz, 3 H); 1.29 (d, J = 6.1 Hz, 6 H); 1.40 (m, 1 H); 1.51 (m, 1 H); 1.73 (m, 2 H); 1.89 (m, 2 H); 2.34 (q, J = 7.1 Hz, 2 H); 2.65 (m, 1 H); 2.85 (t, J = 11.1 Hz, 2 H); 3.70 (s, 3 H); 4.67 (spt, J = 6.0 Hz, 1 H); 6.61 (d, J = 9.0 Hz, 1 H); 6.85 to 6.94 (m, 2 H); 7.13 (t, J = 7.5 Hz, 1 H); 7.20 (d, J = 8.1 Hz, 1 H); 7.48 (m, 2 H); 7.73 (broad s, 1 H); 7.87 (s, 1 H); 8.12 (d, J = 8.1 Hz, 1 H); 9.21 (s, 1 H) | A 546 0.72 |
| I-46 | II-16 | IIIb-3 | 7-(2-Fluorophenyl)-2-{[4-(1-methylpiperidin-4-yl)-2-(propan-2-yloxy)phenyl]amino}thieno[3,2-d]pyrimidine-6-carboxamide | 1.29 (d, J = 5.9 Hz, 6 H); 1.65 (m, 4 H); 1.93 (m, 2 H); 2.19 (s, 3 H); 2.38 (m, 1 H); 2.85 (d, J = 11.2 Hz, 2 H); 4.67 (spt, J = 5.9 Hz, 1 H); 6.64 (d, J = 8.8 Hz, 1 H); 6.88 (s, 1 H); 7.36 (m, 2 H); 7.58 (m, 3 H); 7.78 (broad s, 1 H); 7.94 (s, 1 H); 8.15 (d, J = 8.3 Hz, 1 H); 9.26 (s, 1 H) | A 520 0.69 |
| I-47 | II-32 | IIIb-3 | 2-{[4-(1-Methylpiperidin-4-yl)-2-(propan-2-yloxy)phenyl]amino}-7-(1H-pyrrol-2-yl)thieno[3,2-d]pyrimidine-6-carboxamide | 1.27 (d, J = 5.9 Hz, 6 H); 1.71 (m, 4 H); 1.96 (m, 2 H); 2.20 (s, 3 H); 2.43 (m, 1 H); 2.87 (m, 2 H); 4.66 (spt, J = 6.0 Hz, 1 H); 6.20 (q, J = 2.9 Hz, 1 H); 6.83 (dd, J = 1.7 and 8.1 Hz, 1 H); 6.94 (m, 3 H); 7.95 to 8.04 (m, 3 H); 8.33 (s, 1 H); 9.19 (s, 1 H); 11.74 (broad s, 1 H) | A 491 0.56 |
| I-48 | II-26 | IIIb-3 | 7-[2-Fluoro-5-(hydroxymethyl)phenyl]-2-{[4-(1-methylpiperidin-4-yl)-2-(propan-2-yloxy)phenyl]amino}thieno[3,2-d]pyrimidine-6-carboxamide | 1.30 (d, J = 5.9 Hz, 6 H); 1.56 to 1.74 (m, 4 H); 1.95 (m, 2 H); 2.19 (s, 3 H); 2.36 (m, 1 H); 2.85 (d, J = 11.5 Hz, 2 H); 4.59 (d, J = 5.6 Hz, 2 H); 4.68 (spt, J = 6.1 Hz, 1 H); 5.30 (t, J = 5.9 Hz, 1 H); 6.68 (dd, J = 1.0 and 7.6 Hz, 1 H); 6.88 (d, J = 1.5 Hz, 1 H); 7.30 (dd, J = 8.6 and 10.0 Hz, 1 H); 7.43 to 7.53 (m, 1 H); 7.53 to 7.61 (m, 2 H); 7.75 (broad s, 1 H); 7.93 (s, 1 H); 8.17 (d, J = 8.3 Hz, 1 H); 9.26 (s, 1 H) | A 550 0.64 |
| I-49 | II-5 | IIIb-8 | 2-{[4-(5-Methoxy-1-methyl-1,2,3,6-tetrahydropyridin-4-yl)-2-(propan-2-yloxy)phenyl]amino}-7-(2-methoxyphenyl)thieno[3,2-d]pyrimidine-6-carboxamide | 1.31 (d, J = 6.4 Hz, 6 H); 2.30 (broad s, 3 H); 2.39 (m, 2 H); 2.47 (masked m, 2 H); 3.02 (broad s, 2 H); 3.43 (broad s, 3 H); 3.71 (broad s, 3 H); 4.62 (s, 1 H); 6.76 (d, J = 9.3 Hz, 1 H); 6.91 (broad s, 1 H); 7.10 (m, 2 H); 7.19 (dd, J = 0.6 and 7.9 Hz, 1 H); 7.46 (m, 2 H); 7.74 (broad s, 1 H); 7.91 (d, J = 0.7 Hz, 1 H); 8.18 (d, J = 7.8 Hz, 1 H); 9.23 (broad s, 1 H) | C 560 3.58 |
| I-50 | II-10 | IIIb-25 | 7-(4-Fluoro-2-methoxyphenyl)-2-{[4-(4-methylpiperazin-1-yl)-2-(propan-2-yloxy)phenyl]amino}thieno[3,2-d]pyrimidine-6-carboxamide | 1.26 (d, J = 5.9 Hz, 6 H); 2.22 (s, 3 H); 2.45 (t, J = 4.9 Hz, 4 H); 3.06 (t, J = 4.6 Hz, 4 H); 3.71 (s, 3 H); 4.65 (spt, J = 6.0 Hz, 1 H); 6.36 (dd, J = 2.6 and 8.9 Hz, 1 H); 6.62 (d, J = 2.4 Hz, 1 H); 6.95 (td, J = 2.6 and 8.5 Hz, 1 H); 7.04 (broad s, 1 H); 7.08 (dd, J = 2.4 and 11.5 Hz, 1 H); 7.48 (dd, J = 7.0 and 8.4 Hz, 1 H); 7.69 (broad s, 1 H); 7.78 (s, 1 H); 7.95 (d, J = 9.0 Hz, 1 H); 9.15 (s, 1 H) | C 551 3.39 |
| I-51 | II-5 | IIIb-37 | 2-{[4-(1H-Imidazol-1-yl)-2-(propan-2-yloxy)phenyl]amino}-7-(2-methoxyphenyl)thieno[3,2-d]pyrimidine-6-carboxamide | 1.34 (d, J = 6.0 Hz, 6 H); 3.72 (s, 3 H); 4.87 (m, 1 H); 6.94 (broad s, 1 H); 6.98 (dd, J = 2.5 and 8.7 Hz, 1 H); 7.08 (t, J = 1.2 Hz, 1 H); 7.16 (m, 1 H); 7.21 (d, J = 7.8 Hz, 1 H); 7.29 (d, J = 2.5 Hz, 1 H); 7.48 (m, 2 H); 7.69 (t, J = 1.4 Hz, 1 H); 7.76 (broad s, 1 H); 8.03 (s, 1 H); 8.18 (t, J = 1.2 Hz, 1 H); 8.35 (d, J = 8.7 Hz, 1 H); 9.27 (s, 1 H) | C 501 3.46 |
| I-52 | II-5 | IIIb-58 | 2-Methylpropan-2-yl 4-[5-{[6-carbamoyl-7-(2-methoxyphenyl)thieno[3,2-d]pyrimidin-2-yl]amino}-1-(propan-2-yl)-1H- | 1.23 (d, J = 6.4 Hz, 6 H); 1.32 (m, 2 H); 1.45 (s, 9 H); 1.70 (m, 2 H); 2.62 (m, 1 H); 2.74 to 2.89 (m, 2 H); 3.66 (s, 3 H); 3.99 (m, 2 H); 4.54 (m, 1 H); 6.03 (s, 1 H); 6.72 (broad s, 1 H); 7.05 (t, J = 7.0 Hz, | A 592 0.99 |

| Compound I' | Compound II | Compound IIIb | Name | NMR | MS conditions/ MH+/Tr |
|---|---|---|---|---|---|
| | | | pyrazol-3-yl]piperidine-1-carboxylate | 1 H); 7.13 (d, J = 7.6 Hz, 1 H); 7.37 (dd, J = 1.7 and 7.6 Hz, 1 H); 7.45 (ddd, J = 1.7 and 7.2 and 8.5 Hz, 1 H); 7.75 (broad s, 1 H); 9.22 (s, 1 H); 9.44 (broad s, 1 H) | |
| I-53 | II-5 | IIIb-9 | 7-(2-Methoxyphenyl)-2-{[2-(propan-2-yloxy)-4-(2,2,6,6-tetramethylpiperidin-4-yl)phenyl]amino}thieno[3,2-d]pyrimidine-6-carboxamide | 1.10 (m, 6 H); 1.23 (m, 6 H); 1.29 (m, 2 H); 1.30 (d, J = 6.1 Hz, 6 H); 1.59 (m, 2 H); 2.96 (m, 1 H); 3.71 (s, 3 H); 4.68 (spt, J = 6.1 Hz, 1 H); 6.60 (dd, J = 1.2 and 8.3 Hz, 1 H); 6.89 (m, 2 H); 7.14 (td, J = 1.0 and 7.5 Hz, 1 H); 7.20 (d, J = 7.8 Hz, 1 H); 7.45 (m, 2 H); 7.73 (broad s, 1 H); 7.88 (s, 1 H); 8.14 (d, J = 8.3 Hz, 1 H); 9.22 (s, 1 H) | A 574 0.79 |
| I-54 | II-5 | IIIb-11 | 2-{[4-(2,6-Dimethylpiperidin-4-yl)-2-(propan-2-yloxy)phenyl]amino}-7-(2-methoxyphenyl)thieno[3,2-d]pyrimidine-6-carboxamide | (60/40 diastereoisomer mixture) 0.90 to 1.12 (m, 8.6 H); 1.29 (dd, J = 2.6 and 6.0 Hz, 6 H); 1.41 (m, 0.4 H); 1.63 (m, 0.6 H); 1.99 (d, J = 13.9 Hz, 0.4 H); 2.56 (s, 1 H); 2.64 to 2.82 (m, 2 H); 3.68 to 3.73 (m, 3 H); 4.53 to 4.72 (m, 1 H); 6.57 (dd, J = 1.2 and 7.6 Hz, 0.6 H); 6.70 (d, J = 8.6 Hz, 0.4 H); 6.82 to 6.96 (m, 2 H); 7.08 to 7.22 (m, 2 H); 7.42 to 7.56 (m, 2 H); 7.73 (broad s, 1 H); 7.87 (d, J = 10.5 Hz, 1 H); 8.03 to 8.16 (m, 1 H); 9.21 (s, 1 H) | A 546 0.75 |
| I-55 | II-5 | IIIb-12 | 2-{[4-(2-Ethylpiperidin-4-yl)-2-(propan-2-yloxy)phenyl]amino}-7-(2-methoxyphenyl)thieno[3,2-d]pyrimidine-6-carboxamide | (50/50 diastereoisomer mixture) 0.88 (t, J = 7.4 Hz, 3 H); 1.06 to 1.83 (m, 12 H); 2.35 to 2.43 (m, 0.5 H); 2.52 to 2.86 (m, 5 H); 3.04 (m, 0.5 H); 3.70 (s, 3 H); 4.66 (spt, J = 6.0 Hz, 1 H); 6.57 (m, 1 H); 6.86 (d, J = 8.8 Hz, 1 H); 6.91 (broad s, 1 H); 7.13 (t, J = 7.4 Hz, 1 H); 7.20 (d, J = 8.2 Hz, 1 H); 7.48 (m, 2 H); 7.74 (broad s, 1 H); 7.87 (s, 1 H); 8.13 (d, J = 8.5 Hz, 1 H); 9.21 (s, 1 H) | C 546 3.72 and 3.75 |
| I-56 | II-5 | IIIb-4 | 7-(2-Methoxyphenyl)-2-{[4-(piperidin-4-yl)-2-(propan-2-yloxy)phenyl]amino}thieno[3,2-d]pyrimidine-6-carboxamide | 1.30 (d, J = 6.1 Hz, 6 H); 1.49 (qd, J = 3.9 and 12.3 Hz, 2 H); 1.65 (m, 2 H); 2.48 (masked m, 1 H); 2.59 (m, 2 H); 3.03 (m, 2 H); 3.70 (s, 3 H); 4.66 (spt, J = 6.1 Hz, 2 H); 6.58 (dd, J = 1.7 and 8.6 Hz, 1 H); 6.85 (d, J = 1.2 Hz, 1 H); 6.90 (broad s, 1 H); 7.13 (td, J = 1.1 and 7.4 Hz, 1 H); 7.20 (d, J = 7.6 Hz, 1 H); 7.48 (m, 2 H); 7.74 (broad s, 1 H); 7.87 (s, 1 H); 8.14 (d, J = 8.3 Hz, 1 H); 9.21 (s, 1 H) | A 518 0.68 |
| I-57 | II-10 | IIIb-3 | 7-(4-Fluoro-2-methoxyphenyl)-2-{[4-(1-methylpiperidin-4-yl)-2-(propan-2-yloxy)phenyl]amino}thieno[3,2-d]pyrimidine-6-carboxamide | 1.29 (d, J = 6.0 Hz, 6 H); 1.54 to 1.77 (m, 4 H); 1.97 (td, J = 3.4 and 11.2 Hz, 2 H); 2.20 (s, 3 H); 2.39 (m, 1 H); 2.87 (d, J = 11.8 Hz, 2 H); 3.71 (s, 3 H); 4.67 (spt, J = 6.1 Hz, 1 H); 6.66 (dd, J = 1.7 and 8.4 Hz, 1 H); 6.88 (d, J = 1.7 Hz, 1 H); 6.96 (td, J = 2.5 and 8.5 Hz, 1 H); 7.10 (, 1 H); 7.10 (dd, J = 2.6 and 11.6 Hz, 1 H); 7.49 (dd, J = 7.1 and 8.3 Hz, 1 H); 7.72 (broad s, 1 H); 7.88 (s, 1 H); 8.13 (d, J = 8.4 Hz, 1 H); 9.21 (s, 1 H) | A 550 0.68 |
| I-58 | II-5 | IIIb-27 | 2-{[4-(3,5-Dimethylpiperazin-1-yl)-2-(propan-2-yloxy)phenyl]amino}-7-(2-methoxyphenyl)thieno[3,2-d]pyrimidine-6-carboxamide | 1.13 (m, 6 H); 1.27 (d, J = 6.1 Hz, 6 H); 2.19 (m, 2 H); 2.89 to 3.13 (m, 2 H); 3.52 (broad s, 2 H); 3.70 (s, 3 H); 4.66 (spt, J = 6.1 Hz, 1 H); 6.32 (d, J = 9.0 Hz, 1 H); 6.64 (broad s, 1 H); 6.86 (broad s, 1 H); 7.13 (t, J = 7.3 Hz, 1 H); 7.18 (d, J = 8.3 Hz, 1 H); 7.47 (m, 2 H); 7.71 (broad s, 1 H); 7.78 (s, 1 H); 7.96 (d, J = 8.6 Hz, 1 H); 9.16 (s, 1 H) | A 547 0.69 |
| I-59 | II-5 | IIIb-28 | 7-(2-Methoxyphenyl)-2-{[2-(propan-2-yloxy)-4-(3,4,5-trimethylpiperazin-1-yl)phenyl]amino}thieno[3,2-d]pyrimidine-6-carboxamide | 1.06 (s, 3 H); 1.08 (s, 3 H); 1.26 (d, J = 5.9 Hz, 6 H); 2.19 (s, 3 H); 2.29 (m, 4 H); 3.43 (d, J = 10.8 Hz, 2 H); 3.70 (s, 3 H); 4.66 (spt, J = 6.0 Hz, 1 H); 6.29 (dd, J = 2.3 and 8.7 Hz, 1 H); 6.61 (dd, J = 0.5 and 2.2 Hz, 1 H); 6.85 (broad s, 1 H); 7.13 (t, J = 7.5 Hz, 1 H); 7.18 (d, J = 7.8 Hz, 1 H); 7.47 (m, 2 H); 7.71 (broad s, 1 H); 7.77 (s, 1 H); 7.93 (d, J = 8.8 Hz, 1 H); 9.15 (s, 1 H) | A 561 0.70 |

TABLE 4-continued

| Compound I' | Compound II | Compound IIIb | Name | NMR | MS conditions/ MH+/Tr |
|---|---|---|---|---|---|
| I-60 | II-5 | IIIb-44 | 2-({4-[(8aR)-Hexahydropyrrolo[1,2-a]pyrazin-2(1H)-yl]-2-(propan-2-yloxy)phenyl}amino)-7-(2-methoxyphenyl)thieno[3,2-d]pyrimidine-6-carboxamide | 1.26 (d, J = 6.1 Hz, 6 H); 1.37 (m, 1 H); 1.71 (m, 2 H); 1.83 (m, 1 H); 2.06 (m, 2 H); 2.23 (td, J = 3.2 and 11.1 Hz, 1 H); 2.34 (m, 1 H); 2.67 (td, J = 3.2 and 11.5 Hz, 1 H); 3.00 (m, 2 H); 3.51 (d, J = 11.2 Hz, 1 H); 3.66 (d, J = 10.5 Hz, 1 H); 3.70 (s, 3 H); 4.65 (spt, J = 6.1 Hz, 1 H); 6.31 (dd, J = 2.4 and 9.0 Hz, 1 H); 6.63 (d, J = 2.7 Hz, 1 H); 6.86 (broad s, 1 H); 7.13 (t, J = 7.5 Hz, 1 H); 7.19 (d, J = 7.6 Hz, 1 H); 7.46 (m, 2 H); 7.71 (broad s, 1 H); 7.76 (s, 1 H); 7.96 (d, J = 9.0 Hz, 1 H); 9.15 (s, 1 H) | A 559 0.69 |
| I-61 | II-5 | IIIb-58 | 7-(2-Methoxyphenyl)-2-{[3-(piperidin-4-yl)-1-(propan-2-yl)-1H-pyrazol-5-yl]amino}thieno[3,2-d]pyrimidine-6-carboxamide | 1.23 (d, J = 6.4 Hz, 6 H); 1.68 (m, 2 H); 1.97 (m, 2 H); 2.79 (m, 1 H); 2.98 (m, 2 H); 3.30 (m, 2 H); 3.67 (s, 3 H); 4.52 (spt, J = 6.0 Hz, 1 H); 6.01 (s, 1 H); 6.73 (broad s, 1 H); 7.09 (t, J = 7.3 Hz, 1 H); 7.17 (d, J = 8.3 Hz, 1 H); 7.35 (dd, J = 1.2 and 7.6 Hz, 1 H); 7.47 (t, J = 7.3 Hz, 1 H); 7.78 (broad s, 1 H); 8.49 (m, 1 H); 8.83 (m, 1 H); 9.22 (s, 1 H); 9.44 (s, 1 H) | A 492 0.52 |
| I-62 | II-5 | IIIb-19 | 2-({4-[(3R)-1-Ethylpiperidin-3-yl]-2-(propan-2-yloxy)phenyl}amino)-7-(2-methoxyphenyl)thieno[3,2-d]pyrimidine-6-carboxamide | 1.00 (t, J = 7.2 Hz, 3 H); 1.29 (d, J = 5.9 Hz, 6 H); 1.40 (m, 1 H); 1.55 (ddd, J = 3.8 and 3.9 and 12.3 Hz, 1 H); 1.72 (m, 2 H); 1.89 (m, 2 H); 2.34 (q, J = 7.1 Hz, 2 H); 2.64 (m, 1 H); 2.84 (m, 2 H); 3.70 (s, 3 H); 4.67 (spt, J = 6.1 Hz, 1 H); 6.61 (dd, J = 1.7 and 8.6 Hz, 1 H); 6.90 (broad s, 1 H); 6.90 (d, J = 2.0 Hz, 1 H); 7.13 (td, J = 1.0 and 7.5 Hz, 1 H); 7.20 (d, J = 7.6 Hz, 1 H); 7.47 (m, 2 H); 7.73 (broad s, 1 H); 7.87 (s, 1 H); 8.12 (d, J = 8.3 Hz, 1 H); 9.21 (s, 1 H) | A 546 0.73 |
| I-63 | II-5 | IIIb-19 | 2-({4-[(3S)-1-Ethylpiperidin-3-yl]-2-(propan-2-yloxy)phenyl}amino)-7-(2-methoxyphenyl)thieno[3,2-d]pyrimidine-6-carboxamide | 1.00 (t, J = 7.1 Hz, 3 H); 1.29 (d, J = 5.9 Hz, 6 H); 1.40 (qd, J = 3.7 and 12.1 Hz, 1 H); 1.53 (m, 1 H); 1.72 (m, 2 H); 1.90 (m, 2 H); 2.34 (q, J = 7.3 Hz, 2 H); 2.64 (m, 1 H); 2.84 (m, 2 H); 3.70 (s, 3 H); 4.67 (spt, J = 6.0 Hz, 1 H); 6.61 (dd, J = 1.5 and 8.1 Hz, 1 H); 6.90 (broad s, 1 H); 6.90 (d, J = 1.5 Hz, 1 H); 7.13 (td, J = 1.1 and 7.4 Hz, 1 H); 7.20 (d, J = 7.6 Hz, 1 H); 7.49 (m, 2 H); 7.73 (broad s, 1 H); 7.87 (s, 1 H); 8.12 (d, J = 8.3 Hz, 1 H); 9.21 (s, 1 H) | A 546 0.73 |
| I-64 | II-27 | IIIb-3 | 2-{[4-(1-Methylpiperidin-4-yl)-2-(propan-2-yloxy)phenyl]amino}-7-(thiophen-3-yl)thieno[3,2-d]pyrimidine-6-carboxamide | 1.29 (d, J = 5.9 Hz, 6 H); 1.68 (m, 4 H); 1.96 (m, 2 H); 2.19 (s, 3 H); 2.41 (m, 1 H); 2.86 (m, 2 H); 4.68 (spt, J = 6.1 Hz, 1 H); 6.76 (dt, J = 1.0 and 8.3 Hz, 1 H); 6.92 (d, J = 2.0 Hz, 1 H); 7.53 (dd, J = 1.3 and 5.0 Hz, 1 H); 7.70 (dd, J = 2.9 and 5.1 Hz, 1 H); 7.78 (broad s, 1 H); 7.92 (broad s, 1 H); 8.02 (m, 2 H); 8.20 (d, J = 8.3 Hz, 1 H); 9.22 (s, 1 H) | A 508 0.68 |
| I-65 | II-33 | IIIb-3 | 7-(5-Fluoro-2-methoxypyridin-4-yl)-2-{[4-(1-methylpiperidin-4-yl)-2-(propan-2-yloxy)phenyl]amino}thieno[3,2-d]pyrimidine-6-carboxamide | 1.27 (m, 6 H); 1.55 to 1.83 (m, 4 H); 1.92 to 2.35 (m, 6 H); 2.83 to 3.02 (m, 2 H); 3.94 (broad s, 3 H); 4.66 (m, 1 H); 6.67 (d, J = 8.6 Hz, 1 H); 6.90 (broad s, 1 H); 7.11 (m, 1 H); 7.80 (m, 2 H); 8.04 (broad s, 1 H); 8.12 (d, J = 8.3 Hz, 1 H); 8.26 (broad s, 1 H); 9.28 (broad s, 1 H) | A 551 0.67 |
| I-66 | II-5 | IIIb-15 | 7-(2-Methoxyphenyl)-2-({2-(propan-2-yloxy)-4-[(2R,4S)-2-(propan-2-yl)piperidin-4-yl]phenyl}amino)thieno[3,2-d]pyrimidine-6-carboxamide | 0.89 (t, J = 7.3 Hz, 6 H); 1.15 (m, 1 H); 1.29 (d, J = 5.9 Hz, 6 H); 1.39 to 1.72 (m, 4 H); 2.35 (m, 1 H); 2.53 (d, J = 6.6 Hz, 1 H); 2.65 (m, 1 H); 3.09 (m, 1 H); 3.70 (s, 3 H); 4.66 (spt, J = 6.0 Hz, 1 H); 6.59 (dd, J = 1.6 and 8.2 Hz, 1 H); 6.85 (d, J = 1.5 Hz, 1 H); 6.90 (broad s, 1 H); 7.13 (t, J = 7.5 Hz, 1 H); 7.19 (d, J = 7.8 Hz, 1 H); 7.49 (m, 2 H); 7.73 (broad s, 1 H); 7.87 (s, 1 H); 8.12 (d, J = 8.1 Hz, 1 H); 9.21 (s, 1 H) | A 560 0.77 |

TABLE 4-continued

| Compound I' | Compound II | Compound IIIb | Name | NMR | MS conditions/ MH+/Tr |
|---|---|---|---|---|---|
| I-67 | II-5 | IIIb-15 | 7-(2-Methoxyphenyl)-2-({2-(propan-2-yloxy)-4-[(2R,4R)-2-(propan-2-yl)piperidin-4-yl]phenyl}amino)thieno[3,2-d]pyrimidine-6-carboxamide | 0.86 (d, J = 6.6 Hz, 3 H); 0.92 (d, J = 6.6 Hz, 3 H); 1.30 (d, J = 6.1 Hz, 6 H); 1.55 to 1.82 (m, 4 H); 1.94 (m, 1 H); 2.38 (m, 1 H); 2.61 to 2.91 (m, 3 H); 3.70 (s, 3 H); 4.64 (spt, J = 6.0 Hz, 1 H); 6.62 (d, J = 8.3 Hz, 1 H); 6.87 (s, 1 H); 6.90 (broad s, 1 H); 7.13 (t, J = 7.5 Hz, 1 H); 7.19 (d, J = 8.3 Hz, 1 H); 7.49 (m, 2 H); 7.73 (broad s, 1 H); 7.87 (s, 1 H); 8.13 (d, J = 8.3 Hz, 1 H); 9.21 (s, 1 H) | A 560 0.77 |
| I-68 | II-2 | IIIb-3 | 7-(2-Chlorophenyl)-2-{[4-(1-methylpiperidin-4-yl)-2-(propan-2-yloxy)phenyl]amino}thieno[3,2-d]pyrimidine-6-carboxamide | 1.28 (d, J = 6.1 Hz, 6 H); 1.63 (m, 4 H); 1.93 (m, 2 H); 2.19 (s, 3 H); 2.36 (m, 1 H); 2.84 (m, 2 H); 4.66 (spt, J = 6.1 Hz, 1 H); 6.54 (dd, J = 2.0 and 8.3 Hz, 1 H); 6.86 (d, J = 2.0 Hz, 1 H); 7.19 (broad s, 1 H); 7.52 (m, 3 H); 7.63 (m, 1 H); 7.79 (broad s, 1 H); 7.91 (s, 1 H); 8.01 (d, J = 8.3 Hz, 1 H); 9.25 (s, 1 H) | A 536 0.71 |
| I-69 | II-31 | IIIb-44 | 2-({4-[(8aR)-Hexahydropyrrolo[1,2-a]pyrazin-2(1H)-yl]-2-(propan-2-yloxy)phenyl}amino)-7-(2-methoxypyridin-3-yl)thieno[3,2-d]pyrimidine-6-carboxamide | 1.26 (d, J = 5.9 Hz, 6 H); 1.32 to 1.58 (m, 1 H); 1.65 to 1.76 (m, 1 H); 1.83 (m, 1 H); 2.06 (m, 2 H); 2.23 (m, 1 H); 2.34 (m, 2 H); 2.67 (m, 1 H); 3.02 (m, 2 H); 3.53 (d, J = 11.7 Hz, 1 H); 3.68 (d, J = 11.7 Hz, 1 H); 3.80 (s, 3 H); 4.66 (spt, J = 6.0 Hz, 1 H); 6.35 (d, J = 8.8 Hz, 1 H); 6.64 (d, J = 1.5 Hz, 1 H); 7.17 (dd, J = 5.1 and 7.6 Hz, 1 H); 7.46 (broad s, 1 H); 7.68 (broad s, 1 H); 7.82 (s, 1 H); 7.92 (m, 2 H); 8.26 (d, J = 2.9 Hz, 1 H); 9.18 (s, 1 H) | A 560 0.64 |
| I-70 | II-5 | IIIb-58 | 2-{[3-(1-Ethylpiperidin-4-yl)-1-(propan-2-yl)-1H-pyrazol-5-yl]amino}-7-(2-methoxyphenyl)thieno[3,2-d]pyrimidine-6-carboxamide | 1.04 (t, J = 7.1 Hz, 3 H); 1.22 (d, J = 6.8 Hz, 6 H); 1.48 (m, 2 H); 1.73 (m, 2 H); 1.91 (m, 2 H); 2.37 (m, 3 H); 2.91 (d, J = 11.7 Hz, 2 H); 3.66 (s, 3 H); 4.48 (spt, J = 6.0 Hz, 1 H); 6.00 (s, 1 H); 6.71 (broad s, 1 H); 7.08 (t, J = 7.6 Hz, 1 H); 7.14 (d, J = 8.3 Hz, 1 H); 7.36 (d, J = 7.3 Hz, 1 H); 7.43 (t, J = 7.8 Hz, 1 H); 7.75 (broad s, 1 H); 9.21 (s, 1 H); 9.34 (s, 1 H) | A 520 0.53 |
| I-71 | II-3 | IIIb-3 | 7-(3-Chlorophenyl)-2-{[4-(1-methylpiperidin-4-yl)-2-(propan-2-yloxy)phenyl]amino}thieno[3,2-d]pyrimidine-6-carboxamide | 1.30 (d, J = 5.9 Hz, 6 H); 1.67 (m, 4 H); 1.95 (td, J = 2.3 and 11.8 Hz, 2 H); 2.19 (s, 3 H); 2.40 (m, 1 H); 2.86 (m, 2 H); 4.69 (spt, J = 6.1 Hz, 1 H); 6.76 (dd, J = 2.0 and 8.3 Hz, 1 H); 6.91 (d, J = 1.5 Hz, 1 H); 7.55 (m, 3 H); 7.81 (d, J = 1.5 Hz, 1 H); 7.84 (broad s, 1 H); 7.88 (broad s, 1 H); 8.00 (s, 1 H); 8.24 (d, J = 8.3 Hz, 1 H); 9.26 (s, 1 H) | A 536 0.73 |
| I-72 | II-21 | IIIb-3 | 7-(2-Methylphenyl)-2-{[4-(1-methylpiperidin-4-yl)-2-(propan-2-yloxy)phenyl]amino}thieno[3,2-d]pyrimidine-6-carboxamide | 1.27 (d, J = 6.1 Hz, 6 H); 1.55 to 1.71 (m, 4 H); 1.93 (m, 2H); 2.11 (s, 3 H); 2.19 (s, 3 H); 2.36 (m, 1 H); 2.85 (d, J = 11.7 Hz, 2 H); 4.64 (spt, J = 6.0 Hz, 1 H); 6.52 (dd, J = 1.5 and 8.3 Hz, 1 H); 6.63 (broad s, 1 H); 6.86 (d, J = 1.0 Hz, 1 H); 7.33 (m, 2 H); 7.44 (m, 2 H); 7.84 (broad s, 1 H); 7.90 (s, 1 H); 7.95 (d, J = 8.3 Hz, 1 H); 9.24 (s, 1 H) | A 516 0.73 |
| I-73 | II-34 | IIIb-3 | 2-{[4-(1-Methylpiperidin-4-yl)-2-(propan-2-yloxy)phenyl]amino}-7-(1-methyl-1H-pyrazol-4-yl)thieno[3,2-d]pyrimidine-6-carboxamide | 1.29 (d, J = 5.9 Hz, 6 H); 1.72 (m, 4 H); 1.96 (t, J = 10.5 Hz, 2 H); 2.20 (s, 3 H); 2.45 (m, 1 H); 2.87 (d, J = 11.5 Hz, 2 H); 3.92 (s, 3 H); 4.69 (m, 1 H); 6.84 (d, J = 7.8 Hz, 1 H); 6.95 (s, 1 H); 7.90 (broad s, 1 H); 7.97 (m, 2 H); 8.08 (s, 1 H); 8.14 (d, J = 8.3 Hz, 1 H); 8.32 (s, 1 H); 9.18 (s, 1 H) | A 506 0.60 |
| I-74 | II-8 | IIIb-3 | 7-(2,5-Dimethoxyphenyl)-2-{[4-(1-methylpiperidin-4-yl)-2-(propan-2-yloxy)phenyl]amino}thieno[3,2-d]pyrimidine-6-carboxamide | 1.29 (d, J = 5.9 Hz, 6 H); 1.53 to 1.75 (m, 4 H); 1.94 (m, 2 H); 2.19 (s, 3 H); 2.37 (m, 1 H); 2.85 (m, 2 H); 3.65 (s, 3 H); 3.77 (s, 3 H); 4.67 (spt, J = 5.9 Hz, 1 H); 6.59 (d, J = 8.3 Hz, 1 H); 6.88 (s, 1 H); 6.97 (broad s, 1 H); 7.07 (m, 3 H); 7.72 (broad s, 1 H); 7.88 (s, 1 H); 8.18 (d, J = 8.3 Hz, 1 H); 9.21 (s, 1 H) | A 562 0.69 |

TABLE 4-continued

| Compound I' | Compound II | Compound IIIb | Name | NMR | MS conditions/ MH+/Tr |
|---|---|---|---|---|---|
| I-75 | II-18 | IIIb-3 | 7-[2-(Difluoromethoxy)phenyl]-2-{[4-(1-methylpiperidin-4-yl)-2-(propan-2-yloxy)phenyl]amino}thieno[3,2-d]pyrimidine-6-carboxamide | 1.27 (d, J = 6.1 Hz, 6 H); 1.66 to 1.90 (m, 4 H); 2.38 to 2.57 (partially masked m, 6 H); 3.20 (m, 2 H); 4.62 (m, 1 H); 6.61 (dd, J = 1.3 and 8.5 Hz, 1 H); 6.86 (d, J = 1.3 Hz, 1 H); 6.92 (t, J = 74.1 Hz, 1 H); 7.32 (d, J = 7.8 Hz, 1 H); 7.35 (broad s, 1 H); 7.40 (t, J = 7.8 Hz, 1 H); 7.52 to 7.59 (m, 2 H); 7.77 (broad s, 1 H); 8.01 (m, 2 H); 9.24 (s, 1 H) | A 568 0.70 |
| I-76 | II-35 | IIIb-3 | 2-{[4-(1-Methylpiperidin-4-yl)-2-(propan-2-yloxy)phenyl]amino}-7-(1H-pyrazol-4-yl)thieno[3,2-d]pyrimidine-6-carboxamide | 1.30 (d, J = 5.9 Hz, 6 H); 1.74 (m, 4 H); 2.03 (t, J = 10.5 Hz, 2 H); 2.24 (s, 3 H); 2.44 (m, 1 H); 2.92 (m, 2 H); 4.68 (spt, J = 6.1 Hz, 1 H); 6.81 (dd, J = 1.5 and 8.3 Hz, 1 H); 6.94 (d, J = 1.5 Hz, 1 H); 7.91 (m, 2 H); 8.05 (s, 1 H); 8.19 (m, 3 H); 9.19 (s, 1 H); 12.96 (broad s, 1 H) | A 492 0.59 |
| I-77 | II-5 | IIIb-30 | 2-({4-[3-(2-Hydroxyethyl)-4-methylpiperazin-1-yl]-2-(propan-2-yloxy)phenyl}amino)-7-(2-methoxyphenyl)thieno[3,2-d]pyrimidine-6-carboxamide | 1.26 (d, J = 6.1 Hz, 6 H); 1.52 (dq, J = 7.0 and 14.0 Hz, 1 H); 1.77 (m, 1 H); 2.26 (m, 5 H); 2.48 (masked m, 1 H); 2.74 (m, 2 H); 3.38 (m, 2 H); 3.53 (t, J = 6.7 Hz, 2 H); 3.70 (s, 3 H); 4.44 (broad s, 1 H); 4.64 (spt, J = 6.0 Hz, 1 H); 6.30 (dd, J = 2.3 and 8.9 Hz, 1 H); 6.60 (d, J = 2.4 Hz, 1 H); 6.86 (broad s, 1 H); 7.12 (t, J = 7.5 Hz, 1 H); 7.18 (d, J = 8.3 Hz, 1 H); 7.47 (m, 2 H); 7.71 (broad s, 1 H); 7.77 (s, 1 H); 7.94 (d, J = 9.0 Hz, 1 H); 9.15 (s, 1 H) | A 577 0.64 |
| I-78 | II-31 | IIIb-7 | 7-(2-methoxypyridin-3-yl)-2-{[5-methyl-4-(1-methylpiperidin-4-yl)-2-(propan-2-yloxy)phenyl]amino}thieno[3,2-d]pyrimidine-6-carboxamide | 1.28 (d, J = 5.9 Hz, 6 H); 1.64 (m, 4 H); 1.96 (t, J = 10.3 Hz, 2 H); 2.09 (s, 3 H); 2.19 (s, 3 H); 2.55 (m, 1 H); 2.86 (d, J = 10.8 Hz, 2 H); 3.79 (s, 3 H); 4.62 (spt, J = 6.0 Hz, 1 H); 6.81 (s, 1 H); 7.16 (dd, J = 5.4 and 11.7 Hz, 1 H); 7.46 (broad s, 1 H); 7.71 (broad s, 1 H); 7.86 (s, 1 H); 7.91 (d, J = 6.8 Hz, 1 H); 8.00 (s, 1 H); 8.27 (d, J = 3.9 Hz, 1 H); 9.24 (s, 1 H) | A 547 0.63 |
| I-79 | II-31 | IIIb-25 | 7-(2-Methoxypyridin-3-yl)-2-{[4-(4-methylpiperazin-1-yl)-2-(propan-2-yloxy)phenyl]amino}thieno[3,2-d]pyrimidine-6-carboxamide | 1.26 (d, J = 5.9 Hz, 6 H); 2.22 (s, 3 H); 2.44 (m, 4 H); 3.05 (m, 4 H); 3.80 (s, 3 H); 4.65 (spt, J = 6.0 Hz, 1 H); 6.34 (dd, J = 2.3 and 8.9 Hz, 1 H); 6.62 (d, J = 2.4 Hz, 1 H); 7.17 (dd, J = 4.9 and 7.3 Hz, 1 H); 7.45 (broad s, 1 H); 7.67 (broad s, 1 H); 7.83 (s, 1 H); 7.90 (dd, J = 2.0 and 7.3 Hz, 1 H); 7.94 (d, J = 8.8 Hz, 1 H); 8.26 (dd, J = 2.0 and 5.1 Hz, 1 H); 9.18 (s, 1 H) | A 534 0.60 |
| I-80 | II-5 | IIIb-16 | 2-({4-[1-(2-Hydroxyethyl)piperidin-4-yl]-2-(propan-2-yloxy)phenyl}amino)-7-(2-methoxyphenyl)thieno[3,2-d]pyrimidine-6-carboxamide | 1.29 (d, J = 5.9 Hz, 6 H); 1.64 (m, 4 H); 2.07 (m, 2 H); 2.41 (m, 3 H); 2.98 (d, J = 10.8 Hz, 2 H); 3.52 (broad s, 2 H); 3.70 (s, 3 H); 4.37 (broad s, 1 H); 4.67 (spt, J = 6.0 Hz, 1 H); 6.60 (d, J = 7.8 Hz, 1 H); 6.87 (s, 1 H); 6.92 (broad s, 1 H); 7.13 (t, J = 7.1 Hz, 1 H); 7.20 (d, J = 8.3 Hz, 1 H); 7.49 (m, 2 H); 7.75 (broad s, 1 H); 7.87 (s, 1 H); 8.14 (d, J = 8.3 Hz, 1 H); 9.21 (s, 1 H) | A 562 0.67 |
| I-81 | II-5 | IIIb-48 | 7-(2-Methoxyphenyl)-2-{[4-(3-methoxypyridin-4-yl)-2-(propan-2-yloxy)phenyl]amino}thieno[3,2-d]pyrimidine-6-carboxamide | 1.35 (d, J = 5.9 Hz, 6 H); 3.72 (s, 3 H); 3.91 (s, 3 H); 4.72 (spt, J = 6.0 Hz, 1 H); 6.96 (broad s, 1 H); 6.98 (dd, J = 1.7 and 8.6 Hz, 1 H); 7.15 (t, J = 7.5 Hz, 1 H); 7.21 (d, J = 8.3 Hz, 1 H); 7.26 (d, J = 1.7 Hz, 1 H); 7.37 (d, J = 4.6 Hz, 1 H); 7.51 (m, 2 H); 7.76 (broad s, 1 H); 8.04 (s, 1 H); 8.26 (d, J = 4.6 Hz, 1 H); 8.37 (d, J = 8.3 Hz, 1 H); 8.43 (s, 1 H); 9.29 (s, 1 H) | A 542 0.78 |
| I-82 | II-5 | IIIb-56 | 7-(2-Methoxyphenyl)-2-{[6-(4-methylpiperazin-1-yl)-2-(propan-2-yloxy)pyridin-3-yl]amino}thieno[3,2-d]pyrimidine-6-carboxamide | 1.27 (d, J = 6.1 Hz, 6 H); 2.22 (s, 3 H); 2.40 (t, J = 4.7 Hz, 4 H); 3.37 (m, 4 H); 3.70 (s, 3 H); 5.19 (spt, J = 6.1 Hz, 1 H); 6.16 (d, J = 8.5 Hz, 1 H); 6.85 (broad s, 1 H); 7.11 (t, J = 7.4 Hz, 1 H); 7.17 (d, J = 8.2 Hz, 1 H); 7.42 (d, J = 7.4 Hz, 1 H); 7.47 (t, J = 7.2 Hz, 1 H); 7.73 (broad s, 1 H); 7.83 (s, 1 H); 8.02 (d, J = 7.7 Hz, 1 H); 9.15 (s, 1 H) | A 534 0.68 |

TABLE 4-continued

| Compound I' | Compound II | Compound IIIb | Name | NMR | MS conditions/ MH+/Tr |
|---|---|---|---|---|---|
| I-83 | II-5 | IIIb-10 | 7-(2-Methoxyphenyl)-2-{[4-(1,2,2,6,6-pentamethylpiperidin-4-yl)-2-(propan-2-yloxy)phenyl]amino}thieno[3,2-d]pyrimidine-6-carboxamide | 1.11 (m, 12 H); 1.30 (d, J = 5.9 Hz, 6 H); 1.56 (m, J = 12.7 Hz, 4 H); 2.14 to 2.29 (m, 3 H); 2.88 (broad s, 1 H); 3.71 (s, 3 H); 4.69 (spt, J = 5.9 Hz, 1 H); 6.61 (d, J = 8.8 Hz, 1 H); 6.91 (m, 2 H); 7.14 (t, J = 7.3 Hz, 1 H); 7.20 (d, J = 8.3 Hz, 1 H); 7.49 (m, 2 H); 7.74 (broad s, 1 H); 7.88 (s, 1 H); 8.15 (d, J = 8.3 Hz, 1 H); 9.22 (s, 1 H) | A 588 0.78 |
| I-84 | II-5 | IIIb-13 | 2-({4-[(2S,4S)-2-Ethyl-1-methylpiperidin-4-yl]-2-(propan-2-yloxy)phenyl}amino)-7-(2-methoxyphenyl)thieno[3,2-d]pyrimidine-6-carboxamide | 0.84 (t, J = 7.3 Hz, 3 H); 1.30 (d, J = 5.9 Hz, 6 H); 1.33 to 1.70 (m, 6 H); 1.86 (m, 1 H); 2.12 (m, 1 H); 2.18 (s, 3 H); 2.44 (m, 1 H); 2.89 (dt, J = 2.9 and 11.2 Hz, 1 H); 3.71 (s, 3 H); 4.68 (spt, J = 6.1 Hz, 1 H); 6.60 (dd, J = 1.6 and 8.4 Hz, 1 H); 6.87 (d, J = 1.5 Hz, 1 H); 6.90 (broad s, 1 H); 7.14 (t, J = 7.5 Hz, 1 H); 7.20 (d, J = 7.8 Hz, 1 H); 7.49 (m, 2 H); 7.74 (broad s, 1 H); 7.87 (s, 1 H); 8.13 (d, J = 8.3 Hz, 1 H); 9.22 (s, 1 H) | A 560 0.74 |
| I-85 | II-5 | IIIb-13 | 2-({4-[(2S,4R)-2-Ethyl-1-methylpiperidin-4-yl]-2-(propan-2-yloxy)phenyl}amino)-7-(2-methoxyphenyl)thieno[3,2-d]pyrimidine-6-carboxamide | 0.86 (t, J = 7.5 Hz, 3 H); 1.30 (dd, J = 1.2 and 6.1 Hz, 6 H); 1.43 to 1.84 (m, 6 H); 2.30 (s, 3 H); 2.45 (m, 1 H); 2.55 to 2.74 (m, 3 H); 3.71 (s, 3 H); 4.68 (spt, J = 5.9 Hz, 1 H); 6.62 (dd, J = 1.7 and 8.6 Hz, 1 H); 6.89 (d, J = 1.7 Hz, 1 H); 6.92 (broad s, 1 H); 7.14 (t, J = 7.5 Hz, 1 H); 7.20 (d, J = 8.1 Hz, 1 H); 7.49 (m, 2 H); 7.74 (broad s, 1 H); 7.87 (s, 1 H); 8.13 (d, J = 8.1 Hz, 1 H); 9.22 (s, 1 H) | A 560 0.76 |
| I-86 | II-31 | IIIb-5 | 7-(2-Methoxypyridin-3-yl)-2-({2-(propan-2-yloxy)-4-[1-(propan-2-yl)piperidin-4-yl]phenyl}amino)thieno[3,2-d]pyrimidine-6-carboxamide | 1.00 (d, J = 6.4 Hz, 6 H); 1.30 (d, J = 5.9 Hz, 6 H); 1.58 (m, 2 H); 1.72 (m, 2 H); 2.20 (t, J = 10.6 Hz, 2 H); 2.40 (m, J = 12.0 Hz, 1 H); 2.72 (m, 1 H); 2.88 (d, J = 9.3 Hz, 2 H); 3.80 (s, 3 H); 4.68 (m, 1 H); 6.64 (d, J = 8.1 Hz, 1 H); 6.88 (s, 1 H); 7.19 (t, J = 5.9 Hz, 1 H); 7.48 (broad s, 1 H); 7.70 (broad s, 1 H); 7.92 (m, 2 H); 8.11 (d, J = 8.1 Hz, 1 H); 8.28 (d, J = 3.7 Hz, 1 H); 9.24 (s, 1 H) | A 561 0.69 |
| I-87 | II-36 | IIIb-3 | 7-(5-Fluoro-2-methoxypyridin-3-yl)-2-{[4-(1-methylpiperidin-4-yl)-2-(propan-2-yloxy)phenyl]amino}thieno[3,2-d]pyrimidine-6-carboxamide | 1.29 (d, J = 5.9 Hz, 6 H); 1.56 to 1.75 (m, 4 H); 1.98 (t, J = 11.0 Hz, 2 H); 2.21 (s, 3 H); 2.40 (m, 1 H); 2.87 (d, J = 11.2 Hz, 2 H); 3.78 (s, 3 H); 4.67 (spt, J = 6.1 Hz, 1 H); 6.64 (dd, J = 1.5 and 8.3 Hz, 1 H); 6.89 (d, J = 1.7 Hz, 1 H); 7.66 (m, 2 H); 7.93 (dd, J = 2.9 and 8.8 Hz, 1 H); 7.99 (s, 1 H); 8.09 (d, J = 8.3 Hz, 1 H); 8.26 (d, J = 3.2 Hz, 1 H); 9.25 (s, 1 H) | A 551 0.67 |
| I-88 | II-36 | IIIb-5 | 7-(5-Fluoro-2-methoxypyridin-3-yl)-2-({2-(propan-2-yloxy)-4-[1-(propan-2-yl)piperidin-4-yl]phenyl}amino)thieno[3,2-d]pyrimidine-6-carboxamide | 1.01 (d, J = 6.1 Hz, 6 H); 1.29 (d, J = 6.1 Hz, 6 H); 1.48 to 1.66 (m, 2 H); 1.75 (s, 2 H); 2.14 to 2.29 (m, 2 H); 2.41 (broad s, 1 H); 2.73 (broad s, 1 H); 2.84 to 2.95 (m, 2 H), 3.78 (s, 3 H); 4.67 (spt, J = 6.2 Hz, 1 H); 6.63 (dd, J = 1.6 and 8.4 Hz, 1 H); 6.89 (d, J = 1.2 Hz, 1 H); 7.61 to 7.74 (m, 2 H); 7.93 (dd, J = 3.1 and 8.9 Hz, 1 H); 7.99 (s, 1 H); 8.09 (d, J = 8.3 Hz, 1 H); 8.26 (d, J = 2.9 Hz, 1 H); 9.25 (s, 1 H) | A 579 0.72 |
| I-89 | II-36 | IIIb-7 | 7-(5-Fluoro-2-methoxypyridin-3-yl)-2-{[5-methyl-4-(1-methylpiperidin-4-yl)-2-(propan-2-yloxy)phenyl]amino}thieno[3,2-d]pyrimidine-6-carboxamide | 1.28 (d, J = 6.1 Hz, 6 H); 1.63 (m, 4 H); 1.99 (t, J = 10.5 Hz, 2 H); 2.09 (s, 3 H); 2.20 (s, 3 H); 2.57 (m, 1 H); 2.87 (d, J = 11.0 Hz, 2 H); 3.78 (s, 3 H); 4.62 (spt, J = 6.1 Hz, 1 H); 6.81 (s, 1 H); 7.61 (broad s, 1 H); 7.71 (broad s, 1 H); 7.91 (m, 2 H); 7.98 (s, 1 H); 8.25 (d, J = 2.9 Hz, 1 H); 9.25 (s, 1 H) | A 565 0.68 |
| I-90 | II-37 | IIIb-3 | 7-(6-Methoxypyridin-2-yl)-2-{[4-(1-methylpiperidin-4-yl)-2-(propan-2-yloxy)phenyl]amino}thieno[3,2-d]pyrimidine-6-carboxamide | 1.31 (d, J = 5.9 Hz, 6 H); 1.76 to 2.03 (m, 4 H); 2.55 to 2.63 (masked m, 2 H); 2.68 to 2.79 (m, 4 H); 3.89 (s, 3 H); 4.67 (m, 1 H); 6.79 (d, J = 8.3 Hz, 1 H); 6.88 (dd, J = 3.5 and 5.3 Hz, 1 H); 6.93 (broad s, 1 H); 7.86 to 7.93 (m, 4 H); 8.09 (s, 1 H); 8.25 (s, 3 H); 9.26 (s, 1 H) | A 533 0.70 |

TABLE 4-continued

| Compound I' | Compound II | Compound IIIb | Name | NMR | MS conditions/ MH+/Tr |
|---|---|---|---|---|---|
| I-91 | II-2 | IIIb-16 | 7-(2-Chlorophenyl)-2-({4-[1-(2-hydroxyethyl)piperidin-4-yl]-2-(propan-2-yloxy)phenyl}amino)thieno[3,2-d]pyrimidine-6-carboxamide | 1.28 (d, J = 5.9 Hz, 6 H); 1.53 to 1.72 (m, 4 H); 1.96 to 2.07 (m, 2 H); 2.34 (m, 1 H); 2.40 (t, J = 6.4 Hz, 2 H); 2.95 (d, J = 11.5 Hz, 2 H); 3.51 (q, J = 5.9 Hz, 2 H); 4.31 (t, J = 5.4 Hz, 1 H); 4.66 (spt, J = 6.0 Hz, 1 H); 6.54 (d, J = 8.3 Hz, 1 H); 6.86 (s, 1 H); 7.18 (broad s, 1 H); 7.46 to 7.57 (m, 3 H); 7.63 (m, 1 H); 7.79 (broad s, 1 H); 7.91 (s, 1 H); 8.01 (d, J = 8.3 Hz, 1 H); 9.25 (s, 1 H) | A 566 0.69 |
| I-92 | II-5 | IIIb-57 | 7-(2-Methoxyphenyl)-2-{[6-(1-methylpiperidin-4-yl)-2-(propan-2-yloxy)pyridin-3-yl]amino}thieno[3,2-d]pyrimidine-6-carboxamide | 1.34 (d, J = 6.1 Hz, 6 H); 1.98 (m, 4 H); 2.76 (s, 4 H); 3.02 (s, 2 H); 3.45 (m, J = 5.4 Hz, 2 H); 3.70 (s, 3 H); 5.30 (spt, J = 6.2 Hz, 1 H); 6.66 (d, J = 7.6 Hz, 1 H); 6.92 (broad s, 1 H); 7.12 (td, J = 0.9 and 7.4 Hz, 1 H); 7.19 (d, J = 8.1 Hz, 1 H); 7.45 (dd, J = 1.6 and 7.5 Hz, 1 H); 7.49 (td, J = 1.7 and 8.3 Hz, 1 H); 7.76 (broad s, 1 H); 7.98 (s, 1 H); 8.36 (d, J = 8.1 Hz, 1 H); 9.27 (s, 1 H); 9.74 (broad s, 1 H) | A 533 0.71 |
| I-93 | II-5 | IIIb-45 | 2-{[4-(1,7-Diazaspiro[4.4]non-7-yl)-2-(propan-2-yloxy)phenyl]amino}-7-(2-methoxyphenyl)thieno[3,2-d]pyrimidine-6-carboxamide | 1.27 (d, J = 6.1 Hz, 6 H); 1.54 (m, 1 H); 1.89 (m, 4 H); 2.15 (m, 2 H); 2.35 (m, 1 H); 3.15 (t, J = 7.1 Hz, 1 H); 3.23 (masked m, 2 H); 3.41 (s, 1 H); 3.70 (s, 3 H); 4.63 (spt, J = 6.0 Hz, 1 H); 5.96 (dd, J = 2.6 and 8.9 Hz, 1 H); 6.22 (d, J = 2.2 Hz, 1 H); 6.83 (broad s, 1 H); 7.11 (td, J = 1.1 and 7.5 Hz, 1 H); 7.17 (d, J = 8.1 Hz, 1 H); 7.47 (m, 2 H); 7.71 (broad s, 1 H); 7.73 (s, 1 H); 7.88 (d, J = 8.8 Hz, 1 H); 9.12 (s, 1 H) | A 559 0.71 |
| I-94 | II-31 | IIIb-36 | 2-({4-[3-(Diethylamino)pyrrolidin-1-yl]-2-(propan-2-yloxy)phenyl}amino)-7-(2-methoxypyridin-3-yl)thieno[3,2-d]pyrimidine-6-carboxamide | 0.98 (t, J = 7.1 Hz, 6 H); 1.25 (d, J = 5.9 Hz, 6 H); 1.80 (m, 1 H); 2.12 (m, 1 H); 2.59 (m, 4 H); 2.98 (t, J = 7.8 Hz, 1 H); 3.18 (m, 1 H); 3.38 to 3.42 (partially masked m, 3 H); 3.79 (s, 3 H); 4.63 (spt, J = 5.9 Hz, 1 H); 5.97 (dd, J = 2.4 and 8.8 Hz, 1 H); 6.21 (d, J = 2.4 Hz, 1 H); 7.15 (dd, J = 5.1 and 7.3 Hz, 1 H); 7.43 (broad s, 1 H); 7.66 (broad s, 1 H); 7.77 (s, 1 H); 7.80 (d, J = 8.8 Hz, 1 H); 7.89 (dd, J = 1.7 and 7.3 Hz, 1 H); 8.25 (dd, J = 1.7 and 5.1 Hz, 1 H); 9.13 (s, 1 H) | A 576 0.67 |
| I-95 | II-38 | IIIb-34 | 2-({4-[3-(Dimethylamino)pyrrolidin-1-yl]-2-(propan-2-yloxy)phenyl}amino)-7-(1-methyl-1H-pyrrol-2-yl)thieno[3,2-d]pyrimidine-6-carboxamide | 1.24 (d, J = 6.1 Hz, 6 H); 1.79 (m, 1 H); 2.13 (m, 2 H); 2.21 (s, 6 H); 2.78 (m, 1 H); 3.01 (t, J = 7.8 Hz, 1 H); 3.21 (m, 1 H); 3.28 to 3.44 (partially masked m, 2 H); 3.48 (s, 3 H); 4.61 (spt, J = 6.1 Hz, 1 H); 6.02 (dd, J = 2.4 and 8.8 Hz, 1 H); 6.17 to 6.28 (m, 3 H); 6.80 (broad s, 1 H); 7.04 (t, J = 2.2 Hz, 1 H); 7.74 (d, J = 8.8 Hz, 1 H); 7.86 (s, 1 H); 7.91 (broad s, 1 H); 9.12 (s, 1 H) | A 520 0.67 |
| I-96 | II-38 | IIIb-3 | 2-{[4-(1-Methylpiperidin-4-yl)-2-(propan-2-yloxy)phenyl]amino}-7-(1-methyl-1H-pyrrol-2-yl)thieno[3,2-d]pyrimidine-6-carboxamide | 1.29 (d, J = 5.9 Hz, 6 H); 1.63 to 1.88 (m, 4 H); 2.24 to 2.58 (partially masked m, 6 H); 3.08 (m, 2 H); 3.48 (s, 3 H); 4.66 (m, 1 H); 6.22 (t, J = 3.2 Hz, 1 H); 6.30 (dd, J = 1.3 and 3.8 Hz, 1 H); 6.69 (broad d, J = 8.1 Hz, 1 H); 6.85 (broad s, 1 H); 6.89 (broad s, 1 H); 7.08 (broad s, 1 H); 7.96 (broad s, 1 H); 8.00 (s, 1 H); 8.10 (d, J = 8.1 Hz, 1 H); 9.23 (s, 1 H) | A 505 0.68 |
| I-97 | II-39 | IIIb-3 | 2-{[4-(1-Methylpiperidin-4-yl)-2-(propan-2-yloxy)phenyl]amino}-7-(2-methylpyridin-3-yl)thieno[3,2-d]pyrimidine-6-carboxamide | 1.27 (d, J = 6.1 Hz, 6 H); 1.54 to 1.74 (m, 4 H); 1.97 (m, 2 H); 2.20 (s, 3 H); 2.29 (s, 3 H); 2.38 (m, 1 H); 2.86 (m, 2 H); 4.65 (m, 1 H); 6.55 (dd, J = 2.1 and 8.3 Hz, 1 H); 6.87 (d, J = 2.1 Hz, 1 H); 7.36 (dd, J = 4.9 and 7.6 Hz, 1 H); 7.39 (broad s, 1 H); 7.70 (dd, J = 2.0 and 7.6 Hz, 1 H); 7.79 (broad s, 1 H); 7.92 (d, J = 8.3 Hz, 1 H); 7.95 (s, 1 H); 8.56 (dd, J = 2.0 and 4.9 Hz, 1 H); 9.26 (s, 1 H) | A 517 0.49 |
| I-98 | II-40 | IIIb-3 | 7-(Furan-2-yl)-2-{[4-(1-methylpiperidin-4-yl)-2-(propan-2- | 1.29 (d, J = 6.1 Hz, 6 H); 1.62 to 1.80 (m, 4 H); 1.97 (m, 2 H); 2.20 (s, 3 H); 2.45 (m, 1 H); 2.88 (m, 2 H); 4.68 (m, 1 H); | A 492 0.65 |

TABLE 4-continued

| Compound I' | Compound II | Compound IIIb | Name | NMR | MS conditions/ MH+/Tr |
|---|---|---|---|---|---|
| | | | yloxy)phenyl]amino}thieno[3,2-d]pyrimidine-6-carboxamide | 6.68 (dd, J = 1.8 and 3.3 Hz, 1 H); 6.86 (dd, J = 2.1 and 8.4 Hz, 1 H); 6.95 (d, J = 2.1 Hz, 1 H); 7.33 (broad d, J = 3.3 Hz, 1 H); 7.84 (broad d, J = 1.8 Hz, 1 H); 7.90 (broad s, 1 H); 8.09 (broad s, 1 H); 8.12 (s, 1 H); 8.20 (d, J = 8.1 Hz, 1 H); 9.20 (s, 1 H) | |
| I-99 | II-41 | IIIb-3 | 7-[5-(Aminomethyl)furan-2-yl]-2-{[4-(1-methylpiperidin-4-yl)-2-(propan-2-yloxy)phenyl]amino}thieno[3,2-d]pyrimidine-6-carboxamide | 1,.0 (d, J = 6.1 Hz, 6 H); 1.59 to 1.80 (m, 4 H); 1.98 (m, 2 H); 2.21 (s, 3 H); 2.43 (partially masked m, 1 H); 2.88 (m, 2 H); 3.77 (s, 2 H); 4.69 (m, 1 H); 6.42 (broad d, J = 2.9 Hz, 1 H); 6.84 (broad d, J = 8.3 Hz, 1 H); 6.95 (broad s, 1 H); 7.20 (broad d, J = 2.9 Hz, 1 H); 7.94 (broad s, 1 H); 8.04 (broad s, 1 H); 8.10 (s, 1 H); 8.22 (d, J = 8.3 Hz, 1 H); 9.19 (s, 1 H) | A 521 0.48 |
| I-100 | II-31 | IIIb-26 | 7-(2-Methoxypyridin-3-yl)-2-{[5-methyl-4-(4-methylpiperazin-1-yl)-2-(propan-2-yloxy)phenyl]amino}thieno[3,2-d]pyrimidine-6-carboxamide | 1.28 (d, J = 6.1 Hz, 6 H); 2.05 (s, 3 H); 2.23 (s, 3 H); 2.46 (m, 4 H); 2.78 (m, 4 H); 3.79 (s, 3 H); 4,60 (spt, J = 6.1 Hz, 1 H); 6.69 (s, 1 H); 7.16 (dd, J = 5.1 and 7.3 Hz, 1 H); 7.43 (broad s, 1 H); 7.69 (broad s, 1 H); 7.82 (s, 1 H); 7.91 (dd, J = 2.0 and 7.3 Hz, 1 H); 8.01 (s, 1 H); 8.27 (dd, J = 2.0 and 5.1 Hz, 1 H); 9.22 (s, 1 H) | A 548 0.63 |
| I-101 | II-43 | IIIb-3 | 2-{[4-(1-Methylpiperidin-4-yl]-2-(propan-2-yloxy)phenyl]amino}-7-(1H-pyrrol-3-yl)thieno[3,2-d]pyrimidine-6-carboxamide | 1.32 (d, J = 6.1 Hz, 6 H); 1.61 to 1.79 (m, 4 H); 1.97 (m, 2 H); 2.20 (s, 3 H); 2.42 (m, 1 H); 2.88 (m, 2 H); 4.70 (m, 1 H); 6.56 (m, 1 H); 6.81 (dd, J = 2.0 and 8.5 Hz, 1 H); 6.92 (m, 2 H); 7.51 (m, 1 H); 7.60 (broad s, 1 H); 7.88 (broad s, 1 H); 7.92 (s, 1 H); 8.37 (d, J = 8.5 Hz, 1 H); 9.16 (s, 1 H); 11.18 (broad s, 1 H) | A 491 0.64 |
| I-102 | II-31 | IIIb-34 | 2-({4-[3-(Dimethylamino)pyrrolidin-1-yl]-2-(propan-2-yloxy)phenyl}amino)-7-(2-methoxypyridin-3-yl)thieno[3,2-d]pyrimidine-6-carboxamide | 1.25 (d, J = 6.1 Hz, 6 H); 1.79 (m, 1 H); 2.13 (m, 1 H); 2.21 (s, 6 H); 2.78 (m, 1 H); 3.00 (m, 1 H); 3.21 (m, 1 H); 3.25 to 3.42 (partially masked m, 2 H); 3.79 (s, 3 H); 4.63 (m, 1 H); 5.98 (dd, J = 2.5 and 9.0 Hz, 1 H); 6.21 (d, J = 2.5 Hz, 1 H); 7.15 (dd, J = 5.1 and 7.3 Hz, 1 H); 7.42 (broad s, 1 H); 7.66 (broad s, 1 H); 7.77 (s, 1 H); 7.80 (broad d, J = 9.0 Hz, 1 H); 7.89 (dd, J = 2.1 and 7.3 Hz, 1 H); 8.25 (dd, J = 2.1 and 5.1 Hz, 1 H); 9.13 (s, 1 H) | A 548 0.62 |
| I-103 | II-44 | IIIb-5 | 7-(2-Ethoxypyridin-3-yl)-2-({2-(propan-2-yloxy)-4-[1-(propan-2-yl)piperidin-4-yl]phenyl}amino)thieno[3,2-d]pyrimidine-6-carboxamide | 0.99 (d, J = 6.6 Hz, 6 H); 1.19 (t, J = 7.1 Hz, 3 H); 1.29 (d, J = 6.1 Hz, 6 H); 1.59 (m, 2 H); 1.72 (m, 2 H); 2.18 (m, 2 H); 2.39 (m, 1 H); 2.70 (m, 1 H); 2.87 (m, 2 H); 4.28 (q, J = 7.1 Hz, 2 H); 4.68 (m, 1 H); 6.64 (dd, J = 2.3 and 8.5 Hz, 1 H); 6.88 (d, J = 2.3 Hz, 1 H); 7.17 (dd, J = 5.1 and 7.3 Hz, 1 H); 7.48 (broad s, 1 H); 7.69 (broad s, 1 H); 7.91 (s, 1 H); 7.93 (dd, J = 2.1 and 7.3 Hz, 1 H); 8.13 (d, J = 8.5 Hz, 1 H); 8.25 (dd, J = 2.1 and 5.1 Hz, 1 H); 9.23 (s, 1 H) | A 575 0.72 |
| I-104 | II-44 | IIIb-7 | 7-(2-Ethoxypyridin-3-yl)-2-{[5-methyl-4-(1-methylpiperidin-4-yl)-2-(propan-2-yloxy)phenyl]amino}thieno[3,2-d]pyrimidine-6-carboxamide | 1.17 (t, J = 7.1 Hz, 3 H); 1.28 (d, J = 6.1 Hz, 6 H); 1.50 to 1.71 (m, 4 H); 1.97 (m, 2 H); 2.09 (s, 3 H); 2.19 (s, 3 H); 2.54 (partially masked m, 1 H); 2.86 (m, 2 H); 4.28 (q, J = 7.1 Hz, 2 H); 4.62 (m, 1 H); 6.81 (s, 1 H); 7.14 (dd, J = 5.1 and 7.3 Hz, 1 H); 7.46 (broad s, 1 H); 7.69 (broad s, 1 H); 7.85 (s, 1 H); 7.93 (dd, J = 2.1 and 7.3 Hz, 1 H); 8.02 (s, 1 H); 8.24 (dd, J = 2.1 and 5.1 Hz, 1 H); 9.24 (s, 1 H) | A 561 0.67 |
| I-105 | II-5 | IIIb-26 | 7-(2-Methoxyphenyl)-2-{[5-methyl-4-(4-methylpiperazin-1-yl)-2-(propan-2-yloxy)phenyl]amino}thieno[3,2-d]pyrimidine-6-carboxamide | 1.28 (d, J = 5.9 Hz, 6 H); 2.00 (s, 3 H); 2.22 (s, 3 H); 2.43 (m, 4 H); 2.77 (t, J = 4.4 Hz, 4 H); 3.69 (s, 3 H); 4.59 (spt, J = 6.1, 1 H); 6.68 (s, 1 H); 6.82 (broad s, 1 H); 7.13 (t, J = 7.3 Hz, 1 H); 7.19 (d, J = 8.3 Hz, 1 H); 7.48 (m, 2 H); 7.73 (broad s, 1 H); 7.77 (s, 1 H); 8.03 (s, 1 H); 9.19 (s, 1 H) | A 547 0.68 |

TABLE 4-continued

| Compound I' | Compound II | Compound IIIb | Name | NMR | MS conditions/ MH+/Tr |
|---|---|---|---|---|---|
| I-106 | II-44 | IIIb-3 | 7-(2-Ethoxypyridin-3-yl)-2-{[4-(1-methylpiperidin-4-yl)-2-(propan-2-yloxy)phenyl]amino}thieno[3,2-d]pyrimidine-6-carboxamide | 1.19 (t, J = 7.1 Hz, 3 H); 1.29 (d, J = 6.1 Hz, 6 H); 1.58 to 1.75 (m, 4 H); 1.93 (m, 2 H); 2.19 (s, 3 H); 2.39 (m, 1 H); 2.85 (d, J = 11.0 Hz, 2 H); 4.28 (q, J = 7.1 Hz, 2 H); 4.67 (quin, J = 6.1 Hz, 1 H); 6.64 (dd, J = 1.7 and 8.3 Hz, 1 H); 6.88 (d, J = 1.5 Hz, 1 H); 7.16 (dd, J = 5.1 and 7.3 Hz, 1 H); 7.48 (broad s, 1 H); 7.69 (broad s, 1 H); 7.93 (m, 2 H); 8.13 (d, J = 8.3 Hz, 1 H); 8.24 (dd, J = 2.0 and 5.1 Hz, 1 H); 9.23 (s, 1 H) | A 547 0.67 |
| I-107 | II-44 | IIIb-25 | 7-(2-Ethoxypyridin-3-yl)-2-{[4-(4-methylpiperazin-1-yl)-2-(propan-2-yloxy)phenyl]amino}thieno[3,2-d]pyrimidine-6-carboxamide | 1.20 (t, J = 7.1 Hz, 3 H); 1.26 (d, J = 5.9 Hz, 6 H); 2.22 (s, 3 H); 2.44 (m, 4 H); 3.05 (m, 4 H); 4.28 (q, J = 7.1 Hz, 2 H); 4.65 (m, 1 H); 6.34 (dd, J = 2.5 and 8.8 Hz, 1 H); 6.62 (d, J = 2.5 Hz, 1 H); 7.15 (dd, J = 5.1 and 7.3 Hz, 1 H); 7.46 (broad s, 1 H); 7.67 (broad s, 1 H); 7.82 (s, 1 H); 7.91 (dd, J = 2.2 and 7.3 Hz, 1 H); 7.96 (d, J = 8.8 Hz, 1 H); 8.23 (dd, J = 2.2 and 5.1 Hz, 1 H); 9.18 (s, 1 H) | A 548 0.85 |
| I-108 | II-45 | IIIb-25 | 7-(2-Methoxy-5-methylpyridin-3-yl)-2-{[4-(4-methylpiperazin-1-yl)-2-(propan-2-yloxy)phenyl]amino}thieno[3,2-d]pyrimidine-6-carboxamide | 1.26 (d, J = 5.9 Hz, 6 H); 2.22 (s, 3 H); 2.32 (s, 3 H); 2.45 (m, 4 H); 3.06 (m, 4 H); 3.76 (s, 3 H); 4.65 (spt, J = 6.0 Hz, 1 H); 6.33 (dd, J = 2.4 and 8.8 Hz, 1 H); 6.64 (d, J = 2.4 Hz, 1 H); 7.42 (broad s, 1 H); 7.65 (broad s, 1 H); 7.77 (d, J = 2.2 Hz, 1 H); 7.85 (s, 1 H); 7.94 (d, J = 8.8 Hz, 1 H); 8.07 (d, J = 2.4 Hz, 1 H); 9.17 (s, 1 H) | A 548 0.63 |
| I-109 | II-45 | IIIb-3 | 7-(2-Methoxy-5-methylpyridin-3-yl)-2-{[4-(1-methylpiperidin-4-yl)-2-(propan-2-yloxy)phenyl]amino}thieno[3,2-d]pyrimidine-6-carboxamide | 1.30 (d, J = 6.1 Hz, 6 H); 1.54 to 1.77 (m, 4 H); 1.94 (td, J = 2.3 and 11.6 Hz, 2 H); 2.19 (s, 3 H); 2.34 (s, 3 H); 2.40 (m, 1 H); 2.85 (d, J = 11.2 Hz, 2 H); 3.77 (s, 3 H); 4.68 (spt, J = 6.1 Hz, 1 H); 6.64 (dd, J = 1.5 and 8.3 Hz, 1 H); 6.90 (d, J = 1.7 Hz, 1 H); 7.45 (broad s, 1 H); 7.67 (broad s, 1 H); 7.80 (d, J = 2.2 Hz, 1 H); 7.94 (s, 1 H); 8.09 (dd, J = 0.7 and 2.4 Hz, 1 H); 8.14 (d, J = 8.3 Hz, 1 H); 9.23 (s, 1 H) | A 547 0.67 |
| I-110 | II-36 | IIIb-25 | 7-(5-Fluoro-2-methoxypyridin-3-yl)-2-{[4-(4-methylpiperazin-1-yl)-2-(propan-2-yloxy)phenyl]amino}thieno[3,2-d]pyrimidine-6-carboxamide | 1.25 (d, J = 6.1 Hz, 6 H); 2.22 (s, 3 H); 2.43 (m, 4 H); 3.06 (m, 4 H); 3.78 (s, 3 H); 4.64 (spt, J = 6.0 Hz, 1 H); 6.33 (dd, J = 2.4 and 8.8 Hz, 1 H); 6.63 (d, J = 2.4 Hz, 1 H); 7.62 (broad s, 1 H); 7.68 (broad s, 1 H); 7.87 to 7.93 (m, 3 H); 8.24 (d, J = 2.9 Hz, 1 H); 9.19 (s, 1 H) | A 552 0.63 |
| I-111 | II-45 | IIIb-7 | 7-(2-Methoxy-5-methylpyridin-3-yl)-2-{[5-methyl-4-(1-methylpiperidin-4-yl)-2-(propan-2-yloxy)phenyl]amino}thieno[3,2-d]pyrimidine-6-carboxamide | 1.28 (d, J = 6.1 Hz, 6 H); 1.65 (m, 4 H); 2.05 (s, 3 H); 2.25 (m, 8 H); 2.55 (t, J = 8.3 Hz, 1 H); 2.90 (d, J = 8.6 Hz, 2 H); 3.76 (s, 3 H); 4.61 (spt, J = 6.1 Hz, 1 H); 6.80 (s, 1 H); 7.35 (broad s, 1 H); 7.68 (d, J = 2.4 Hz, 1 H); 7.71 (broad s, 1 H); 7.88 (s, 1 H); 7.96 (s, 1 H); 8.09 (d, J = 1.5 Hz, 1 H); 9.23 (s, 1 H) | A 561 0.67 |
| I-112 | II-46 | IIIb-3 | 2-{[4-(1-Methylpiperidin-4-yl)-2-(propan-2-yloxy)phenyl]amino}-7-(1-methyl-1H-pyrazol-3-yl)thieno[3,2-d]pyrimidine-6-carboxamide | 1.30 (d, J = 6.1 Hz, 6 H); 1.68 (m, 4 H); 1.97 (m, 2 H); 2.20 (s, 3 H); 2.41 (m, 1 H); 2.87 (d, J = 11.2 Hz, 2 H); 3.99 (s, 3 H); 4.68 (spt, J = 6.1 Hz, 1 H); 6.79 (dd, J = 1.6 and 8.4 Hz, 1 H); 6.93 (d, J = 1.7 Hz, 1 H); 7.17 (d, J = 2.2 Hz, 1 H); 7.98 (d, J = 2.2 Hz, 1 H); 8.02 (s, 1 H); 8.04 (broad s, 1 H); 8.26 (d, J = 8.3 Hz, 1 H); 9.23 (s, 1 H); 9.85 (broad s, 1 H) | A 506 0.66 |
| I-113 | II-5 | IIIb-31 | 2-({4-[3-(2-Methoxyethyl)-4-methylpiperazin-1-yl]-2-(propan-2-yloxy)phenyl}amino)-7-(2-methoxyphenyl)thieno[3,2-d]pyrimidine-6-carboxamide | 1.26 (d, J = 5.8 Hz, 6 H); 1.62 (m, 1 H); 1.86 (m, 1 H); 2.13 to 2.31 (m, 5 H); 2.71 (t, J = 9.6 Hz, 1 H); 2.79 (d, J = 11.5 Hz, 1 H); 3.26 to 3.49 (m, 5 H); 3.70 (s, 3 H); 4.59 to 4.72 (m, 1 H); 6.30 (d, J = 8.5 Hz); 1 H). 6.60 (s, 1 H); 6.91 (broad s, 1 H); 7.12 (t, J = 7.4 Hz, 1 H); 7.18 (d, J = 8.2 Hz, 1 H); 7.48 (m, 2 H); 7.74 (broad s, 1 H); 7.79 (s, 1 H); 7.95 (d, J = 9.6 Hz, 1 H); 9.16 (s, 1 H) | A 591 0.71 |

TABLE 4-continued

| Compound I' | Compound II | Compound IIIb | Name | NMR | MS conditions/ MH+/Tr |
|---|---|---|---|---|---|
| I-114 | II-5 | IIIb-47 | 7-(2-Methoxyphenyl)-2-{[4-{(3R)-3-[methyl(oxetan-3-yl)amino]piperidin-1-yl}-2-(propan-2-yloxy)phenyl]amino}thieno[3,2-d]pyrimidine-6-carboxamide | 1.26 (d, J = 6.1 Hz, 7 H); 1.51 (m, 1 H); 1.71 (d, J = 8.8 Hz, 2 H); 2.21 (s, 3 H); 2.46 (broad s, 3 H); 3.48 (m, 2 H); 3.70 (s, 3 H); 4.00 (quin, J = 6.8 Hz, 1 H); 4.50 (m, 4 H); 4.65 (spt, J = 5.9 Hz, 1 H); 6.28 (d, J = 7.1 Hz, 1 H); 6.58 (d, J = 2.0 Hz, 1 H); 6.86 (broad s, 1 H); 7.12 (t, J = 7.6 Hz, 1 H); 7.18 (d, J = 8.3 Hz, 1 H); 7.38 to 7.53 (m, 2 H); 7.71 (broad s, 1 H); 7.76 (s, 1 H); 7.94 (d, J = 8.8 Hz, 1 H); 9.15 (s, 1 H) | A 603 0.70 |
| I-115 | II-42 | IIIb-3 | 7-(2-Methylfuran-3-yl)-2-{[4-(1-methylpiperidin-4-yl)-2-(propan-2-yloxy)phenyl]amino}thieno[3,2-d]pyrimidine-6-carboxamide | 1.30 (d, J = 6.1 Hz, 6 H); 1.57 to 1.77 (m, 4 H); 1.95 (m, 2 H); 2.19 (s, 3 H); 2.21 (s, 3 H); 2.40 (m, 1 H); 2.86 (m, 2 H); 4.68 (m, 1 H); 6.68 (d, J = 2.0 Hz, 1 H); 6.73 (dd, J = 2.3 and 8.3 Hz, 1 H); 6.90 (d, J = 2.3 Hz, 1 H); 7.30 (broad s, 1 H); 7.71 (d, J = 2.0 Hz, 1 H); 7.90 (broad s, 1 H); 7.95 (s, 1 H); 8.24 (d, J = 8.3 Hz, 1 H); 9.22 (s, 1 H) | A 506 0.68 |
| I-116 | II-37 | IIIb-7 | 7-(6-Methoxypyridin-2-yl)-2-{5-methyl-4-(1-methylpiperidin-4-yl)-2-(propan-2-yloxy)phenyl]amino}thieno[3,2-d]pyrimidine-6-carboxamide | 1.29 (d, J = 6.1 Hz, 6 H); 1.62 (m, 4 H); 1.95 to 2.06 (m, 2 H); 2.20 (s, 3 H); 2.21 (s, 3 H); 2.60 (m, 1 H); 2.88 (d, J = 11.0 Hz, 2 H); 3.88 (s, 3 H); 4.64 (dt, J = 6.1 and 11.9 Hz, 1 H); 6.85 (s, 1 H); 6.89 (d, J = 7.8 Hz, 1 H); 7.88 (m, 3 H); 7.97 (s, 1 H); 8.14 (s, 1 H); 8.20 (broad s, 1 H); 9.25 (s, 1 H) | A 547 0.70 |
| I-117 | II-31 | IIIb-35 | 2-({4-[3-(Dimethylamino)pyrrolidin-1-yl]-5-methyl-2-(propan-2-yloxy)phenyl}amino)-7-(2-methoxypyridin-3-yl)thieno[3,2-d]pyrimidine-6-carboxamide | 1.28 (dd, J = 1.0 and 5.9 Hz, 6 H); 1.58 (m, 1 H); 1.86 (m, 1 H); 2.06 (s, 3 H); 2.18 (s, 3 H); 2.23 (dd, J = 6.0 and 9.2 Hz, 1 H); 2.41 (m, 5 H); 2.59 (m, 1 H); 3.61 (m, 1 H); 3.79 (m, 3 H); 4.60 (dt, J = 6.3 and 12.2 Hz, 1 H); 6.77 (s, 1 H); 7.16 (dd, J = 5.0 and 7.2 Hz, 1 H); 7.44 (broad s, 1 H); 7.70 (broad s, 1 H); 7.84 (s, 1 H); 7.91 (dd, J = 2.0 and 7.3 Hz, 1 H); 8.01 (s, 1 H); 8.27 (dd, J = 1.8 and 5.0 Hz, 1 H); 9.22 (s, 1 H) | A 562 0.70 |
| I-118 | II-5 | IIIb-35 | 2-({4-[3-(Dimethylamino)pyrrolidin-1-yl]-5-methyl-2-(propan-2-yloxy)phenyl}amino)-7-(2-methoxyphenyl)thieno[3,2-d]pyrimidine-6-carboxamide | 1.28 (dd, J = 1.0 and 5.9 Hz, 6 H); 1.57 (m, 1 H); 1.85 (m, 1 H); 2.02 (s, 3 H); 2.18 (s, 3 H); 2.21 (dd, J = 6.0 and 9.2 Hz, 1 H); 2.38 (m, 1 H); 2.46 (s, 4 H); 2.58 (dd, J = 7.2 and 8.9 Hz, 1 H); 3.60 (m, 1 H); 3.70 (s, 3 H); 4.60 (spt, J = 6.1 Hz, 1 H); 6.76 (s, 1 H); 6.82 (broad s, 1 H); 7.13 (t, J = 7.5 Hz, 1 H); 7.20 (d, J = 8.1 Hz, 1 H); 7.49 (m, 2 H); 7.73 (broad s, 1 H); 7.79 (s, 1 H); 8.03 (s, 1 H); 9.20 (s, 1 H) | A 561 0.75 |
| I-119 | II-19 | IIIb-58 | 2-({3-[1-(Oxetan-3-yl)piperidin-4-yl]-1-(propan-2-yl)-1H-pyrazol-5-yl}amino)-7-[2-(trifluoromethoxy)phenyl]thieno[3,2-d]pyrimidine-6-carboxamide | 1.22 (d, J = 6.4 Hz, 6 H); 1.50 (qd, J = 3.4 and 12.2 Hz, 2 H); 1.74 (d, J = 11.5 Hz, 2 H); 1.83 (m, 2 H); 2.42 (tt, J = 3.8 and 11.6 Hz, 1 H); 2.73 (d, J = 11.2 Hz, 2 H); 3.39 (s, 1 H); 4.43 to 4.51 (m, 4 H); 4.57 (m, 2 H); 6.01 (s, 1 H); 7.36 (broad s, 1 H); 7.47 (m, 2 H); 7.60 (m, 2 H); 7.74 (broad s, 1 H); 9.26 (s, 1 H); 9.40 (broad s, 1 H) | A 602 0.59 |
| I-120 | II-47 | IIIb-7 | 7-(2-Methoxy-6-methylpyridin-3-yl)-2-{[5-methyl-4-(1-methylpiperidin-4-yl)-2-(propan-2-yloxy)phenyl]amino}thieno[3,2-d]pyrimidine-6-carboxamide | 1.29 (d, J = 6.1 Hz, 6 H); 1.56 to 1.73 (m, 4 H); 2.03 (m, 2 H), 2.10 (s, 3 H); 2.23 (s, 3 H); 2.49 (s, 3 H); 2.58 (m, 1 H); 2.90 (d, J = 10.5 Hz, 2 H); 3.77 (s, 3 H); 4.62 (spt, J = 6.0 Hz, 1 H); 6.80 (s, 1 H); 7.01 (d, J = 7.3 Hz, 1 H); 7.31 (broad s, 1 H); 7.71 (broad s, 1 H); 7.77 (d, J = 7.6 Hz, 1 H); 7.84 (s, 1 H); 8.03 (s, 1 H); 9.22 (s, 1 H) | A 561 0.68 |
| I-121 | II-47 | IIIb-25 | 7-(2-Methoxy-6-methylpyridin-3-yl)-2-{[4-(4-methylpiperazin-1-yl)-2-(propan-2-yloxy)phenyl]amino}thieno[3,2-d]pyrimidine-6-carboxamide | 1.26 (d, J = 6.1 Hz, 6 H); 2.25 (s, 3 H); 2.46 (masked m, 7 H); 3.07 (m, 4 H); 3.77 (s, 3 H); 4.64 (spt, J = 6.0 Hz, 1 H); 6.35 (dd, J = 2.6 and 8.9 Hz, 1 H); 6.62 (d, J = 2.4 Hz, 1 H); 7.01 (d, J = 7.6 Hz, 1 H); 7.33 (broad s, 1 H); 7.66 (broad s, 1 H); 7.78 (d, J = 7.3 Hz, 1 H); 7.82 (s, 1 H); 7.92 (d, J = 8.8 Hz, 1 H); 9.16 (s, 1 H) | A 548 0.64 |

TABLE 4-continued

| Compound I' | Compound II | Compound IIIb | Name | NMR | MS conditions/ MH+/Tr |
|---|---|---|---|---|---|
| I-122 | II-47 | IIIb-3 | 7-(2-Methoxy-6-methylpyridin-3-yl)-2-{[4-(1-methylpiperidin-4-yl)-2-(propan-2-yloxy)phenyl]amino}thieno[3,2-d]pyrimidine-6-carboxamide | 1.29 (d, J = 6.1 Hz, 6 H); 1.55 to 1.78 (m, 4 H); 2.00 (t, J = 10.8 Hz, 2 H); 2.22 (s, 3 H); 2.41 (m, 1 H); 2.50 (masked s, 3 H); 2.89 (d, J = 11.2 Hz, 2 H); 3.78 (s, 3 H); 4.67 (spt, J = 6.0 Hz, 1 H); 6.65 (dd, J = 1.6 and 8.4 Hz, 1 H); 6.89 (d, J = 1.5 Hz, 1 H); 7.03 (d, J = 7.3 Hz, 1 H); 7.36 (broad s, 1 H); 7.69 (broad s, 1 H); 7.80 (d, J = 7.3 Hz, 1 H); 7.91 (s, 1 H); 8.11 (d, J = 8.3 Hz, 1 H); 9.22 (s, 1 H) | A 547 0.68 |
| I-123 | II-19 | IIIb-58 | 2-{[3-(1-Ethylpiperidin-4-yl)-1-(propan-2-yl)-1H-pyrazol-5-yl]amino}-7-[2-(trifluoromethoxy)phenyl]thieno[3,2-d]pyrimidine-6-carboxamide | 1.04 (t, J = 7.3 Hz, 3 H); 1.22 (d, J = 6.8 Hz, 6 H); 1.48 (qd, J = 3.4 and 12.7 Hz, 2 H); 1.73 (d, J = 11.7 Hz, 2 H); 1.93 (m, 2 H); 2.37 (m, 3 H); 2.90 (d, J = 11.7 Hz, 2 H); 4.47 (dt, J = 6.8 and 13.3 Hz, 1 H); 5.98 (s, 1 H); 7.33 (broad s, 1 H); 7.46 (m, 1 H); 7.57 (m, 2 H); 7.72 (broad s, 1 H); 9.25 (s, 1 H); 9.35 (s, 1 H) | A 572 0.61 |
| I-124 | II-5 | IIIb-8 | 2-({4-[(3R,4S)-3-Hydroxy-1-methylpiperidin-4-yl]-2-(propan-2-yloxy)phenyl}amino)-7-(2-methoxyphenyl)thieno[3,2-d]pyrimidine-6-carboxamide | ¹H NMR spectrum (500 MHz, d in ppm, CHLOROFORM-d): 1.37 (d, J = 5.5 Hz, 6 H); 1.65 (d, J = 11.0 Hz, 1 H); 2.06 (m, 1 H); 2.21 (m, 2 H); 2.32 (s, 3 H); 2.36 (broad s, 1 H); 2.55 (d, J = 12.6 Hz, 1 H); 2.95 (d, J = 11.0 Hz, 1 H); 3.01 (d, J = 11.0 Hz, 1 H); 3.76 (s, 3 H); 3.87 (broad s, 1 H); 4.61 (dt, J = 6.0 and 12.1 Hz, 1 H); 5.49 (broad s, 1 H); 6.03 (broad s, 1 H); 6.64 (d, J = 8.5 Hz, 1 H); 6.88 (s, 1 H); 7.11 (d, J = 8.2 Hz, 1 H); 7.18 (t, J = 7.4 Hz, 1 H); 7.47 (d, J = 7.7 Hz, 1 H); 7.54 (t, J = 7.8 Hz, 1 H); 7.86 (s, 1 H); 8.31 (d, J = 8.2 Hz, 1 H); 8.97 (s, 1 H) | A 548 0.64 |
| I-125 | II-31 | IIIb-20 | 7-(2-Methoxypyridin-3-yl)-2-({4-[(8S,8aS)-octahydroindolizin-8-yl]-2-(propan-2-yloxy)phenyl}amino)thieno[3,2-d]pyrimidine-6-carboxamide | 1.24 (m, J = 6.1 Hz, 7 H); 1.35 to 1.80 (m, 7 H); 1.91 (td, J = 6.1 and 9.8 Hz, 1 H); 2.07 (m, 2 H); 2.31 (m, 1 H); 3.01 (m, 2 H); 3.80 (s, 3 H); 4.67 (spt, J = 6.0 Hz, 1 H); 6.62 (dd, J = 1.5 and 8.3 Hz, 1 H); 6.87 (d, J = 1.5 Hz, 1 H); 7.18 (dd, J = 5.1 and 7.3 Hz, 1 H); 7.47 (broad s, 1 H); 7.69 (broad s, 1 H); 7.91 (dd, J = 2.0 and 7.3 Hz, 1 H); 7.93 (s, 1 H); 8.08 (d, J = 8.3 Hz, 1 H); 8.28 (dd, J = 2.0 and 5.1 Hz, 1 H); 9.24 (s, 1 H) | A 559 0.67 |
| I-126 | II-31 | IIIb-20 | 7-(2-Methoxypyridin-3-yl)-2-({4-[(8R,8aS)-octahydroindolizin-8-yl]-2-(propan-2-yloxy)phenyl}amino)thieno[3,2-d]pyrimidine-6-carboxamide | 1.25 to 1.34 (m, 6 H); 1.39 to 1.74 (m, 8 H); 1.96 (m, 2 H); 2.21 (broad s, 1 H); 3.00 (d, J = 16.9 Hz, 2 H); 3.12 (d, J = 10.0 Hz, 1 H); 3.79 (s, 3 H); 4.52 (spt, J = 6.0 Hz, 1 H); 6.84 (d, J = 8.1 Hz, 1 H); 7.14 (dd, J = 5.0 and 7.2 Hz, 1 H); 7.47 (broad s, 1 H); 7.53 (broad s, 1 H); 7.69 (broad s, 1 H); 7.90 (m, 2 H); 8.03 (d, J = 8.3 Hz, 1 H); 8.26 (dd, J = 2.0 and 4.9 Hz, 1 H); 9.23 (s, 1 H) | A 559 0.68 |
| I-127 | II-5 | IIIb-49 | 7-(2-Methoxyphenyl)-2-{[4-(1-methyl-1H-pyrazol-4-yl)-2-(propan-2-yloxy)phenyl]amino}thieno[3,2-d]pyrimidine-6-carboxamide | 1.33 (d, J = 5.9 Hz, 6 H); 3.72 (s, 3 H); 3.85 (s, 3 H); 4.78 (spt, J = 6.0 Hz, 1 H); 6.92 (d, J = 6.8.Hz, 2 H); 7.19 (m, 3 H); 7.51 (m, 2 H); 7.74 (broad s, 1 H); 7.81 (s, 1 H); 7.92 (s, 1 H); 8.08 (s, 1 H); 8.23 (d, J = 8.6 Hz, 1 H); 9.24 (s, 1 H) | A 484 0.97 |
| I-128 | II-31 | IIIb-52 | 7-(2-Methoxypyridin-3-yl)-2-[(1-methyl-2-oxo-2,3,4,5-tetrahydro-1H-1-benzazepin-8-yl)amino]thieno[3,2-d]pyrimidine-6-carboxamide | 1.99 (m, 2 H); 2.13 (m, 2 H); 2.55 (t, J = 6.8 Hz, 2 H); 2.97 (s, 3 H); 3.77 (s, 3 H); 7.06 (m, 2 H); 7.38 (m, 2 H); 7.67 (broad s, 1 H); 7.75 (s, 1 H); 7.86 (m, 1 H); 8.22 (d, J = 4.9 Hz, 1 H); 9.27 (s, 1 H); 9.75 (s, 1 H) | A 475 0.70 |
| I-129 | II-31 | IIIb-38 | 7-(2-Methoxypyridin-3-yl)-2-{[4-(2-methyl-1H-imidazol-1-yl)-2-(propan-2-yloxy)phenyl]amino}thieno[3,2-d]pyrimidine-6-carboxamide | 1.32 (d, J = 6.4 Hz, 6 H); 2.27 (s, 3 H); 3.80 (s, 3 H); 4.77 (spt, J = 6.1 Hz, 1 H); 6.79 (dd, J = 2.0 and 8.8 Hz, 1 H); 6.88 (s, 1 H); 7.10 (s, 1 H); 7.19 (dd, J = 4.9 and 7.3 Hz, 1 H); 7.22 (s, 1 H); 7.48 (broad s, 1 H); 7.70 (broad s, 1 H); 7.93 (d, J = 7.3 Hz, 1 H); 8.12 (s, 1 H); 8.25 (d, J = 4.9 Hz, 1 H); 8.34 (d, J = 8.8 Hz, 1 H); 9.30 (s, 1 H) | A 561 0.63 |

TABLE 4-continued

| Compound I' | Compound II | Compound IIIb | Name | NMR | MS conditions/ MH+/Tr |
|---|---|---|---|---|---|
| I-130 | II-5 | IIIb-17 | 2-{5-Fluoro-4-(1-methylpiperidin-4-yl)-2-(propan-2-yloxy)phenyl]amino}-7-(2-methoxyphenyl)thieno[3,2-d]pyrimidine-6-carboxamide | 1.29 (d, J = 6.0 Hz, 6 H); 1.54 to 1.81 (m, 4 H); 1.95 (m, 2 H); 2.19 (s, 3 H); 2.63 (m, 1 H); 2.85 (d, J = 11.3 Hz, 2 H); 3.71 (s, 3 H); 4.65 (spt, J = 6.2 Hz, 1 H); 6.89 (d, J = 6.8 Hz, 1 H); 6.95 (broad s, 1 H); 7.11 (t, J = 7.5 Hz, 1 H); 7.19 (d, J = 8.1 Hz, 1 H); 7.49 (m, 2 H); 7.77 (broad s, 1 H); 7.93 (s, 1 H); 8.14 (d, J = 13.2 Hz, 1 H); 9.27 (s, 1 H) | A 550 0.71 |
| I-131 | II-31 | IIIb-17 | 2-{[5-Fluoro-4-(1-methylpiperidin-4-yl)-2-(propan-2-yloxy)phenyl]amino}-7-(2-methoxypyridin-3-yl)thieno[3,2-d]pyrimidine-6-carboxamide | 1.30 (d, J = 5.9 Hz, 6 H); 1.59 to 1.81 (m, 4 H); 1.94 (m, 2 H); 2.19 (s, 3 H); 2.66 (m, 1 H); 2.85 (d, J = 11.2 Hz, 2 H); 3.81 (s, 3 H); 4.65 (spt, J = 6.0 Hz, 1 H); 6.90 (d, J = 7.1 Hz, 1 H); 7.14 (dd, J = 4.9 and 7.3 Hz, 1 H); 7.49 (broad s, 1 H); 7.72 (broad s, 1 H); 7.93 (dd, J = 1.8 and 7.2 Hz, 1 H); 7.97 (s, 1 H); 8.11 (d, J = 13.0 Hz, 1 H); 8.28 (dd, J = 1.8 and 5.0 Hz, 1 H); 9.29 (s, 1 H) | A 551 0.56 |
| I-132 | II-31 | IIIb-39 | 7-(2-Methoxypyridin-3-yl)-2-{[5-methyl-4-(2-methyl-1H-imidazol-1-yl)-2-(propan-2-yloxy)phenyl]amino}thieno[3,2-d]pyrimidine-6-carboxamide | 1.30 (d, J = 6.0 Hz, 6 H); 1.79 (s, 3 H); 2.08 (s, 3 H); 3.80 (s, 3 H); 4.70 (m, 1 H); 6.89 (s, 1 H); 6.98 (s, 1 H); 7.08 (s, 1 H); 7.18 (m, 1 H); 7.49 (s, 1 H); 7.73 (s, 1 H); 7.92 (d, J = 7.3 Hz, 1 H); 8.03 (s, 1 H); 8.25 (d, J = 5.0 Hz, 1 H); 8.30 (s, 1 H); 9.30 (s, 1 H) | A 530 0.66 |
| I-133 | II-5 | IIIb-42 | 7-(2-Methoxyphenyl)-2-{[2-(propan-2-yloxy)-4-(1H-1,2,4-triazol-1-yl)phenyl]amino}thieno[3,2-d]pyrimidine-6-carboxamide | 1.35 (d, J = 6.0 Hz, 6 H); 3.71 (s, 3 H); 4.81 (m, 1 H); 6.85 (broad s, 1 H); 7.12 to 7.25 (m, 3 H); 7.45 to 7.55 (m, 3 H); 7.78 (broad s, 1 H); 8.07 (s, 1 H); 7.19 (s, 1 H); 8.42 (d, J = 8.0 Hz, 1 H); 9.22 (s, 1 H); 9.29 (s, 1 H) | A 502 0.91 |
| I-134 | II-5 | IIIb-60 | 7-(2-Methoxyphenyl)-2-[[(1-phenyl-1H-pyrazol-5-yl)amino]thieno[3,2-d]pyrimidine-6-carboxamide | 3.78 (s, 3 H); 6.31 (d, J = 1.9 Hz, 1 H); 6.24 (broad s, 1 H); 7.05 (t, J = 7.7 Hz, 1 H); 7.12 (d, J = 8.0 Hz, 1 H); 8.26 (m, 2 H); 7.38 (t, J = 7.6 Hz, 2 H); 7.44 (m, 3 H); 7.59 (d, J = 1.9 Hz, 1 H); 7.71 (broad s, 1 H); 9.10 (s, 1 H); 9.29 (broad s, 1 H) | A 443 0.76 |
| I-135 | II-5 | IIIb-50 | 7-(2-Methoxyphenyl)-2-{[4-(1-methyl-1H-pyrazol-3-yl)-2-(propan-2-yloxy)phenyl]amino}thieno[3,2-d]pyrimidine-6-carboxamide | 1.35 (d, J = 6.0 Hz, 6 H); 3.71 (s, 3 H); 3.88 (s, 3 H); 4.75 (m, 1 H); 6.63 (d, J = 1.9 Hz, 1 H) 6.92 (broad s, 1 H); 7.16 (m, 2 H); 7.22 (d, J = 8.0 Hz, 1 H); 7.39 (d, J = 1.7 Hz, 1 H); 7.48 to 7.56 (m, 2 H); 7.69 (d, J = 1.9 Hz, 1 H); 7.75 (broad s, 1 H); 7.98 (s, 1 H); 8.30 (d, J = 8.5 Hz, 1 H); 9.26 (s, 1 H) | A 515 1.0 |
| I-136 | II-31 | IIIb-64 | 7-(2-Methoxypyridin-3-yl)-2-{[3-methyl-1-(propan-2-yl)-1H-pyrazol-5-yl]amino}thieno[3,2-d]pyrimidine-6-carboxamide | 1.22 (d, J = 6.0 Hz, 6 H); 2.09 (s, 3 H); 3.78 (s, 3 H); 4.45 (m, 1 H); 5.93 (s, 1 H); 7.10 (dd, J = 5.0 and 7.2 Hz, 1 H); 7.39 (broad m, 1 H); 7.69 (broad m, 1 H); 7.80 (dd, J = 2.2 and 7.2 Hz, 1 H); 8.22 (dd, J = 2.2 and 5.0 Hz, 1 H); 9.21 (s, 1 H); 9.32 (s, 1 H) | A 424 0.58 |
| I-137 | II-16 | IIIb-7 | 7-(2-Fluorophenyl)-2-{[5-methyl-4-(1-methylpiperidin-4-yl)-2-(propan-2-yloxy)phenyl]amino}thieno[3,2-d]pyrimidine-6-carboxamide | 1.29 (d, J = 6.0 Hz, 6 H); 1.53 to 1.70 (m, 4 H); 1.97 (m, 2 H); 2.08 (s, 3 H); 2.20 (s, 3 H); 2.52 (partially masked m, 1 H); 2.85 (m, 2 H); 4.62 (m, 1 H); 6.80 (s, 1 H); 7.35 (m, 2 H); 7.48 to 7.67 (m, 3 H); 7.78 (broad m, 1 H); 7.88 (s, 1 H); 8.02 (s, 1 H); 9.28 (s, 1 H) | B 534 0.83 |
| I-138 | II-5 | IIIb-52 | 7-(2-Methoxyphenyl)-2-[[(1-methyl-2-oxo-2,3,4,5-tetrahydro-1H-1-benzazepin-8-yl)amino]thieno[3,2-d]pyrimidine-6-carboxamide | 1.99 (m, 2 H); 2.11 (t, J = 6.9 Hz, 2 H); 2.52 (t, J = 6.9 Hz, 2 H); 2.72 (s, 3 H); 3.68 (s, 3 H); 6.72 (broad m, 1 H); 7.05 (m, 2 H); 7.15 (d, J = 8.5 Hz, 1 H); 7.38 (dd, J = 2.5 and 8.5 Hz, 1 H); 7.40 to 7.49 (m, 2 H); 7.73 (broad m, 1 H); 7.79 (d, J = 2.5 Hz, 1 H); 9.23 (s, 1 H); 9.73 (s, 1 H) | B 474 1.01 |
| I-139 | II-10 | IIIb-59 | 7-(4-Fluoro-2-methoxyphenyl)-2-{[3-(piperidin-3-yl)-1-(propan-2-yl)-1H-pyrazol-5-yl]amino}thieno[3,2-d]pyrimidine-6-carboxamide | 1.21 (broad d, J = 6.0 Hz, 6 H); 1.30 to 1.53 (m, 2 H); 1.63 (m, 1 H); 1.88 (m, 1 H); 2.40 to 2.60 (partially masked m, 3 H); 2.90 to 3.08 (m, 2 H); 3.58 (broad m, 1 H); 3.68 (s, 3 H); 4.52 (m, 1 H); 6.00 (s, 1 H); 6.89 (dt, J = 2.5 and 8.5 Hz, 1 H); 6.93 (broad m, 1 H); 7.04 (dd, | B 510 0.74 |

TABLE 4-continued

| Compound I' | Compound II | Compound IIIb | Name | NMR | MS conditions/ MH+/Tr |
|---|---|---|---|---|---|
| | | | | J = 2.5 and 11.4 Hz, 1 H); 7.39 (dd, J = 7.1 and 8.5 Hz, 1 H); 7.72 (broad m, 1 H); 9.21 (s, 1 H); 9.39 (broad s, 1 H) | |
| I-140 | II-31 | IIIb-63 | 2-{[3-Cyclopropyl-1-(propan-2-yl)-1H-pyrazol-5-yl]amino}-7-(2-methoxypyridin-3-yl)thieno[3,2-d]pyrimidine-6-carboxamide | 0.49 (m, 2 H); 0.80 (m, 2 H); 1.22 (d, J = 6.0 Hz, 6 H); 1.78 (m, 1 H); 3.78 (s, 3 H); 4.49 (m, 1 H); 5.79 (s, 1 H); 7.10 (dd, J = 5.0 and 7.3 Hz, 1 H); 7.38 (broad m, 1 H); 7.70 (broad m, 1 H); 7.79 (dd, J = 2.0 and 7.3 Hz, 1 H); 8.23 (dd, J = 2.0 and 5.0 Hz, 1 H); 9.21 (s, 1 H); 9.31 (broad s, 1 H) | B 450 0.92 |
| I-141 | II-10 | IIIb-62 | 7-(4-Fluoro-2-methoxyphenyl)-2-{[1-(propan-2-yl)-3-(pyridin-3-yl)-1H-pyrazol-5-yl]amino}thieno[3,2-d]pyrimidine-6-carboxamide | 1.33 (d, J = 6.0 Hz, 6 H); 3.68 (s, 3 H); 4.69 (m, 1 H); 6.71 (s, 1 H); 6.89 (dt, J = 2.9 and 8.8 Hz, 1 H); 6.97 (broad m, 1 H); 7.05 (dd, J = 2.9 and 11.9 Hz, 1 H); 7.39 to 7.49 (m, 2 H); 7.73 (broad m, 1 H); 7.99 (td, J = 1.7 and 7.5 Hz, 1 H); 8.50 (dd, J = 1.7 and 5.0 Hz, 1 H); 8.90 (d, J = 1.7 Hz, 1 H); 9.27 (s, 1 H); 9.65 (broad s, 1 H) | B 504 0.86 |
| I-142 | II-31 | IIIb-53 | 7-(2-Methoxypyridin-3-yl)-2-[(1-methyl-2-oxo-2,3,4,5-tetrahydro-1H-1-benzazepin-7-yl)amino]thieno[3,2-d]pyrimidine-6-carboxamide | 2.00 (m, 2 H); 2.11 (m, 2 H); 2.48 (partially masked m, 2 H); 3.28 (s, 3 H); 3.80 (s, 3 H); 7.12 (d, J = 8.8 Hz, 1 H); 7.18 (dd, J = 5.0 and 7.3 Hz, 1 H); 6.91 (broad m, 1 H); 7.48 (dd, J = 2.6 and 8.8 Hz, 1 H); 7.71 (broad m, 1 H); 7.82 (d, J = 2.6 Hz, 1 H); 7.90 (dd, J = 1.8 and 7.3 Hz, 1 H); 8.28 (dd, J = 1.8 and 5.0 Hz, 1 H); 9.28 (s, 1 H); 9.80 (broad s, 1 H) | B 475 0.88 |
| I-143 | II-10 | IIIb-42 | 7-(4-Fluoro-2-methoxyphenyl)-2-{[2-(propan-2-yloxy)-4-(1H-1,2,4-triazol-1-yl)phenyl]amino}thieno[3,2-d]pyrimidine-6-carboxamide | 1.35 (d, J = 6.0 Hz, 6 H); 3.72 (s, 3 H); 4.73 (m, 1 H); 6.99 (m, 1 H); 7.08 to 7.19 (m, 2 H); 7.28 (d, J = 8.5 Hz, 1 H); 7.51 (m, 2 H); 7.73 (s, 1 H); 8.09 (s, 1 H); 8.20 (s, 1 H); 8.42 (d, J = 8.5 Hz, 1 H); 9.22 (s, 1 H); 9.29 (s, 1 H) | B 520 1.19 |
| I-144 | II-31 | IIIb-41 | 2-{[4-(2,4-Dimethyl-1H-imidazol-1-yl)-2-(propan-2-yloxy)phenyl]amino}-7-(2-methoxypyridin-3-yl)thieno[3,2-d]pyrimidine-6-carboxamide | 1.30 (d, J = 6.0 Hz, 6 H); 2.09 (s, 3 H); 2.21 (s, 3 H); 3.80 (s, 3 H); 4.75 (m, 1 H); 6.76 (d, J = 8.5 Hz, 1 H); 6.90 (s, 1 H); 7.05 (s, 1 H); 7.20 (m, 1 H); 7.49 (broad m, 1 H); 7.70 (broad m, 1 H); 7.92 (m, 1 H); 8.10 (m, 1 H); 8.25 (m, 1 H); 8.30 (d, J = 8.5 Hz, 1 H); 9.30 (s, 1 H) | B 530 0.89 |
| I-145 | II-31 | IIIb-51 | 2-{[4-Methoxy-2-(propan-2-yloxy)phenyl]amino}-7-(2-methoxypyridin-3-yl)thieno[3,2-d]pyrimidine-6-carboxamide | 1.28 (d, J = 6.0 Hz, 6 H); 3.71 (s, 3 H); 3.80 (s, 3 H); 4.63 (m, 1 H); 6.35 (broad d, J = 8.5 Hz, 1 H); 6.61 (broad s, 1 H); 7.17 (m, 1 H); 7.43 (broad m, 1 H); 7.68 (broad m, 1 H); 7.88 (m, 2 H); 7.97 (d, J = 8.5 Hz, 1 H); 8.25 (s, 1 H); 9.19 (s, 1 H) | B 466 1.26 |
| I-146 | II-5 | IIIb-61 | 2-[(3-Cyclopropyl-1-phenyl-1H-pyrazol-5-yl)amino]-7-(2-methoxyphenyl)thieno[3,2-d]pyrimidine-6-carboxamide | 0.61 (m, 2 H); 0.89 (m, 2 H); 1.36 (m, 1 H); 3.68 (s, 3 H); 6.04 (s, 1 H); 6.75 (broad m, 1 H); 7.08 (t, J = 7.8 Hz, 1 H); 7.24 (d, J = 8.0 Hz, 1 H); 7.27 (tt, J = 1.7 and 7.5 Hz, 1 H); 7.29 (dd, J = 2.0 and 8.0 Hz, 1 H); 7.37 (t, J = 7.8 Hz, 2 H); 7.45 (m, 3 H); 7.71 (broad m, 1 H); 9.11 (s, 1 H); 9.22 (broad s, 1 H) | B 483 1.17 |
| I-147 | II-31 | IIIb-29 | 2-{[4-(5,6-Dihydroimidazo[1,2-a]pyrazin-7(8H)-yl)-2-(propan-2-yloxy)phenyl]amino}-7-(2-methoxypyridin-3-yl)thieno[3,2-d]pyrimidine-6-carboxamide | 1.29 (d, J = 6.0 Hz, 6 H); 3.61 (m, 2 H); 3.80 (s, 3 H); 4.08 (m, 2 H); 4.31 (s, 2 H); 4.72 (m, 1 H); 6.48 (dd, J = 3.0 and 8.9 Hz, 1 H); 6.79 (d, J = 3.0 Hz, 1 H); 6.90 (d, J = 10 Hz, 1 H); 7.10 (d, J = 1.0 Hz, 1 H); 7.19 (dd, J = 5.0 and 7.3 Hz, 1 H); 7.46 (broad m, 1 H); 7.69 (broad m, 1 H); 7.88 (s, 1 H); 7.90 (dd, J = 2.0 and 7.3 Hz, 1 H); 8.00 (d, J = 8.9 Hz, 1 H); 8.28 (dd, J = 2.0 and 5.0 Hz, 1 H); 9.20 (s, 1 H) | B 557 0.84 |
| I-148 | II-5 | IIIb-6 | 2-{[4-(1-Cyclopropylpiperidin-4-yl)-2-(propan-2-yloxy)phenyl]amino}-7-(2-methoxyphenyl)thieno[3,2- | 0.30 (m, 2 H); 0.42 (m, 2 H); 1.29 (d, J = 6.0 Hz, 6 H); 1.48 to 1.72 (m, 5 H); 2.21 (m, 2 H); 2.41 (m, 1 H); 3.00 (m, 2 H); 3.70 (s, 3 H); 4.68 (m, 1 H); 6.59 (dd, J = 1.7 and 8.6 Hz, 1 H); 6.86 (d, J = 1.7 Hz, | B 558 0.95 |

TABLE 4-continued

| Compound I' | Compound II | Compound IIIb | Name | NMR | MS conditions/ MH+/Tr |
|---|---|---|---|---|---|
| | | | d]pyrimidine-6-carboxamide | 1 H); 6.90 (broad m, 1 H); 7.13 (t, J = 7.8 Hz, 1 H); 7.20 (d, J = 8.0 Hz, 1 H); 7.42 to 7.52 (m, 2 H); 7.74 (broad m, 1 H); 7.86 (s, 1 H); 8.12 (d, J = 8.6 Hz, 1 H); 9.20 (s, 1 H) | |
| I-149 | II-11 | IIIb-6 | 2-{[4-(1-Cyclopropylpiperidin-4-yl)-2-(propan-2-yloxy)phenyl]amino}-7-(5-fluoro-2-methoxyphenyl)thieno[3,2-d]pyrimidine-6-carboxamide | 0.30 (m, 2 H); 0.42 (m, 2 H); 1.29 (d, J = 6.0 Hz, 6 H); 1.48 to 1.72 (m, 5 H); 2.21 (m, 2 H); 2.42 (m, 1 H); 3.00 (m, 2 H); 3.69 (s, 3 H); 4.68 (m, 1 H); 6.60 (dd, J = 1.7 and 8.6 Hz, 1 H); 6.89 (d, J = 1.7 Hz, 1 H); 7.15 (dd, J = 4.5 and 9.2 Hz, 1 H); 7.24 (broad m, 1 H); 7.30 (dt, J = 3.0 and 9.02 Hz, 1 H); 7.38 (dd, J = 3.0 and 9.4 Hz, 1 H); 7.70 (broad m, 1 H); 7.90 (s, 1 H); 8.15 (d, J = 8.6 Hz, 1 H); 9.21 (s, 1 H) | B 576 0.96 |
| I-150 | II-31 | IIIb-6 | 2-{[4-(1-Cyclopropylpiperidin-4-yl)-2-(propan-2-yloxy)phenyl]amino}-7-(2-methoxypyridin-3-yl)thieno[3,2-d]pyrimidine-6-carboxamide | 0.30 (m, 2 H); 0.42 (m, 2 H); 1.29 (d, J = 6.0 Hz, 6 H); 1.48 to 1.72 (m, 5 H); 2.22 (m, 2 H); 2.42 (m, 1 H); 3.01 (m, 2 H); 3.80 (s, 3 H); 4.68 (m, 1 H); 6.61 (dd, J = 1.7 and 8.4 Hz, 1 H); 6.89 (d, J = 1.7 Hz, 1 H); 7.19 (dd, J = 4.9 and 7.4 Hz, 1 H); 7.48 (broad m, 1 H); 7.70 (broad m, 1 H); 7.81 (m, 2 H); 8.10 (d, J = 8.4 Hz, 1 H); 8.29 (dd, J = 1.9 and 4.9 Hz, 1 H); 9.22 (s, 1 H) | B 559 0.89 |
| I-151 | II-31 | IIIb-40 | 7-(2-Methoxypyridin-3-yl)-2-{[4-(4-methyl-1H-imidazol-1-yl)-2-(propan-2-yloxy)phenyl]amino}thieno[3,2-d]pyrimidine-6-carboxamide | 1.32 (d, J = 6.0 Hz, 6 H); 2.25 (s, 3 H); 3.80 (s, 3 H); 3.83 (m, 1 H); 6.98 (dd, J = 2.1 and 8.7 Hz, 1 H); 7.21 (dd, J = 5.0 and 7.5 Hz, 1 H); 8.24 (d, J = 2.1 Hz, 1 H); 7.40 (s, 1 H); 7.50 (broad m, 1 H); 7.71 (broad m, 1 H); 7.92 (dd, J = 1.9 and 7.5 Hz, 1 H); 8.08 (s, 2 H); 8.28 (m, 2 H); 9.29 (s, 1 H) | B 516 0.87 |
| I-152 | II-10 | IIIb-53 | 7-(4-Fluoro-2-methoxyphenyl)-2-[(1-methyl-2-oxo-2,3,4,5-tetrahydro-1H-1-benzazepin-7-yl)amino]thieno[3,2-d]pyrimidine-6-carboxamide | 2.00 (m, 2 H); 2.10 (m, 2 H); 2.48 (m, 2 H); 3.18 (s, 3 H); 3.70 (s, 3 H); 6.90 to 7.16 (m, 4 H); 7.48 (m, 2 H); 7.72 (broad m, 1 H); 7.82 (d, J = 2.1 Hz, 1 H); 9.22 (s, 1 H); 9.78 (s, 1 H) | B 492 0.99 |
| I-153 | II-30 | IIIb-25 | 2-{[4-(4-Methylpiperazin-1-yl)-2-(propan-2-yloxy)phenyl]amino}-7-(1-oxidopyridin-2-yl)thieno[3,2-d]pyrimidine-6-carboxamide | 1.25 (d, J = 6.0 Hz, 6 H); 2.21 (s, 3 H); 2.43 (m, 4 H); 3.05 (m, 4 H); 4.65 (m, 1 H); 6.40 (dd, J = 2.2 and 9.0 Hz, 1 H); 6.60 (d, J = 2.1 Hz, 1 H); 7.62 (m, 2 H); 7.76 (m, 2 H); 7.80 (d, J = 9.0 Hz, 1 H); 7.89 (s, 1 H); 8.50 (m, 1 H); 9.00 (broad m, 1 H); 9.29 (s, 1 H) | B 520 0.68 |
| I-154 | II-5 | IIIb-46 | 2-{[4-(1-Ethyl-1,7-diazaspiro[4.4]non-7-yl)-2-(propan-2-yloxy)phenyl]amino}-7-(2-methoxyphenyl)thieno[3,2-d]pyrimidine-6-carboxamide | 1.02 (t, J = 7.0 Hz, 3 H); 1.23 (d, J = 6.0 Hz, 6 H); 1.64 (m, 1 H); 1.76 (m, 4 H); 2.08 (m, 1 H); 2.40 to 2.65 (partially masked m, 3 H); 2.82 (m, 1 H); 2.92 (d, J = 9.3 Hz, 1 H); 3.10 to 3.38 (partially masked m, 3 H); 3.70 (s, 3 H); 4.61 (m, 1 H); 5.92 (dd, J = 2.1 and 9.0 Hz, 1 H); 6.19 (d, J = 2.1 Hz, 1 H); 6.82 (broad m, 1 H); 7.11 (t, J = 7.8 Hz, 1 H); 7.19 (d, J = 8.0 Hz, 1 H); 7.41 to 7.51 (m, 2 H); 7.70 (m, 2 H); 7.82 (d, J = 9.0 Hz, 1 H); 9.10 (s, 1 H) | B 587 0.96 |
| I-155 | II-44 | IIIb-26 | 7-(2-Ethoxypyridin-3-yl)-2-{[5-methyl-4-(4-methylpiperazin-1-yl)-2-(propan-2-yloxy)phenyl]amino}thieno[3,2-d]pyrimidine-6-carboxamide | 1.08 (t, J = 7.0 Hz, 3 H); 1.29 (d, J = 6.0 Hz, 6 H); 2.03 (s, 3 H); 2.22 (s, 3 H); 2.45 (m, 4 H); 2.79 (m, 4 H); 4.29 (q, J = 7.0 Hz, 2 H); 4.60 (m, 1 H); 6.70 (s, 1 H); 7.13 (dd, J = 5.1 and 7.4 Hz, 1 H); 7.47 (broad m, 1 H); 7.70 (broad m, 1 H); 7.81 (s, 1 H); 7.92 (dd, J = 2.1 and 7.4 Hz, 1 H); 8.03 (s, 1 H); 8.23 (dd, J = 2.1 and 5.1 Hz, 1 H); 9.21 (s, 1 H) | B 562 0.88 |
| I-156 | II-5 | IIIb-67 | 2-{[4-(3,5-Dimethyl-1H-1,2,4-triazol-1-yl)-2-(propan-2-yloxy)phenyl]amino}-7-(2- | 1.31 (d, J = 6.0 Hz, 6 H); 2.25 (s, 3 H); 2.39 (s, 3 H); 3.70 (s, 3 H); 4.76 (m, 1 H); 6.85 (dd, J = 2.1 and 8.8 Hz, 1 H); 6.95 (broad m, 1 H); 7.13 (t, J = 7.8 Hz, | B 530 1.13 |

TABLE 4-continued

| Compound I' | Compound II | Compound IIIb | Name | NMR | MS conditions/ MH+/Tr |
|---|---|---|---|---|---|
| | | | methoxyphenyl)thieno[3,2-d]pyrimidine-6-carboxamide | 1 H); 7.19 (d, J = 2.1 Hz, 1 H); 7.20 (d, J = 8.0 Hz, 1 H); 7.49 (m, 2 H); 7.78 (broad m, 1 H); 8.09 (s, 1 H); 8.40 (d, J = 8.8 Hz, 1 H); 9.29 (s, 1 H) | |
| I-157 | II-36 | IIIb-26 | 7-(5-Fluoro-2-methoxypyridin-3-yl)-2-{5-methyl-4-(4-methylpiperazin-1-yl)-2-(propan-2-yloxy)phenyl]amino}thieno[3,2-d]pyrimidine-6-carboxamide | 1.28 (d, J = 6.1 Hz, 6 H); 2.05 (s, 3 H); 2.23 (s, 3 H); 2.46 (m, 4 H); 2.78 (m, 4 H); 3.78 (s, 3 H); 4.60 (m, 1 H); 6.70 (s, 1 H); 7.55 to 7.74 (broad m, 2 H); 7.86 to 7.94 (m, 2 H); 7.98 (s, 1 H); 8.25 (d, J = 3.1 Hz, 1 H); 9.23 (s, 1 H) | B 566 0.88 |
| I-158 | II-47 | IIIb-38 | 7-(2-Methoxy-6-methylpyridin-3-yl)-2-{[4-(2-methyl-1H-imidazol-1-yl)-2-(propan-2-yloxy)phenyl]amino}thieno[3,2-d]pyrimidine-6-carboxamide | 1.31 (d, J = 6.0 Hz, 6 H); 2.29 (s, 3 H); 2.47 (s, 3 H); 3.79 (s, 3 H); 4.79 (m, 1 H); 6.81 (dd, J = 2.2 and 8.6 Hz, 1 H); 6.90 (d, J = 1.0 Hz, 1 H); 7.04 (d, J = 7.6 Hz, 1 H); 7.11 (d, J = 2.1 Hz, 1 H); 7.22 (d, J = 1.0 Hz, 1 H); 7.40 (broad m, 1 H); 7.70 (broad m, 1 H); 7.81 (d, J = 7.6 Hz, 1 H); 8.11 (s, 1 H); 8.36 (d, J = 8.6 Hz, 1 H); 9.29 (s, 1 H) | B 530 0.89 |
| I-159 | II-5 | IIIb-66 | 7-(2-Methoxyphenyl)-2-({4-[(4-methylpiperazin-1-yl)methyl]-2-(propan-2-yloxy)phenyl}amino)thieno[3,2-d]pyrimidine-6-carboxamide | 1.30 (d, J = 6.0 Hz, 6 H); 2.13 (s, 3 H); 2.30 (broad m, 8 H); 3.38 (s, 2 H); 3.70 (s, 3 H); 4.61 (m, 1 H); 6.82 (dd, J = 1.9 and 8.8 Hz, 1 H); 6.89 (broad m, 1 H); 6.91 (d, J = 1.9 Hz, 1 H); 7.11 (t, J = 7.8 Hz, 1 H); 7.19 (d, J = 8.0 Hz, 1 H); 7.42 to 7.52 (m, 2 H); 7.71 (broad m, 1 H); 7.90 (s, 1 H); 8.17 (d, J = 8.8 Hz, 1 H); 9.21 (s, 1 H) | B 547 0.82 |
| I-160 | II-47 | IIIb-26 | 7-(2-Methoxy-6-methylpyridin-3-yl)-2-{[5-methyl-4-(4-methylpiperazin-1-yl)-2-(propan-2-yloxy)phenyl]amino}thieno[3,2-d]pyrimidine-6-carboxamide | 1.30 (d, J = 6.0 Hz, 6 H); 2.03 (s, 3 H); 2.22 (s, 3 H); 2.40 to 2.53 (partially masked m, 7 H); 2.79 (m, 4 H); 3.78 (s, 3 H); 4.60 (m, 1 H); 6.70 (s, 1 H); 7.01 (d, J = 7.7 Hz, 1 H); 7.30 (broad m, 1 H); 7.70 (broad m, 1 H); 7.78 (d, J = 7.7 Hz, 1 H); 7.80 (s, 1 H); 8.03 (s, 1 H); 9.20 (s, 1 H) | B 562 0.89 |
| I-161 | II-5 | IIIb-65 | 7-(2-Methoxyphenyl)-2-{[1-methyl-2-oxo-6-(propan-2-yloxy)-2,3,4,5-tetrahydro-1H-1-benzazepin-7-yl]amino}thieno[3,2-d]pyrimidine-6-carboxamide | 1.22 (d, J = 6.0 Hz, 6 H); 2.04 (m, 2 H); 2.16 (m, 2 H); 2.69 (m, 2 H); 3.20 (s, 3 H); 3.70 (s, 3 H); 4.18 (m, 1 H); 6.90 (m, 2 H); 7.11 (t, J = 8.0 Hz, 1 H); 7.19 (d, J = 8.0 Hz, 1 H); 7.48 (m, 2 H); 7.72 (broad m, 1 H); 8.03 (d, J = 8.0 Hz, 1 H); 8.13 (s, 1 H); 9.22 (s, 1 H) | B 532 1.18 |
| I-162 | II-31 | IIIb-65 | 7-(2-Methoxypyridin-3-yl)-2-{[1-methyl-2-oxo-6-(propan-2-yloxy)-2,3,4,5-tetrahydro-1H-1-benzazepin-7-yl]amino}thieno[3,2-d]pyrimidine-6-carboxamide | 1.21 (d, J = 6.0 Hz, 6 H); 2.04 (m, 2 H); 2.17 (m, 2 H); 2.69 (m, 2 H); 3.20 (s, 3 H); 3.70 (s, 3 H); 4.16 (m, 1 H); 6.95 (d, J = 8.8 Hz, 1 H); 7.18 (dd, J = 5.0 and 7.3 Hz, 1 H); 7.48 (broad m, 1 H); 7.70 (broad m, 1 H); 7.91 (dd, J = 2.0 and 7.3 Hz, 1 H); 8.00 (d, J = 8.8 Hz, 1 H); 8.23 (m, 2 H); 9.26 (s, 1 H) | B 533 1.09 |
| I-163 | II-5 | IIIb-68 | 7-(2-Methoxyphenyl)-2-{[5-(4-methylpiperazin-1-yl)-2-(propan-2-yloxy)phenyl]amino}thieno[3,2-d]pyrimidine-6-carboxamide | 1.28 (d, J = 6.1 Hz, 6 H); 2.24 (s, 3 H); 2.34 (m, 4 H); 2.68 (m, 4 H); 3.68 (s, 3 H); 4.49 (m, 1 H); 6.43 (dd, J = 2.9 and 9.0 Hz, 1 H); 6.64 (broad s, 1 H); 6.89 (d, J = 9.0 Hz, 1 H); 7.09 (broad t, J = 7.8 Hz, 1 H); 7.19 (broad d, J = 7.8 Hz, 1 H); 7.38 (dd, J = 1.8 and 7.8 Hz, 1 H); 7.48 (m, 1 H); 7.74 (d, J = 2.9 Hz, 1 H); 7.78 (broad s, 1 H); 7.92 (s, 1 H); 9.26 (s, 1 H) | B 533 0.93 |
| I-164 | II-5 | IIIb-69 | 7-(2-Methoxyphenyl)-2-{[2-(propan-2-yloxy)-4-(tetrahydro-2H-pyran-4-ylamino)phenyl]amino}thieno[3,2-d]pyrimidine-6-carboxamide | 1.24 (d, J = 6.1 Hz, 6 H); 1.33 (m, 2 H); 1.85 (m, 2 H); 3.41 (m, 3 H); 3.70 (s, 3 H); 3.86 (m, 2 H); 4.49 (m, 1 H); 5.17 (broad d, J = 8.3 Hz, 1 H); 6.03 (dd, J = 2.5 and 8.5 Hz, 1 H); 6.31 (d, J = 2.5 Hz, 1 H); 6.82 (broad s, 1 H); 7.09 (t, J = 7.8 Hz, 1 H); 7.15 (d, J = 7.8 Hz, 1 H); 7.40 to 7.50 (m, 2 H); 7.65 to 7.75 (m, 3 H); 9.10 (s, 1 H) | B 534 0.98 |
| I-165 | II-48 | IIIb-26 | 7-(3-Methoxypyridin-2-yl)-2-{[5-methyl-4-(4-methylpiperazin-1-yl)- | 1.28 (m, 6 H); 2.00 (s, 3 H); 2.23 (s, 3 H); 2.50 (masked m, 4 H); 2.77 (m, 4 H); 3.70 (s, 3 H); 4.59 (m, 1 H); 6.68 (s, | B 548 0.82 |

TABLE 4-continued

| Compound I' | Compound II | Compound IIIb | Name | NMR | MS conditions/ MH+/Tr |
|---|---|---|---|---|---|
| | | | (propan-2-yloxy)phenyl]amino}thieno[3,2-d]pyrimidine-6-carboxamide | 1 H); 7.49 to 7.97 (m, 6 H); 8.35 (m, 1 H); 9.23 (s, 1 H) | |
| I-166 | II-31 | IIIb-70 | 2-{[4-(4-Hydroxypiperidin-1-yl)-2-(propan-2-yloxy)phenyl]amino}-7-(2-methoxypyridin-3-yl)thieno[3,2-d]pyrimidine-6-carboxamide | 1.26 (d, J = 6.1 Hz, 6 H); 1.49 (m, 2 H); 1.82 (m, 2 H); 2.75 (m, 2 H); 3.42 (m, 2 H); 3.60 (m, 1 H); 3.80 (s, 3 H); 4.57 to 4.68 (m, 2 H); 6.34 (dd, J = 2.1 and 8.4 Hz, 1 H); 6.61 (d, J = 2.1 Hz, 1 H); 7.17 (dd, J = 5.1 and 8.3 Hz, 1 H); 7.45 (broad m, 1 H); 7.67 (broad m, 1 H); 7.81 (s, 1 H); 7.87 to 7.93 (m, 2 H); 8.26 (dd, J = 2.0 and 5.1 Hz, 1 H); 9.17 (s, 1 H) | B 535 0.83 |
| I-167 | II-5 | IIIb-73 | 7-(2-Methoxyphenyl)-2-({4-[(1-methylpiperidin-4-yl)amino]-2-(propan-2-yloxy)phenyl}amino)thieno[3,2-d]pyrimidine-6-carboxamide | 1.24 (d, J = 6.1 Hz, 6 H); 1.35 (m, 2 H); 1.85 (m, 2 H); 2.02 (m, 2 H); 2.17 (s, 3 H); 2.71 (m, 2 H); 3.13 (m, 1 H); 3.69 (s, 3 H); 4.48 (m, 1 H); 5.09 (broad d, J = 8.6 Hz, 1 H); 6.00 (dd, J = 2.5 and 8.5 Hz, 1 H); 6.28 (d, J = 2.5 Hz, 1 H); 6.82 (broad s, 1 H); 7.08 (t, J = 7.8 Hz, 1 H); 7.15 (d, J = 7.8 Hz, 1 H); 7.39 to 7.48 (m, 2 H); 7.62 to 7.76 (m, 3 H); 9.09 (s, 1 H) | B 547 0.86 |
| I-168 | II-10 | IIIb-74 | 2-{[1-Cyclobutyl-3-(1-ethylpiperidin-4-yl)-1H-pyrazol-5-yl]amino}-7-(4-fluoro-2-methoxyphenyl)thieno[3,2-d]pyrimidine-6-carboxamide | 1.03 (t, J = 7.3 Hz, 3 H); 1.44 to 1.82 (m, 6 H); 1.94 (m, 2 H); 2.16 (m, 2 H); 2.34 (q, J = 7.3 Hz, 2 H); 2.42 (m, 3 H); 2.91 (m, 2 H); 3.67 (s, 3 H); 4.78 (m, 1 H); 6.02 (s, 1 H); 6.88 (td, J = 2.4 and 8.6 Hz, 1 H); 6.94 (broad m, 1 H); 7.03 (dd, J = 2.4 and 11.5 Hz, 1 H); 7.39 (dd, J = 6.8 and 8.6 Hz, 1 H); 7.72 (broad m, 1 H); 9.21 (s, 1 H); 9.42 (broad s, 1 H) | B 550 0.84 |
| I-169 | II-31 | IIIb-66 | 7-(2-Methoxypyridin-3-yl)-2-({4-[(4-methylpiperazin-1-yl)methyl]-2-(propan-2-yloxy)phenyl}amino)thieno[3,2-d]pyrimidine-6-carboxamide | 1.30 (d, J = 6.1 Hz, 6 H); 2.15 (s, 3 H); 2.55 to 2.45 (broad m, 8 H); 3.38 (s, 2 H); 3.80 (s, 3 H); 4.63 (m, 1 H); 6.68 (dd, J = 1.7 and 8.3 Hz, 1 H); 6.94 (d, J = 1.7 Hz, 1 H); 7.17 (dd, J = 5.0 and 7.3 Hz, 1 H); 7.48 (broad s, 1 H); 7.71 (broad s, 1 H); 7.91 (dd, J = 2.0 and 7.3 Hz, 1 H); 7.96 (s, 1 H); 8.14 (d, J = 8.3 Hz, 1 H); 8.28 (dd, J = 2.0 and 5.0 Hz, 1 H); 9.25 (s, 1 H) | B 548 0.83 |
| I-170 | II-31 | IIIb-71 | 7-(2-Methoxypyridin-3-yl)-2-{[4-(1-methylpyrrolidin-3-yl)-2-(propan-2-yloxy)phenyl]amino}thieno[3,2-d]pyrimidine-6-carboxamide | 1.29 (d, J = 6.1 Hz, 6 H); 1.73 (m, 1 H); 2.20 (m, 1 H); 2.30 (s, 3 H); 2.39 (dd, J = 5.7 and 8.5 Hz, 1 H); 2.61 (m, 2 H); 2.83 (t, J = 8.5 Hz, 1 H); 3.27 (partially masked m, 1 H); 3.80 (s, 3 H); 4.64 (m, 1 H); 6.66 (dd, J = 2.1 and 8.3 Hz, 1 H); 6.92 (d, J = 2.1 Hz, 1 H); 7.17 (dd, J = 5.1 and 7.3 Hz, 1 H); 7.47 (broad m, 1 H); 7.70 (broad m, 1 H); 7.91 (dd, J = 2.0 and 7.3 Hz, 1 H); 7.93 (s, 1 H); 8.08 (d, J = 8.3 Hz, 1 H); 8.28 (dd, J = 2.0 and 5.1 Hz, 1 H); 9.24 (s, 1 H) | B 519 0.89 |
| I-171 | II-5 | IIIb-75 | 7-(2-Methoxyphenyl)-2-{[3-(4-methylpiperazin-1-yl)-2-(propan-2-yloxy)phenyl]amino}thieno[3,2-d]pyrimidine-6-carboxamide | 1.20 (d, J = 6.1 Hz, 6 H); 2.22 (s, 3 H); 2.47 (partially masked broad m, 4 H); 2.99 (broad m, 4 H); 3.70 (s, 3 H); 4.85 (m, 1 H); 6.59 (dd, J = 1.5 and 8.3 Hz, 1 H); 6.81 (t, J = 8.3 Hz, 1 H); 7.00 (broad s, 1 H); 7.12 (t, J = 7.8 Hz, 1 H); 7.19 (d, J = 7.8 Hz, 1 H); 7.45 to 7.52 (m, 2 H); 7.79 (broad s, 1 H); 7.99 (dd, J = 1.5 and 8.3 Hz, 1 H); 8.03 (s, 1 H); 9.25 (s, 1 H) | B 533 0.83 |
| I-172 | II-36 | IIIb-72 | 7-(5-Fluoro-2-methoxypyridin-3-yl)-2-{[1-(propan-2-yl)-3-(tetrahydro-2H-pyran-4-yl)-1H-pyrazol-5-yl]amino}thieno[3,2-d]pyrimidine-6-carboxamide | 1.23 (d, J = 6.6 Hz, 6 H); 1.54 (m, 2 H); 1.71 (m, 2 H); 2.70 (m, 1 H); 3.41 (m, 2 H); 3.75 (s, 3 H); 3.89 (m, 2 H); 4.50 (m, 1 H); 6.02 (s, 1 H); 7.48 to 7.72 (broad m, 2 H); 7.78 (dd, J = 2.9 and 8.6 Hz, 1 H); 8.19 (d, J = 2.9 Hz, 1 H); 9.25 (s, 1 H); 9.43 (broad s, 1 H) | B 512 1.01 |
| I-173 | II-36 | IIIb-64 | 7-(5-Fluoro-2-methoxypyridin-3-yl)-2-{[3-methyl-1-(propan-2-yl)-1H-pyrazol-5- | 1.23 (d, J = 6.6 Hz, 6 H); 2.10 (s, 3 H); 3.76 (s, 3 H); 4.46 (m, 1 H); 5.98 (s, 1 H); 7.53 to 7.72 (broad m, 2 H); 7.82 (dd, J = 3.1 and 8.7 Hz, 1 H); 8.21 (d, | B 442 0.95 |

TABLE 4-continued

| Compound I' | Compound II | Compound IIIb | Name | NMR | MS conditions/ MH+/Tr |
|---|---|---|---|---|---|
| | | | yl]amino}thieno[3,2-d]pyrimidine-6-carboxamide | J = 3.1 Hz, 1 H); 9.23 (s, 1 H); 9.39 (broad s, 1 H) | |
| I-174 | II-31 | IIIb-76 | 7-(2-Methoxypyridin-3-yl)-2-[(5-methyl-2,3,4,5-tetrahydro-1,5-benzoxazepin-7-yl)amino]thieno[3,2-d]pyrimidine-6-carboxamide | 1.88 (m, 2 H); 2.52 (s, 3 H); 3.00 (m, 2 H); 3.78 (s, 3 H); 3.87 (m, 2 H); 6.66 (d, J = 8.6 Hz, 1 H); 7.07 to 7.16 (m, 2 H); 7.23 (d, J = 2.1 Hz, 1 H); 7.33 (broad s, 1 H); 7.67 (broad s, 1 H); 7.82 (dd, J = 2.0 and 7.3 Hz, 1 H); 8.25 (dd, J = 2.0 and 5.1 Hz, 1 H); 9.21 (s, 1 H); 9.45 (broad s, 1 H) | B 463 0.90 |
| I-175 | II-19 | IIIb-72 | 2-{[1-(Propan-2-yl)-3-(tetrahydro-2H-pyran-4-yl)-1H-pyrazol-5-yl]amino}-7-[2-(trifluoromethoxy)phenyl]thieno[3,2-d]pyrimidine-6-carboxamide | 1.23 (d, J = 6.5 Hz, 6 H); 1.50 (m, 2 H); 1.68 (m, 2 H); 2.68 (m, 1 H); 3.40 (m, 2 H); 3.89 (m, 2 H); 4.49 (m, 1 H); 5.99 (s, 1 H); 7.36 (broad m, 1 H); 7.41 to 7.50 (m, 2 H); 7.57 (m, 2 H); 7.74 (broad m, 1 H); 9.26 (s, 1 H); 9.41 (broad s, 1 H) | B 547 1.14 |
| I-176 | II-31 | IIIb-75 | 7-(2-Methoxypyridin-3-yl)-2-{[3-(4-methylpiperazin-1-yl)-2-(propan-2-yloxy)phenyl]amino}thieno[3,2-d]pyrimidine-6-carboxamide | For this batch, all the signals are broad with: 1.20 (d, J = 6.0 Hz, 6 H); 2.22 (s, 3 H); 2.48 (partially masked m, 4 H); 2.99 (m, 4 H); 3.80 (s, 3 H); 4.83 (m, 1 H); 6.60 (d, J = 80 Hz, 1 H); 6.84 (t, J = 8.2 Hz, 1 H); 7.19 (m, 1 H); 7.53 (s, 1 H); 7.75 (s, 1 H); 7.90 to 8.00 (m, 2 H); 8.08 (s, 1 H); 8.28 (d, J = 5.0 Hz, 1 H); 9.28 (s, 1 H) | B 534 0.74 |
| I-177 | II-31 | IIIb-68 | 7-(2-Methoxypyridin-3-yl)-2-{[5-(4-methylpiperazin-1-yl)-2-(propan-2-yloxy)phenyl]amino}thieno[3,2-d]pyrimidine-6-carboxamide | For this batch, all the signals are broad with: 1.19 (d, J = 6.0 Hz, 6 H); 2.25 (s, 3 H); 2.39 (m, 4 H); 2.71 (m, 4 H); 3.78 (s, 3 H); 4.50 (m, 1 H); 6.45 (dd, J = 2.1 and 8.5 Hz, 1 H); 6.90 (d, J = 8.5 Hz, 1 H); 7.11 (m, 1 H); 7.41 (s, 1 H); 7.72 (s, 1 H); 7.76 (d, J = 2.1 Hz, 1 H); 7.81 (d, J = 7.4 Hz, 1 H); 7.96 (s, 1 H); 8.27 (d, J = 5.0 Hz, 1 H); 9.29 (s, 1 H) | B 534 0.82 |
| I-178 | II-31 | IIIb-73 | 7-(2-Methoxypyridin-3-yl)-2-({4-[(1-methylpiperidin-4-yl)amino]-2-(propan-2-yloxy)phenyl}amino)thieno[3,2-d]pyrimidine-6-carboxamide | 1.24 (d, J = 6.1 Hz, 6 H); 1.36 (m, 2 H); 1.85 (m, 2 H); 2.01 (m, 2 H); 2.17 (s, 3 H); 2.70 (m, 2 H); 3.13 (m, 1 H); 3.79 (s, 3 H); 4.48 (m, 1 H); 5.11 (d, J = 8.3 Hz, 1 H); 6.03 (dd, J = 2.4 and 8.8 Hz, 1 H); 6.29 (d, J = 2.4 Hz, 1 H); 7.11 (dd, J = 5.1 and 7.3 Hz, 1 H); 7.42 (broad s, 1 H); 7.65 (partially masked broad s, 1 H); 7.68 (d, J = 8.8 Hz, 1 H); 7.72 (s, 1 H); 7.87 (dd, J = 2.0 and 7.3 Hz, 1 H); 8.23 (dd, J = 2.0 and 5.1 Hz, 1 H); 9.12 (s, 1 H) | B 548 0.73 |
| I-179 | II-31 | IIIb-77 | 2-{[4-(4-Ethylpiperazin-1-yl)-2-(propan-2-yloxy)phenyl]amino}-7-(2-methoxypyridin-3-yl)thieno[3,2-d]pyrimidine-6-carboxamide | 1.03 (t, J = 7.2 Hz, 3 H); 1.26 (d, J = 6.1 Hz, 6 H); 2.37 (q, J = 7.2 Hz, 2 H); 2.50 (masked m, 4 H); 3.06 (m, 4 H); 3.80 (s, 3 H); 4.64 (m, 1 H); 6.34 (dd, J = 2.5 and 8.8 Hz, 1 H); 6.62 (d, J = 2.5 Hz, 1 H); 7.17 (dd, J = 4.9 and 7.3 Hz, 1 H); 7.44 (broad s, 1 H); 7.67 (broad s, 1 H); 7.83 (s, 1 H); 7.90 (dd, J = 2.0 and 7.3 Hz, 1 H); 7.93 (d, J = 8.8 Hz, 1 H); 8.26 (dd, J = 2.0 and 4.9 Hz, 1 H); 9.18 (s, 1 H) | B 548 0.79 |
| I-180 | II-5 | IIIb-78 | 7-(2-Methoxyphenyl)-2-{[1-methyl-2-oxo-8-(propan-2-yloxy)-2,3,4,5-tetrahydro-1H-1-benzazepin-7-yl]amino}thieno[3,2-d]pyrimidine-6-carboxamide | 1.32 (d, J = 6.0 Hz, 6 H); 1.96 (m, 2 H); 2.10 (t, J = 6.5 Hz, 2 H); 2.35 (broad t, J = 6.5 Hz, 2 H); 3.19 (s, 3 H); 3.69 (s, 3 H); 4.71 (m, 1 H); 6.82 (broad m, 1 H); 7.00 (s, 1 H); 7.13 (t, J = 7.8 Hz, 1 H); 7.20 (d, J = 7.8 Hz, 1 H); 7.41 to 7.55 (m, 2 H); 7.76 (broad m, 1 H); 7.91 (s, 1 H); 8.14 (s, 1 H); 9.25 (s, 1 H) | B 532 1.3 |
| I-181 | II-5 | IIIb-72 | 7-(2-Methoxyphenyl)-2-{[1-(propan-2-yl)-3-(tetrahydro-2H-pyran-4-yl)-1H-pyrazol-5-yl]amino}thieno[3,2-d]pyrimidine-6-carboxamide | 1.23 (d, J = 6.5 Hz, 6 H); 1.52 (m, 2 H); 1.68 (m, 2 H); 2.68 (m, 1 H); 3.40 (m, 2 H); 3.67 (s, 3 H); 3.90 (m, 2 H); 4.50 (m, 1 H); 6.01 (broad m, 1 H); 6.70 (broad m, 1 H); 7.07 (t, J = 7.8 Hz, 1 H); 7.15 (d, J = 7.8 Hz, 1 H); 7.36 (dd, J = 1.8 and 7.8 Hz, 1 H); 7.45 (td, J = 1.8 and 7.8 Hz, 1 H); 7.75 (broad m, 1 H); 9.21 (s, 1 H); 9.37 (broad s, 1 H) | B 493 1.03 |

TABLE 4-continued

| Compound I' | Compound II | Compound IIIb | Name | NMR | MS conditions/ MH+/Tr |
|---|---|---|---|---|---|
| I-182 | II-31 | IIIb-78 | 7-(2-Methoxypyridin-3-yl)-2-{[1-methyl-2-oxo-8-(propan-2-yloxy)-2,3,4,5-tetrahydro-1H-1-benzazepin-7-yl]amino}thieno[3,2-d]pyrimidine-6-carboxamide | 1.32 (d, J = 6.0 Hz, 6 H); 1.99 (m, 2 H); 2.11 (t, J = 6.5 Hz, 2 H); 2.41 (broad t, J = 6.5 Hz, 2 H); 3.19 (s, 3 H); 3.79 (s, 3 H); 4.71 (m, 1 H); 7.01 (s, 1 H); 7.15 (dd, J = 5.0 and 7.3 Hz, 1 H); 7.45 (broad m, 1 H); 7.73 (broad m, 1 H); 7.89 (dd, J = 2.0 and 7.3 Hz, 1 H); 7.95 (s, 1 H); 8.12 (s, 1 H); 8.27 (dd, J = 2.0 and 5.0 Hz, 1 H); 9.27 (s, 1 H) | B 533 1.31 |
| I-183 | II-31 | IIIb-49 | 7-(2-Methoxypyridin-3-yl)-2-{[4-(1-methyl-1H-pyrazol-4-yl)-2-(propan-2-yloxy)phenyl]amino}thieno[3,2-d]pyrimidine-6-carboxamide | 1.33 (d, J = 6.1 Hz, 6 H); 3.81 (s, 3 H); 3.85 (s, 3 H); 4.78 (m, 1 H); 6.96 (dd, J = 2.1 and 8.6 Hz, 1 H); 7.17 to 7.23 (m, 2 H); 7.49 (broad m, 1 H); 7.71 (broad m, 1 H); 7.82 (s, 1 H); 7.94 (dd, J = 2.1 and 7.3 Hz, 1 H); 7.98 (s, 1 H); 8.09 (s, 1 H); 8.20 (d, J = 8.6 Hz, 1 H); 8.29 (dd, J = 2.1 and 5.0 Hz, 1 H); 9.26 (s, 1 H) | B 516 1.19 |

Note 1:
Examples I-1 to I-8 were prepared in hydrochloride form.

Note 2:
Examples I-54, I-55, I-56, I-66, I-67, I-99 and I-139 of Table 4 are obtained after deprotection of the piperidinyl ring, protected on the nitrogen atom with a tert-butyloxycarbonyl group, by treatment with an acid as described in the example below:

7-(2-Methoxyphenyl)-2-{[4-(piperidin-4-yl)-2-(propan-2-yloxy)phenyl]amino}thieno[3,2-d]pyrimidine-6-carboxamide A 1M solution of hydrochloric acid in ethyl acetate (90 ml) is added slowly to a mixture of 536 mg of 2-methylpropan-2-yl 4-[4-{[6-carbamoyl-7-(2-methoxyphenyl)thieno[3,2-d]pyrimidin-2-yl]amino}-3-(propan-2-yloxy)phenyl]piperidine-1-carboxylate in 5 ml of cold ethyl acetate in an ice bath. After the addition, the mixture is stirred at ambient temperature for 18 h, and then the precipitate is filtered off and rinsed with ether. The solid is suspended in 60 ml of water and 40 ml of a 1M sodium hydroxide solution are added and the mixture is left to stir for 5 min. The mixture is extracted three times with 100 ml of ethyl acetate. The organic phases are washed with 50 ml of water and then with 50 ml of a saturated sodium chloride solution. The organic phases are dried over magnesium sulfate, filtered and concentrated under vacuum. The residue is taken up with ether and the solid is filtered off and dried under vacuum, so as to obtain 321 mg of 7-(2-methoxyphenyl)-2-{[4-(piperidin-4-yl)-2-(propan-2-yloxy)phenyl]amino}thieno[3,2-d]pyrimidine-6-carboxamide in the form of a yellow solid.

Note 3: Example I-61 was prepared from Example I-52 according to the following method: 140 mg of 2-methylpropan-2-yl 4-[5-{[6-carbamoyl-7-(2-methoxyphenyl)thieno[3,2-d]pyrimidin-2-yl]amino}-1-(propan-2-yl)-1H-pyrazol-3-yl]piperidine-1-carboxylate are added to a solution of 4 ml of 4N hydrochloric acid in dioxane at a temperature of about 20° C. and the mixture is left to stir for 30 minutes. After concentration of the mixture under reduced pressure, a solid is obtained which is washed successively with ethyl ether, with dichloromethane, with dioxane and to finish with dichloromethane. The solid is dried under reduced pressure, so as to obtain 112 mg of 7-(2-methoxyphenyl)-2-{[3-(piperidin-4-yl)-1-(propan-2-yl)-1H-pyrazol-5-yl]amino}thieno[3,2-d]pyrimidine-6-carboxamide hydrochloride.

Note 4: Example I-70 was prepared from Example I-61 according to the following method: 57 microliters of triethylamine and 14 microliters of iodoethane are added, at a temperature of about 20° C., to a solution of 69 mg of 7-(2-methoxyphenyl)-2-{[3-(piperidin-4-yl)-1-(propan-2-yl)-1H-pyrazol-5-yl]amino}thieno[3,2-d]pyrimidine-6-carboxamide hydrochloride in 1.7 ml of DMF, under an argon atmosphere, and the mixture is left to stir for 15 h at ambient temperature. 30 microliters of triethylamine and 6 microliters of iodoethane are then added and then, after stirring for 15 h, a further addition of 30 microliters of triethylamine and of 16 microliters of iodoethane is carried out, while leaving the mixture to stir for a further 48 hours. The reaction medium is diluted with 30 ml of ethyl acetate and then the organic phase is washed three times with 15 ml of water.

The aqueous phase is extracted twice with 25 ml of ethyl acetate. The combined organic phases are dried over magnesium sulfate, filtered and concentrated under vacuum, so as to obtain a yellow solid. The residue is purified by flash chromatography on silica gel, using a dichloromethane/methanol/ $NH_4OH$ (95/5/0.05% to 90/10/0.1%) elution gradient, so as to obtain 40 mg of 2-{[3-(1-ethylpiperidin-4-yl)-1-(propan-2-yl)-1H-pyrazol-5-yl]amino}-7-(2-methoxyphenyl)thieno[3,2-d]pyrimidine-6-carboxamide in the form of a yellow solid.

Note 5: Example I-119 was prepared from 2-methylpropan-2-yl 4-[5-({6-carbamoyl-7-[2-(trifluoromethoxy)phenyl]thieno[3,2-d]pyrimidin-2-yl}amino)-1-(propan-2-yl)-1H-pyrazol-3-yl]piperidine-1-carboxylate, obtained according to Example 10, according to the following steps:

220 mg of 2-methylpropan-2-yl 4-[5-({6-carbamoyl-7-[2-(trifluoromethoxy)phenyl]thieno[3,2-d]pyrimidin-2-yl}amino)-1-(propan-2-yl)-1H-pyrazol-3-yl]piperidine-1-carboxylate are added to 5 ml of a 1N solution of hydrochloric acid in ethyl acetate at a temperature of about 20° C. and the mixture is left to stir for 30 minutes. A further addition of 3 ml of the 1N acid solution is carried out and the mixture is left to stir for 15 h. After concentration of the mixture under reduced pressure, a solid is obtained which is washed successively with dichloromethane and then with ether. The solid is dried under reduced pressure, so as to obtain 139 mg of 2-{[3-(piperidin-4-yl)-1-(propan-2-yl)-1H-pyrazol-5-yl]amino}-7-[2-(trifluoromethoxy)phenyl]thieno[3,2-d]pyrimidine-6-carboxamide hydrochloride.

10 ml of 1N sodium hydroxide are added to a solution of 50 mg of 2-{[3-(piperidin-4-yl)-1-(propan-2-yl)-1H-pyrazol-5-yl]amino}-7-[2-(trifluoromethoxy)phenyl]thieno[3,2-d]pyrimidine-6-carboxamide hydrochloride in 10 ml of ethyl acetate. The mixture is stirred, and then the aqueous phase is extracted twice with 30 ml of ethyl acetate. The combined organic phases are dried over magnesium sulfate, filtered and concentrated under vacuum, so as to obtain 42 mg of 2-{[3-(piperidin-4-yl)-1-(propan-2-yl)-1H-pyrazol-5-yl]amino}-7-[2-(trifluoromethoxy)phenyl]thieno[3,2-d]pyrimidine-6-carboxamide.

1 ml of acetic acid, 6 microliters of 3-oxetanone and 190 mg of amberlite resin IRA400 cyanoborohydride (Aldrich, loading $2 \times 10^{-3}$ mol/g) are added, at ambient temperature, to a solution of 50 mg of 2-{[3-(piperidin-4-yl)-1-(propan-2-yl)-1H-pyrazol-5-yl]amino}-7-[2-(trifluoromethoxy)phenyl]thieno[3,2-d]pyrimidine-6-carboxamide in 3 ml of anhydrous THF, under an argon atmosphere. After stirring for 4 h at ambient temperature, 10 microliters of 3-oxetanone and 186 mg of the same amberlite resin IRA400 cyanoborohydride are added and the mixture is left to stir for a further 15 h. A further 6 microliters of 3-oxetanone and 100 mg of amberlite resin IRA400 cyanoborohydride are added and the mixture is then left to stir for 2 h. The mixture is filtered and the resin is washed with 50 ml of ethyl acetate then 20 ml of ethanol. The filtrate is concentrated under vacuum and the crude product is purified by flash chromatography on silica gel, elution being carried out with a dichloromethane/methanol/NH$_4$OH (96/4/0.1%) mixture, so as to obtain 30 mg of 2-({3-[1-(oxetan-3-yl)piperidin-4-yl]-1-(propan-2-yl)-1H-pyrazol-5-yl}amino)-7-[2-(trifluoromethoxy)phenyl]thieno[3,2-d]pyrimidine-6-carboxamide in the form of a yellow solid.

Note 6: Example I-123 was prepared from 2-{[3-(piperidin-4-yl)-1-(propan-2-yl)-1H-pyrazol-5-yl]amino}-7-[2-(trifluoromethoxy)phenyl]thieno[3,2-d]pyrimidine-6-carboxamide hydrochloride (see note 5), according to the following steps:

70 microliters of triethylamine and 17 microliters of iodoethane are added, at a temperature of about 20° C., to a solution of 100 mg of 2-{[3-(piperidin-4-yl)-1-(propan-2-yl)-1H-pyrazol-5-yl]amino}-7-[2-(trifluoromethoxy)phenyl]thieno[3,2-d]pyrimidine-6-carboxamide hydrochloride in 2.5 ml of DMF under an argon atmosphere, and the mixture is left to stir for 4 h. 70 microliters of triethylamine and 10 microliters of iodoethane are then added and then, after stirring for 15 h, a further addition of 70 microliters of triethylamine and 10 microliters of iodoethane is carried out and the mixture is left to stir for a further 24 hours. The reaction medium is diluted with 40 ml of ethyl acetate and then the organic phase is washed three times with 15 ml of water. The aqueous phase is extracted twice with 20 ml of ethyl acetate. The combined organic phases are dried over magnesium sulfate, filtered and concentrated under vacuum, so as to obtain a yellow solid. The crude product is purified by flash chromatography on silica gel, elution being carried out with a dichloromethane/methanol/NH$_4$OH (96/4/0.1%) mixture, so as to obtain 57 mg of 2-{[3-(1-ethylpiperidin-4-yl)-1-(propan-2-yl)-1H-pyrazol-5-yl]amino}-7-[2-(trifluoromethoxy)phenyl]thieno[3,2-d]pyrimidine-6-carboxamide in the form of a yellow solid.

Note 7:

Examples I-62 and I-63 are isolated by separation of the enantiomers of Example I-45 by chiral chromatography according to the following conditions: Chiralpak IC, 5 µm, 20×250 mm column, detection at λ=254 nm, elution with 60 MTBE/15 heptane/5 methanol/0.1 TEA at a flow rate of 20 ml/min. This separation produces I-62 (TR 14.2 min, OR (589 nm) 20.1 (c=1.635 mg/0.5 ml DMSO)) and I-63 (TR 19.3 min, OR (589 nm) 20.1 (c=1.793 mg/0.5 ml DMSO)).

Note 8: 2-[2-Isopropy-4-(tetrahydropyran-4-ylamino)phenylamino]-7-(2-methoxyphenyl)thieno[3,2-d]pyrimidine-6-carboxamide Example I-164 was obtained from 2-{4-[formyl-(tetrahydropyran-4-yl)amino]-2-isopropoxyphenylamino}-7-(2-methoxyphenyl)thieno[3,2-d]pyrimidine-6-carboxamide, obtained according to Example 10, according to the following steps:

A mixture of 0.3 g of 2-{4-[formyl-tetrahydropyran-4-yl)amino]-2-isopropoxyphenylamino}-7-(2-methoxyphenyl)thieno[3,2-d]pyrimidine-6-carboxamide and 30 ml of a 1.25 M hydrochloric acid solution in methanol is stirred in an autoclave at 60° C. for 15 h. The mixture is concentrated to dryness under reduced pressure. The residue is taken up in water and alkalinized with an ammonical solution, and then extracted three times with 30 ml of ethyl acetate. The organic phases are combined, dried over magnesium sulfate and concentrated to dryness under reduced pressure. The residue is purified by chromatography on a 50 g silica column, elution being carried out with a dichloromethane/methanol/acetonitrile (95/5/5 v/v/v) mixture, so as to obtain an impure batch of 0.23 g which is subjected to a second purification on 50 g of silica, with the same eluent, so as to obtain 0.20 g of 2-[2-isopropy-4-(tetrahydropyran-4-ylamino)phenylamino]-7-(2-methoxyphenyl)thieno[3,2-d]pyrimidine-6-carboxamide. The latter is taken up with stirring in a mixture of 5 ml of diethyl ether and 5 ml of petroleum ether and then filtered. The yellow solid obtained is dried under vacuum (20 mbar/1 h) at 40° C., so as to obtain 0.19 g of 2-[2-isopropy-4-(tetrahydropyran-4-ylamino)phenylamino]-7-(2-methoxyphenyl)-thieno[3,2-d]pyrimidine-6-carboxamide, in the form of an orangey-coloured solid (melting point: 192° C.).

Retention time Tr (min)=0.98; [M+H]+: m/z 534 (method B).

Note 9: 2-[2-Isopropoxy-4-(1-methylpiperidin-4-ylamino)phenylamino]-7-(2-methoxy-phenyl)thieno[3,2-d]pyrimidine-6-carboxamide Example I-167 was obtained from 2-{4-[formyl-(1-methylpiperidin-4-yl)amino]-2-isopropoxyphenylamino}-7-(2-methoxyphenyl)thieno[3,2-d]pyrimidine-6-carboxamide, obtained according to Example 10, according to the following steps:

A 5N hydrochloric acid solution (6.25 ml) is added to a single-necked round-bottomed flask containing 0.25 g of 2-{4-[formyl-(1-methylpiperidin-4-yl)amino]-2-isopropoxyphenylamino}-7-(2-methoxyphenyl)thieno[3,2-d]pyrimidine-6-carboxamide. The reaction mixture is stirred at ambient temperature for 40 h, and then a further 2.0 ml of 5N hydrochloric acid solution are added and the stirring is continued for 20 h. The mixture is then poured into 25 ml of water and alkalinized by adding a solution of aqueous ammonia at 28% (8 ml). After extraction with ethyl acetate (3×30 ml), the organic extracts are combined, washed with water (3×20 ml) to neutral pH, dried over magnesium sulfate, and then concentrated to dryness under reduced pressure. The residue is purified by chromatography on a 25 g cartridge of 15-40 µm silica, elution being carried out successively with 94/3/3 v/v/v then 90/5/5 v/v/v dichloromethane/methanol/acetonitrile mixtures, and then a dichloromethane/methanol/acetonitrile/28% aqueous ammonia mixture (93/3/3/1 v/v/v/v) at a flow rate of 20 ml/min. The pasty orange solid obtained is triturated from diisopropyl ether and reconcentrated to dryness under reduced pressure, and then triturated from petroleum ether and filtered. The solid obtained is stove-dried under reduced pressure (40° C., 10-3 mbar), so as to obtain 0.13 g of 2-[2-isopropoxy-4-(1-methylpiperidin-4-ylamino)phenylamino]-7-(2-methoxyphenyl)thieno[3,2-d]pyrimidine-6-carboxamide in the form of a dark orange solid.

Retention time Tr (min)=0.86; [M+H]+: m/z 547 (method B).

Note 10: Example I-93 was obtained from 2-{[4-(1-formyl-1,7-diazaspiro[4.4]non-7-yl)-2-(propan-2-yloxy)phenyl]amino}-7-(2-methoxyphenyl)thieno[3,2-d]pyrimidine-6-carboxamide, obtained according to Example 10, according to the following steps:

A mixture of 76 mg of 2-{[4-(1-formyl-1,7-diazaspiro[4.4]non-7-yl)-2-(propan-2-yloxy)phenyl]amino}-7-(2-methoxyphenyl)thieno[3,2-d]pyrimidine-6-carboxamide and 2 ml of 5N sodium hydroxide in 15 ml of methanol is stirred at ambient temperature for 3 hours, and then maintained at reflux for 1 h 30. The mixture is stirred at AT for 15 h and then again maintained at reflux for 5 h 30. The reaction medium is then run into 20 ml of water and then the methanol is eliminated by concentration under reduced pressure. The resulting aqueous phase is washed several times with dichloromethane (3 times 20 ml) and then acidified so as to obtain a pH with a value of about 7/8, and then the aqueous phase is extracted a further three times with 20 ml of dichloromethane. The combined organic phases are dried over magnesium sulfate, filtered and concentrated under vacuum, so as to obtain 72 mg of 2-{[4-(1,7-diazaspiro[4.4]non-7-yl)-2-(propan-2-yloxy)phenyl]amino}-7-(2-methoxyphenyl)thieno[3,2-d]pyrimidine-6-carboxylic acid in the form of a brown solid.

A mixture of 40 mg of 2-{[4-(1,7-diazaspiro[4.4]non-7-yl)-2-(propan-2-yloxy)phenyl]amino}-7-(2-methoxyphenyl)thieno[3,2-d]pyrimidine-6-carboxylic acid, 63 mg of BOP and 68 mg of HOBt in 20 ml of DMF is stirred at ambient temperature for 20 minutes. 23 mg of ammonium chloride and 74 mg of N,N-diisopropylethylamine are then added. The mixture is stirred at AT for 48 h. The residue is purified by flash chromatography on silica gel, using a dichloromethane/methanol (100/0 to 90/10) elution gradient. After concentration of the fractions to dryness, a brown solid is obtained which is repurified by reverse-phase HPLC (Macherey-Nagel 250×40 mm, reverse phase C18 Nucleodur 10 μm column; eluent: MeCN containing 0.07% TFA, $H_2O$ containing 0.07% TFA; elution gradient from 10 to 95% of MeCN; flow rate 70 ml/min and collection by UV detection at 254 nm).

The fractions containing the expected product are loaded on to a Varian Bond Elut SCX cartridge (2 g) conditioned with methanol. The phase is washed with methanol and then methanol/$NH_3$ 7N. After concentration of the solvent to dryness, 7 mg of 2-{[4-(1,7-diazaspiro[4.4]non-7-yl)-2-(propan-2-yloxy)phenyl]amino}-7-(2-methoxyphenyl)thieno[3,2-d]pyrimidine-6-carboxamide are obtained in the form of an orangey-coloured solid.

Example 13

[7-(2-Methoxyphenyl)-2-{[4-(4-methylpiperazin-1-yl)-2-(propan-2-yloxy)phenyl]amino}thieno[3,2-d]pyrimidin-6-yl]methanol (I-185)

A mixture of 1.80 g of methyl 7-(2-methoxyphenyl)-2-(methylsulfonyl)thieno[3,2-d]pyrimidine-6-carboxylate, 1.37 g of N-[4-(4-methylpiperazin-1-yl)-2-(propan-2-yloxy)phenyl]formamide and 4.44 g of 1-[N-(2-methylpropan-2-yl)-P,P-di(pyrrolidin-1-yl)phosphorimidoyl]pyrrolidine (BTPP) in 50 ml of anhydrous DMF is stirred at ambient temperature for 16 h. The mixture is then evaporated under vacuum at a temperature of 55° C., and the residue is diluted with ethyl acetate and water. The aqueous phase is extracted three times with ethyl acetate. The organic phases are washed with a saturated sodium chloride solution, dried over magnesium sulfate, filtered and concentrated under vacuum. The crude product is purified on 100 g of silica, elution being carried out with 0-2.5% of methanol containing 10% by volume of 28% aqueous ammonia solution in dichloromethane, so as to obtain 2.264 g of methyl 2-{formyl[4-(4-methylpiperazin-1-yl)-2-(propan-2-yloxy)phenyl]amino}-7-(2-methoxyphenyl)thieno[3,2-d]pyrimidine-6-carboxylate in the form of a brown solid.

A 1M solution of hydrido[bis(2-methylpropyl)]aluminium in toluene is added dropwise to a solution of 2.26 g of methyl 2-{formyl[4-(4-methylpiperazin-1-yl)-2-(propan-2-yloxy)phenyl]amino}-7-(2-methoxyphenyl)thieno[3,2-d]pyrimidine-6-carboxylate in 30 ml of toluene and 30 ml of THF, cooled to −70° C. under argon. After 5 min, the bath is replaced with a bath of ice-cold water and the mixture is stirred for 2 h. The mixture is then cooled to −40° C. and treated with 10 ml of a saturated ammonium chloride solution, 10 ml of water and 30 ml of ethyl acetate. The resulting suspension is filtered on Clarcel and the Clarcel is rinsed with ethyl acetate. The aqueous phase is saturated with sodium chloride and extracted three times with ethyl acetate. The organic phases are washed with a saturated sodium chloride solution, dried over magnesium sulfate, filtered and concentrated under vacuum, so as to obtain 1.47 g of a mixture containing mainly {[6-(hydroxymethyl)-7-(2-methoxyphenyl)thieno[3,2-d]pyrimidin-2-yl][4-(4-methylpiperazin-1-yl)-2-(propan-2-yloxy)phenyl]amino}methanol in the form of an orangey-coloured solid.

A solution of 1.47 g of {[6-(hydroxymethyl)-7-(2-methoxyphenyl)thieno[3,2-d]pyrimidin-2-yl][4-(4-methylpiperazin-1-yl)-2-(propan-2-yloxy)phenyl]amino}methanol mixture in 30 ml of THF and 13.4 ml of 1M sodium hydroxide is stirred at ambient temperature for 1 h 40. The mixture is diluted with 80 ml of ethyl acetate and 10 ml of an aqueous 10% citric acid solution. The aqueous phase is extracted three times with ethyl acetate. The aqueous phase is saturated with sodium chloride and again extracted twice with ethyl acetate. The organic phases are washed with a saturated sodium chloride solution, dried over magnesium sulfate, filtered and concentrated under vacuum. The crude product is purified on 50 g of silica, elution being carried out with 50-100% of acetone in dichloromethane, and then with 2-4% of methanol containing 10% by volume of 28% aqueous ammonia solution in dichloromethane, so as to obtain a brown solid. Trituration from ethyl ether gives 457 mg of [7-(2-methoxyphenyl)-2-{[4-(4-methylpiperazin-1-yl)-2-(propan-2-yloxy)phenyl]amino}thieno[3,2-d]pyrimidin-6-yl]methanol in the form of a yellow solid.

Example 14

2-[2-{[2-Methoxy-4-(4-methylpiperazin-1-yl)phenyl]amino}-7-(2-methoxyphenyl)thieno[3,2-d]pyrimidin-6-yl]propan-2-ol (I-210)

A 3M solution of methylmagnesium bromide (11.2 ml) is added slowly to a solution of 2.60 g of methyl 7-(2-methoxyphenyl)-2-(methylsulfanyl)thieno[3,2-d]pyrimidine-6-carboxylate in 30 ml of THF, cooled to −70° C. The mixture is stirred while allowing the temperature to come back up to ambient temperature. After 1 h at ambient temperature, the mixture is treated with a saturated ammonium chloride solution and the aqueous phase is extracted with ethyl acetate. The organic phases are dried over sodium sulfate, filtered and concentrated under vacuum, so as to obtain 2.58 g of 2-[7-(2-methoxyphenyl)-2-(methylsulfanyl)thieno[3,2-d]pyrimidin- 6-yl]propan-2-ol in the form of a yellow powder. A mixture of 2.58 g of 2-[7-(2-methoxyphenyl)-2-(methylsulfanyl)thieno[3,2-d]pyrimidin-6-yl]propan-2-ol and 4.08 g of sodium perborate hydrate in 15 ml of acetic acid is heated at 95° C. for 1 h, and then concentrated under reduced pressure. The residue is diluted with 1M sodium hydroxide and extracted with ethyl acetate. The organic phases are washed with water, dried over sodium sulfate, filtered and concentrated under vacuum. The residue is purified on 80 g of silica, elution being carried out with dichloromethane, so as to obtain 1.57 g of 2-[7-(2-methoxyphenyl)-2-(methylsulfonyl)thieno[3,2-d]pyrimidin-6-yl]propan-2-ol in the form of a yellow powder.

170 mg of sodium hydride at 60% are added to a solution of 424 mg of N-[2-methoxy-4-(4-methylpiperazin-1-yl)phenyl]formamide in 7 ml of DMSO. The mixture is stirred at ambient temperature for 30 min, and then 643 mg of 2-[7-(2-methoxyphenyl)-2-(methylsulfonyl)thieno[3,2-d]pyrimidin-6-yl]propan-2-ol are added. The mixture is stirred at ambient temperature for 4 h. The mixture is purified on 40 g of silica (solid deposition), elution being carried out with 2% methanol in dichloromethane. The fractions containing the expected product are combined and concentrated under reduced pressure. The residue is purified by reverse-phase HPLC, elution being carried out with acetonitrile/0.001 M hydrochloric acid, so as to obtain 180 mg of 2-[2-{[2-methoxy-4-(4-methylpiperazin-1-yl)phenyl]amino}-7-(2-methoxyphenyl)thieno[3,2-d]pyrimidin-6-yl]propan-2-ol hydrochloride in the form of a yellow powder.

Example 15

2-[7-(4-Fluoro-2-methoxyphenyl)-2-{[2-methoxy-4-(4-methylpiperazin-1-yl)phenyl]amino}thieno[3,2-d]pyrimidin-6-yl]propan-2-ol (I-211)

170 mg of sodium hydride at 60% are added to a solution of 424 mg of N-[2-methoxy-4-(4-methylpiperazin-1-yl)phenyl]formamide in 7 ml of DMSO. The mixture is stirred at ambient temperature for 30 min, and then 674 mg of methyl 7-(4-fluoro-2-methoxyphenyl)-2-(methylsulfonyl)thieno[3,2-d]pyrimidine-6-carboxylate are added. The mixture is stirred at ambient temperature for 4 h. The mixture is purified on silica (solid deposition), elution being carried out with dichloromethane/cyclohexane (1/1), and then with dichloromethane/methanol/NH$_4$OH (96/4/0.4). The compound is again purified on 80 g of silica, elution being carried out with dichloromethane/methanol/NH$_4$OH (98/2/0.2), so as to obtain 217 mg of methyl 7-(4-fluoro-2-methoxyphenyl)-2-{[4-(4-methylpiperazin-1-yl)-2-(propan-2-yloxy)phenyl]amino}thieno[3,2-d]pyrimidine-6-carboxylate in the form of a beige powder.

A 3M solution of methylmagnesium bromide (0.44 ml) is added slowly to a solution of 158 mg of methyl 7-(4-fluoro-2-methoxyphenyl)-2-{[4-(4-methylpiperazin-1-yl)-2-(propan-2-yloxy)phenyl]amino}thieno[3,2-d]pyrimidine-6-carboxylate in 1.2 ml of THF, cooled to 0° C. The mixture is stirred while allowing the temperature to come back up to ambient temperature. After 1 h at ambient temperature, the mixture is treated with a saturated ammonium chloride solution and the aqueous phase is extracted with ethyl acetate. The organic phases are dried over sodium sulfate, filtered and concentrated under vacuum. The crude product is purified by chromatography on 40 g of silica, elution being carried out with dichloromethane/methanol (98/2), so as to obtain 150 mg of 2-[7-(4-fluoro-2-methoxyphenyl)-2-{[2-methoxy-4-(4-methylpiperazin-1-yl)phenyl]amino}thieno[3,2-d]pyrimidin-6-yl]propan-2-ol. The solid is treated with one equivalent of a 1M solution of hydrochloric acid in dioxane and the mixture is concentrated under vacuum, so as to obtain 130 mg of 2-[7-(4-fluoro-2-methoxyphenyl)-2-{[2-methoxy-4-(4-methylpiperazin-1-yl)phenyl]amino}thieno[3,2-d]pyrimidin-6-yl]propan-2-ol hydrochloride in the form of an orange powder.

Example 16

[7-(2-Methoxy-6-methylpyridin-3-yl)-2-{[5-methyl-4-(4-methylpiperazin-1-yl)-2-(propan-2-yloxy)phenyl]amino}thieno[3,2-d]pyrimidin-6-yl]methanol (I-191)

0.7 ml of 1-[N-(2-methylpropan-2-yl)-P,P-di(pyrrolidin-1-yl)phosphorimidoyl]pyrrolidine (BTPP) is added to a mixture of 300 mg of methyl 7-(2-methoxy-6-methylpyridin-3-yl)-2-(methylsulfonyl)thieno[3,2-d]pyrimidine-6-carboxylate and 231 mg of N-[5-methyl-4-(4-methylpiperazin-1-yl)-2-(propan-2-yloxy)phenyl]formamide in 8 ml of anhydrous DMF. The mixture is stirred at ambient temperature for 16 h, and then evaporated under vacuum at a temperature of 55° C., and the residue is diluted with ethyl acetate and water. The aqueous phase is extracted three times with ethyl acetate. The organic phases are washed with a saturated sodium chloride solution, dried over magnesium sulfate, filtered and concentrated under vacuum. The crude product is purified on 25 g of silica, elution being carried out with 50-100% of acetone in dichloromethane so as to obtain 422 mg of methyl 2-{formyl[5-methyl-4-(4-methylpiperazin-1-yl)-2-(propan-2-yloxy)phenyl]amino}-7-(2-methoxy-6-methylpyridin-3-yl)thieno[3,2-d]pyrimidine-6-carboxylate in the form of an orangey-coloured solid.

4.85 ml of a 1M solution of hydrido[bis(2-methylpropyl)]aluminium in toluene are added dropwise to a solution of 419 mg of methyl 2-{formyl[5-methyl-4-(4-methylpiperazin-1-yl)-2-(propan-2-yloxy)phenyl]amino}-7-(2-methoxy-6-methylpyridin-3-yl)thieno[3,2-d]pyrimidine-6-carboxylate in 15 ml of toluene and 15 ml of THF, cooled to −70° C. under argon. After 5 min, the bath is replaced with a bath of ice-cold water and the mixture is stirred for 2 h. The mixture is then cooled to −40° C. and treated with 30 ml of a saturated ammonium chloride solution and 30 ml of ethyl acetate. The aqueous phase is extracted three times with 15 ml of ethyl acetate. The organic phases are combined with the organic phases of another reaction carried out under the same conditions, but starting from 145 mg of methyl 2-{[5-methyl-4-(4-methylpiperazin-1-yl)-2-(propan-2-yloxy)phenyl]amino}-7-(2-methoxy-6-methylpyridin-3-yl)thieno[3,2-d]pyrimidine-6-carboxylate. The combined organic phases are washed with a saturated sodium chloride solution, dried over magnesium sulfate, filtered and concentrated under vacuum, so as to obtain 457 mg of a mixture containing mainly {[6-(hydroxymethyl)-7-(2-methoxy-6-methylpyridin-3-yl)thieno[3,2-d]pyrimidin-2-yl][5-methyl-4-(4-methylpiperazin-1-yl)-2-(propan-2-yloxy)phenyl]amino}methanol in the form of a beige solid.

A solution of 457 mg of the {[6-(hydroxymethyl)-7-(2-methoxy-6-methylpyridin-3-yl)thieno[3,2-d]pyrimidin-2-yl][5-methyl-4-(4-methylpiperazin-1-yl)-2-(propan-2-yloxy)phenyl]amino}methanol mixture in 30 ml of THF and 4.75 ml of 1 M sodium hydroxide is stirred at ambient temperature for 2 h 15. The mixture is diluted with 80 ml of ethyl acetate, 40 ml of water and 5 ml of an aqueous 10% citric acid solution. The aqueous phase is extracted three times with 40 ml of ethyl acetate. The organic phases are washed with 50 ml of a saturated sodium chloride solution, dried over magnesium sulfate, filtered and concentrated under vacuum. The crude product is purified on 25 g of silica, elution being carried out with 1-5% of methanol (containing 10% by volume of 28% ammonium hydroxide) in dichloromethane, so as to obtain a brown oil. Placing the oil in solution in 1 ml of acetonitrile and adding diisopropyl ether and pentane gives a suspension which is concentrated under vacuum. After trituration with pentane, the resulting solid is filtered off and dried under vacuum, so as to obtain 177 mg of [7-(2-methoxy-6-methylpyridin-3-yl)-2-{[5-methyl-4-(4-methylpiperazin-1-yl)-2-(propan-2-yloxy)phenyl]amino}thieno[3,2-d]pyrimidin-6-yl]methanol in the form of a beige solid.

Example 17

[7-(5-Fluoro-2-methoxyphenyl)-2-{[4-(4-methylpiperazin-1-yl)-2-(propan-2-yloxy)phenyl]amino}thieno[3,2-d]pyrimidin-6-yl]methanol (I-202)

0.7 ml of 1-[N-(2-methylpropan-2-yl)-P,P-di(pyrrolidin-1-yl)phosphorimidoyl]pyrrolidine (BTPP) is added to a solution of 245 mg of N-[4-(4-methylpiperazin-1-yl)-2-(propan-2-yloxy)phenyl]formamide in 5 ml of anhydrous DMF. After 10 min, a solution of 350 mg of methyl 7-(5-fluoro-2-methoxyphenyl)-2-(methylsulfonyl)thieno[3,2-d]pyrimidine-6-carboxylate in 6.5 ml of anhydrous DMF is added and the mixture is stirred at ambient temperature for 42 h. The mixture is then evaporated under vacuum at a temperature of 60° C., and the residue is purified on 120 g of silica, elution being carried out with 5% of methanol in dichloromethane, so as to obtain 503 mg of methyl 2-{formyl[4-(4-methylpiperazin-1-yl)-2-(propan-2-yloxy)phenyl]amino}-7-(5-fluoro-2-methoxyphenyl)thieno[3,2-d]pyrimidine-6-carboxylate in the form of an orangey-coloured solid.

5.47 ml of a 1M solution of hydrido[bis(2-methylpropyl)] aluminium in toluene are added dropwise to a solution of 500 mg of methyl 2-{formyl[4-(4-methylpiperazin-1-yl)-2-(propan-2-yloxy)phenyl]amino}-7-(5-fluoro-2-methoxyphenyl)thieno[3,2-d]pyrimidine-6-carboxylate in 13 ml of anhydrous toluene, cooled to −70° C. under argon. After 3 h at −70° C., 10 ml of a 5N sodium hydroxide solution are added. After returning to ambient temperature, the mixture is extracted three times with 10 ml of ethyl acetate. The organic phases are washed with a mixture of 10 ml of water and 6 ml of 5N sodium hydroxide. The aqueous phase is extracted twice with 10 ml of ethyl acetate and the combined organic phases are dried over magnesium sulfate, filtered and concentrated under vacuum, so as to obtain 517 mg of a mixture containing mainly {[6-(hydroxymethyl)-7-(5-fluoro-2-methoxyphenyl)thieno[3,2-d]pyrimidin-2-yl][4-(4-methylpiperazin-1-yl)-2-(propan-2-yloxy)phenyl]amino}methanol in the form of an orangey-coloured solid.

A solution of 517 mg of the {[6-(hydroxymethyl)-7-(5-fluoro-2-methoxyphenyl)thieno[3,2-d]pyrimidin-2-yl][4-(4-methylpiperazin-1-yl)-2-(propan-2-yloxy)phenyl]amino}methanol mixture in 24 ml of THF and 10 ml of 1M sodium hydroxide is stirred at ambient temperature for 4 h. The mixture is extracted three times with 10 ml of ethyl acetate. The organic phases are washed with 10 ml of water and the organic phases are concentrated under vacuum. The crude product is purified on 80 g of silica, elution being carried out with 5-8% of methanol in dichloromethane, so as to obtain a yellow foam. After trituration with ether, the resulting solid is filtered off and dried under vacuum, so as to obtain 247 mg of [7-(5-fluoro-2-methoxyphenyl)-2-{[4-(4-methylpiperazin-1-yl)-2-(propan-2-yloxy)phenyl]amino}thieno[3,2-d]pyrimidin-6-yl]methanol in the form of a yellow solid.

The compounds (I″) obtained according to Examples 13 to 17 are described in Table 5.

TABLE 5

| Compound I″ | Compound II | Compound IIIb | Name | NMR | MS conditions/ MH +/Tr |
|---|---|---|---|---|---|
| I-184 | II-5 | IIIb-3 | [7-(2-Methoxyphenyl)-2-{[4-(1-methylpiperidin-4-yl)-2-(propan-2-yloxy)phenyl]amino}thieno[3,2-d]pyrimidin-6-yl]methanol | 1.30 (d, J = 6.1 Hz, 6H); 1.53 to 1.74 (m, m, 4H); 1.93 (m, 2H); 2.18 (s, 3H); 2.37 (m, 1H); 2.84 (m, 2H); 3.74 (s, 3H); 4.66 (m, 3H); 5.86 (t, J = 5.6 Hz, 1H); 6.60 (dd, J = 1.7 and 8.3 Hz, 1H); 6.86 (d, J = 1.7 Hz, 1H); 7.10 (t, J = 7.8 Hz, 1H); 7.19 (d, J = 7.8 Hz, 1H); 7.38 (dd, J = 1.8 and 7.8 Hz, 1H); 7.47 (dt, J = 1.8 and 7.8 Hz, 1H); 7.72 (s, 1H); 8.21 (d, J = 8.3 Hz, 1H); 9.06 (s, 1H) | A 519 0.73 |
| I-185 | II-5 | IIIb-25 | [7-(2-Methoxyphenyl)-2-{[4-(4-methylpiperazin-1-yl)-2-(propan-2-yloxy)phenyl]amino}thieno[3,2-d]pyrimidin-6-yl]methanol | 1.27 (d, J = 6.1 Hz, 6H); 2.22 (s, 3H); 2.44 (m, 4H); 3.04 (m, 4H); 3.74 (s, 3H); 4.53 to 4.71 (m, 3H); 5.84 (broad t, J = 5.7 Hz, 1H); 6.31 (dd, J = 1.9 and 8.8 Hz, 1H); 6.61 (d, J = 1.9 Hz, 1H); 7.09 (t, J = 8.0 Hz, 1H); 7.18 (d, J = 8.0 Hz, 1H); 7.37 (dd, J = 1.7 and 8.0 Hz, 1H); 7.45 (td, J = 1.7 and 8.0 Hz, 1H); 7.61 (s, 1H); 8.05 (d, J = 8.8 Hz, 1H); 9.01 (s, 1H) | B 520 0.79 |
| I-186 | II-47 | IIIb-25 | [7-(2-Methoxy-6-methylpyridin-3-yl)-2-{[4-(4-methylpiperazin-1-yl)-2-(propan-2-yloxy)phenyl]amino}thieno[3,2-d]pyrimidin-6-yl]methanol | 1.26 (d, J = 6.1 Hz, 6H); 2.22 (s, 3H); 2.45 (m, 4H); 2.50 (masked s, 3H); 3.05 (m, 4H); 3.83 (s, 3H); 4.64 (m, 3H); 5.88 (broad s, 1H); 6.34 (dd, J = 1.9 and 8.8 Hz, 1H); 6.61 (d, J = 1.9 Hz, 1H); 7.01 (d, J = 7.6 Hz, 1H); 7.65 (s, 1H); 7.69 (d, J = 7.6 Hz, 1H); 7.97 (d, J = 8.8 Hz, 1H); 9.02 (s, 1H) | B 535 0.79 |

TABLE 5-continued

| Compound I" | Compound II | Compound IIIb | Name | NMR | MS conditions/ MH +/Tr |
|---|---|---|---|---|---|
| I-187 | II-36 | IIIb-25 | [7-(5-Fluoro-2-methoxypyridin-3-yl)-2-{[4-(4-methylpiperazin-1-yl)-2-(propan-2-yloxy)phenyl]amino}thieno[3,2-d]pyrimidin-6-yl]methanol | 1.26 (d, J = 6.1 Hz, 6H); 2.22 (s, 3H); 2.45 (m, 4H); 3.04 (m, 4H); 3.84 (s, 3H); 4.64 (spt, J = 6.1 Hz, 1H); 4.69 (d, J = 5.8 Hz, 1H); 5.94 (t, J = 5.8 Hz, 1H); 6.31 (dd, J = 2.5 and 9.0 Hz, 1H); 6.62 (d, J = 2.5 Hz, 1H); 7.72 (s, 1H); 7.87 (dd, J = 2.9 and 8.8 Hz, 1H); 7.95 (d, J = 9.0 Hz, 1H); 8.28 (d, J = 2.9 Hz, 1H); 9.04 (s, 1H) | B 539 0.91 |
| I-188 | II-44 | IIIb-25 | [7-(2-Ethoxypyridin-3-yl)-2-{[4-(4-methylpiperazin-1-yl)-2-(propan-2-yloxy)phenyl]amino}thieno[3,2-d]pyrimidin-6-yl]methanol | 1.21 (t, J = 7.2 Hz, 3H); 1.27 (d, J = 6.1 Hz, 6H); 2.22 (s, 3H); 2.44 (m, 4H); 3.04 (m, 4H); 4.34 (q, J = 7.2 Hz, 2H); 4.65 (spt, J = 6.1 Hz, 1H); 4.69 (broad s, 2H); 5.92 (broad s, 1H); 6.32 (dd, J = 2.6 and 8.9 Hz, 1H); 6.62 (d, J = 2.6 Hz, 1H); 7.15 (dd, J = 5.0 and 7.3 Hz, 1H); 7.66 (s, 1H); 7.83 (dd, J = 2.0 and 7.3 Hz, 1H); 8.00 (d, J = 8.9 Hz, 1H); 8.26 (dd, J = 2.0 and 5.0 Hz, 1H); 9.03 (s, 1H) | B 535 0.91 |
| I-189 | II-31 | IIIb-26 | [7-(2-Methoxypyridin-3-yl)-2-{[5-methyl-4-(4-methylpiperazin-1-yl)-2-(propan-2-yloxy)phenyl]amino}thieno[3,2-d]pyrimidin-6-yl]methanol | 1.28 (d, J = 6.1 Hz, 6H); 2.03 (s, 3H); 2.22 (s, 3H); 2.45 (broad m, 4H); 2.77 (m, 4H); 3.85 (s, 3H); 4.59 (m, 1H); 4.67 (d, J = 5.7 Hz, 2H); 5.92 (t, J = 5.7 Hz, 1H); 6.68 (s, 1H); 7.17 (dd, J = 4.9 and 7.3 Hz, 1H); 7.68 (s, 1H); 7.85 (dd, J = 2.1 and 7.3 Hz, 1H); 8.07 (s, 1H); 8.29 (dd, J = 2.1 and 4.9 Hz, 1H); 9.07 (s, 1H) | B 535 0.89 |
| I-190 | II-36 | IIIb-26 | [7-(5-Fluoro-2-methoxypyridin-3-yl)-2-{[5-methyl-4-(4-methylpiperazin-1-yl)-2-(propan-2-yloxy)phenyl]amino}thieno[3,2-d]pyrimidin-6-yl]methanol | 1.28 (d, J = 6.1 Hz, 6H); 2.04 (s, 3H); 2.23 (s, 3H); 2.45 (broad m, 4H); 2.77 (m, 4H); 3.84 (s, 3H); 4.59 (m, 1H); 4.70 (d, J = 5.7 Hz, 2H); 5.95 (t, J = 5.7 Hz, 1H); 6.69 (s, 1H); 7.73 (s, 1H); 7.89 (dd, J = 2.9 and 8.7 Hz, 1H); 8.04 (s, 1H); 8.29 (d, J = 2.9 Hz, 1H); 9.08 (s, 1H) | B 553 0.95 |
| I-191 | II-47 | IIIb-26 | [7-(2-Methoxy-6-methylpyridin-3-yl)-2-{[5-methyl-4-(4-methylpiperazin-1-yl)-2-(propan-2-yloxy)phenyl]amino}thieno[3,2-d]pyrimidin-6-yl]methanol | 1.28 (d, J = 6.1 Hz, 6H); 2.04 (s, 3H); 2.23 (s, 3H); 2.45 (m, 4H); 2.50 (masked s, 3H); 2.78 (m, 4H); 3.82 (s, 3H); 4.59 (m, 1H); 4.67 (d, J = 5.7 Hz, 2H); 5.90 (t, J = 5.7 Hz, 1H); 6.69 (s, 1H); 7.01 (d, J = 7.6 Hz, 1H); 7.67 (s, 1H); 7.71 (d, J = 7.6 Hz, 1H); 8.09 (s, 1H); 9.05 (s, 1H) | B 549 0.84 |
| I-192 | II-47 | IIIb-72 | [7-(2-Methoxy-6-methylpyridin-3-yl)-2-{[1-(propan-2-yl)-3-(tetrahydro-2H-pyran-4-yl)-1H-pyrazol-5-yl]amino}thieno[3,2-d]pyrimidin-6-yl]methanol | 1.25 (d, J = 6.1 Hz, 6H); 1.53 (m, 2H); 1.69 (m, 2H); 2.47 (s, 3H); 2.69 (m, 1H); 3.41 (m, 2H); 3.80 (s, 3H); 3.90 (m, 2H); 4.55 (m, 1H); 4.64 (d, J = 5.6 Hz, 2H); 5.89 (t, J = 5.6 Hz, 1H); 6.06 (s, 1H); 6.96 (d, J = 7.6 Hz, 1H); 7.63 (d, J = 7.6 Hz, 1H); 9.07 (s, 1H); 9.27 (s, 1H) | B 495 1.11 |
| I-193 | II-44 | IIIb-26 | [7-(2-Ethoxypyridin-3-yl)-2-{[5-methyl-4-(4-methylpiperazin-1-yl)-2-(propan-2-yloxy)phenyl]amino}thieno[3,2-d]pyrimidin-6-yl]methanol | 1.18 (t, J = 7.2 Hz, 2H); 1.28 (d, J = 6.1 Hz, 4H); 2.03 (s, 3H); 2.23 (s, 3H); 2.45 (broad m, 4H); 2.77 (m, 4H); 4.34 (q, J = 7.2 Hz, 2H); 4.59 (m, 1H); 4.69 (broad m, 1H); 5.93 (broad t, J = 5.6 Hz, 1H); 6.69 (s, 1H); 7.15 (dd, J = 5.0 and 7.5 Hz, 1H); 7.68 (s, 1H); 7.85 (dd, J = 2.1 and 7.5 Hz, 1H); 8.07 (s, 1H); 8.27 (dd, J = 2.1 and 5.0 Hz, 1H); 9.07 (s, 1H) | B 549 0.98 |
| I-194 | II-5 | IIIb-26 | [7-(2-Methoxyphenyl)-2-{[5-methyl-4-(4-methylpiperazin-1-yl)-2-(propan-2-yloxy)phenyl]amino}thieno[3,2-d]pyrimidin-6-yl]methanol | 1.28 (d, J = 6.1 Hz, 6H); 2.01 (s, 3H); 2.22 (s, 3H); 2.44 (m, 4H); 2.76 (m, 4H); 3.73 (s, 3H); 4.54 to 4.69 (m, 3H); 5.85 (t, J = 5.7 Hz, 1H); 6.68 (s, 1H); 7.10 (t, J = 7.8 Hz, 1H); 7.18 (d, J = 7.8 Hz, 1H); 7.39 (dd, J = 1.7 and 7.8 Hz, 1H); 7.45 (dt, J = 1.7 and 7.8 Hz, 1H); 7.64 (s, 1H); 8.12 (s, 1H); 9.04 (s, 1H) | B 534 0.85 |

TABLE 5-continued

| Compound I" | Compound II | Compound IIIb | Name | NMR | MS conditions/ MH +/Tr |
|---|---|---|---|---|---|
| I-195 | II-47 | IIIb-80 | [7-(2-Methoxy-6-methylpyridin-3-yl)-2-{4-(1-methyl-1,7-diazaspiro[4.4]non-7-yl)-2-(propan-2-yloxy)phenyl]amino}thieno[3,2-d]pyrimidin-6-yl]methanol | 1.25 (d, J = 6.1 Hz, 6H); 1.65 (m, 1H); 1.69 to 1.81 (m, 4H); 2.08 (m, 1H); 2.24 (s, 3H); 2.50 (masked s, 3H); 2.64 (m, 1H); 2.74 (m, 1H); 2.91 (d, J = 9.5 Hz, 1H); 3.19 (m, 1H); 3.26 (partially masked d, J = 9.5 Hz, 1H); 3.33 (m, 1H); 3.83 (s, 3H); 4.57 to 4.65 (m, 3H); 5.86 (t, J = 5.8 Hz, 1H); 5.97 (dd, J = 2.2 and 8.6 Hz, 1H); 6.19 (d, J = 2.2 Hz, 1H); 7.00 (d, J = 7.5 Hz, 1H); 7.58 (s, 1H); 7.68 (d, J = 7.5 Hz, 1H); 7.83 (d, J = 8.6 Hz, 1H); 8.97 (s, 1H) | B 575 1.01 |
| I-196 | II-31 | IIIb-79 | [2-{[4-Chloro-2-(propan-2-yloxy)phenyl]amino}-7-(2-methoxypyridin-3-yl)thieno[3,2-d]pyrimidin-6-yl]methanol | 1.30 (d, J = 6.1 Hz, 6H); 3.85 (s, 3H); 4.66 to 4.77 (m, 3H); 5.95 (broad s, 1H); 6.78 (dd, J = 2.2 and 8.8 Hz, 1H); 7.09 (d, J = 2.2 Hz, 1H); 7.19 (dd, J = 5.1 and 7.4 Hz, 1H); 7.85 (dd, J = 1.7 and 7.4 Hz, 1H); 7.88 (s, 1H); 8.27 (d, J = 8.8 Hz, 1H); 8.30 (dd, J = 1.7 and 5.1 Hz, 1H); 9.14 (s, 1H) | B 457 1.59 |
| I-197 | II-19 | IIIb-64 | (2-{[3-Methyl-1-(propan-2-yl)-1H-pyrazol-5-yl]amino}-7-[2-(trifluoromethoxy)phenyl]thieno[3,2-d]pyrimidin-6-yl)methanol | 1.22 (d, J = 6.6 Hz, 6H); 2.07 (s, 3H); 4.41 (spt, J = 6.6 Hz, 1H); 4.63 (broad m, 2H); 5.89 (s, 1H); 5.98 (broad t, J = 5.6 Hz, 1H); 7.46 to 7.62 (m, 4H); 9.06 (s, 1H); 9.12 (broad s, 1H) | B 464 1.22 |
| I-198 | II-36 | IIIb-64 | [7-(5-Fluoro-2-methoxypyridin-3-yl)-2-{[3-methyl-1-(propan-2-yl)-1H-pyrazol-5-yl]amino}thieno[3,2-d]pyrimidin-6-yl]methanol | 1.23 (d, J = 6.6 Hz, 6H); 2.08 (s, 3H); 3.81 (s, 3H); 4.44 (spt, J = 6.6 Hz, 1H); 4.66 (d, J = 5.4 Hz, 2H); 5.94 (m, 2H); 7.80 (dd, J = 2.9 and 8.6 Hz, 1H); 8.24 (d, J = 2.9 Hz, 1H); 9.07 (s, 1H); 9.19 (broad s, 1H) | B 429 1.05 |
| I-199 | II-19 | IIIb-72 | (2-{[1-(Propan-2-yl)-3-(tetrahydro-2H-pyran-4-yl)-1H-pyrazol-5-yl]amino}-7-[2-(trifluoromethoxy)phenyl]thieno[3,2-d]pyrimidin-6-yl)methanol | 1.23 (broad m, 6H); 1.50 (m, 2H); 1.69 (m, 2H); 2.68 (m, 1H); 3.39 (m, 2H); 3.88 (m, 2H); 4.48 (spt, J = 6.6 Hz, 1H); 4.64 (broad m, 2H); 5.98 (broad s, 1H); 6.01 (s, 1H); 7.45 to 7.63 (m, 4H); 9.09 (s, 1H); 9.22 (broad s, 1H) | B 534 1.27 |
| I-200 | II-5 | IIIb-72 | [7-(2-Methoxyphenyl)-2-{[1-(propan-2-yl)-3-(tetrahydro-2H-pyran-4-yl)-1H-pyrazol-5-yl]amino}thieno[3,2-d]pyrimidin-6-yl]methanol | 1.23 (d, J = 6.6 Hz, 6H); 1.52 (m, 2H); 1.69 (m, 2H); 2.69 (m, 1H); 3.40 (m, 2H); 3.69 (s, 3H); 3.89 (d, J = 14.0 Hz, 2H); 4.49 (dt, J = 6.6 and 13.0 Hz, 1H); 4.60 (broad m, 2H); 5.85 (broad t, J = 5.7 Hz, 1H); 6.03 (s, 1H); 7.04 (t, J = 7.8 Hz, 1H); 7.12 (d, J = 7.8 Hz, 1H); 7.29 (dd, J = 1.8 and 7.5 Hz, 1H); 7.40 (m, 1H); 9.05 (s, 1H); 9.17 (s, 1H) | B 480 1.2 |
| I-201 | II-11 | IIIb-64 | [7-(5-Fluoro-2-methoxyphenyl)-2-{[3-methyl-1-(propan-2-yl)-1H-pyrazol-5-yl]amino}thieno[3,2-d]pyrimidin-6-yl]methanol | 1.23 (d, J = 6.5 Hz, 6H); 2.08 (s, 3H); 3.69 (s, 3H); 4.45 (spt, J = 6.5 Hz, 1H); 4.61 (broad s, 2H); 5.88 (broad s, 1H); 5.95 (s, 1H); 7.12 (dd, J = 4.6 and 9.0 Hz, 1H); 7.17 (dd, J = 3.2 and 9.0 Hz, 1H); 7.24 (dt, J = 3.2 and 9.0 Hz, 1H); 9.04 (s, 1H); 9.14 (s, 1H) | B 428 1.04 |
| I-202 | II-11 | IIIb-25 | [7-(5-Fluoro-2-methoxyphenyl)-2-{[4-(4-methylpiperazin-1-yl)-2-(propan-2-yloxy)phenyl]amino}thieno[3,2-d]pyrimidin-6-yl]methanol | 1.27 (d, J = 6.1 Hz, 6H); 2.22 (s, 3H); 2.44 (m, 4H); 3.04 (m, 4H); 3.72 (s, 3H); 4.64 (m, 3H); 5.87 (t, J = 5.7 Hz, 1H); 6.31 (dd, J = 2.6 and 8.9 Hz, 1H); 6.62 (d, J = 2.6 Hz, 1H); 7.17 (dd, J = 4.6 and 9.0 Hz, 1H); 7.23 to 7.33 (m, 2H); 7.66 (broad s, 1H); 8.02 (d, J = 8.9 Hz, 1H); 9.02 (s, 1H) | B 538 0.82 |
| I-203 | II-19 | IIIb-25 | (2-{[4-(4-Methylpiperazin-1-yl)-2-(propan-2-yloxy)phenyl]amino}-7-[2-(trifluoromethoxy)phenyl]thieno[3,2-d]pyrimidin-6-yl)methanol | 1.25 (d, J = 6.1 Hz, 6H); 2.22 (s, 3H); 2.44 (m, 4H); 3.04 (m, 4H); 4.56 to 4.76 (m, 3H); 5.97 (t, J = 5.7 Hz, 1H); 6.30 (dd, J = 2.5 and 8.8 Hz, 1H); 6.60 (d, J = 2.5 Hz, 1H); 7.49 to 7.65 (m, 4H); 7.66 (s, 1H); 7.94 (d, J = 8.8 Hz, 1H); 9.05 (s, 1H) | B 574 0.89 |

TABLE 5-continued

| Compound I" | Compound II | Compound IIIb | Name | NMR | MS conditions/ MH +/Tr |
|---|---|---|---|---|---|
| I-204 | II-31 | IIIb-49 | [7-(2-Methoxypyridin-3-yl)-2-{[4-(1-methyl-1H-pyrazol-4-yl)-2-(propan-2-yloxy)phenyl]amino}thieno[3,2-d]pyrimidin-6-yl]methanol | 1.33 (d, J = 6.1 Hz, 6H); 3.85 (s, 3H); 3.87 (s, 3H); 4.69 (broad d, J = 5.3 Hz, 2H); 4.78 (spt, J = 6.1 Hz, 1H); 5.94 (broad t, J = 5.3 Hz, 1H); 6.94 (dd, J = 2.0 and 8.6 Hz, 1H); 7.18 to 7.23 (m, 2H); 7.80 (s, 1H); 7.83 (s, 1H); 7.87 (dd, J = 2.0 and 7.3 Hz, 1H); 8.08 (s, 1H); 8.24 (d, J = 8.3 Hz, 1H); 8.32 (dd, J = 2.0 and 4.9 Hz, 1H); 9.11 (s, 1H) | B 503 1.28 |
| I-205 | II-5 | IIIb-49 | [7-(2-Methoxyphenyl)-2-{[4-(1-methyl-1H-pyrazol-4-yl)-2-(propan-2-yloxy)phenyl]amino}thieno[3,2-d]pyrimidin-6-yl]methanol | 1.33 (d, J = 6.1 Hz, 6H); 3.75 (s, 3H); 3.85 (s, 3H); 4.66 (broad m, 2H); 4.77 (spt, J = 6.1 Hz, 1H); 5.87 (broad t, J = 5.7 Hz, 1H); 6.93 (d, J = 7.8 Hz, 1H); 7.12 (t, J = 7.8 Hz, 1H); 7.17 to 7.24 (m, 2H); 7.40 (d, J = 7.8 Hz, 1H); 7.48 (t, J = 7.8 Hz, 1H); 7.79 (s, 1H); 7.80 (s, 1H); 8.07 (s, 1H); 8.30 (d, J = 8.6 Hz, 1H); 9.09 (s, 1H) | B 502 1.34 |
| I-206 | II-49 | IIIb-26 | [2-{[5-Methyl-4-(4-methylpiperazin-1-yl)-2-(propan-2-yloxy)phenyl]amino}-7-(6-methylpyridin-3-yl)thieno[3,2-d]pyrimidin-6-yl]methanol | 1.29 (d, J = 6.1 Hz, 6H); 2.11 (s, 3H); 2.25 to 2.93 (partially masked broad m, 8H); 2.56 (s, 3H); 4.61 (spt, J = 6.1 Hz, 1H); 4.87 (d, J = 5.6 Hz, 2H); 6.00 (t, J = 5.6 Hz, 1H); 6.71 (s, 1H); 7.42 (d, J = 8.1 Hz, 1H); 7.75 (s, 1H); 7.94 (dd, J = 2.4 and 8.1 Hz, 1H); 8.17 (s, 1H); 8.70 (d, J = 2.4 Hz, 1H); 9.11 (s, 1H) | B 519 0.59 |
| I-207 | II-31 | IIIb-25 | [7-(2-Methoxypyridin-3-yl)-2-{[4-(4-methylpiperazin-1-yl)-2-(propan-2-yloxy)phenyl]amino}thieno[3,2-d]pyrimidin-6-yl]methanol | 1.27 (d, J = 6.1 Hz, 6H); 2.22 (s, 3H); 2.44 (m, 4H); 3.05 (m, 4H); 3.85 (s, 3H); 4.57 to 4.72 (m, 3H); 5.89 (t, J = 5.7 Hz, 1H); 6.31 (dd, J = 2.6 and 8.8 Hz, 1H); 6.61 (d, J = 2.6 Hz, 1H); 7.17 (dd, J = 5.0 and 7.4 Hz, 1H); 7.66 (s, 1H); 7.83 (dd, J = 2.0 and 7.4 Hz, 1H); 7.98 (d, J = 8.8 Hz, 1H); 8.29 (dd, J = 2.0 and 5.0 Hz, 1H); 9.03 (s, 1H) | B 521 0.72 |
| I-208 | II-5 | IIIb-71 | [7-(2-Methoxyphenyl)-2-{[4-(1-methylpyrrolidin-3-yl)-2-(propan-2-yloxy)phenyl]amino}thieno[3,2-d]pyrimidin-6-yl]methanol | 1.30 (d, J = 6.1 Hz, 6H); 1.72 (m, 1H); 2.19 (m, 1H); 2.29 (s, 3H); 2.37 (t, J = 8.6 Hz, 1H); 2.60 (m, 2H); 2.82 (t, J = 8.6 Hz, 1H); 3.23 (partially masked m, 1H); 3.74 (s, 3H); 4.56 to 4.72 (m, 3H); 5.85 (broad t, J = 5.7 Hz, 1H); 6.63 (broad d, J = 8.3 Hz, 1H); 6.90 (broad s, 1H); 7.10 (t, J = 7.8 Hz, 1H); 7.18 (d, J = 7.8 Hz, 1H); 7.38 (d, J = 7.8 Hz, 1H); 7.47 (t, J = 7.8 Hz, 1H); 7.73 (s, 1H); 8.19 (d, J = 8.3 Hz, 1H); 9.07 (s, 1H) | B 505 0.81 |
| I-209 | II-1 | IIIb-24 | 2-(2-{[2-Methoxy-4-(4-methylpiperazin-1-yl)phenyl]amino}-7-phenylthieno[3,2-d]pyrimidin-6-yl)propan-2-ol | 1.36 (s, 6H); 2.81 (d, J = 4.8 Hz, 3H); 3.02 (m, 2H); 3.13 (m, 2H); 3.45 (partially masked m, 2H); 3.72 (m, 2H); 3.81 (s, 3H); 6.29 (dd, J = 2.5 and 8.8 Hz, 1H); 6.66 (d, J = 2.5 Hz, 1H); 7.31 (m, 2H); 7.43 to 7.54 (m, 3H); 7.78 (d, J = 8.8 Hz, 1H); 7.84 (broad m, 1H); 9.01 (s, 1H); 10.72 (broad m, 1H) | E 490 0.75 |
| I-210 | II-5 | IIIb-24 | 2-[2-{[2-Methoxy-4-(4-methylpiperazin-1-yl)phenyl]amino}-7-(2-methoxyphenyl)thieno[3,2-d]pyrimidin-6-yl]propan-2-ol | 1.25 (s, 3H); 1.37 (s, 3H); 2.72 (broad s, 3H); 3.00 to 3.50 (partially masked broad m, 8H); 3.65 (s, 3H); 3.80 (s, 3H); 6.28 (dd, J = 2.5 and 8.8 Hz, 1H); 6.64 (d, J = 2.5 Hz, 1H); 7.04 (td, J = 1.3 and 7.5 Hz, 1H); 7.10 to 7.16 (m, 2H); 7.25 (broad m, 1H); 7.45 (ddd, J = 2.0 and 7.5 and 8.3 Hz, 1H); 7.78 (d, J = 8.8 Hz, 1H); 8.95 (s, 1H); 10.64 (broad m, 1H) | E 520 0.82 |

TABLE 5-continued

| Compound I" | Compound II | Compound IIIb | Name | NMR | MS conditions/ MH +/Tr |
|---|---|---|---|---|---|
| I-211 | II-10 | IIIb-24 | 2-[7-(4-Fluoro -2-methoxyphenyl)-2-{[2-methoxy-4-(4-methylpiperazin-1-yl)phenyl]amino]thieno[3,2-d]pyrimidin-6-yl]propan-2-ol | Spectrum at 500 MHz: 1.25 (s, 3H); 1.37 (s, 3H); 2.82 (d, J = 4.7 Hz, 3H); 3.00 (m, 2H); 3.15 (m, 2H); 3.48 (m, 2H); 3.67 (s, 3H); 3.74 (m, 2H); 3.81 (s, 3H); 6.34 (dd, J = 2.5 and 8.8 Hz, 1H); 6.67 (d, J = 2.5 Hz, 1H); 6.88 (dt, J = 2.5 and 8.5 Hz, 1H); 7.07 (dd, J = 2.5 and 11.5 Hz, 1H); 7.16 (dd, J = 7.0 and 8.5 Hz, 1H); 7.75 (d, J = 8.8 Hz, 1H); 7.87 (broad m, 1H); 8.97 (s, 1H); 10.47 (broad m, 1H) | E 538 0.85 |

The compounds according to the invention were the subject of pharmacological tests for determining their ALK kinase-inhibiting effect.

Tests consisted in measuring the in vitro activity of the compounds of the invention on ALK.

A first test uses a GST-Alk protein (wild-type form 1058-1620), obtained from Carna Biosciences (reference 08-518).

The reagents used have the following composition:
Enzyme buffer (EB): 50 mM HEPES (pH: 7.0) (Sigma H7523), 100 mM NaCl (Sigma S7653), $NaN_3$ at 0.01% (Sigma S8032), BSA at 0.005% (Sigma A2153), 0.05 mM sodium orthovanadate (Calbiochem 567540).
Detection buffer (DB): 50 mM HEPES (pH: 7.0), BSA at 0.1%, 0.8 M KF (Fluka 60239), 20 mM EDTA (Sigma E5134).

The peptide used is the one described in *Biochemistry*, 2005, 44, 8533-8542; A-21-K(biotin)$NH_2$, obtained from NeoMPS (reference SP081233). All the HTRF reagents Mab PT66-K (61T66KLB) and streptavidin-XL665 (610SAXLB), and the SEB reagent, are purchased from Cisbio.

The test is carried out in a 384-well plate (Greiner 784076). The serial dilutions are carried out in pure DMSO, and then an intermediate one-in-three dilution in water is carried out, with 1 microliter of each concentration being distributed, all these operations being performed using the Zephyr apparatus (Caliper Life Sciences). The substrate/ATP mixture is prepared in the following way: addition of ATP (final concentration 400 microM, Sigma A7699), of the peptide (final concentration 1 microM) and of the SEB reagent (final concentration 1.56 nM) to the EB, which is then distributed as 7 μl. The enzymatic reaction is initiated by adding 2 μl of enzymatic mixture (final concentration 2 nM) in EB supplemented with DTT (final concentration 1 mM, Sigma D5545). These two distributions are carried out with a multichannel pipette (biohit). The plate is incubated at 30° C. for 1 hour. In order to stop the enzymatic reaction, 10 microliters of the detection mixture, prepared by adding the two antibodies, Mab PT66-K and streptavidin-XL665, to the DB, are added. The incubation time before reading is overnight at 4° C. The HTRF signal is detected on a Rubystar apparatus (BMG Labtech).

A second test uses a commercial GST-Alk protein (mutant L1196M 1058-1620) from Carnabio Sciences (08-529). The protocol is the same as the one for the wild-type form, but the final ATP concentration is 200 microM and the final enzyme concentration is 1 nM.

The inhibitory activity with respect to ALK in these tests is given by the concentration which inhibits 50% of the ALK activity (or $IC_{50}$).

The $IC_{50}$ values for the compounds according to the invention are less than 1 μM, preferably less than 10 μM, and more particularly less than 100 nM.

The table hereinafter indicates the activity results for compounds according to the invention.

| Ex. No. | Name | ALK (nM) | ALK L1196M (nM) |
|---|---|---|---|
| I-7 | 2-({2-Methoxy-4-[4-(propan-2-yl)piperazin-1-yl]phenyl}amino)-7-phenylthieno[3,2-d]pyrimidine-6-carboxamide | 28 | NT |
| I-13 | 2-{[2-Methoxy-5-methyl-4-(1-methylpiperidin-4-yl)phenyl]amino}-7-phenylthieno[3,2-d]pyrimidine-6-carboxamide | 14 | NT |
| I-16 | 7-(2-Methoxyphenyl)-2-{[4-(1-methylpiperidin-4-yl)-2-(propan-2-yloxy)phenyl]amino}thieno[3,2-d]pyrimidine-6-carboxamide | 7 | NT |
| I-26 | 2-{[4-(1-Methylpiperidin-4-yl)-2-(propan-2-yloxy)phenyl]amino}-7-[2-(trifluoromethoxy)phenyl]thieno[3,2-d]pyrimidine-6-carboxamide | 0.5 | NT |
| I-38 | 7-(2-Methoxyphenyl)-2-{[6-(1-methylpiperidin-4-yl)-4-(propan-2-yloxy)pyridin-3-yl]amino}thieno[3,2-d]pyrimidine-6-carboxamide | 7 | NT |
| I-100 | 7-(2-Methoxypyridin-3-yl)-2-{[5-methyl-4-(4-methylpiperazin-1-yl)-2-(propan-2-yloxy)phenyl]amino}thieno[3,2-d]pyrimidine-6-carboxamide | 3 | 3 |
| I-115 | 7-(2-Methylfuran-3-yl)-2-{[4-(1-methylpiperidin-4-yl)-2-(propan-2-yloxy)phenyl]amino}thieno[3,2-d]pyrimidine-6-carboxamide | 13 | 17 |
| I-118 | 2-({4-[3-(Dimethylamino)pyrrolidin-1-yl]-5-methyl-2-(propan-2-yloxy)phenyl}amino)-7-(2-methoxyphenyl)thieno[3,2-d]pyrimidine-6-carboxamide | 2 | 2 |
| I-123 | 2-{[3-(1-Ethylpiperidin-4-yl)-1-(propan-2-yl)-1H-pyrazol-5-yl]amino}-7-[2-(trifluoromethoxy)phenyl]-thieno[3,2-d]pyrimidine-6-carboxamide | 0.5 | 4 |
| I-127 | 7-(2-Methoxyphenyl)-2-{[4-(1-methyl-1H-pyrazol-4-yl)-2-(propan-2-yloxy)phenyl]amino}thieno[3,2-d]pyrimidine-6-carboxamide | 43 | 54 |
| I-131 | 2-{[5-Fluoro-4-(1-methylpiperidin-4-yl)-2-(propan-2-yloxy)phenyl]amino}-7-(2-methoxypyridin-3-yl)thieno[3,2-d]pyrimidine-6-carboxamide | 3 | 1 |
| I-132 | 7-(2-Methoxypyridin-3-yl)-2-{[5-methyl-4-(2-methyl-1H-imidazol-1-yl)-2-(propan-2-yloxy)phenyl]amino}thieno[3,2-d]pyrimidine-6-carboxamide | 17 | 65 |

-continued

| Ex. No. | Name | ALK (nM) | ALK L1196M (nM) |
|---|---|---|---|
| I-159 | 7-(2-Methoxyphenyl)-2-({4-[(4-methylpiperazin-1-yl)methyl]-2-(propan-2-yloxy)phenyl}amino)thieno[3,2-d]pyrimidine-6-carboxamide | 4 | 9 |
| I-164 | 7-(2-Methoxyphenyl)-2-{[2-(propan-2-yloxy)-4-(tetrahydro-2H-pyran-4-ylamino)phenyl]amino}thieno[3,2-d]pyrimidine-6-carboxamide | 35 | 57 |
| I-172 | 7-(5-Fluoro-2-methoxypyridin-3-yl)-2-{[1-(propan-2-yl)-3-(tetrahydro-2H-pyran-4-yl)-1H-pyrazol-5-yl]amino}thieno[3,2-d]pyrimidine-6-carboxamide | 8 | 13 |
| I-176 | 7-(2-Methoxypyridin-3-yl)-2-{[3-(4-methylpiperazin-1-yl)-2-(propan-2-yloxy)phenyl]amino}thieno[3,2-d]pyrimidine-6-carboxamide | 23 | 43 |
| I-180 | 7-(2-Methoxyphenyl)-2-{[1-methyl-2-oxo-8-(propan-2-yloxy)-2,3,4,5-tetrahydro-1H-1-benzazepin-7-yl]amino}thieno[3,2-d]pyrimidine-6-carboxamide | 310 | 424 |
| I-191 | [7-(2-Methoxy-6-methylpyridin-3-yl)-2-{[5-methyl-4-(4-methylpiperazin-1-yl)-2-(propan-2-yloxy)phenyl]amino]thieno[3,2-d]pyrimidin-6-yl]methanol | 12 | 14 |
| I-202 | [7-(5-Fluoro-2-methoxyphenyl)-2-{[4-(4-methylpiperazin-1-yl)-2-(propan-2-yloxy)phenyl]amino}thieno[3,2-d]pyrimidin-6-yl]methanol | 27 | 29 |
| I-210 | 2-[2-{[2-Methoxy-4-(4-methylpiperazin-1-yl)phenyl]amino}-7-(2-methoxyphenyl)thieno[3,2-d]pyrimidin-6-yl]propan-2-ol | 130 | NT |

NT: not tested

It therefore appears that the compounds according to the invention have an ALK-inhibiting activity.

The compounds according to the invention can therefore be used for preparing medicaments, in particular ALK-inhibiting medicines.

Thus, according to another of its aspects, a subject of the invention is medicaments which comprise a compound of formula (I), (I') or (I''), or an addition salt thereof with a pharmaceutically acceptable acid.

The present invention also relates to a medicament comprising a compound of formula (I), (I') or (I'') as defined above, or a pharmaceutically acceptable salt thereof.

These medicaments are of use in therapy, in particular in the treatment of cancer.

Among these cancers, attention is given to the treatment of solid or liquid tumours, and to the treatment of cancers which are resistant to cytotoxic agents.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, and also at least one pharmaceutically acceptable excipient.

Said excipients are selected, according to the pharmaceutical form and the mode of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I), (I') or (I'') above, or the salt thereof, can be administered in unit administration form, as a mixture with conventional pharmaceutical excipients, to animals and to human beings for the treatment of the disorders and diseases above.

The suitable unit administration forms include oral forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions. By way of example, a unit administration form of a compound according to the invention in tablet form can comprise the following constituents:

| Compound according to the invention | 50.0 mg |
|---|---|
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

According to the usual practice, the dosage suitable for each patient is determined by the physician according to the mode of administration and the weight and response of said patient.

The present invention relates to a compound of the formula (I), (I') or (I'') according to the present invention, for use in treating cancer.

The present invention relates to a compound of formula (I), (I') or (I'') as defined above, or an addition salt of this compound with a pharmaceutically acceptable acid, for use as a medicine.

The present invention relates to a compound of formula (I), (I') or (I'') as defined above, or a pharmaceutically acceptable salt of this compound, for use as a drug.

The present invention, according to another of its aspects, also relates to a method for treating the pathological conditions indicated above, which comprises the administration, to a patient, of an effective dose of a compound according to the invention, or a pharmaceutically acceptable salt thereof.

Thus, the present invention also relates to a method for treating cancer comprising the administration, to a patient in need thereof, of a pharmaceutically acceptable amount of a compound of formula (I), (I') or (I'') as defined above, or a pharmaceutically acceptable salt thereof.

The invention claimed is:

1. A compound of formula (I):

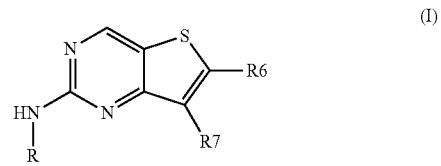

wherein:
R6 is —CONH$_2$ or a —C(R$_\alpha$)(R$_\beta$)(OH) group in which R$_\alpha$ and R$_\beta$ are, independently of one another, a hydrogen atom or a (C$_1$-C$_6$) alkyl group or together form, with the carbon atom which bears them, a 3- to 5-membered carbocycle;

R is a phenyl or heteroaryl group substituted with R1, R'1, R2 and R3;

R1 is a hydrogen atom or is selected from the following groups: $(C_1-C_6)$alkyl, $(C_1-C_6)$alkoxy, $(C_3-C_7)$cycloalkyl and aryl, these groups being optionally substituted with one or several substituents selected, independently in each instance, from: amino, hydroxyl, thiol, halogen, $(C_1-C_6)$alkyl, $(C_1-C_6)$alkoxy, $(C_1-C_6)$alkylthio, $(C_1-C_6)$alkylamino, aryloxy, aryl$(C_1-C_6)$alkoxy, cyano, halo$(C_1-C_6)$alkyl, carboxyl and carboxy$(C_1-C_6)$alkyl;

R'1 is a hydrogen atom or a $(C_1-C_6)$alkoxy group;

R2 is selected from:
  a hydrogen atom, a halogen atom, or a $(C_1-C_6)$alkyl, $(C_3-C_7)$cycloalkyl or $(C_1-C_6)$alkoxy group;
  a heterocycloalkyl, heterocycloalkyl-$CH_2$— or heteroaryl group;
    wherein each said heterocycloalkyl, heterocycloalkyl-$CH_2$— and heteroaryl group is optionally substituted with one or several substituents selected, independently in each instance, from: $(C_1-C_6)$alkyl, $(C_3-C_7)$cycloalkyl, $(C_1-C_6)$alkoxy, heterocycloalkyl, carboxy$(C_1-C_6)$alkyl, NR4R5 and OR4;
    said $(C_1-C_6)$alkyl group being optionally substituted with a halogen atom or a $(C_1-C_6)$alkoxy, heterocycloalkyl, $NH_2$ or OH group; and
    R4 and R5 being each, independently of one another, a hydrogen atom, a $(C_1-C_6)$alkyl group or a heterocycloalkyl group;
    or else R4 and R5 together form, with the nitrogen atom which bears them, a 4- to 7-membered ring;
  an NRaRb group, where Ra and Rb are, independently of one another:
    a hydrogen atom;
    a heterocycloalkyl group, said heterocycloalkyl group being optionally Substituted with a $(C_1-C_6)$alkyl group; or
    a $(C_1-C_6)$alkyl group, said alkyl group being optionally substituted with an NR4R5 group;
      R4 and R5 being each, independently of one another, a hydrogen atom, a (C1-C6)alkyl group or a heterocycloalkyl group;
      or else R4 and R5 together form, with the nitrogen atom which bears them, a 4- to 7-membered ring;

R3 is a hydrogen atom, a halogen atom or a $(C_1-C_6)$alkyl group;

wherein when R is a phenyl group, two adjacent substituents on the phenyl group may together form a heterocycloalkyl ring fused with the phenyl bearing them, this heterocycloalkyl being optionally substituted with one or several substituents selected, independently in each instance, from: an oxo group and a $(C_1-C_6)$alkyl group;

R7 is an aryl group or heteroaryl group, this group being optionally substituted with one or several substituents selected, independently in each instance, from: cyano, halogen, $(C_1-C_6)$alkyl, OR'4, $CH_2OH$, $CH_2NH_2$, $S(O)_nR'4$, R8 and OR8;
  wherein:
    R'4 is a hydrogen atom or a $(C_1-C_6)$alkyl or aryl group, said ($C_1-C_6$alkyl and aryl groups being optionally substituted with a halogen atom or an $NH_2$ or OH group;
    n is 1 or 2; and
    R8 is a halo$(C_1-C_6)$alkyl group;
wherein each of the nitrogen atom(s) of the compounds of formula (I) may be, independently of one another, optionally in oxidized form (N-oxide);
or a pharmaceutically acceptable salt thereof.

2. A compound according to claim 1, wherein:
$R_6$ is —$CONH_2$ or a —$C(R_\alpha)(R_\beta)(OH)$ group wherein $R_\alpha$ and $R_\beta$ are, independently of one another, a hydrogen atom or a $(C_1-C_6)$alkyl group;
or a pharmaceutically acceptable salt thereof.

3. A compound according to claim 1, wherein:
R is a phenyl, pyridinyl or pyrazolyl group substituted with R1, R'1, R2 and R3;
or a pharmaceutically acceptable salt thereof.

4. A compound according to claim 1, wherein R is selected from the following groups:

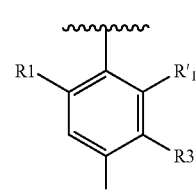
(A)

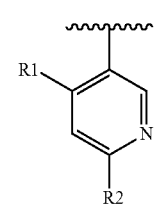
(B)

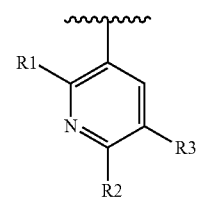
(C)

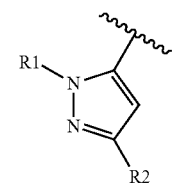
(D)

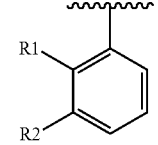
(E)

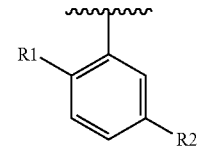
(F)

or a pharmaceutically acceptable salt thereof.

5. A compound according to claim 1, wherein R1 is a hydrogen atom or is selected from the following groups: $(C_1-C_6)$alkyl, $(C_1-C_6)$alkoxy, $(C_3-C_7)$cycloalkyl and aryl;
or a pharmaceutically acceptable salt thereof.

6. A compound according to claim 1, wherein R'1 is a hydrogen atom or an isopropyloxy group;
or a pharmaceutically acceptable salt thereof.

7. A compound according to claim 4, wherein:

R2 is selected from:
- a hydrogen or chlorine atom or a methyl, cyclopropyl or methoxy group;
- a pyrrolidinyl, piperidinyl, tetrahydropyridinyl, piperazinyl, tetrahydropyranyl, 1,4-diazepan-1-yl, diazabicycloheptanyl, (8aR)-hexahydropyrrolo[1,2-a]pyrazin-2(1H) -yl, 1,7-diazaspiro[4.4]non-7-yl, octahydroindolizinyl, dihydroimidazo-pyrazinyl, piperazinyl-$CH_2$, pyrazolyl, imidazolyl, triazolyl or pyridinyl group; these groups being optionally substituted with one or more substituents selected, independently in each instance, from: $(C_1-C_6)$alkyl, $(C_3-C_7)$cycloalkyl, $(C_1-C_6)$alkoxy, heterocycloalkyl, carboxy$(C_1-C_6)$alkyl, NR4R5 and OR4;
    - said $(C_1-C_6)$alkyl group being optionally substituted with a halogen atom or a $(C_1-C_6)$alkoxy, heterocycloalkyl, $NH_2$ or OH group;
        - wherein:
            - R4 and R5 each is, independently of one another, a hydrogen atom, a $(C_1 C_6)$alkyl group or a heterocycloalkyl group;
            - or else R4 and R5 together form, with the nitrogen atom bearing them, a 4- to 7-membered ring; and
- an NRaRb group, where Ra and Rb are, independently of one another:
    - a hydrogen atom;
    - a piperidinyl group or tetrahydropyranyl group, wherein each of said piperidinyl and tetrahydropyranyl groups is independently optionally substituted with a $(C_1-C_6)$alkyl group; or
    - a methyl or ethyl group, said alkyl group being optionally substituted with an NR4R5 group;
        - wherein:
            - R4 and R5 each is, independently of one another, a hydrogen atom, a $(C_1-C_6)$alkyl group or a heterocycloalkyl group;
            - or else R4 and R5 together form, with the nitrogen atom bearing them, a 4- to 7-membered ring; and R3 is a hydrogen atom, a halogen atom or a $(C_1-C_6)$alkyl group;

wherein when R corresponds to formula (A), R2 and R3 can together form an azepinyl or oxazepinyl ring fused with the phenyl bearing them, this azepinyl or oxazepinyl being optionally substituted with one or more substituents selected, independently in each instance, from: an oxo group and a $(C_1-C_6)$alkyl group;

or a pharmaceutically acceptable salt thereof.

8. A compound according to claim 1, wherein:

R7 is a phenyl, pyridinyl, thienyl, furanyl, pyrazolyl or pyrolyl group, this group being optionally substituted with one or more substituents selected, independently in each instance, from: cyano, halogen, $(C_1-C_6)$alkyl, OR'4, $CH_2OH$, $CH_2NH_2$, $S(O)_n$R'4, R8 and OR8;

wherein:
- R'4 is a hydrogen atom or a $(C_1-C_6)$alkyl group or aryl group, said $(C_1-C_6)$alkyl and aryl groups being optionally substituted with a halogen atom or an $NH_2$ or OH group;
- n is 1 or 2;
- R8 is a halo$(C_1-C_6)$alkyl group;

or a pharmaceutically acceptable salt thereof.

9. A compound according to claim 4, wherein $R_6$ is —$CONH_2$ or a —$C(R_\alpha)(R_\beta)(OH)$ group wherein $R_\alpha$ and $R_\beta$ are, independently of one another, a hydrogen atom or a $(C_1-C_6)$alkyl group;

R is a phenyl, pyridinyl or pyrazolyl group substituted with R1, R'1, R2 and R3;

R1 is a hydrogen atom or is selected from the following groups: $(C_1-C_6)$alkyl, $(C_1-C_6)$alkoxy, $(C_3-C_7)$cycloalkyl and aryl;

R'1 is a hydrogen atom or an isopropyloxy group;

R2 is selected from:
- a hydrogen or chlorine atom or a methyl, cyclopropyl or methoxy group;
- a pyrrolidinyl, piperidinyl, tetrahydropyridinyl, piperazinyl, tetrahydropyranyl, 1,4-diazepan-1-yl, diazabicycloheptanyl, (8aR)-hexahydropyrrolo[1,2-a]pyrazin -2(1H)-yl, 1,7-diazaspiro[4.4]non-7-yl, octahydroindolizinyl, dihydroimidazopyrazinyl, Piperazinyl -$CH_2$, pyrazolyl, imidazolyl, triazolyl or pyridinyl group; these groups being optionally substituted with one or more substituents independently selected from: $(C_1-C_6)$alkyl, $(C_3-C_7)$cycloalkyl, $(C_1-C_6)$alkoxy, heterocycloalkyl, carboxy$(C_1-C_6)$alkyl, NR4R5 and OR4;
    - said $(C_1-C_6)$alkyl group being optionally substituted with a halogen atom or a $(C_1-C_6)$alkoxy, heterocycloalkyl, $NH_2$ or OH group;
    - and wherein:
        - R4 and R5 each is, independently of one another, a hydrogen atom, a $(C_1-C_6)$alkyl group or a heterocycloalkyl group;
        - or else R4 and R5 together form, with the nitrogen atom which bears them, a 4- to 7-membered ring; and
- an NRaRb group, where Ra and Rb are, independently of one another:
    - a hydrogen atom;
    - a piperidinyl or tetrahydropyranyl group, said group being optionally Substituted with a $(C_1-C_6)$alkyl group; or
    - a methyl or ethyl group, said group being optionally substituted with an NR4R5 group;
        - wherein:
            - R4 and R5 each is, independently of one another, a hydrogen atom, a $(C_1-C_6)$alkyl group or a heterocycloalkyl group;
            - or else R4 and R5 together form, with the nitrogen atom which bears them, a 4- to 7-membered ring; and R3 is a hydrogen atom, a halogen atom or a $(C_1-C_6)$alkyl group;

wherein when R corresponds to formula (A), R2 and R3 may together form an azepinyl or oxazepinyl ring fused with the phenyl bearing them, this azepinyl or oxazepinyl ring being optionally substituted with at least one substituent selected from: an oxo group and a $(C_1-C_6)$ alkyl group;

R7 is a phenyl, pyridinyl, thienyl, furanyl, pyrazolyl or pyrolyl group, this group being optionally substituted with one or more substituents selected, independently in each instance, from: cyano, halogen, $(C_1-C_6)$alkyl, OR'4, $CH_2OH$, $CH_2NH_2$, $S(O)_n$R'4, R8 and OR8;

wherein:
- R'4 is a hydrogen atom or a $(C_1-C_6)$alkyl or aryl group, said $(C_1-C_6$ alkyl and aryl groups being optionally substituted with a halogen atom or an $NH_2$ or OH group;
- n is 1 or 2; and
- R8 is a halo$(C_1-C_6)$alkyl group;

or a pharmaceutically acceptable salt thereof.

10. A compound according to claim 1, wherein:
$R_6$ is —$CONH_2$ or a —$C(R_\alpha)(R_\beta)(OH)$ group wherein $R_\alpha$ and $R_\beta$ are, independently of one another, a hydrogen atom or a ($C_1$-$C_6$)alkyl group;
R is selected from the following groups:

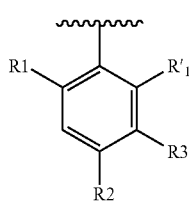
(A)

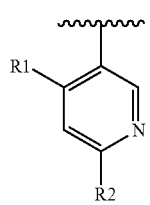
(B)

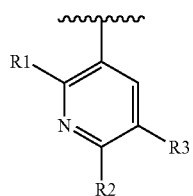
(C)

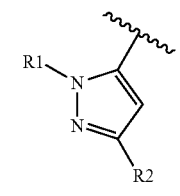
(D)

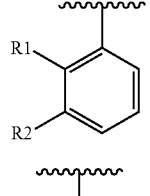
(E)

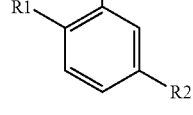
(F)

R1 is a hydrogen atom or is selected from the following groups: ($C_1$-$C_6$)alkyl, ($C_1$-$C_6$)alkoxy, ($C_3$-$C_7$)cycloalkyl and aryl;
R'1 is a hydrogen atom or an isopropyloxy group;
R2 is a pyrrolidinyl, piperidinyl, tetrahydropyridinyl, piperazinyl, tetrahydropyranyl, 1,4-diazepan-1-yl, diazabicycloheptanyl, (8aR)-hexahydropyrrolo[1,2-a]pyrazin-2(1H)-yl, 1,7-diazaspiro[4.4]non-7-yl, octahydroindolizinyl, dihydroimidazopyrazinyl, piperazinyl-$CH_2$, pyrazolyl, imidazolyl, triazolyl or pyridinyl group; these groups being optionally substituted with one or more substituents selected, independently in each instance, from: ($C_1$-$C_6$)alkyl, ($C_3$-$C_7$)cycloalkyl, ($C_1$-$C_6$)alkoxy, heterocycloalkyl, carboxy($C_1$-$C_6$)alkyl, NR4R5 and OH;

said ($C_1$-$C_6$)alkyl group being optionally substituted with a ($C_1$-$C_6$)alkoxy group or OH;
wherein:
R4 and R5 each is, independently of one another, a hydrogen atom, a ($C_1$-$C_6$)alkyl group or a heterocycloalkyl group;
or else R4 and R5 together form, with the nitrogen atom which bears them, a 4- to 7-membered ring;
R3 is a hydrogen atom, a halogen atom or a ($C_1$-$C_6$)alkyl group;
R7 is a phenyl, pyridinyl, thienyl, furanyl, pyrazolyl or pyrolyl group, this group being optionally substituted with one or more substituents selected, independently in each instance, from: cyano, halogen, ($C_1$-$C_6$)alkyl, OR'4, $CH_2OH$, $CH_2NH_2$, $S(O)_nR'4$, R8 and OR8;
wherein:
R'4 is a hydrogen atom or a ($C_1$-$C_6$)alkyl or aryl group, said ($C_1$-$C_6$)alkyl and aryl groups being optionally substituted with a halogen atom or an $NH_2$ or OH group;
n is 1 or 2; and
R8 is a halo($C_1$-$C_6$)alkyl group;
or a pharmaceutically acceptable salt thereof.

11. A compound according to claim 1, wherein:
$R_6$ is —$CONH_2$ or a —$C(R_\alpha)(R_\beta)(OH)$ group wherein $R_\alpha$ and $R_\beta$ are, independently of one another, a hydrogen atom or a ($C_1$-$C_6$)alkyl group;
R is an (A), (E) or (F) group

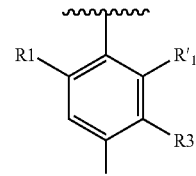
(A)

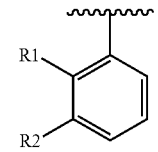
(E)

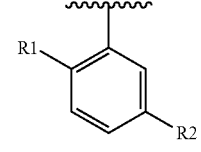
(F)

R1 is an isopropyloxy group;
R'1 is a hydrogen atom;
R2 is a piperidinyl or piperazinyl group, these groups being optionally substituted with one or more substituents selected, independently in each instance, from: a methyl, ethyl, isopropyl, cyclopropyl, OH, oxetanyl, pyrrolidinyl, $C(O)O(CH_3)_3$, NR4R5 and OR4 group;
said methyl, ethyl and isopropyl groups being optionally substituted with a ($C_1$-$C_6$)alkoxy group or with an OH;
wherein R4 and R5 each is, independently of one another, a hydrogen atom, a (C1-C6)alkyl group or a heterocycloalkyl group;
R3 is a hydrogen or fluorine atom or a methyl;

R7 is a phenyl, pyridinyl, thienyl, furanyl, pyrazolyl or pyrolyl group, this group being optionally substituted with one or more substituents selected, independently in each instance, from: cyano, halogen, $(C_1-C_6)$alkyl, OR'4, CH$_2$OH, CH$_2$NH$_2$, S(O)$_n$R'4 and OR8;
wherein:
R'4 is a $(C_1-C_6)$alkyl group;
n is equal to 1; and
R8 is a halo$(C_1-C_6)$alkyl group;
or a pharmaceutically acceptable salt thereof.

12. A compound according to claim 1, wherein it is selected from the following compounds:
- 2-({2-methoxy-4-[4-(pyrrolidin-1-yl)piperidin-1-yl]phenyl}amino)-7-phenylthieno-[3,2-d]pyrimidine-6-carboxamide;
- 2-({2-methyl-4-[4-(pyrrolidin-1-yl)piperidin-1-yl]phenyl}amino)-7-phenylthieno-[3,2-d]pyrimidine-6-carboxamide;
- 7-(3-chlorophenyl)-2-({2-methoxy-4-[4-(pyrrolidin-1-yl)piperidin-1-yl]phenyl}-amino)thieno[3,2-d]pyrimidine-6-carboxamide;
- 7-(4-chlorophenyl)-2-({2-methoxy-4-[4-(pyrrolidin-1-yl)piperidin-1-yl]phenyl}-amino)thieno[3,2-d]pyrimidine-6-carboxamide;
- 2-({2-methoxy-4-[4-(pyrrolidin-1-yl)piperidin-1-yl]phenyl}amino)-7-(thiophen-3-yl)thieno[3,2-d]pyrimidine-6-carboxamide;
- 2-({2-methoxy-4-[4-(pyrrolidin-1-yl)piperidin-1-yl]phenyl}amino)-7-(thiophen-2-yl)thieno[3,2-d]pyrimidine-6-carboxamide;
- 2-({2-methoxy-4-[4-(propan-2-yl)piperazin-1-yl]phenyl}amino)-7-phenylthieno-[3,2-d]pyrimidine-6-carboxamide;
- 2-({2-methoxy-4-[4-(propan-2-yl)piperidin-4-yl]phenyl}amino)-7-phenylthieno-[3,2-d]pyrimidine-6-carboxamide;
- 7-(2-methoxyphenyl)-2-{[4-(4-methylpiperazin-1-yl)-2-(propan-2-yloxy)phenyl]-amino}thieno[3,2-d]pyrimidine-6-carboxamide;
- 7-(4-fluoro-3-methoxyphenyl)-2-{[4-(4-methylpiperazin-1-yl)-2-(propan-2-yloxy)-phenyl]amino}thieno[3,2-d]pyrimidine-6-carboxamide;
- 7-(4-methoxyphenyl)-2-{[4-(4-methylpiperazin-1-yl)-2-(propan-2-yloxy)-phenyl]-amino}thieno[3,2-d]pyrimidine-6-carboxamide;
- 7-(4-fluorophenyl)-2-{[4-(4-methylpiperazin-1-yl)-2-(propan-2-yloxy)phenyl]-amino}thieno[3,2-d]pyrimidine-6-carboxamide;
- 2-{[2-methoxy-5-methyl-4-(1-methylpiperidin-4-yl)phenyl]amino}-7-phenylthieno[3,2-d]pyrimidine-6-carboxamide;
- 7-(4-fluoro-2-methoxyphenyl)-2-{[2-methoxy-4-(4-methylpiperazin-1-yl)phenyl]-amino}thieno[3,2-d]pyrimidine-6-carboxamide;
- 2-{[2-methoxy-4-(4-methylpiperazin-1-yl)phenyl]amino}-7-(3-methoxyphenyl)-thieno[3,2-d]pyrimidine-6-carboxamide;
- 7-(2-methoxyphenyl)-2-{[4-(1-methylpiperidin-4-yl)-2-(propan-2-yloxy)phenyl]-amino}thieno[3,2-d]pyrimidine-6-carboxamide;
- 2-{[5-methyl-4-(1-methylpiperidin-4-yl)-2-(propan-2-yloxy)phenyl]amino}-7-phenylthieno[3,2-d]pyrimidine-6-carboxamide;
- 2-{[2-methoxy-5-methyl-4-(1-methylpiperidin-3-yl)phenyl]amino}-7-phenylthieno[3,2-d]pyrimidine-6-carboxamide;
- 2-({2-methoxy-4-[1-(propan-2-yl)piperidin-4-yl]phenyl}amino)-7-phenylthieno-[3,2-d]pyrimidine-6-carboxamide;
- 2-{[4-(1-methylpiperidin-4-yl)-2-(propan-2-yloxy)phenyl]amino}-7-(1-methyl-1H-pyrazol-5-yl)thieno[3,2-d]pyrimidine-6-carboxamide;
- 7-(2-ethoxyphenyl)-2-{[4-(1-methylpiperidin-4-yl)-2-(propan-2-yloxy)phenyl]-amino}thieno[3,2-d]pyrimidine-6-carboxamide;
- 7-(3-methoxyphenyl)-2-{[4-(1-methylpiperidin-4-yl)-2-(propan-2-yloxy)phenyl]-amino}thieno[3,2-d]pyrimidine-6-carboxamide;
- 2-{[5-methyl-4-(1-methylpiperidin-4-yl)-2-(propan-2-yloxy)phenyl]amino}-7-(pyridin-2-yl)thieno[3,2-d]pyrimidine-6-carboxamide;
- 2-{[4-(4-methyl-1,4-diazepan-1-yl)-2-(propan-2-yloxy)phenyl]amino}-7-phenylthieno[3,2-d]pyrimidine-6-carboxamide;
- 7-(2-fluoro-5-methoxyphenyl)-2-{[4-(1-methylpiperidin-4-yl)-2-(propan-2-yloxy)-phenyl]amino}thieno[3,2-d]pyrimidine-6-carboxamide;
- 7-(3-cyanophenyl)-2-{[4-(1-methylpiperidin-4-yl)-2-(propan-2-yloxy)phenyl]-amino}thieno[3,2-d]pyrimidine-6-carboxamide;
- 2-{[4-(1-methylpiperidin-4-yl)-2-(propan-2-yloxy)phenyl]amino}-7-[2-(trifluoromethoxy)phenyl]thieno[3,2-d]pyrimidine-6-carboxamide;
- 2-{[4-(1-methylpiperidin-4-yl)-2-(propan-2-yloxy)phenyl]amino}-7-phenylthieno[3,2-d]pyrimidine-6-carboxamide;
- 2-({4-[(1S,4S)-5-methyl-2,5-diazabicyclo[2.2.1]hept-2-yl]-2-(propan-2-yloxy)-phenyl}amino)-7-phenylthieno[3,2-d]pyrimidine-6-carboxamide;
- 2-{[4-(1-methylpiperidin-4-yl)-2-(propan-2-yloxy)phenyl]amino}-7-(1-methyl-1,2,3,6-tetrahydropyridin-4-yl)thieno[3,2-d]pyrimidine-6-carboxamide;
- 7-(2-methoxyphenyl)-2-{[5-methyl-4-(1-methylpiperidin-4-yl)-2-(propan-2-yloxy)phenyl]amino}thieno[3,2-d]pyrimidine-6-carboxamide;
- 2-{[4-methoxy-2-(propan-2-yloxy)phenyl]amino}-7-phenylthieno[3,2-d]pyrimidine-6-carboxamide;
- 2-{[4-(1-methylpiperidin-4-yl)-2-(propan-2-yloxy)phenyl]amino}-7-[3-(methylsulfinyl)phenyl]thieno[3,2-d]pyrimidine-6-carboxamide;
- 7-(2-methoxypyridin-3-yl)-2-{[4-(1-methylpiperidin-4-yl)-2-(propan-2-yloxy)-phenyl]amino}thieno[3,2-d]pyrimidine-6-carboxamide;
- 7-(2-cyanophenyl)-2-{[4-(1-methylpiperidin-4-yl)-2-(propan-2-yloxy)phenyl]-amino}thieno[3,2-d]pyrimidine-6-carboxamide;
- 2-{[4-(1H-imidazol-1-yl)-2-(propan-2-yloxy)phenyl]amino}-7-phenylthieno[3,2-d]pyrimidine-6-carboxamide;
- 2-{[4-{methyl[2-(pyrrolidin-1-yl)ethyl]amino}-2-(propan-2-yloxy)phenyl]amino}-7-phenylthieno[3,2-d]pyrimidine-6-carboxamide;
- 7-(2-methoxyphenyl)-2-{[6-(4-methylpiperazin-1-yl)-4-(propan-2-yloxy)pyridin-3-yl]amino}thieno[3,2-d]pyrimidine-6-carboxamide;
- 7-(2-methoxyphenyl)-2-{[6-(1-methylpiperidin-4-yl)-4-(propan-2-yloxy)pyridin-3-yl]amino}thieno[3,2-d]pyrimidine-6-carboxamide;
- 7-(5-fluoro-2-methoxyphenyl)-2-{[4-(1-methylpiperidin-4-yl)-2-(propan-2-yloxy)-phenyl]amino}thieno[3,2-d]pyrimidine-6-carboxamide;

7-(3-fluoro-2-methoxyphenyl)-2-{[4-(1-methylpiperidin-4-yl)-2-(propan-2-yloxy)-phenyl]amino}thieno[3,2-d]pyrimidine-6-carboxamide;

2-{[4-(1-methylpiperidin-4-yl)-2-(propan-2-yloxy)phenyl]amino}-7-[2-(methylsulfinyl)phenyl]thieno[3,2-d]pyrimidine-6-carboxamide;

2-({4-[3-(dimethylamino)pyrrolidin-1-yl]-2-(propan-2-yloxy)phenyl}amino)-7-(2-methoxyphenyl)thieno[3,2-d]pyrimidine-6-carboxamide;

7-(2-methoxyphenyl)-2-{[4-{methyl[2-(pyrrolidin-1-yl)ethyl]amino}-2-(propan-2-yloxy)phenyl]amino}thieno[3,2-d]pyrimidine-6-carboxamide;

7-(2-fluoro-3-methoxyphenyl)-2-{[4-(1-methylpiperidin-4-yl)-2-(propan-2-yloxy)-phenyl]amino}thieno[3,2-d]pyrimidine-6-carboxamide;

2-{[4-(1-ethylpiperidin-3-yl)-2-(propan-2-yloxy)phenyl]amino}-7-(2-methoxyphenyl)thieno[3,2-d]pyrimidine-6-carboxamide;

7-(2-fluorophenyl)-2-{[4-(1-methylpiperidin-4-yl)-2-(propan-2-yloxy)phenyl]-amino}thieno[3,2-d]pyrimidine-6-carboxamide;

2-{[4-(1-methylpiperidin-4-yl)-2-(propan-2-yloxy)phenyl]amino}-7-(1H-pyrrol-2-yl)thieno[3,2-d]pyrimidine-6-carboxamide;

7-[2-fluoro-5-(hydroxymethyl)phenyl]-2-{[4-(1-methylpiperidin-4-yl)-2-(propan-2-yloxy)phenyl]amino}thieno[3,2-d]pyrimidine-6-carboxamide;

2-{[4-(5-methoxy-1-methyl-1,2,3,6-tetrahydropyridin-4-yl)-2-(propan-2-yloxy)-phenyl]amino}-7-(2-methoxyphenyl)thieno[3,2-d]pyrimidine-6-carboxamide;

7-(4-fluoro-2-methoxyphenyl)-2-{[4-(4-methylpiperazin-1-yl)-2-(propan-2-yloxy)-phenyl]amino}thieno[3,2-d]pyrimidine-6-carboxamide;

2-{[4-(1H-imidazol-1-yl)-2-(propan-2-yloxy)phenyl]amino}-7-(2-methoxyphenyl)-thieno[3,2-d]pyrimidine-6-carboxamide;

2-methylpropan-2-yl 4-[5-{[6-carbamoyl-7-(2-methoxyphenyl)thieno-[3,2-d]pyrimidin-2-yl]amino}-1-(propan-2-yl)-1H-pyrazol-3-yl]piperidine-1-carboxylate;

7-(2-methoxyphenyl)-2-{[2-(propan-2-yloxy)-4-(2,2,6,6-tetramethylpiperidin-4-yl)phenyl]amino}thieno[3,2-d]pyrimidine-6-carboxamide;

2-{[4-(2,6-dimethylpiperidin-4-yl)-2-(propan-2-yloxy)phenyl]amino}-7-(2-methoxyphenyl)thieno[3,2-d]pyrimidine-6-carboxamide;

2-{[4-(2-ethylpiperidin-4-yl)-2-(propan-2-yloxy)phenyl]amino}-7-(2-methoxyphenyl)thieno[3,2-d]pyrimidine-6-carboxamide;

7-(2-methoxyphenyl)-2-{[4-(piperidin-4-yl)-2-(propan-2-yloxy)phenyl]amino}-thieno[3,2-d]pyrimidine-6-carboxamide;

7-(4-fluoro-2-methoxyphenyl)-2-{[4-(1-methylpiperidin-4-yl)-2-(propan-2-yloxy)-phenyl]amino}thieno[3,2-d]pyrimidine-6-carboxamide;

2-{[4-(3,5-dimethylpiperazin-1-yl)-2-(propan-2-yloxy)phenyl]amino}-7-(2-methoxyphenyl)thieno[3,2-d]pyrimidine-6-carboxamide;

7-(2-methoxyphenyl)-2-{[2-(propan-2-yloxy)-4-(3,4,5-trimethylpiperazin-1-yl)-phenyl]amino}thieno[3,2-d]pyrimidine-6-carboxamide;

2-({4-[(8aR)-hexahydropyrrolo[1,2-a]pyrazin-2(1H)-yl]-2-(propan-2-yloxy)-phenyl}amino)-7-(2-methoxyphenyl)thieno[3,2-d]pyrimidine-6-carboxamide;

7-(2-methoxyphenyl)-2-{[3-(piperidin-4-yl)-1-(propan-2-yl)-1H-pyrazol-5-yl]amino}thieno[3,2-d]pyrimidine-6-carboxamide;

2-({4-[(3R)-1-ethylpiperidin-3-yl]-2-(propan-2-yloxy)phenyl}amino)-7-(2-methoxyphenyl)thieno[3,2-d]pyrimidine-6-carboxamide;

2-({4-[(3S)-1-ethylpiperidin-3-yl]-2-(propan-2-yloxy)phenyl}amino)-7-(2-methoxyphenyl)thieno[3,2-d]pyrimidine-6-carboxamide;

2-{[4-(1-methylpiperidin-4-yl)-2-(propan-2-yloxy)phenyl]amino}-7-(thiophen-3-yl)thieno[3,2-d]pyrimidine-6-carboxamide;

7-(5-fluoro-2-methoxypyridin-4-yl)-2-{[4-(1-methylpiperidin-4-yl)-2-(propan-2-yloxy)phenyl]amino}thieno[3,2-d]pyrimidine-6-carboxamide;

7-(2-methoxyphenyl)-2-({2-(propan-2-yloxy)-4-[(2R,4S)-2-(propan-2-yl)-piperidin-4-yl]phenyl}amino)thieno[3,2-d]pyrimidine-6-carboxamide;

7-(2-methoxyphenyl)-2-({2-(propan-2-yloxy)-4-[(2R,4R)-2-(propan-2-yl)-piperidin-4-yl]phenyl}amino)thieno[3,2-d]pyrimidine-6-carboxamide;

7-(2-chlorophenyl)-2-{[4-(1-methylpiperidin-4-yl)-2-(propan-2-yloxy)phenyl]-amino}thieno[3,2-d]pyrimidine-6-carboxamide;

2-({4-[(8aR)-hexahydropyrrolo[1,2-a]pyrazin-2(1H)-yl]-2-(propan-2-yloxy)-phenyl}amino)-7-(2-methoxypyridin-3-yl)thieno[3,2-d]pyrimidine-6-carboxamide;

7-(3-chlorophenyl)-2-{[4-(1-methylpiperidin-4-yl)-2-(propan-2-yloxy)phenyl]-amino}thieno[3,2-d]pyrimidine-6-carboxamide;

7-(2-methylphenyl)-2-{[4-(1-methylpiperidin-4-yl)-2-(propan-2-yloxy)phenyl]-amino}thieno[3,2-d]pyrimidine-6-carboxamide;

2-{[4-(1-methylpiperidin-4-yl)-2-(propan-2-yloxy)phenyl]amino}-7-(1-methyl-1H-pyrazol-4-yl)thieno[3,2-d]pyrimidine-6-carboxamide;

7-(2,5-dimethoxyphenyl)-2-{[4-(1-methylpiperidin-4-yl)-2-(propan-2-yloxy)-phenyl]amino}thieno[3,2-d]pyrimidine-6-carboxamide;

7-[2-(difluoromethoxy)phenyl]-2-{[4-(1-methylpiperidin-4-yl)-2-(propan-2-yloxy)-phenyl]amino}thieno[3,2-d]pyrimidine-6-carboxamide;

2-{[4-(1-methylpiperidin-4-yl)-2-(propan-2-yloxy)phenyl]amino}-7-(1H-pyrazol-4-yl)thieno[3,2-d]pyrimidine-6-carboxamide;

2-({4-[3-(2-hydroxyethyl)-4-methylpiperazin-1-yl]-2-(propan-2-yloxy)-phenyl}amino)-7-(2-methoxyphenyl)thieno[3,2-d]pyrimidine-6-carboxamide;

7-(2-methoxypyridin-3-yl)-2-{[5-methyl-4-(1-methylpiperidin-4-yl)-2-(propan-2-yloxy)phenyl]amino}thieno[3,2-d]pyrimidine-6-carboxamide;

7-(2-methoxypyridin-3-yl)-2-{[4-(4-methylpiperazin-1-yl)-2-(propan-2-yloxy)-phenyl]amino}thieno[3,2-d]pyrimidine-6-carboxamide;

2-({4-[1-(2-hydroxyethyl)piperidin-4-yl]-2-(propan-2-yloxy)phenyl}amino)-7-(2-methoxyphenyl)thieno[3,2-d]pyrimidine-6-carboxamide;

7-(2-methoxyphenyl)-2-{[4-(3-methoxypyridin-4-yl)-2-(propan-2-yloxy)phenyl]-amino}thieno[3,2-d]pyrimidine-6-carboxamide;

7-(2-methoxyphenyl)-2-{[6-(4-methylpiperazin-1-yl)-2-(propan-2-yloxy)pyridin-3-yl]amino}thieno[3,2-d]pyrimidine-6-carboxamide;

7-(2-methoxyphenyl)-2-{[4-(1,2,2,6,6-pentamethylpiperidin-4-yl)-2-(propan-2-yloxy)phenyl]amino}thieno[3,2-d]pyrimidine-6-carboxamide;

2-({4-[(2S,4S)-2-ethyl-1-methylpiperidin-4-yl]-2-(propan-2-yloxy)phenyl}-amino)-7-(2-methoxyphenyl)thieno[3,2-d]pyrimidine-6-carboxamide;

2-({4-[(2S,4R)-2-ethyl-1-methylpiperidin-4-yl]-2-(propan-2-yloxy)phenyl}-amino)-7-(2-methoxyphenyl)thieno[3,2-d]pyrimidine-6-carboxamide;

7-(2-methoxypyridin-3-yl)-2-({2-(propan-2-yloxy)-4-[1-(propan-2-yl)piperidin-4-yl]phenyl}amino)thieno[3,2-d]pyrimidine-6-carboxamide;

7-(5-fluoro-2-methoxypyridin-3-yl)-2-{[4-(1-methylpiperidin-4-yl)-2-(propan-2-yloxy)phenyl]amino}thieno[3,2-d]pyrimidine-6-carboxamide;

7-(5-fluoro-2-methoxypyridin-3-yl)-2-({2-(propan-2-yloxy)-4-[1-(propan-2-yl)-piperidin-4-yl]phenyl}amino)thieno[3,2-d]pyrimidine-6-carboxamide;

7-(5-fluoro-2-methoxypyridin-3-yl)-2-{[5-methyl-4-(1-methylpiperidin-4-yl)-2-(propan-2-yloxy)phenyl]amino}thieno[3,2-d]pyrimidine-6-carboxamide;

7-(6-methoxypyridin-2-yl)-2-{[4-(1-methylpiperidin-4-yl)-2-(propan-2-yloxy)-phenyl]amino}thieno[3,2-d]pyrimidine-6-carboxamide;

7-(2-chlorophenyl)-2-({4-[1-(2-hydroxyethyl)piperidin-4-yl]-2-(propan-2-yloxy)-phenyl}amino)thieno[3,2-d]pyrimidine-6-carboxamide;

7-(2-methoxyphenyl)-2-{[6-(1-methylpiperidin-4-yl)-2-(propan-2-yloxy)pyridin-3-yl]amino}thieno[3,2-d]pyrimidine-6-carboxamide;

2-{[4-(1,7-diazaspiro[4.4]non-7-yl)-2-(propan-2-yloxy)phenyl]amino}-7-(2-methoxyphenyl)thieno[3,2-d]pyrimidine-6-carboxamide;

2-({4-[3-(diethylamino)pyrrolidin-1-yl]-2-(propan-2-yloxy)phenyl}amino)-7-(2-methoxypyridin-3-yl)thieno[3,2-d]pyrimidine-6-carboxamide;

2-({4-[3-(dimethylamino)pyrrolidin-1-yl]-2-(propan-2-yloxy)phenyl}amino)-7-(1-methyl-1H-pyrrol-2-yl)thieno[3,2-d]pyrimidine-6-carboxamide;

2-{[4-(1-methylpiperidin-4-yl)-2-(propan-2-yloxy)phenyl]amino}-7-(1-methyl-1H-pyrrol-2-yl)thieno[3,2-d]pyrimidine-6-carboxamide;

2-{[4-(1-methylpiperidin-4-yl)-2-(propan-2-yloxy)phenyl]amino}-7-(2-methylpyridin-3-yl)thieno[3,2-d]pyrimidine-6-carboxamide;

7-(furan-2-yl)-2-{[4-(1-methylpiperidin-4-yl)-2-(propan-2-yloxy)phenyl]amino}thieno[3,2-d]pyrimidine-6-carboxamide;

7-[5-(aminomethyl)furan-2-yl]-2-{[4-(1-methylpiperidin-4-yl)-2-(propan-2-yloxy)phenyl]amino}thieno[3,2-d]pyrimidine-6-carboxamide;

7-(2-methoxypyridin-3-yl)-2-{[5-methyl-4-(4-methylpiperazin-1-yl)-2-(propan-2-yloxy)phenyl]amino}thieno[3,2-d]pyrimidine-6-carboxamide;

2-{[4-(1-methylpiperidin-4-yl)-2-(propan-2-yloxy)phenyl]amino}-7-(1H-pyrrol-3-yl)thieno[3,2-d]pyrimidine-6-carboxamide;

2-({4-[3-(dimethylamino)pyrrolidin-1-yl]-2-(propan-2-yloxy)phenyl}amino)-7-(2-methoxypyridin-3-yl)thieno[3,2-d]pyrimidine-6-carboxamide;

7-(2-ethoxypyridin-3-yl)-2-({2-(propan-2-yloxy)-4-[1-(propan-2-yl)piperidin-4-yl]-phenyl}amino)thieno[3,2-d]pyrimidine-6-carboxamide;

7-(2-ethoxypyridin-3-yl)-2-{[5-methyl-4-(1-methylpiperidin-4-yl)-2-(propan-2-yloxy)phenyl]amino}thieno[3,2-d]pyrimidine-6-carboxamide;

7-(2-methoxyphenyl)-2-{[5-methyl-4-(4-methylpiperazin-1-yl)-2-(propan-2-yloxy)phenyl]amino}thieno[3,2-d]pyrimidine-6-carboxamide;

7-(2-ethoxypyridin-3-yl)-2-{[4-(1-methylpiperidin-4-yl)-2-(propan-2-yloxy)phenyl]amino}thieno[3,2-d]pyrimidine-6-carboxamide;

7-(2-ethoxypyridin-3-yl)-2-{[4-(4-methylpiperazin-1-yl)-2-(propan-2-yloxy)phenyl]amino}thieno[3,2-d]pyrimidine-6-carboxamide;

7-(2-methoxy-5-methylpyridin-3-yl)-2-{[4-(4-methylpiperazin-1-yl)-2-(propan-2-yloxy)phenyl]amino}thieno[3,2-d]pyrimidine-6-carboxamide;

7-(2-methoxy-5-methylpyridin-3-yl)-2-{[4-(1-methylpiperidin-4-yl)-2-(propan-2-yloxy)phenyl]amino}thieno[3,2-d]pyrimidine-6-carboxamide;

7-(5-fluoro-2-methoxypyridin-3-yl)-2-{[4-(4-methylpiperazin-1-yl)-2-(propan-2-yloxy)phenyl]amino}thieno[3,2-d]pyrimidine-6-carboxamide;

7-(2-methoxy-5-methylpyridin-3-yl)-2-{[5-methyl-4-(1-methylpiperidin-4-yl)-2-(propan-2-yloxy)phenyl]amino}thieno[3,2-d]pyrimidine-6-carboxamide;

2-{[4-(1-methylpiperidin-4-yl)-2-(propan-2-yloxy)phenyl]amino}-7-(1-methyl-1H-pyrazol-3-yl)thieno[3,2-d]pyrimidine-6-carboxamide;

2-({4-[3-(2-methoxyethyl)-4-methylpiperazin-1-yl]-2-(propan-2-yloxy)-phenyl}amino)-7-(2-methoxyphenyl)thieno[3,2-d]pyrimidine-6-carboxamide;

7-(2-methoxyphenyl)-2-{[4-{(3R)-3-[methyl(oxetan-3-yl)amino]piperidin-1-yl}-2-(propan-2-yloxy)phenyl]amino}thieno[3,2-d]pyrimidine-6-carboxamide;

7-(2-methylfuran-3-yl)-2-{[4-(1-methylpiperidin-4-yl)-2-(propan-2-yloxy)-phenyl]amino}thieno[3,2-d]pyrimidine-6-carboxamide;

7-(6-methoxypyridin-2-yl)-2-{[5-methyl-4-(1-methylpiperidin-4-yl)-2-(propan-2-yloxy)phenyl]amino}thieno[3,2-d]pyrimidine-6-carboxamide;

2-({4-[3-(dimethylamino)pyrrolidin-1-yl]-5-methyl-2-(propan-2-yloxy)-phenyl}amino)-7-(2-methoxypyridin-3-yl)thieno[3,2-d]pyrimidine-6-carboxamide;

2-({4-[3-(dimethylamino)pyrrolidin-1-yl]-5-methyl-2-(propan-2-yloxy)-phenyl}amino)-7-(2-methoxyphenyl)thieno[3,2-d]pyrimidine-6-carboxamide;

2-({3-[1-(oxetan-3-yl)piperidin-4-yl]-1-(propan-2-yl)-1H-pyrazol-5-yl}amino)-7-[2-(trifluoromethoxy)phenyl]thieno[3,2-d]pyrimidine-6-carboxamide;

7-(2-methoxy-6-methylpyridin-3-yl)-2-{[5-methyl-4-(1-methylpiperidin-4-yl)-2-(propan-2-yloxy)phenyl]amino}thieno[3,2-d]pyrimidine-6-carboxamide;

7-(2-methoxy-6-methylpyridin-3-yl)-2-{[4-(4-methylpiperazin-1-yl)-2-(propan-2-yloxy)phenyl]amino}thieno[3,2-d]pyrimidine-6-carboxamide;

7-(2-methoxy-6-methylpyridin-3-yl)-2-{[4-(1-methylpiperidin-4-yl)-2-(propan-2-yloxy)phenyl]amino}thieno[3,2-d]pyrimidine-6-carboxamide;

2-{[3-(1-ethylpiperidin-4-yl)-1-(propan-2-yl)-1H-pyrazol-5-yl]amino}-7-[2-(trifluoromethoxy)phenyl]thieno[3,2-d]pyrimidine-6-carboxamide;

2-({4-[(3R,4S)-3-hydroxy-1-methylpiperidin-4-yl]-2-(propan-2-yloxy)-phenyl}amino)-7-(2-methoxyphenyl)thieno[3,2-d]pyrimidine-6-carboxamide;

7-(2-methoxypyridin-3-yl)-2-({4-[(8S,8aS)-octahydroindolizin-8-yl]-2-(propan-2-yloxy)phenyl}amino)thieno[3,2-d]pyrimidine-6-carboxamide;

7-(2-methoxypyridin-3-yl)-2-({4-[(8R,8aS)-octahydroindolizin-8-yl]-2-(propan-2-yloxy)phenyl}amino)thieno[3,2-d]pyrimidine-6-carboxamide 7-(2-methoxyphenyl)-2-{[4-(1-methyl-1H-pyrazol-4-yl)-2-(propan-2-yloxy)-phenyl]amino}thieno[3,2-d]pyrimidine-6-carboxamide;

7-(2-methoxypyridin-3-yl)-2-[(1-methyl-2-oxo-2,3,4,5-tetrahydro-1H-1-benzazepin-8-yl)amino]thieno[3,2-d]pyrimidine-6-carboxamide;

7-(2-methoxypyridin-3-yl)-2-{[4-(2-methyl-1H-imidazol-1-yl)-2-(propan-2-yloxy)-phenyl]amino}thieno[3,2-d]pyrimidine-6-carboxamide;

2-{[5-fluoro-4-(1-methylpiperidin-4-yl)-2-(propan-2-yloxy)phenyl]amino}-7-(2-methoxyphenyl)thieno[3,2-d]pyrimidine-6-carboxamide;

2-{[5-fluoro-4-(1-methylpiperidin-4-yl)-2-(propan-2-yloxy)phenyl]amino}-7-(2-methoxypyridin-3-yl)thieno[3,2-d]pyrimidine-6-carboxamide;

7-(2-methoxypyridin-3-yl)-2-{[5-methyl-4-(2-methyl-1H-imidazol-1-yl)-2-(propan-2-yloxy)phenyl]amino}thieno[3,2-d]pyrimidine-6-carboxamide;

7-(2-methoxyphenyl)-2-{[2-(propan-2-yloxy)-4-(1H-1,2,4-triazol-1-yl)phenyl]-amino}thieno[3,2-d]pyrimidine-6-carboxamide;

7-(2-methoxyphenyl)-2-[(1-phenyl-1H-pyrazol-5-yl)amino]thieno[3,2-d]pyrimidine-6-carboxamide;

7-(2-methoxyphenyl)-2-{[4-(1-methyl-1H-pyrazol-3-yl)-2-(propan-2-yloxy)-phenyl]amino}thieno[3,2-d]pyrimidine-6-carboxamide;

7-(2-methoxypyridin-3-yl)-2-{[3-methyl-1-(propan-2-yl)-1H-pyrazol-5-yl]amino}-thieno[3,2-d]pyrimidine-6-carboxamide;

7-(2-fluorophenyl)-2-{[5-methyl-4-(1-methylpiperidin-4-yl)-2-(propan-2-yloxy)-phenyl]amino}thieno[3,2-d]pyrimidine-6-carboxamide;

7-(2-methoxyphenyl)-2-[(1-methyl-2-oxo-2,3,4,5-tetrahydro-1H-1-benzazepin-8-yl)amino]thieno[3,2-d]pyrimidine-6-carboxamide;

7-(4-fluoro-2-methoxyphenyl)-2-{[3-(piperidin-3-yl)-1-(propan-2-yl)-1H-pyrazol-5-yl]amino}thieno[3,2-d]pyrimidine-6-carboxamide;

2-{[3-cyclopropyl-1-(propan-2-yl)-1H-pyrazol-5-yl]amino}-7-(2-methoxypyridin-3-yl)thieno[3,2-d]pyrimidine-6-carboxamide;

7-(4-fluoro-2-methoxyphenyl)-2-{[1-(propan-2-yl)-3-(pyridin-3-yl)-1H-pyrazol-5-yl]amino}thieno[3,2-d]pyrimidine-6-carboxamide;

7-(2-methoxypyridin-3-yl)-2-[(1-methyl-2-oxo-2,3,4,5-tetrahydro-1H-1-benzazepin-7-yl)amino]thieno[3,2-d]pyrimidine-6-carboxamide;

7-(4-fluoro-2-methoxyphenyl)-2-{[2-(propan-2-yloxy)-4-(1H-1,2,4-triazol-1-yl)-phenyl]amino}thieno[3,2-d]pyrimidine-6-carboxamide;

2-{[4-(2,4-dimethyl-1H-imidazol-1-yl)-2-(propan-2-yloxy)phenyl]amino}-7-(2-methoxypyridin-3-yl)thieno[3,2-d]pyrimidine-6-carboxamide;

2-{[4-methoxy-2-(propan-2-yloxy)phenyl]amino}-7-(2-methoxypyridin-3-yl)-thieno[3,2-d]pyrimidine-6-carboxamide;

2-[(3-cyclopropyl-1-phenyl-1H-pyrazol-5-yl)amino]-7-(2-methoxyphenyl)-thieno[3,2-d]pyrimidine-6-carboxamide;

2-{[4-(5,6-dihydroimidazo[1,2-a]pyrazin-7(8H)-yl)-2-(propan-2-yloxy)-phenyl]amino}-7-(2-methoxypyridin-3-yl)thieno[3,2-d]pyrimidine-6-carboxamide;

2-{[4-(1-cyclopropylpiperidin-4-yl)-2-(propan-2-yloxy)phenyl]amino}-7-(2-methoxyphenyl)thieno[3,2-d]pyrimidine-6-carboxamide;

2-{[4-(1-cyclopropylpiperidin-4-yl)-2-(propan-2-yloxy)phenyl]amino}-7-(5-fluoro-2-methoxyphenyl)thieno[3,2-d]pyrimidine-6-carboxamide;

2-{[4-(1-cyclopropylpiperidin-4-yl)-2-(propan-2-yloxy)phenyl]amino}-7-(2-methoxypyridin-3-yl)thieno[3,2-d]pyrimidine-6-carboxamide;

7-(2-methoxypyridin-3-yl)-2-{[4-(4-methyl-1H-imidazol-1-yl)-2-(propan-2-yloxy)-phenyl]amino}thieno[3,2-d]pyrimidine-6-carboxamide;

7-(4-fluoro-2-methoxyphenyl)-2-[(1-methyl-2-oxo-2,3,4,5-tetrahydro-1H-1-benzazepin-7-yl)amino]thieno[3,2-d]pyrimidine-6-carboxamide;

2-{[4-(4-methylpiperazin-1-yl)-2-(propan-2-yloxy)phenyl]amino}-7-(1-oxidopyridin-2-yl)thieno[3,2-d]pyrimidine-6-carboxamide;

2-{[4-(1-ethyl-1,7-diazaspiro[4.4]non-7-yl)-2-(propan-2-yloxy)phenyl]amino}-7-(2-methoxyphenyl)thieno[3,2-d]pyrimidine-6-carboxamide;

7-(2-ethoxypyridin-3-yl)-2-{[5-methyl-4-(4-methylpiperazin-1-yl)-2-(propan-2-yloxy)phenyl]amino}thieno[3,2-d]pyrimidine-6-carboxamide;

2-{[4-(3,5-dimethyl-1H-1,2,4-triazol-1-yl)-2-(propan-2-yloxy)phenyl]amino}-7-(2-methoxyphenyl)thieno[3,2-d]pyrimidine-6-carboxamide;

7-(5-fluoro-2-methoxypyridin-3-yl)-2-{[5-methyl-4-(4-methylpiperazin-1-yl)-2-(propan-2-yloxy)phenyl]amino}thieno[3,2-d]pyrimidine-6-carboxamide;

7-(2-methoxy-6-methylpyridin-3-yl)-2-{[4-(2-methyl-1H-imidazol-1-yl)-2-(propan-2-yloxy)phenyl]amino}thieno[3,2-d]pyrimidine-6-carboxamide;

7-(2-methoxyphenyl)-2-({4-[(4-methylpiperazin-1-yl)methyl]-2-(propan-2-yloxy)phenyl}amino)thieno[3,2-d]pyrimidine-6-carboxamide;

7-(2-methoxy-6-methylpyridin-3-yl)-2-{[5-methyl-4-(4-methylpiperazin-1-yl)-2-(propan-2-yloxy)phenyl]amino}thieno[3,2-d]pyrimidine-6-carboxamide;

7-(2-methoxyphenyl)-2-{[1-methyl-2-oxo-6-(propan-2-yloxy)-2,3,4,5-tetrahydro-1H-1-benzazepin-7-yl]amino}thieno[3,2-d]pyrimidine-6-carboxamide;

7-(2-methoxypyridin-3-yl)-2-{[1-methyl-2-oxo-6-(propan-2-yloxy)-2,3,4,5-tetrahydro-1H-1-benzazepin-7-yl]amino}thieno[3,2-d]pyrimidine-6-carboxamide;

7-(2-methoxyphenyl)-2-{[5-(4-methylpiperazin-1-yl)-2-(propan-2-yloxy)-phenyl]amino}thieno[3,2-d]pyrimidine-6-carboxamide;

7-(2-methoxyphenyl)-2-{[2-(propan-2-yloxy)-4-(tetrahydro-2H-pyran-4-ylamino)phenyl]amino}thieno[3,2-d]pyrimidine-6-carboxamide;

7-(3-methoxypyridin-2-yl)-2-{[5-methyl-4-(4-methylpiperazin-1-yl)-2-(propan-2-yloxy)phenyl]amino}thieno[3,2-d]pyrimidine-6-carboxamide;

2-{[4-(4-hydroxypiperidin-1-yl)-2-(propan-2-yloxy)phenyl]amino}-7-(2-methoxypyridin-3-yl)thieno[3,2-d]pyrimidine-6-carboxamide;

7-(2-methoxyphenyl)-2-({4-[(1-methylpiperidin-4-yl)amino]-2-(propan-2-yloxy)phenyl}amino)thieno[3,2-d]pyrimidine-6-carboxamide;

2-{[1-cyclobutyl-3-(1-ethylpiperidin-4-yl)-1H-pyrazol-5-yl]amino}-7-(4-fluoro-2-methoxyphenyl)thieno[3,2-d]pyrimidine-6-carboxamide;

7-(2-methoxypyridin-3-yl)-2-({4-[(4-methylpiperazin-1-yl)methyl]-2-(propan-2-yloxy)phenyl}amino)thieno[3,2-d]pyrimidine-6-carboxamide;

7-(2-methoxypyridin-3-yl)-2-{[4-(1-methylpyrrolidin-3-yl)-2-(propan-2-yloxy)phenyl]amino}thieno[3,2-d]pyrimidine-6-carboxamide;

7-(2-methoxyphenyl)-2-{[3-(4-methylpiperazin-1-yl)-2-(propan-2-yloxy)phenyl]amino}thieno[3,2-d]pyrimidine-6-carboxamide;

7-(5-fluoro-2-methoxypyridin-3-yl)-2-{[1-(propan-2-yl)-3-(tetrahydro-2H-pyran-4-yl)-1H-pyrazol-5-yl]amino}thieno[3,2-d]pyrimidine-6-carboxamide;

7-(5-fluoro-2-methoxypyridin-3-yl)-2-{[3-methyl-1-(propan-2-yl)-1H-pyrazol-5-yl]amino}thieno[3,2-d]pyrimidine-6-carboxamide;

7-(2-methoxypyridin-3-yl)-2-[(5-methyl-2,3,4,5-tetrahydro-1,5-benzoxazepin-7-yl)amino]thieno[3,2-d]pyrimidine-6-carboxamide;

2-{[1-(propan-2-yl)-3-(tetrahydro-2H-pyran-4-yl)-1H-pyrazol-5-yl]amino}-7-[2-(trifluoromethoxy)phenyl]thieno[3,2-d]pyrimidine-6-carboxamide;

7-(2-methoxypyridin-3-yl)-2-{[3-(4-methylpiperazin-1-yl)-2-(propan-2-yloxy)phenyl]amino}thieno[3,2-d]pyrimidine-6-carboxamide;

7-(2-methoxypyridin-3-yl)-2-{[5-(4-methylpiperazin-1-yl)-2-(propan-2-yloxy)phenyl]amino}thieno[3,2-d]pyrimidine-6-carboxamide;

7-(2-methoxypyridin-3-yl)-2-({4-[(1-methylpiperidin-4-yl)amino]-2-(propan-2-yloxy)phenyl}amino)thieno[3,2-d]pyrimidine-6-carboxamide;

2-{[4-(4-ethylpiperazin-1-yl)-2-(propan-2-yloxy)phenyl]amino}-7-(2-methoxypyridin-3-yl)thieno[3,2-d]pyrimidine-6-carboxamide;

7-(2-methoxyphenyl)-2-{[1-methyl-2-oxo-8-(propan-2-yloxy)-2,3,4,5-tetrahydro-1H-1-benzazepin-7-yl]amino}thieno[3,2-d]pyrimidine-6-carboxamide;

7-(2-methoxyphenyl)-2-{[1-(propan-2-yl)-3-(tetrahydro-2H-pyran-4-yl)-1H-pyrazol-5-yl]amino}thieno[3,2-d]pyrimidine-6-carboxamide;

7-(2-methoxypyridin-3-yl)-2-{[1-methyl-2-oxo-8-(propan-2-yloxy)-2,3,4,5-tetrahydro-1H-1-benzazepin-7-yl]amino}thieno[3,2-d]pyrimidine-6-carboxamide;

7-(2-methoxypyridin-3-yl)-2-{[4-(1-methyl-1H-pyrazol-4-yl)-2-(propan-2-yloxy)phenyl]amino}thieno[3,2-d]pyrimidine-6-carboxamide;

[7-(2-methoxyphenyl)-2-{[4-(1-methylpiperidin-4-yl)-2-(propan-2-yloxy)phenyl]amino}thieno[3,2-d]pyrimidin-6-yl]methanol;

[7-(2-methoxyphenyl)-2-{[4-(4-methylpiperazin-1-yl)-2-(propan-2-yloxy)phenyl]amino}thieno[3,2-d]pyrimidin-6-yl]methanol;

[7-(2-methoxy-6-methylpyridin-3-yl)-2-{[4-(4-methylpiperazin-1-yl)-2-(propan-2-yloxy)phenyl]amino}thieno[3,2-d]pyrimidin-6-yl]methanol;

[7-(5-fluoro-2-methoxypyridin-3-yl)-2-{[4-(4-methylpiperazin-1-yl)-2-(propan-2-yloxy)phenyl]amino}thieno[3,2-d]pyrimidin-6-yl]methanol;

[7-(2-ethoxypyridin-3-yl)-2-{[4-(4-methylpiperazin-1-yl)-2-(propan-2-yloxy)phenyl]amino}thieno[3,2-d]pyrimidin-6-yl]methanol;

[7-(2-methoxypyridin-3-yl)-2-{[5-methyl-4-(4-methylpiperazin-1-yl)-2-(propan-2-yloxy)phenyl]amino}thieno[3,2-d]pyrimidin-6-yl]methanol;

[7-(5-fluoro-2-methoxypyridin-3-yl)-2-{[5-methyl-4-(4-methylpiperazin-1-yl)-2-(propan-2-yloxy)phenyl]amino}thieno[3,2-d]pyrimidin-6-yl]methanol;

[7-(2-methoxy-6-methylpyridin-3-yl)-2-{[5-methyl-4-(4-methylpiperazin-1-yl)-2-(propan-2-yloxy)phenyl]amino}thieno[3,2-d]pyrimidin-6-yl]methanol;

[7-(2-methoxy-6-methylpyridin-3-yl)-2-{[1-(propan-2-yl)-3-(tetrahydro-2H-pyran-4-yl)-1H-pyrazol-5-yl]amino}thieno[3,2-d]pyrimidin-6-yl]methanol;

[7-(2-ethoxypyridin-3-yl)-2-{[5-methyl-4-(4-methylpiperazin-1-yl)-2-(propan-2-yloxy)phenyl]amino}thieno[3,2-d]pyrimidin-6-yl]methanol;

[7-(2-methoxyphenyl)-2-{[5-methyl-4-(4-methylpiperazin-1-yl)-2-(propan-2-yloxy)phenyl]amino}thieno[3,2-d]pyrimidin-6-yl]methanol;

[7-(2-methoxy-6-methylpyridin-3-yl)-2-{[4-(1-methyl-1,7-diazaspiro[4.4]non-7-yl)-2-(propan-2-yloxy)phenyl]amino}thieno[3,2-d]pyrimidin-6-yl]methanol;

[2-{[4-chloro-2-(propan-2-yloxy)phenyl]amino}-7-(2-methoxypyridin-3-yl)thieno[3,2-d]pyrimidin-6-yl]methanol;

(2-{[3-methyl-1-(propan-2-yl)-1H-pyrazol-5-yl]amino}-7-[2-(trifluoromethoxy)phenyl]thieno[3,2-d]pyrimidin-6-yl)methanol;

[7-(5-fluoro-2-methoxypyridin-3-yl)-2-{[3-methyl-1-(propan-2-yl)-1H-pyrazol-5-yl]amino}thieno[3,2-d]pyrimidin-6-yl]methanol;

(2-{[1-(propan-2-yl)-3-(tetrahydro-2H-pyran-4-yl)-1H-pyrazol-5-yl]amino}-7-[2-(trifluoromethoxy)phenyl]thieno[3,2-d]pyrimidin-6-yl)methanol;

[7-(2-methoxyphenyl)-2-{[1-(propan-2-yl)-3-(tetrahydro-2H-pyran-4-yl)-1H-pyrazol-5-yl]amino}thieno[3,2-d]pyrimidin-6-yl]methanol;

[7-(5-fluoro-2-methoxyphenyl)-2-{[3-methyl-1-(propan-2-yl)-1H-pyrazol-5-yl]amino}thieno[3,2-d]pyrimidin-6-yl]methanol;

[7-(5-fluoro-2-methoxyphenyl)-2-{[4-(4-methylpiperazin-1-yl)-2-(propan-2-yloxy)phenyl]amino}thieno[3,2-d]pyrimidin-6-yl]methanol;

(2-{[4-(4-methylpiperazin-1-yl)-2-(propan-2-yloxy)phenyl]amino}-7-[2-(trifluoromethoxy)phenyl]thieno[3,2-d]pyrimidin-6-yl)methanol;

[7-(2-methoxypyridin-3-yl)-2-{[4-(1-methyl-1H-pyrazol-4-yl)-2-(propan-2-yloxy)phenyl]amino}thieno[3,2-d]pyrimidin-6-yl]methanol;

[7-(2-methoxyphenyl)-2-{[4-(1-methyl-1H-pyrazol-4-yl)-2-(propan-2-yloxy)phenyl]amino}thieno[3,2-d]pyrimidin-6-yl]methanol;

[2-{[5-methyl-4-(4-methylpiperazin-1-yl)-2-(propan-2-yloxy)phenyl]amino}-7-(6-methylpyridin-3-yl)thieno[3,2-d]pyrimidin-6-yl]methanol;

[7-(2-methoxypyridin-3-yl)-2-{[4-(4-methylpiperazin-1-yl)-2-(propan-2-yloxy)phenyl]amino}thieno[3,2-d]pyrimidin-6-yl]methanol;

[7-(2-methoxyphenyl)-2-{[4-(1-methylpyrrolidin-3-yl)-2-(propan-2-yloxy)phenyl]amino}thieno[3,2-d]pyrimidin-6-yl]methanol;

2-(2-{[2-methoxy-4-(4-methylpiperazin-1-yl)phenyl]amino}-7-phenylthieno[3,2-d]pyrimidin-6-yl)propan-2-ol;

2-[2-{[2-methoxy-4-(4-methylpiperazin-1-yl)phenyl]amino}-7-(2-methoxyphenyl)thieno[3,2-d]pyrimidin-6-yl]propan-2-ol; and 2-[7-(4-fluoro-2-methoxyphenyl)-2-{[2-methoxy-4-(4-methylpiperazin-1-yl)phenyl]amino}thieno[3,2-d]pyrimidin-6-yl]propan-2-ol;

or a pharmaceutically acceptable salt thereof.

13. A pharmaceutical composition, comprising a compound according to claim 1, or a pharmaceutically acceptable salt thereof, and also at least one pharmaceutically acceptable excipient.

14. A compound according to claim 1, wherein the compound is selected from the following compounds:

2-({2-methoxy-4-[4-(propan-2-yl)piperazin-1-yl]phenyl}amino)-7-phenylthieno-[3,2-d]pyrimidine-6-carboxamide;

2-{[2-methoxy-5-methyl-4-(1-methylpiperidin-4-yl)phenyl]amino}-7-phenylthieno[3,2-d]pyrimidine-6-carboxamide;

7-(2-methoxyphenyl)-2-{[4-(1-methylpiperidin-4-yl)-2-(propan-2-yloxy)phenyl]-amino}thieno[3,2-d]pyrimidine-6-carboxamide;

2-{[4-(1-methylpiperidin-4-yl)-2-(propan-2-yloxy)phenyl]amino}-7-[2-(trifluoromethoxy)phenyl]thieno[3,2-d]pyrimidine-6-carboxamide;

7-(2-methoxyphenyl)-2-{[6-(1-methylpiperidin-4-yl)-4-(propan-2-yloxy)pyridin-3-yl]amino}thieno[3,2-d]pyrimidine-6-carboxamide;

7-(2-methoxypyridin-3-yl)-2-{[5-methyl-4-(4-methylpiperazin-1-yl)-2-(propan-2-yloxy)phenyl]amino}thieno[3,2-d]pyrimidine-6-carboxamide;

7-(2-methylfuran-3-yl)-2-{[4-(1-methylpiperidin-4-yl)-2-(propan-2-yloxy)-phenyl]amino}thieno[3,2-d]pyrimidine-6-carboxamide;

2-({4-[3-(dimethylamino)pyrrolidin-1-yl]-5-methyl-2-(propan-2-yloxy)-phenyl}amino)-7-(2-methoxyphenyl)thieno[3,2-d]pyrimidine-6-carboxamide;

2-{[3-(1-ethylpiperidin-4-yl)-1-(propan-2-yl)-1H-pyrazol-5-yl]amino}-7-[2-(trifluoromethoxy)phenyl]thieno[3,2-d]pyrimidine-6-carboxamide;

7-(2-methoxyphenyl)-2-{[4-(1-methyl-1H-pyrazol-4-yl)-2-(propan-2-yloxy)-phenyl]amino}thieno[3,2-d]pyrimidine-6-carboxamide;

2-{[5-fluoro-4-(1-methylpiperidin-4-yl)-2-(propan-2-yloxy)phenyl]amino}-7-(2-methoxypyridin-3-yl)thieno[3,2-d]pyrimidine-6-carboxamide;

7-(2-methoxypyridin-3-yl)-2-{[5-methyl-4-(2-methyl-1H-imidazol-1-yl)-2-(propan-2-yloxy)phenyl]amino}thieno[3,2-d]pyrimidine-6-carboxamide;

7-(2-methoxyphenyl)-2-({4-[(4-methylpiperazin-1-yl)methyl]-2-(propan-2-yloxy)phenyl}amino)thieno[3,2-d]pyrimidine-6-carboxamide;

7-(2-methoxyphenyl)-2-{[2-(propan-2-yloxy)-4-(tetrahydro-2H-pyran-4-ylamino)phenyl]amino}thieno[3,2-d]pyrimidine-6-carboxamide;

7-(5-fluoro-2-methoxypyridin-3-yl)-2-{[1-(propan-2-yl)-3-(tetrahydro-2H-pyran-4-yl)-1H-pyrazol-5-yl]amino}thieno[3,2-d]pyrimidine-6-carboxamide;

7-(2-methoxypyridin-3-yl)-2-{[3-(4-methylpiperazin-1-yl)-2-(propan-2-yloxy)phenyl]amino}thieno[3,2-d]pyrimidine-6-carboxamide;

7-(2-methoxyphenyl)-2-{[1-methyl-2-oxo-8-(propan-2-yloxy)-2,3,4,5-tetrahydro-1H-1-benzazepin-7-yl]amino}thieno[3,2-d]pyrimidine-6-carboxamide;

[7-(2-methoxy-6-methylpyridin-3-yl)-2-{[5-methyl-4-(4-methylpiperazin-1-yl)-2-(propan-2-yloxy)phenyl]amino}thieno[3,2-d]pyrimidin-6-yl]methanol;

[7-(5-fluoro-2-methoxyphenyl)-2-{[4-(4-methylpiperazin-1-yl)-2-(propan-2-yloxy)phenyl]amino}thieno[3,2-d]pyrimidin-6-yl]methanol; and 2-[2-{[2-methoxy-4-(4-methylpiperazin-1-yl)phenyl]amino}-7-(2-methoxyphenyl)thieno[3,2-d]pyrimidin-6-yl]propan-2-ol;

or a pharmaceutically acceptable salt thereof.

15. A compound according to claim 1, wherein the compound is selected from the following compounds:

7-(2-methoxypyridin-3-yl)-2-{[5-methyl-4-(4-methylpiperazin-1-yl)-2-(propan-2-yloxy)phenyl]amino}thieno[3,2-d]pyrimidine-6-carboxamide;

7-(2-methylfuran-3-yl)-2-{[4-(1-methylpiperidin-4-yl)-2-(propan-2-yloxy)-phenyl]amino}thieno[3,2-d]pyrimidine-6-carboxamide;

2-({4-[3-(dimethylamino)pyrrolidin-1-yl]-5-methyl-2-(propan-2-yloxy)-phenyl}amino)-7-(2-methoxyphenyl)thieno[3,2-d]pyrimidine-6-carboxamide;

2-{[3-(1-ethylpiperidin-4-yl)-1-(propan-2-yl)-1H-pyrazol-5-yl]amino}-7-[2-(trifluoromethoxy)phenyl]thieno[3,2-d]pyrimidine-6-carboxamide;

7-(2-methoxyphenyl)-2-{[4-(1-methyl-1H-pyrazol-4-yl)-2-(propan-2-yloxy)-phenyl]amino}thieno[3,2-d]pyrimidine-6-carboxamide;

2-{[5-fluoro-4-(1-methylpiperidin-4-yl)-2-(propan-2-yloxy)phenyl]amino}-7-(2-methoxypyridin-3-yl)thieno[3,2-d]pyrimidine-6-carboxamide;

7-(2-methoxypyridin-3-yl)-2-{[5-methyl-4-(2-methyl-1H-imidazol-1-yl)-2-(propan-2-yloxy)phenyl]amino}thieno[3,2-d]pyrimidine-6-carboxamide;

7-(2-methoxyphenyl)-2-({4-[(4-methylpiperazin-1-yl)methyl]-2-(propan-2-yloxy)phenyl}amino)thieno[3,2-d]pyrimidine-6-carboxamide;

7-(2-methoxyphenyl)-2-{[2-(propan-2-yloxy)-4-(tetrahydro-2H-pyran-4-ylamino)phenyl]amino}thieno[3,2-d]pyrimidine-6-carboxamide;

7-(5-fluoro-2-methoxypyridin-3-yl)-2-{[1-(propan-2-yl)-3-(tetrahydro-2H-pyran-4-yl)-1H-pyrazol-5-yl]amino}thieno[3,2-d]pyrimidine-6-carboxamide;

7-(2-methoxypyridin-3-yl)-2-{[3-(4-methylpiperazin-1-yl)-2-(propan-2-yloxy)phenyl]amino}thieno[3,2-d]pyrimidine-6-carboxamide;

7-(2-methoxyphenyl)-2-{[1-methyl-2-oxo-8-(propan-2-yloxy)-2,3,4,5-tetrahydro-1H-1-benzazepin-7-yl]amino}thieno[3,2-d]pyrimidine-6-carboxamide;

[7-(2-methoxy-6-methylpyridin-3-yl)-2-{[5-methyl-4-(4-methylpiperazin-1-yl)-2-(propan-2-yloxy)phenyl]amino}thieno[3,2-d]pyrimidin-6-yl]methanol;

[7-(5-fluoro-2-methoxyphenyl)-2-{[4-(4-methylpiperazin-1-yl)-2-(propan-2-yloxy)phenyl]amino}thieno[3,2-d]pyrimidin-6-yl]methanol; and or a pharmaceutically acceptable salt thereof.

\* \* \* \* \*